US012577294B2

(12) United States Patent
Weisbart et al.

(10) Patent No.: US 12,577,294 B2
(45) Date of Patent: *Mar. 17, 2026

(54) ANTIBODY-MEDIATED TRANSDUCTION OF HEAT SHOCK PROTEINS INTO LIVING CELLS

(71) Applicant: United States Government As Represented By The Department of Veterans Affairs, Washington, DC (US)

(72) Inventors: Richard H. Weisbart, Sepulveda, CA (US); Robert N. Nishimura, Sepulveda, CA (US); James E. Hansen, Guilford, CT (US)

(73) Assignee: THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 917 days.

This patent is subject to a terminal disclaimer.

(21) Appl. No.: 16/884,942

(22) Filed: May 27, 2020

(65) Prior Publication Data

US 2020/0385447 A1 Dec. 10, 2020

Related U.S. Application Data

(60) Continuation of application No. 15/650,752, filed on Jul. 14, 2017, now Pat. No. 10,703,807, which is a division of application No. 13/815,829, filed on Mar. 15, 2013, now Pat. No. 9,732,146.

(60) Provisional application No. 61/618,594, filed on Mar. 30, 2012.

(51) Int. Cl.
*C07K 16/18* (2006.01)
*C07K 14/47* (2006.01)
*A61K 38/00* (2006.01)

(52) U.S. Cl.
CPC .............. *C07K 16/18* (2013.01); *C07K 14/47* (2013.01); *A61K 38/00* (2013.01); *C07K 2317/56* (2013.01); *C07K 2317/622* (2013.01); *C07K 2317/77* (2013.01); *C07K 2319/33* (2013.01)

(58) Field of Classification Search
CPC .... C07K 16/18; C07K 14/47; C07K 2317/56; C07K 2317/622; C07K 2317/77; C07K 2319/33; A61K 38/00
See application file for complete search history.

(56) References Cited

U.S. PATENT DOCUMENTS 9,701,740 B2 7/2017 Hansen et al.

FOREIGN PATENT DOCUMENTS

| WO | WO2010/138769 A1 | 12/2010 | |
| WO | WO2010/148010 A1 | 12/2010 | |
| WO | WO 2012/091564 * | 12/2011 | ............. C07K 16/28 |
| WO | WO2012/091564 A2 | 7/2012 | |

OTHER PUBLICATIONS

Mariuzza (Annu. Rev. Biophys. Biophys. Chem., 16: 139-159, 1987).*
Hansen et al. (Brain Research, 1088: 187-196, 2006).*
List of references, Form 892 issued Dec. 12, 2016.
List of references, Form 892 issued Jul. 10, 2015.
Amin V, Cumming DV, Latchman DS. (1996) Over-expression of heat shock protein 70 protects neuronal cells against both thermal and ischemic stress but with different efficiencies. Neurosci. Lett. 206(1):45-48.
An JJ, Lee YP, Kim SY, Lee SH, Lee MJ, Jeong MS, Kim DW, Jang SH, Yoo K-Y, Won MH, Kang T-C, et al. (2008) Transduced human PEP-1-heat shock protein 27 efficiently protects against brain ischemic insult. FEBS J. 275:1296-1308.
Arrigo A-P, Landry J. (1994) Expression and function of the low-molecular weight heat shock proteins. In: Morimoto RI, Tissieres A, Georgopoulos C (eds.) The Biology of Heat Shock Proteins and Molecular Chaperones, Cold Spring Harbor Laboratory Press, Cold Spring Harbor, NY pp. 335-373.
Arrigo A-P, Firdaus WJ, Melller G, Moulin M, Paul C, Diaz-Latoud C, Kretz-Remy C. (2005) Cytotoxic effects induced by oxidative stress in cultured mammalian cells and protection provided by Hsp27 expression. Methods. 35, 126-138.
Arrigo A-P. (2011) Structure-Function of HspB1 (Hsp27). In Mol. Chaperones: Methods and Protocols, Methods in Mol. Biol. vol. 787, pp. 105-119.
Avalos BR et al., Human Granulocyte Colony-Stimulating Factor: Biologic Activities and Receptor Characterization on Hematopoietic Cells and Small Cell Lung Cancer Cell Lines. Blood Journal, 1990. 75(4):851-857.
Beckman RP, Mizzen LE, Welch WJ. (1990) Interaction of Hsp70 with newly synthesized proteins: implication for protein folding and assembly. Science 248(4957:850-854.
Beere HM, Wolf BB, Cain K, Mosser DD, Mahboubi A, Kuwana T, Tailor P, Morimoto RI, Cohen GM, Green DR. (2000) Heat shock protein 70 inhibits apoptosis by preventing recruitment of procaspase-9 to the Apaf-1 apoptosome. Nat. Cell. Biol. 2(8):469-475.
Bellyei S, Szigeti A, Pozsgai E, Boronkai A, Gomori E, Hocsak E, Farkas R, Sumegi B, Gallyas F. (2007) Preventing apoptotic cell death by a novel small heat shock protein. Eur. J. Cell Biol. 86, 161-171.
Brar BK, Stephanou A, Wagstaff MJ, Coffin RL, Marber MS, Engelmann G, Latchman DS. (1999) Heat shock proteins delivered with a virus vector can protect cardiac cells against apoptosis as well as against thermal or hypoxic stress. J. Mol. Cell. Cardiol. 31(1):135-146.

(Continued)

*Primary Examiner* — Nelson B Moseley, II
(74) *Attorney, Agent, or Firm* — BALLARD SPAHR LLP

(57) ABSTRACT

The invention provides for a fusion protein comprising a 3E10 Fv joined to a Hsp-70, Hsp-27, Hsp-90 or GRP-78 or portion thereof, and optionally, the 3E10 Fv comprising an amino acid sequence AGIH at its amino terminus.

14 Claims, 76 Drawing Sheets

Specification includes a Sequence Listing.

(56)         References Cited

OTHER PUBLICATIONS

Bruey JM, Ducasse C, Bonniaud P, Ravagnan L, Susin SA, Diaz-Latoud C, Gurbuxani S, Arrigo A-P, Kroemer G, Solary E, et al. (2000) Hsp27 negatively regulates cell death by interacting with cytochrome c. *Nat. Cell Biol.* 2(9):645-652.

Cheetham ME, Anderton BH, Jackson AP. (1996) Inhibition of hsc70-catalysed clathrin uncoating by HSJ1 proteins. *Biochem J* 319(Pt1):103-108.

Chen J, Graham SH, Zhu RL, Simon RP. (1996) Stress proteins and tolerance to focal cerebral ischemia. *J. Cereb. Blood Flow Metab.* 16(4)566-577.

Demand J, Luders J, Hohfeld J. (1998) The carboxy-terminal domain of Hsc70 provides binding sites for a distinct set of chaperone cofactors. *Mol. Cell. Biol.* 18(4):2023-2028.

Gabai VL, Merlin AB, Mosser DD, Caron AW, Rits S, Shifrin VI, Sherman MY. (1997) Hsp70 prevents activation of stress kinases. A novel pathway of cellular thermotolerance. *J. Biol. Chem.* 272(29):18033-18037.

Gebauer M, Zeiner M., Gehring U. (1997) Proteins interacting with the molecular chaperone hsp70/hsc70: physical associations and effects on refolding activity. *FEBS Lett.* 417(1):109-113.

Gasson JC et al., High-affinity binding of granulocyte-macrophage colony-stimulating factor to normal and leukemic human myeloid cells. *Proc. Natl. Acad. Sci. USA*, 1986. vol. 83, pp. 669-673.

Fleischmann J et al., Granulocyte-macrophage colony-stimulating factor enhances phagocytosis of bacteria by human neutrophils. *Blood Journal*, 1986. 68(3): 708-711.

Hansen JE et al., Intranuclear protein transduction through a nucleoside salvage pathway. *J Biol Chem.* 2007. 282(29):20790-3. Epub May 24, 2007.

Hansen JE et al., Antibody-Mediated p53 Protein Therapy Prevents Liver Metastasis In vivo. *Cancer Res*, 2007; 67:(4).

Heinze E et al., Tumor suppressor and T-regulatory functions of Foxp3 are mediated through separate signaling pathways. *Oncology Letters*, 2011. 2(4):665-668. Epub May 13, 2011.

Hansen JE et al., Targeting cancer with a lupus autoantibody. *Science Translational Medicine*, 2012. 4(157): 157ra142.

Hansen JE, Sohn W, Kim C, Chang SS, Huang NC, Santos DG, Chan G, Weisbart RH, Nishimura RN. (2006) Antibody-mediated Hsp70 protein therapy. *Brain Res.* 1088:187-196.

Kurucz I et al., Retargeting of CTL by an efficiently refolded bispecific single-chain Fv dimer produced in bacteria. *Journal of Immunology*, 1995. 154:4576-4582.

Lee GJ, Roseman AM, Saibil HR, Vierling E. (1997) A small heat shock protein stably binds heat-denatured model substrates and can maintain a substrate in a folding-competent state. *EMBO J.* 16, 221-229.

Lee JE, Yenari MA, Sun GH Xu L, Emond MR, Cheng D, Steinberg GK, Giffard RG. (2001) Differential neuroprotection from human heat shock protein 70 overexpression in in-vitro and in-vivo models of ischemia and ischemia-like conditions. *Exp. Neurol.* 170(1):129-139.

Lindquist S. (1992) Heat shock proteins and stress tolerance in microorganisms. *Curr. Opin. Genet. Dev.* 2(5):748-755.

Liu JP, Schlosser R, Ma WY, Dong Z, Feng H, Liu L, Huang XQ, Liu Y, Li DW. (2004) Human alphaA- and alphaB-crystallins prevent UVA-induced apoptosis through regulation of PKCalpha, RAF/MEK/ERK and AKT signaling pathways. *Exp. Eye Res.* 79, 393-403.

Mariuzza, R.A. et al., The Structural Basis of Antigen-Antibody Recognition, Annu. Rev. Biophys. Biophys. Chem., 1987, 16: 139-59.

Martin JL, Mestril R, Hilal-Dandan R, Brunton LL, Dillmann WH. (1997) Small heat shock proteins and protection against ischemic injury in cardiac myocytes. *Circulation* 96:4343-4348.

Martin-Ventura JL, Duran MC, Blanco-Colio LM, Meilhac O, Leclercq A, Michel JB, Jensen ON, Hernandez-Merida S, Tuñón J, Vivanco F, Egido J. (2004) Identification by a differential proteomic approach of heat shock protein 27 as a potential marker of atherosclerosis. Circulation 110:2216-2219.

Mehlen P, Carole K-R, Preville X, Arrigo A-P. (1996) Human hsp27, *Drosophila* hsp27 and human alphabeta-crystallin expression-mediated increase in glutathione is essential for the protective activity of these proteins against TNFalpha-induced cell death. *EMBO J.* 15, 2695-2706.

Ni M , Zhang Y, and Lee AS, (2011) Beyond the endoplasmic reticulum: atypical GRP78 in cell viability, signaling and therapeutic targeting, *Biochemical J.* 434(2): 181-188.

Nicholl ID, Quinlan RA. (1994) Chaperone activity of alpha-crystallins modulates intermediate filament assembly. *EMBO J.* 13, 945-953.

Noritake DT et al., Rheumatoid factors specific for active rheumatoid Arthritis. *Annals of the Rheumatic Diseases*, 1990; 49: 910-915.

Pandey P, Saleh A, Nakazawa A, Kumar S, Srinivasula SM, Kumar V, Weichselbaum R, Nalin C, Alnemri ES, Kufe D, et al. (2000) Negative regulation of cytochrome c-mediated oligomerization of Apaf-1 and activation of procaspase-9 by heat shock protein 90. *EMBO J.* 19(16):4310-4322.

Rane MJ, Pan Y, Singh, Poell D, Wu R, Cummins T, Chen Q, McLeish KR, Klein JB. (2003) Heat shock protein 27 controls apoptosis by regulating Akt activation. *J. Biol. Chem.* 279, 27828-27835.

Samali A and Orrenius S. (1998) Heat shock proteins: regulators of stress response and apoptosis. *Cell Stress Chaperones* 3(4):228-236.

Schumacher RJ, Hansen WJ, Freeman BC, Alnemri E, Litwack G, Toft DO. (1996) Cooperative action of Hsp70, Hsp90, and DnaJ proteins in protein renaturation. *Biochem.* 35(7):14889-14898.

Shi Y, Mosser DD, Morimoto RI. (1998) Molecular chaperones as HSF1 specific transcriptional repressors. *Genes Dev.* 12(5):654-666.

Stetler RA Signore AP, Gao Y, Cao G, Chen J. (2009) Hsp27: Mechanisms of cellular protection against neuronal injury. *Curr. Mol. Med.* 9:863-872.

Stevens FJ, Argon Y. (1999) Protein folding in the ER. *Semin. Cell. Dev. Biol.* 10(5):443-454.

Tsaytler PA Krijgsveld J Goerdayal SS Rudiger S, Egmond MR. (2009) Novel Hsp90 partners discovered using complementary proteomic approaches. *Cell Stress Chaperones* 4:629-638.

Van der Weerd L Akbar MT, Badin RA, Vanentim LM, Thomas DL, Wells DJ, Latchman DS, Gadian DG, Lythgoe MF, de Belleroche JS. (2010) Overexpression of heat shock protein 27 reduces cortical damage after cerebral ischemia. *J. Cereb. Blood Flow Metab.* 30:849-856.

Wang W, Peng Y, Wang Y, Zhao X, Yuan Z. (2009) Anti-apoptotic effect of heat shock protein 90 on hypoxia-mediated cardiomyocyte damage is mediated via the phosphatidylinositol 3-kinase/AKT pathway. Clin. Exp. Pharmacol. Physiol. 36:899-903.

Welch WJ, Brown CR. (1996) Influence of molecular and chemical chaperones on protein folding. Cell Stress Chaperones 1(2):109-115.

Weisbart RH et al., Construction and expression of a bispecific single-chain antibody that penetrates mutant p53 colon cancer cells and binds p53. *International Journal of Oncology*, 2004. 25: 1113-1118.

Weisbart RH et al., Human GM-CSF primes neutrophils for enhanced oxidative metabolism in response to the major physiological chemoattractants. *Blood Journal*, 1987. 69(1):18-21.

Weisbart RH et al., Novel Protein Transfection of Primary Rat Cortical Neurons Using an Antibody That Penetrates Living Cells. *Journal of Immunology* 2000; 164:6020-6026.

Weisbart RH et al., A cell-Penetrating Bispecific Antibody for Therapeutic Regulation of Intracellular Targets. *Mol Cancer Ther.* Oct. 2012;11(10):2169-73. doi: 10.1158/1535-7163.MCT-12-0476-T. Epub Aug. 3, 2012.

Yenari MA, Fink SL, Sun GH, Chang LK, Patel MK, Kunis DM, Olney D, Ho DY, Sapolsky RM, Steinberg GK. (1998) Gene therapy with HSP72 is neuroprotective in rat models of stroke and epilepsy. *Ann. Neurol.* 44(4):584-591.

Zack DJ et al., Novel structural features of autoantibodies in murine lupus: A possible superantigen binding site? *Immunology and Cell Biology*, 1994. 72, 51 3-520.

(56) References Cited

OTHER PUBLICATIONS

Zhan X, Ander BP, Liao IH, Hansen JE, Kim C, Clements D, Weisbart RH, Nishimura RN, Sharp FR. (2010) Recombinant Fv-Hsp70 protein mediates neuroprotection after focal cerebral ischemia in rats. *Stroke* 41:538-543.

Zou J, Guo Y, Guettouche T, Smith DF, Voellmy R. (1998) Repression of heat shock transcription factor HSF1 activation by HSP90 (HSP90 complex) that forms a stress-sensitive complex with HSF1. *Cell* 94:471-480.

U.S. Appl. No. 15/650,752 (U.S. Pat. No. 10,703,807), filed Jul. 14, 2017, Weisbart.

U.S. Appl. No. 13/815,829 (U.S. Pat. No. 9,732,146), filed Mar. 15, 2013, Weisbart.

U.S. Appl. No. 61/618,594, filed Mar. 30, 2012, Weisbart.

* cited by examiner

3E10-Fv-HSP27 in pPiczαA (Human linker)

↓Begin pPiczαA signal sequence
```
ATG AGA TTT CCT TCA CTT TTT ACT GCT GTT TTA TTC GCA GCA TCC
 M   R   F   P   S   L   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ACT ATT GCC AGC ATT GCT GCT
 N   G   L   L   F   I   N   T   T   I   A   S   I   A   A
```

Kex2 signal cleavage →　End signal seq →

```
AAA GAA GAA GGG GTA TCT CTC GAG AAA AGA GAG GCT GAA GCT
 K   E   E   G   V   S   L   E   K   R   E   A   E   A
```

Ste13 signal cleavage

Figure 4

EcoRI  HIS6 tag  ↑solubility ↓Begin Fv

```
GAA TTC CAT CAC CAT CAC CAT CAC GCA GGG ATT CAC GAC ATT GTC
 E   F   H   H   H   H   H   H   A   G   I   H   D   I   V

CTG ACA CAG TCT CCT GCT TCC TTA GCT GTA TCT CTG GGG CAG AGG
 L   T   Q   S   P   A   S   L   A   V   S   L   G   Q   R

GCC ACC ATC TCC TGC AGG GCC AGC AAA AGT GTC AGT ACA TCT AGC
 A   T   I   S   C   R   A   S   K   S   V   S   T   S   S
                    3E10 Vk CDR1
TAT AGT TAC ATG CAC TGG TAC CAA CAG AAA CCA GGA CAG CCA CCC
 Y   S   Y   M   H   W   Y   Q   Q   K   P   G   Q   P   P
                         3E10 Vk CDR2
AAA CTC CTC ATC AAG TAT GCA TCC TAC CTA GAA TCT GGG GTT CCT
 K   L   L   I   K   Y   A   S   Y   L   E   S   G   V   P

GCC AGG TTC AGT GGC AGT GGG TCT GGG ACA GAC TTC ACC CTC AAC
 A   R   F   S   G   S   G   S   G   T   D   F   T   L   N
                         3E10 Vk CDR3
ATC CAT CCT GTG GAG GAG GAT GCT GCA ACA TAT TAC TGT CAG
 I   H   P   V   E   E   D   A   A   T   Y   Y   C   Q

CAC AGT AGG GAG TTT CCG TGG ACG TTC GGT GGA GGC ACC AAG CTG
 H   S   R   E   F   P   W   T   F   G   G   G   T   K   L
```

```
                                                    (GGGGS)₃ Linker
GAA ATC AAA CGG GCT GAT GCT GCA CCC GGG GCT GGC GGT TCT GGC
 E   I   K   R   A   D   A   A   P   G   G   G   S   G GGT GGC GGT TCT GGA GGC GGT GGC TCT GAG GTG CAG CTG GTG GAG
 G   G   G   S   G   G   G   S   E   V   Q   L   V   E TCT GGG GGA GGC TTA GTG AAG CCT GGA GGG TCC CGG AAA CTC TCC
 S   G   G   G   L   V   K   P   G   G   S   R   K   L   S 3E10 VH CDR1
TGT GCA GCC TCT GGA TTC ACT TTC AGT AAC TAT GGA ATG CAC TGG
 C   A   A   S   G   F   T   F   S   N   Y   G   M   H   W
                (D31N mutation 3E10 VH enhances cell penetration)

GTC CGT CAG GCT CCA GAG AAG GGG CTG GAG TGG GTT GCA TAC ATT
 V   R   Q   A   P   E   K   G   L   E   W   V   A   Y   I

3E10 VH CDR2
AGT AGT GGC AGT AGT ACC ATC TAC TAT GCA GAC ACA GTG AAG GGC
 S   S   G   S   S   T   I   Y   Y   A   D   T   V   K   G

CGA TTC ACC ATC TCC AGA GAC AAT GCC AAG AAC ACC CTG TTC CTG
 R   F   T   I   S   R   D   N   A   K   N   T   L   F   L
```

3E10 VH CDR3

```
    CAA ATG ACC AGT CTA AGG TCT GAG GAC ACA GCC ATG CGG GGG TTA
    Q   M   T   S   L   R   S   E   D   T   A   M   R   G   L
```

End 3E10 Fv →

```
    CTA CTT GAC TAC TGG GGC CAA GGC ACC ACT CTC ACA GTC TCC TCA
    L   L   D   Y   W   G   Q   G   T   T   L   T   V   S   S
```

Myc tag

```
    CTA GAA CAA AAA CTC ATC TCA GAA GAG GAT CTG AAT AGC GCC GTC
    L   E   Q   K   L   I   S   E   E   D   L   N   S   A   V
```

↓Human CH1 Linker

```
    GAC GCT TCC ACC AAG GGC CCA TCC GTC TTC CCC CTG GCG CCC
    D   A   S   T   K   G   P   S   V   F   P   L   A   P
```

↓Swivel seq     ↓Begin Human HSP27

```
    CTG GAG TCT TCC GGA TCC ATG ACC GAG CGC CGC GTC CCC TTC TCG
    L   E   S   S   G   S   M   T   E   R   R   V   P   F   S
```

```
    CTC CTG CGG GGC CCC AGC TGG GAC CCC TTC CGC GAC TGG TAC CCG
    L   L   R   G   P   S   W   D   P   F   R   D   W   Y   P
```

```
    CAT AGC CGC CTC TTC GAC CAG GCC TTC GGG CTG CCC CGG CTG CCG
    H   S   R   L   F   D   Q   A   F   G   L   P   R   L   P
```

```
    GAG GAG TGG TCG CAG TGG TTA GGC GGC AGC AGC TGG CCA GGC TAC
    E   E   W   S   Q   W   L   G   G   S   S   W   P   G   Y
```

```
GTG CGC CCC CTG CCC CCC GCC ATC GAG AGC CCC GCA GTG GCC
 V   R   P   L   P   P   A   I   E   S   P   A   V   A

GCG CCC GCC TAC AGC CGC GCG CTC AGC CGG CAA CTC AGC AGC GGG
 A   P   A   Y   S   R   A   L   S   R   Q   L   S   S   G

GTC TCG GAG ATC CGG CAC ACT GCG GAC CGC TGG CGC GTG TCC CTG
 V   S   E   I   R   H   T   A   D   R   W   R   V   S   L

GAT GTC AAC CAC TTC GCC CCG GAC GAG ATC ACC GGC AAG
 D   V   N   H   F   A   P   D   E   I   T   G   K

GAT GGC GTG GAG ATC ACC AAG CAC GAG GAG CGG CAG GAC
 D   G   V   E   I   T   K   H   E   E   R   Q   D

GAG CAT GGC TAC ATC TCC CGG TGC TTC ACG CGG AAA TAC ACG CTG
 E   H   G   Y   I   S   R   C   F   T   R   K   Y   T   L

CCC CCC GGT GTG GAC CCC ACC CAA GTT TCC TCC CTG TCC CCT
 P   P   G   V   D   P   T   Q   V   S   S   L   S   P

GAG GGC ACA CTG ACC GTG GAG GCC ATG CCC AAG CTA GCC ACG
 E   G   T   L   T   V   E   A   M   P   K   L   A   T
```

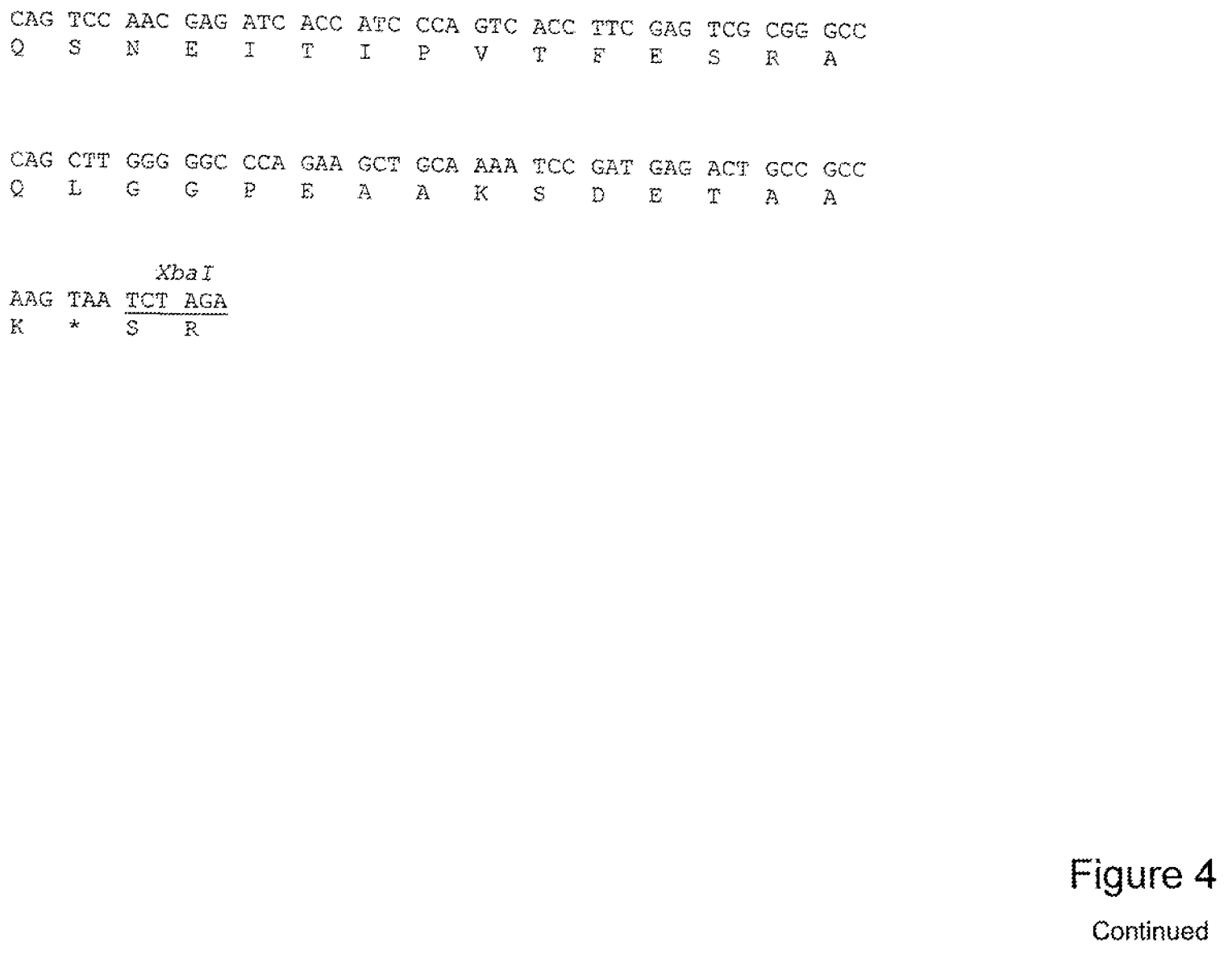

```
CAG TCC AAC GAG ATC ACC ATC CCA GTC ACC TTC GAG TCG CGG GCC
 Q   S   N   E   I   T   I   P   V   T   F   E   S   R   A

CAG CTT GGG GGC CCA GAA GCT GCA AAA TCC GAT GAG ACT GCC GCC
 Q   L   G   G   P   E   A   A   K   S   D   E   T   A   A

XbaI
AAG TAA TCT AGA
 K   *   S   R
```

Figure 4
Continued

3E10-Fv-HSP70 in pPiczαA (Human linker)

↓Begin pPiczαA signal sequence
```
ATG AGA TTT CCT TCA CTT TTT ACT GCT GTT TTA TTC GCA GCA TCC
 M   R   F   P   S   L   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ACT ATT GCC AGC ATT GCT GCT
 N   G   L   L   F   I   N   T   T   I   A   S   I   A   A
```

Kex2 signal cleavage→   End signal seq→
```
AAA GAA GAA GGG GTA TCT CTC GAG AAA AGA GAG GCT GAA GCT
 K   E   E   G   V   S   L   E   K   R   E   A   E   A
```

Ste13 signal cleavage

```
EcoRI    HIS6 tag              ↑solubility  ↓Begin Fv
GAA TTC CAT CAC CAT CAC CAT CAC GCA GGG ATT CAC GAC ATT GTC
 E   F   H   H   H   H   H   H   A   G   I   H   D   I   V CTG ACA CAG TCT CCT GCT TCC TTA GCT GTA TCT CTG GGG CAG AGG
 L   T   Q   S   P   A   S   L   A   V   S   L   G   Q   R GCC ACC ATC TCC TGC AGG GCC AGC AAA AGT GTC AGT ACA TCT AGC
 A   T   I   S   C   R   A   S   K   S   V   S   T   S   S
                    3E10 Vk CDR1

TAT AGT TAC ATG CAC TGG TAC CAA CAG AAA CCA GGA CAG CCA CCC
 Y   S   Y   M   H   W   Y   Q   Q   K   P   G   Q   P   P

AAA CTC CTC ATC AAG TAT GCA TCC TAC CTA GAA TCT GGG GTT CCT
 K   L   L   I   K   Y   A   S   Y   L   E   S   G   V   P
                        3E10 Vk CDR2

GCC AGG TTC AGT GGC AGT GGG TCT GGG ACA GAC TTC ACC CTC AAC
 A   R   F   S   G   S   G   S   G   T   D   F   T   L   N

ATC CAT CCT GTG GAG GAG GAT GCT GCA ACA TAT TAC TGT CAG
 I   H   P   V   E   E   D   A   A   T   Y   Y   C   Q
                                        3E10 Vk CDR3

CAC AGT AGG GAG TTT CCG TGG ACG TTC GGT GGA GGC ACC AAG CTG
 H   S   R   E   F   P   W   T   F   G   G   G   T   K   L
```

```
                                                              (GGGGS)₃ Linker
GAA ATC AAA CGG GCT GAT GCT GCA CCC GGG GGT GGC GGT TCT GGC
 E   I   K   R   A   D   A   A   P   G   G   G   G   S   G GGT GGC GGT TCT GGA GGC GGT GGC TCT GAG GTG CAG CTG GTG GAG
 G   G   G   S   G   G   G   G   S   E   V   Q   L   V   E TCT GGG GGA GGC TTA GTG AAG CCT GGA GGG TCC CGG AAA CTC TCC
 S   G   G   G   L   V   K   P   G   G   S   R   K   L   S 3E10 VH CDR1
TGT GCA GCC TCT GGA TTC ACT TTC AGT AAC TAT GGA ATG CAC TGG
 C   A   A   S   G   F   T   F   S   N   Y   G   M   H   W
                          (D31N mutation 3E10 VH enhances cell penetration)

GTC CGT CAG GCT CCA GAG AAG GGG CTG GAG TGG GTT GCA TAC ATT
 V   R   Q   A   P   E   K   G   L   E   W   V   A   Y   I

3E10 VH CDR2
AGT AGT GGC AGT AGT ACC ATC TAC TAT GCA GAC ACA GTG AAG GGC
 S   S   G   S   S   T   I   Y   Y   A   D   T   V   K   G

CGA TTC ACC ATC TCC AGA GAC AAT GCC AAG AAC ACC CTG TTC CTG
 R   F   T   I   S   R   D   N   A   K   N   T   L   F   L
```

Figure 5
Continued

3E10 VH CDR3
```
CAA ATG ACC AGT CTA AGG TCT GAG GAC ACA GCC ATG | CGG GGG TTA
 Q   M   T   S   L   R   S   E   D   T   A   M      R   G   L
```

End 3E10 Fv →

```
CTA CTT GAC TAC TGG GGC CAA GGC ACC ACT CTC ACA GTC TCC TCA
 L   L   D   Y   W   G   Q   G   T   T   L   T   V   S   S
```

Myc tag
```
CTA GAA CAA AAA CTC ATC TCA GAA GAG GAT CTG AAT AGC GCC GTC
 L   E   Q   K   L   I   S   E   E   D   L   N   S   A   V
```

→Human CH1 Linker
```
GAC GCT TCC ACC AAG GGC CCA TCC GTC TTC CCC CTG GCG CCC
 D   A   S   T   K   G   P   S   V   F   P   L   A   P
```

→Swivel seq
```
CTG GAG TCT TCC GGA TCC
 L   E   S   S   G   S
```

→Begin Human HSP70
```
ATG GCC AAA GCC GCG GCG ATC GGC ATC GAC CTG GGC ACC ACC TAC
 M   A   K   A   A   A   I   G   I   D   L   G   T   T   Y
```

```
TCC TGC GTG GGG GTG TTC CAA CAC GGC AAG GTG GAG ATC ATC GCC
 S   C   V   G   V   F   Q   H   G   K   V   E   I   I   A
```

```
AAC GAC CAG GGC AAC CGC ACC ACC CCC AGC TAC GTG GCC TTC ACG
 N   D   Q   G   N   R   T   T   P   S   Y   V   A   F   T
```

```
GAC ACC GAG CGG CTC ATC GGG GAT GCG GCC AAG AAC CAG GTG GCG
 D   T   E   R   L   I   G   D   A   A   K   N   Q   V   A

CTG AAC CCG CAG AAC ACC GTG TTT GAC GCG AAG CGG CTG ATC GGC
 L   N   P   Q   N   T   V   F   D   A   K   R   L   I   G

CGC AAG TTC GGC GAC CCG GTG GTG CAG TCG GAC ATG AAG CAC TGG
 R   K   F   G   D   P   V   V   Q   S   D   M   K   H   W

CCT TTC CAG GTG ATC AAC GAC GGA GAC AAG CCC AAG GTG CAG GTG
 P   F   Q   V   I   N   D   G   D   K   P   K   V   Q   V

AGC TAC AAG GGG GAG ACC AAG GCA TTC TAC CCC GAG GAG ATC TCG
 S   Y   K   G   E   T   K   A   F   Y   P   E   E   I   S

TCC ATG GTG CTG ACC AAG ATG AAG GAG ATC GCC GAG GCG TAC CTG
 S   M   V   L   T   K   M   K   E   I   A   E   A   Y   L

GGC TAC CCG GTG ACC AAC GCG GTG ATC ACC GTG CCG TAC TTC
 G   Y   P   V   T   N   A   V   I   T   V   P   Y   F

AAC GAC TCG CAG CGC CAG GCC ACC AAG GAT GCG GGT GTG ATC GCG
 N   D   S   Q   R   Q   A   T   K   D   A   G   V   I   A
```

```
GGG CTC AAC GTG CTG CGG ATC ATC AAC GAG CCC ACG GCC GCC GCC
 G   L   N   V   L   R   I   I   N   E   P   T   A   A   A

ATC GCC TAC GGC CTG GAC AGA ACG GGC AAG GAG CGC AAC GTG
 I   A   Y   G   L   D   R   T   G   K   E   R   N   V

CTC ATC TTT GAC CTG GGC GGC ACC TTC GAC GTG TCC ATC CTG
 L   I   F   D   L   G   G   T   F   D   V   S   I   L

ACG ATC GAC GAC GGC GGG GGC AAG GCC ACG GCC GGG GAC
 T   I   D   D   G   G   G   K   A   T   A   G   D

ACC CAC CTG GGT GGG GAG GAC TTT GAC AAC AGG CTG AAC CAC
 T   H   L   G   G   E   D   F   D   N   R   L   N   H

TTC GTG GAG GAG TTC AAG AGA AAA CAC AAG AAG GAC ATC AGC CAG
 F   V   E   E   F   K   R   K   H   K   K   D   I   S   Q

AAC AAG CGA GCC GTG AGG CGG CTG CGC ACC GCC TGC GAG AGG GCC
 N   K   R   A   V   R   R   L   R   T   A   C   E   R   A

AAG AGG ACC CTG TCG TCC AGC ACC CAG GCC AGC ACC CTG GAG ATC GAC
 K   R   T   L   S   S   S   T   Q   A   S   T   L   E   I   D
```

```
TCC CTG TTT GAG GGC ATC GAC TTC TAC ACG TCC ATC ACC AGG GCG
 S   L   F   E   G   I   D   F   Y   T   S   I   T   R   A

AGG TTC GAG GAG CTG TGC TCC GAC CTG TTC CGA AGC ACC CTG GAG
 R   F   E   E   L   C   S   D   L   F   R   S   T   L   E

CCC GTG GAG AAG GCT CTG CGC GAC GCC AAG CTG GAC AAG GCC CAG
 P   V   E   K   A   L   R   D   A   K   L   D   K   A   Q

ATT CAC GAC CTG GTC GGG GGC TCC ACC CGC ATC CCC AAG
 I   H   D   L   V   G   G   S   T   R   I   P   K

GTG CAG AAG CTG CTG CAG GAC TTC AAC GGG CGC GAC CTG AAC
 V   Q   K   L   L   Q   D   F   N   G   R   D   L   N

AAG AGC ATC AAC CCC GAC GAG GCT GTG GCC TAC GGG GCG GCG GTG
 K   S   I   N   P   D   E   A   V   A   Y   G   A   A   V

CAG GCG GCC ATC CTG ATG GGG GAC AAG TCC GAG AAC GTG CAG GAC
 Q   A   A   I   L   M   G   D   K   S   E   N   V   Q   D
```

Figure 5
Continued

```
CTG CTG CTG CTG GAC GTG GCT CCC CTG TCG CTG GGG CTG GAG ACG
 L   L   L   L   D   V   A   P   L   S   L   G   L   E   T

GCC GGA GGC GTG ATG ACT GCC CTG ATC AAG CGC AAC TCC ACC ATC
 A   G   G   V   M   T   A   L   I   K   R   N   S   T   I

CCC ACC AAG CAG ACG CAG ATC TTC ACC TAC TCC GAC AAC CAA
 P   T   K   Q   T   Q   I   F   T   Y   S   D   N   Q

CCC GGG GTG CTG ATC CAG GTG TAC GAG GGC GCC ATG ACG
 P   G   V   L   I   Q   V   Y   E   G   A   M   T

AAA GAC AAC AAT CTG TTG GGG CGC TTC GAG CTG AGC ATC CCT
 K   D   N   N   L   L   G   R   F   E   L   S   I   P

CCG GCC CCC AGG GGC GTG CCC CAG ATC GAG GTG ACC TTC GAC ATC
 P   A   P   R   G   V   P   Q   I   E   V   T   F   D   I

GAT GCC AAC GGC ATC CTG AAC GTC ACG GCC ACG GAC AAG AGC ACC
 D   A   N   G   I   L   N   V   T   A   T   D   K   S   T

GGC AAG GCC AAC AAC ATC ACC ATC ACC AAC AAG GAC AAG GGC CGC CTG
 G   K   A   N   N   K   I   T   I   T   N   D   K   G   R   L
```

```
AGC AAG GAG GAG ATC GAG CGC ATG GTG CAG GAG GCG GAG AAG TAC
 S   K   E   E   I   E   R   M   V   Q   E   A   E   K   Y

AAA GCG GAG GAC GAG GTG CAG CGC GAG AGC GTG TCA GCC AAG AAC
 K   A   E   D   E   V   Q   R   E   R   V   S   A   K   N

GCC CTG GAG TCC TAC GCC TTC AAC ATG AAG AGC GCC GTG GAG GAT
 A   L   E   S   Y   A   F   N   M   K   S   A   V   E   D

GAG GGG CTC AAG GGC AAG ATC AGC GAG GCG GAC AAG AAG AAG GTT
 E   G   L   K   G   K   I   S   E   A   D   K   K   K   V

CTG GAC AAG TGT CAA GAG GTC ATC TCG TGG CTG GAC GCC AAC ACC
 L   D   K   C   Q   E   V   I   S   W   L   D   A   N   T

TTG GCC GAG AAG GAC GAG TTT GAG CAC AAG AAG AGG AAG GAG CTG GAG
 L   A   E   K   D   E   F   E   H   K   K   R   K   E   L   E

CAG GTG TGT AAC CCC ATC ATC AGC GGA CTG TAC CAG GGT GCC GGT
 Q   V   C   N   P   I   I   S   G   L   Y   Q   G   A   G

GGT CCC GGG CCT GGC GGC TTC GGG TTC GCT CAG GGT CCC AAG GGA GGG
 G   P   G   P   G   G   F   G   F   A   Q   G   P   K   G   G
```

TCT GGG TCA GGC CCT ACC ATT GAG GAG GTG GAT TAG
 S   G   S   G   P   T   I   E   E   V   D   *

Figure 5
Continued

Figure 6:
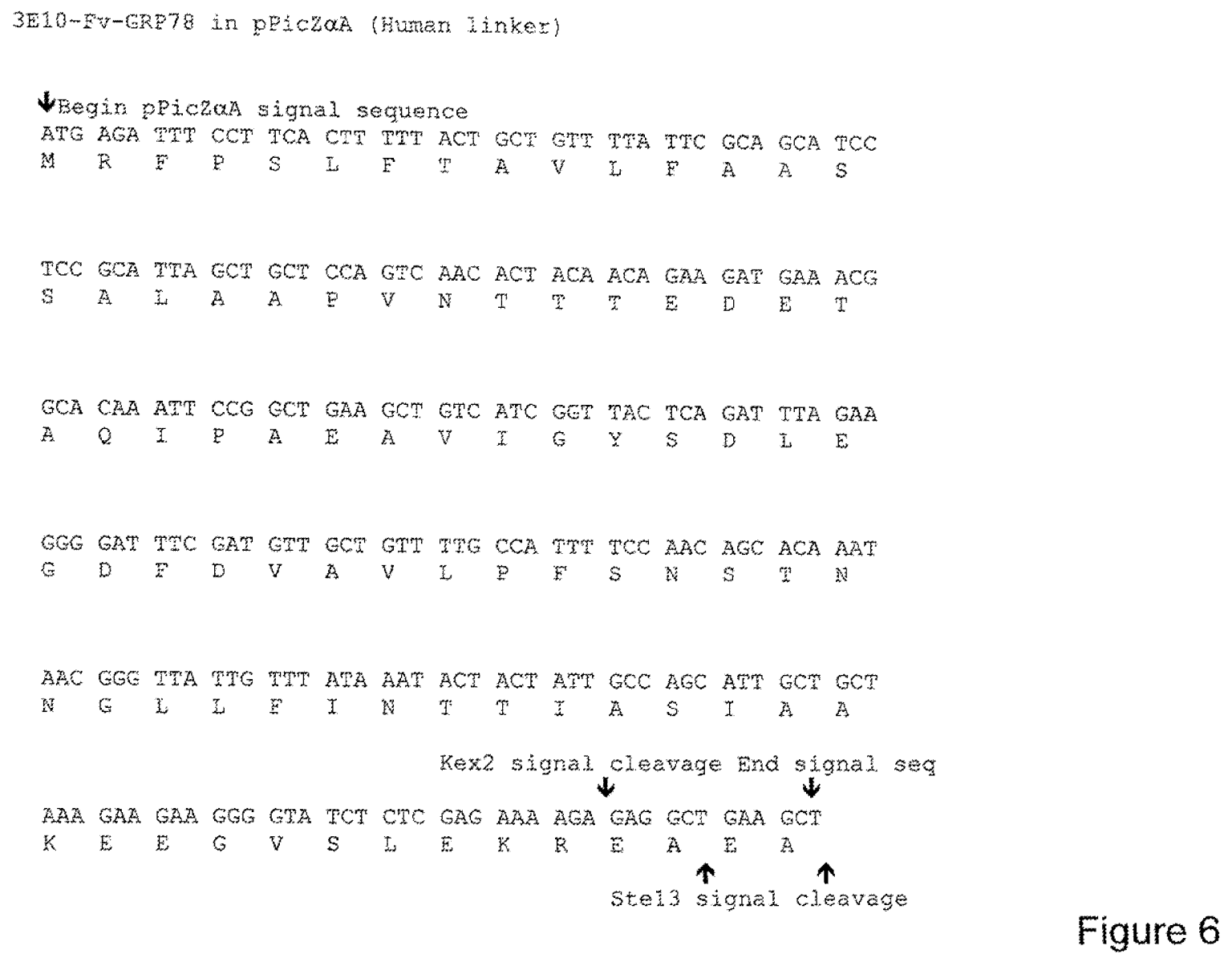

3E10-Fv-GRP78 in pPiczαA (Human linker)

↓Begin pPiczαA signal sequence
```
ATG AGA TTT CCT TCA CTT TTT ACT GCT GTT TTA TTC GCA GCA TCC
 M   R   F   P   S   L   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ACT ATT GCC AGC ATT GCT GCT
 N   G   L   L   F   I   N   T   T   I   A   S   I   A   A Kex2 signal cleavage   End signal seq
                                        ↓                  ↓
AAA GAA GAA GGG GTA TCT CTC GAG AAA AGA GAG GCT GAA GCT
 K   E   E   G   V   S   L   E   K   R   E   A   E   A
                                ↑                    ↑
                            Ste13 signal cleavage
```

```
EcoRI     HIS6 tag                              ↑solubility   ↓Begin Fv
GAA TTC CAT CAC CAT CAC CAT CAC GCA GGG ATT CAC GAC ATT GTC
 E   F   H   H   H   H   H   H   A   G   I   H   D   I   V CTG ACA CAG TCT CCT GCT TCC TTA GCT GTA TCT CTG GGG CAG AGG
 L   T   Q   S   P   A   S   L   A   V   S   L   G   Q   R GCC ACC ATC TCC TGC AGG GCC AGC AAA AGT GTC AGT ACA TCT AGC
 A   T   I   S   C   R   A   S   K   S   V   S   T   S   S
                  3E10 Vk CDR1
TAT AGT TAC ATG CAC TGG TAC CAA CAG AAA CCA GGA CAG CCA CCC
 Y   S   Y   M   H   W   Y   Q   Q   K   P   G   Q   P   P
                          3E10 Vk CDR2
AAA CTC CTC ATC AAG TAT GCA TCC TAC CTA GAA TCT GGG GTT CCT
 K   L   L   I   K   Y   A   S   Y   L   E   S   G   V   P GCC AGG TTC AGT GGC AGT GGG TCT GGG ACA GAC TTC ACC CTC AAC
 A   R   F   S   G   S   G   S   G   T   D   F   T   L   N
          3E10 Vk CDR3
ATC CAT CCT GTG GAG GAG GAG GAT GCT GCA ACA TAT TAC TGT CAG
 I   H   P   V   E   E   E   D   A   A   T   Y   Y   C   Q CAC AGT AGG GAG TTT CCG TGG ACG TTC GGT GGA GGC ACC AAG CTG
 H   S   R   E   F   P   W   T   F   G   G   G   T   K   L
```

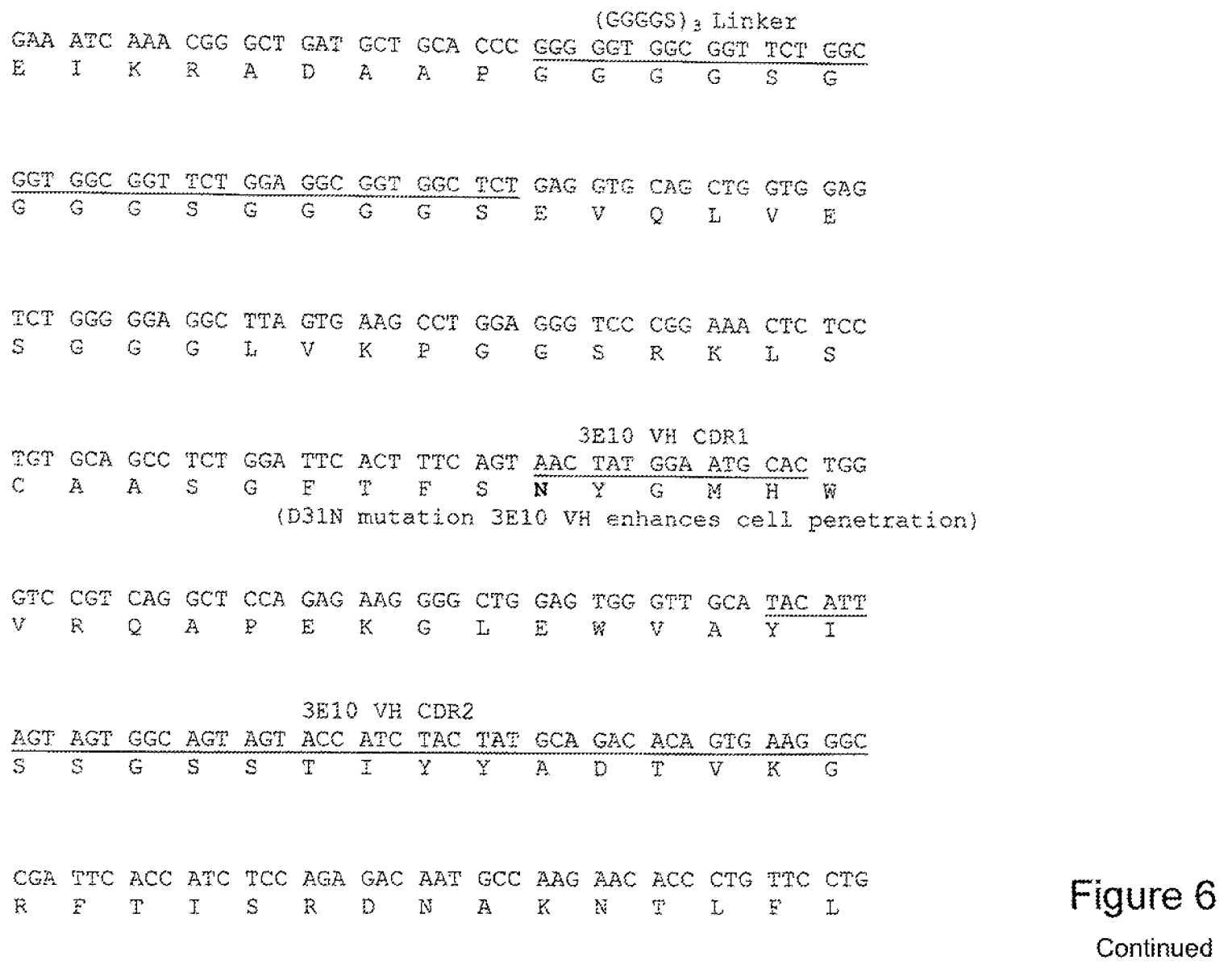

Figure 6
Continued (GGGGS)₃ Linker

```
GAA ATC AAA CGG GCT GAT GCT GCA CCC GGG GGT GGC GGT TCT GGC
 E   I   K   R   A   D   A   A   P   G   G   G   G   S   G

GGT GGC GGT TCT GGA GGC GGT GGC TCT GAG GTG CAG CTG GTG GAG
 G   G   G   S   G   G   G   G   S   E   V   Q   L   V   E

TCT GGG GGA GGC TTA GTG AAG CCT GGA GGG TCC CGG AAA CTC TCC
 S   G   G   G   L   V   K   P   G   G   S   R   K   L   S
```

3E10 VH CDR1

```
TGT GCA GCC TCT GGA TTC ACT TTC AGT AAC TAT GGA ATG CAC TGG
 C   A   A   S   G   F   T   F   S   N   Y   G   M   H   W
```
(D31N mutation 3E10 VH enhances cell penetration)

```
GTC CGT CAG GCT CCA GAG AAG GGG CTG GAG TGG GTT GCA TAC ATT
 V   R   Q   A   P   E   K   G   L   E   W   V   A   Y   I
```

3E10 VH CDR2

```
AGT AGT GGC AGT AGT ACC ATC TAC TAT GCA GAC ACA GTG AAG GGC
 S   S   G   S   S   T   I   Y   Y   A   D   T   V   K   G

CGA TTC ACC ATC TCC AGA GAC AAT GCC AAG AAC ACC CTG TTC CTG
 R   F   T   I   S   R   D   N   A   K   N   T   L   F   L
```

Figure 6
Continued

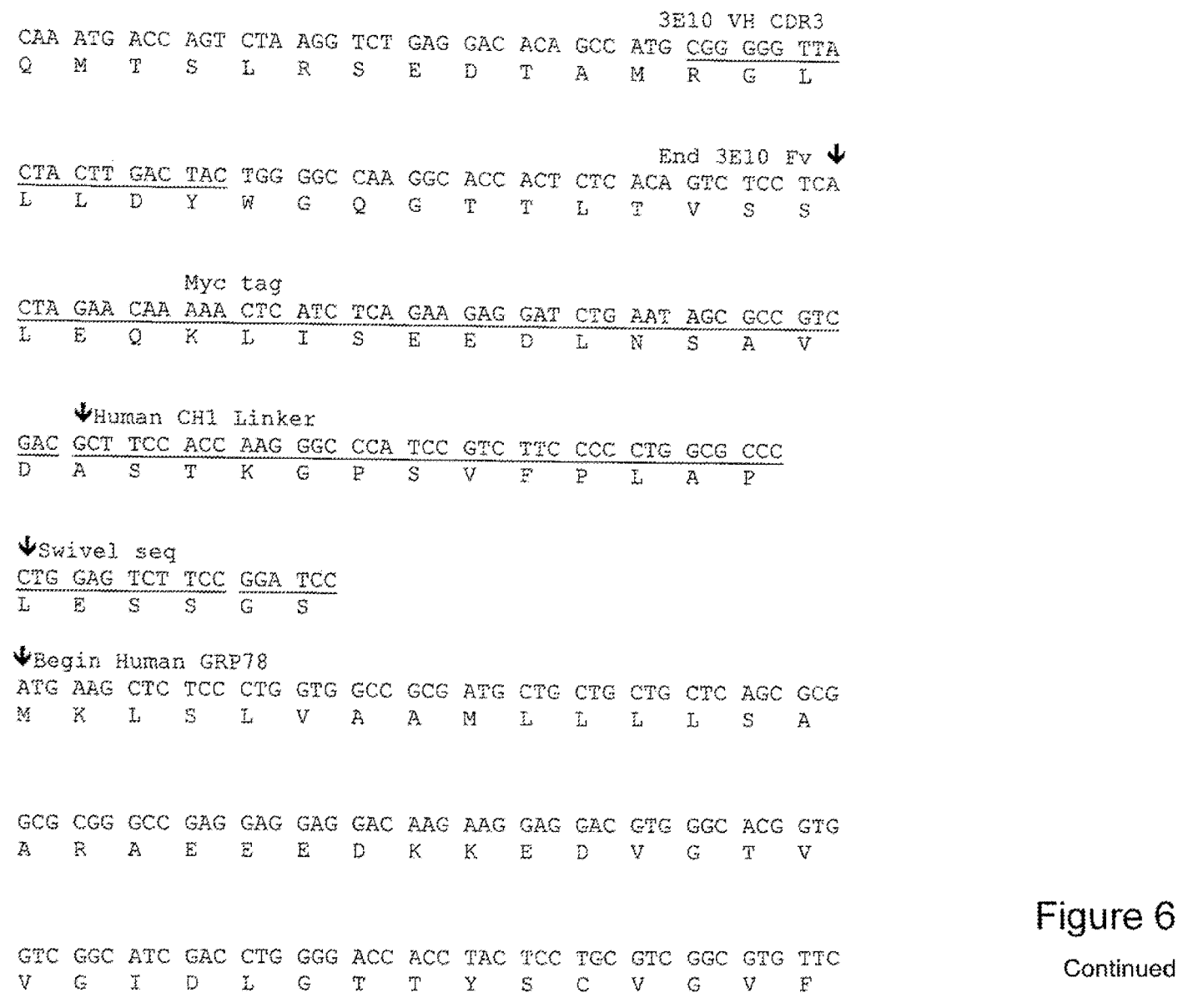

3E10 VH CDR3
```
CAA ATG ACC AGT CTA AGG TCT GAG GAC ACA GCC ATG CGG GGG TTA
 Q   M   T   S   L   R   S   E   D   T   A   M   R   G   L
```

End 3E10 Fv →
```
CTA CTT GAC TAC TGG GGC CAA GGC ACC ACT CTC ACA GTC TCC TCA
 L   L   D   Y   W   G   Q   G   T   T   L   T   V   S   S
```

Myc tag
```
CTA GAA CAA AAA CTC ATC TCA GAA GAG GAT CTG AAT AGC GCC GTC
 L   E   Q   K   L   I   S   E   E   D   L   N   S   A   V
```

↓Human CH1 linker
```
GAC GCT TCC ACC AAG GGC CCA TCC GTC TTC CCC CTG GCG CCC
 D   A   S   T   K   G   P   S   V   F   P   L   A   P
```

↓Swivel seq
```
CTG GAG TCT TCC GGA TCC
 L   E   S   S   G   S
```

↓Begin Human GRP78
```
ATG AAG CTC TCC CTG GTG GCC GCG ATG CTC CTG CTC AGC GCG
 M   K   L   S   L   V   A   A   M   L   L   L   S   A
```

```
GCG CGG GCC GAG GAG GAG GAC AAG AAG GAG GAC GTG GGC ACG GTG
 A   R   A   E   E   E   D   K   K   E   D   V   G   T   V
```

```
GTC GGC ATC GAC CTG GGG ACC ACC TAC TCC TGC GTC GGC GTG TTC
 V   G   I   D   L   G   T   T   Y   S   C   V   G   V   F
```

Figure 6:
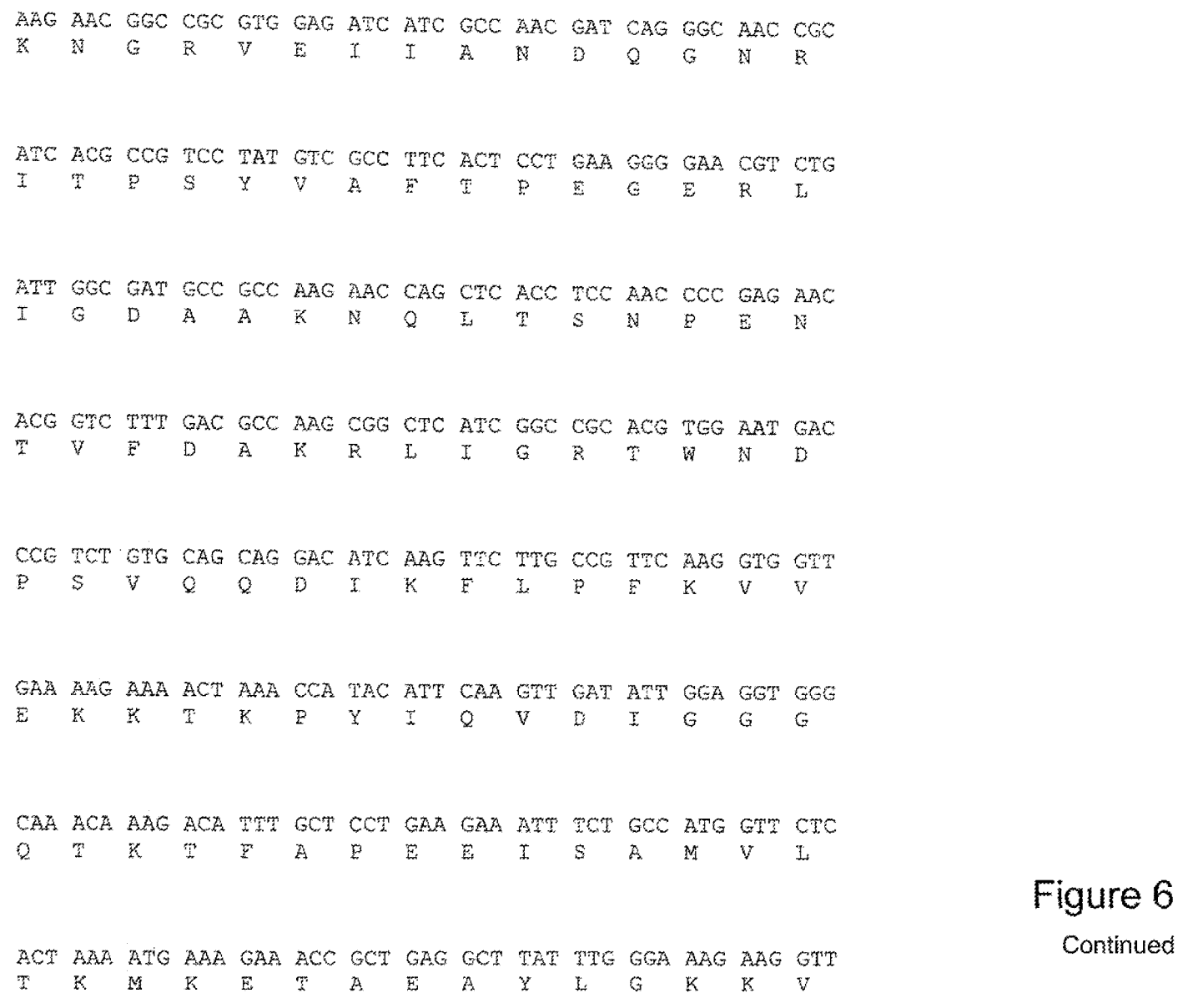

```
AAG AAC GGC CGC GTG GAG ATC ATC GCC AAC GAT CAG GGC AAC CGC
 K   N   G   R   V   E   I   I   A   N   D   Q   G   N   R

ATC ACG CCG TCC TAT GTC GCC TTC ACT CCT GAA GGG GAA CGT CTG
 I   T   P   S   Y   V   A   F   T   P   E   G   E   R   L

ATT GGC GAT GCC GCC AAG AAC CAG CTC ACC TCC AAC CCC GAG AAC
 I   G   D   A   A   K   N   Q   L   T   S   N   P   E   N

ACG GTC TTT GAC GCC AAG CGG CTC ATC GGC CGC ACG TGG AAT GAC
 T   V   F   D   A   K   R   L   I   G   R   T   W   N   D

CCG TCT GTG CAG CAG GAC ATC AAG TTC TTG CCG TTC AAG GTG GTT
 P   S   V   Q   Q   D   I   K   F   L   P   F   K   V   V

GAA AAG AAA ACT AAA CCA TAC ATT CAA GTT GAT ATT GGA GGT GGG
 E   K   K   T   K   P   Y   I   Q   V   D   I   G   G   G

CAA ACA AAG ACA TTT GCT CCT GAA ATT TCT GCC ATG GTT CTC
 Q   T   K   T   F   A   P   E   I   S   A   M   V   L

ACT AAA ATG AAA GAA ACC GCT GAG GCT TAT TTG GGA AAG AAG GTT
 T   K   M   K   E   T   A   E   A   Y   L   G   K   K   V
```

```
ACC CAT GCA GTT GTT ACT GTA CCA GCC TAT TTT AAT GAT GCC CAA
 T   H   A   V   V   T   V   P   A   Y   F   N   D   A   Q

CGC CAA GCA ACC AAA GAC GCT GGA ACT ATT GCT GGC CTA AAT GTT
 R   Q   A   T   K   D   A   G   T   I   A   G   L   N   V

ATG AGG ATC ATC AAC GAG CCT ACG GCA GCT ATT GCT TAT GGC
 M   R   I   I   N   E   P   T   A   A   I   A   Y   G

CTG GAT AAG AGG GAG GGG GAG AAG AAC ATC CTG GTG TTT GAC CTG
 L   D   K   R   E   G   E   K   N   I   L   V   F   D   L

GGT GGC GGA ACC TTC GAT GTG TCT CTT CTC ACC ATT GAC CTG
 G   G   G   T   F   D   V   S   L   L   T   I   D   L

GTC TTC GAA GTT GTG GCC ACT AAT GGA GAT ACT CAT CTG GGT GGA
 V   F   E   V   V   A   T   N   G   D   T   H   L   G   G

GAA GAC TTT GAC CGT GTC ATG GAA CAC TTC ATC AAA CTG TAC
 E   D   F   D   R   V   M   E   H   F   I   K   L   Y

AAA AAG ACG GGC AAA GAT GTC AGG AAA GAC AAT AGA GCT GTG
 K   K   T   G   K   D   V   R   K   D   N   R   A   V
```

Figure 6
Continued

```
CAG AAA CTC CGG CGC GAG GTA GAA AAG GCC AAA CGG GCC CTG TCT
 Q   K   L   R   R   E   V   E   K   A   K   R   A   L   S

TCT CAG CAT CAA GCA AGA ATT GAA ATT GAG TCC TTC TAT GAA GGA
 S   Q   H   Q   A   R   I   E   I   E   S   F   Y   E   G

GAA GAC TTT TCT GAG ACC CTG ACT CGG GCC AAA TTT GAA GAG CTC
 E   D   F   S   E   T   L   T   R   A   K   F   E   E   L

AAC ATG GAT CTG TTC CGG TCT ACT ATG AAG CCC GTC CAG AAA GTG
 N   M   D   L   F   R   S   T   M   K   P   V   Q   K   V

TTG GAA GAT TCT GAT TTG AAG AAG TCT GAT ATT GAT GAA ATT GTT
 L   E   D   S   D   L   K   K   S   D   I   D   E   I   V

CTT GTT GGT GGC TCC ACT CGA ATT CCA AAG ATT CAG CAA CTG GTT
 L   V   G   G   S   T   R   I   P   K   I   Q   Q   L   V

AAA GAG TTC TTC AAT GGC AAG GAA CCA TCC CGT GGC ATA AAC CCA
 K   E   F   F   N   G   K   E   P   S   R   G   I   N   P
```

```
GAT GAA GCT GTA GCG TAT GGT GCT GTC CAG GCT GGT GTG CTC
 D   E   A   V   A   Y   G   A   V   Q   A   G   V   L

TCT GGT GAT CAA GAT ACA GGT GAC CTG GTA CTG CTT GAT GTA TGT
 S   G   D   Q   D   T   G   D   L   V   L   L   D   V   C

CCC CTT ACA CTT GGT ATT GAA ACT GTG GGA GGT GTC ATG ACC AAA
 P   L   T   L   G   I   E   T   V   G   G   V   M   T   K

CTG ATT CCA AGG AAC ACA GTG CCT ACC AAG AAG TCT CAG ATC
 L   I   P   R   N   T   V   P   T   K   K   S   Q   I

TTT TCT ACA GCT TCT GAT AAT CAA CCA ACT GTT ACA ATC AAG GTC
 F   S   T   A   S   D   N   Q   P   T   V   T   I   K   V

TAT GAA GGT GAA AGA CCC CTG ACA AAA GAC AAT CAT CTT CTG GGT
 Y   E   G   E   R   P   L   T   K   D   N   H   L   L   G

ACA TTT GAT CTG ACT GGA ATT CCT CCT GCT CCT CGT GGG GTC CCA
 T   F   D   L   T   G   I   P   P   A   P   R   G   V   P

CAG ATT GAA GTC ACC TTT GAG ATA GAT GTG AAT GGT ATT CTT CGA
 Q   I   E   V   T   F   E   I   D   V   N   G   I   L   R
```

Figure 6
Continued

Figure 6:
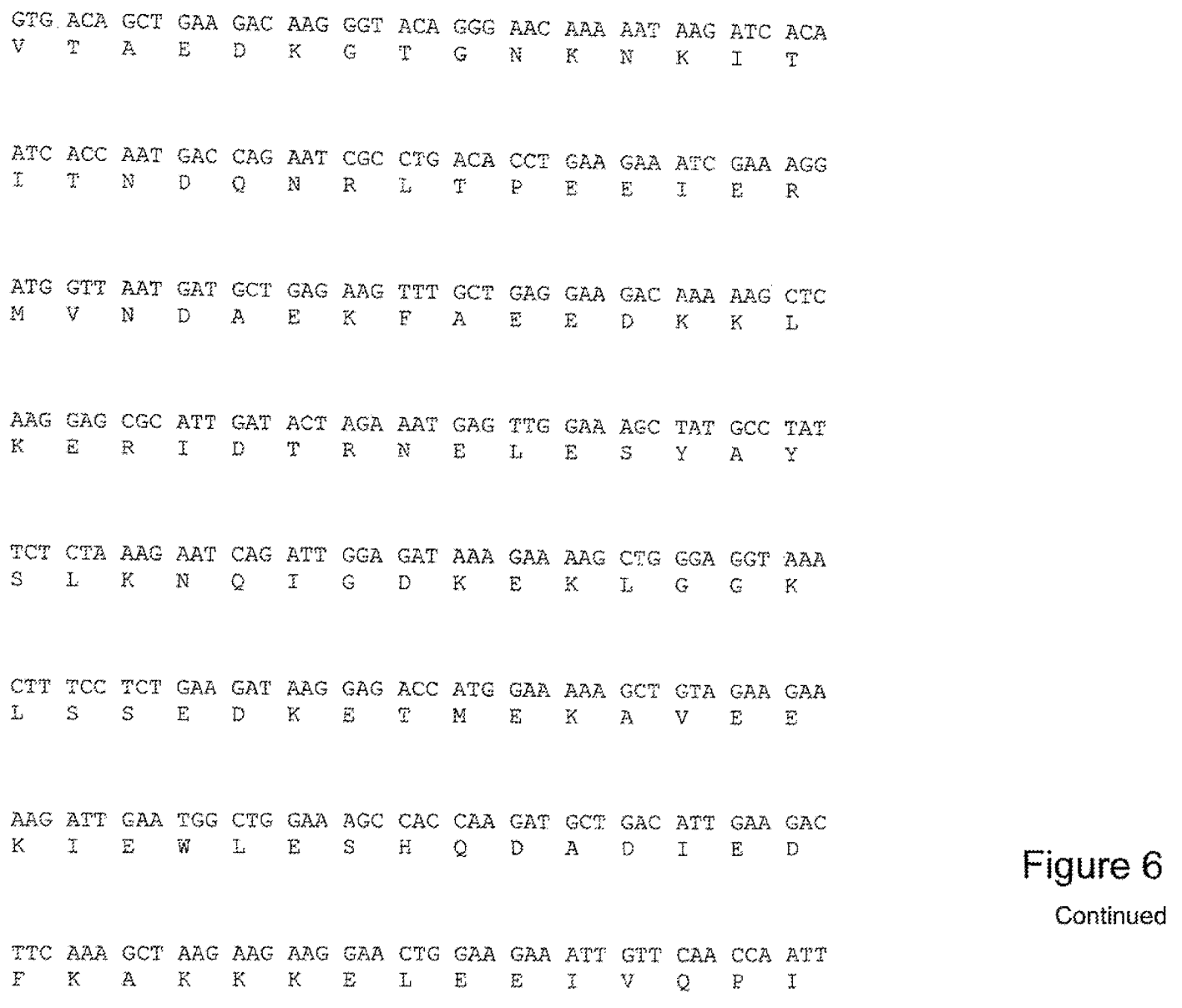

```
GTG ACA GCT GAA GAC AAG GGT ACA GGG AAC AAA AAT AAG ATC ACA
 V   T   A   E   D   K   G   T   G   N   K   N   K   I   T

ATC ACC AAT GAC CAG AAT CGC CTG ACA CCT GAA GAA ATC GAA AGG
 I   T   N   D   Q   N   R   L   T   P   E   E   I   E   R

ATG GTT AAT GAT GCT GAG AAG TTT GCT GAG GAA GAC AAA AAG CTC
 M   V   N   D   A   E   K   F   A   E   E   D   K   K   L

AAG GAG CGC ATT GAT ACT AGA AAT GAG TTG GAA AGC TAT GCC TAT
 K   E   R   I   D   T   R   N   E   L   E   S   Y   A   Y

TCT CTA AAG AAT CAG ATT GGA GAT AAA GAA AAG CTG GGA GGT AAA
 S   L   K   N   Q   I   G   D   K   E   K   L   G   G   K

CTT TCC TCT GAA GAT AAG GAG ACC ATG GAA AAA GCT GTA GAA GAA
 L   S   S   E   D   K   E   T   M   E   K   A   V   E   E

AAG ATT GAA TGG CTG GAA AGC CAC CAA GAT GCT GAC ATT GAA GAC
 K   I   E   W   L   E   S   H   Q   D   A   D   I   E   D

TTC AAA GCT AAG AAG GAA CTG GAA ATT GTT CAA CCA ATT
 F   K   A   K   K   E   L   E   I   V   Q   P   I
```

```
ATC AGC AAA CTC TAT GGA AGT GCA GGC CCT CCC CCA ACT GGT GAA
 I   S   K   L   Y   G   S   A   G   P   P   P   T   G   E

XbaI
GAG GAT ACA GCA GAA AAA GAT GAG TTG TAG TCT AGA
 E   D   T   A   E   K   D   E   L   *
```

Figure 7:
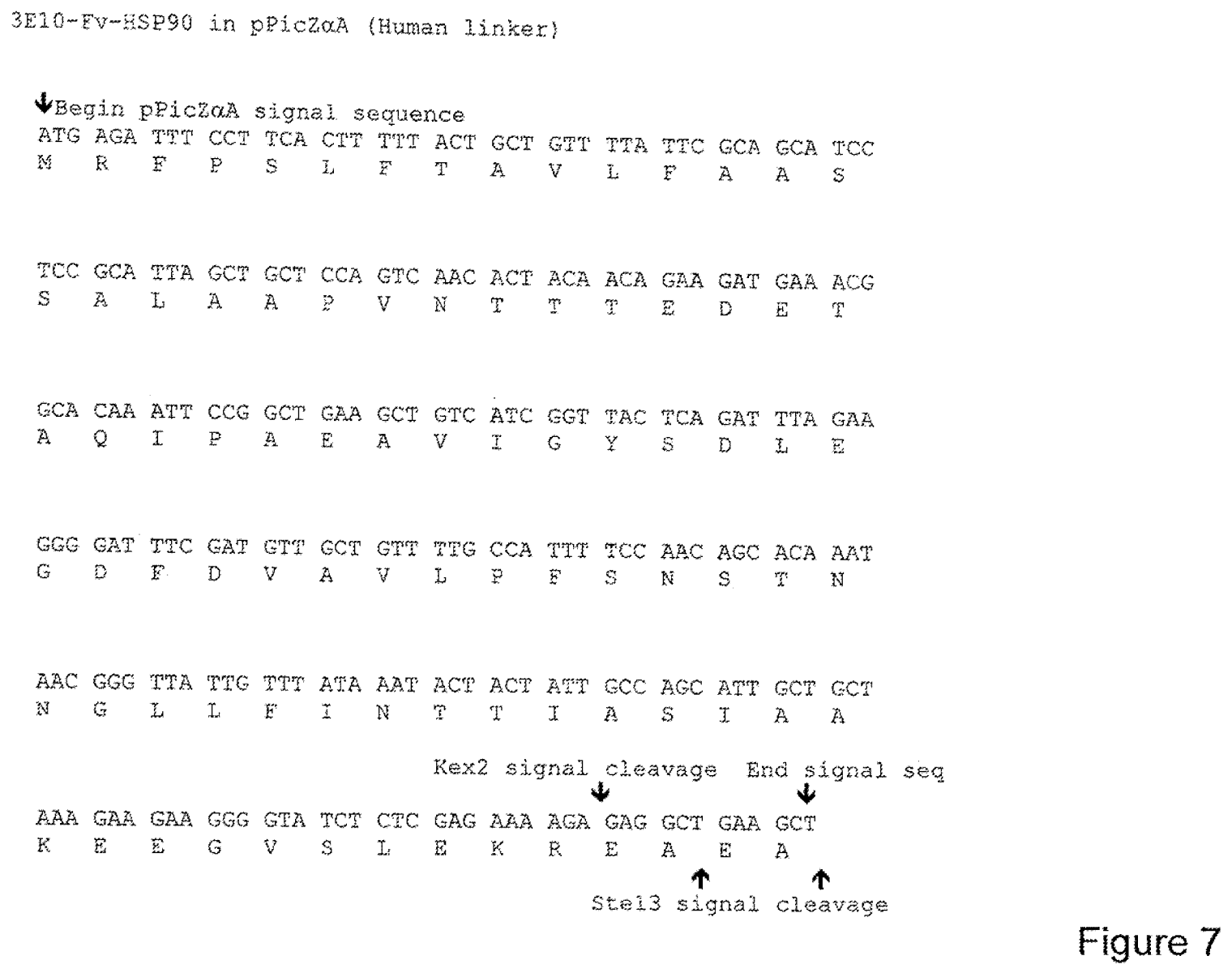

3E10-Fv-HSP90 in pPiczαA (Human linker)

↓Begin pPiczαA signal sequence
ATG AGA TTT CCT TCA CTT TTT ACT GCT GTT TTA TTC GCA GCA TCC
M   R   F   P   S   L   F   T   A   V   L   F   A   A   S TCC GCA TTA GCT GCT CCA GTC AAC ACT ACA ACA GAA GAT GAA ACG
S   A   L   A   A   P   V   N   T   T   T   E   D   E   T GCA CAA ATT CCG GCT GAA GCT GTC ATC GGT TAC TCA GAT TTA GAA
A   Q   I   P   A   E   A   V   I   G   Y   S   D   L   E GGG GAT TTC GAT GTT GCT GTT TTG CCA TTT TCC AAC AGC ACA AAT
G   D   F   D   V   A   V   L   P   F   S   N   S   T   N AAC GGG TTA TTG TTT ATA AAT ACT ACT ATT GCC AGC ATT GCT GCT
N   G   L   L   F   I   N   T   T   I   A   S   I   A   A Kex2 signal cleavage   End signal seq→
AAA GAA GGG GTA TCT CTC GAG AAA AGA GAG GCT GAA GCT
K   E   G   V   S   L   E   K   R   E   A   E   A Ste13 signal cleavage

```
EcoRI    HIS6 tag                    ↑solubility  ↓Begin Fv
GAA TTC CAT CAC CAT CAC CAT CAC GCA GGG ATT CAC GAC ATT GTC
 E   F   H   H   H   H   H   H   A   G   I   H   D   I   V CTG ACA CAG TCT CCT GCT TCC TTA GCT GTA TCT CTG GGG CAG AGG
 L   T   Q   S   P   A   S   L   A   V   S   L   G   Q   R GCC ACC ATC TCC TGC AGG GCC AGC AAA AGT GTC AGT ACA TCT AGC
 A   T   I   S   C   R   A   S   K   S   V   S   T   S   S
                            3E10 Vk CDR1
TAT AGT TAC ATG CAC TGG TAC CAA CAG AAA CCA GGA CAG CCA CCC
 Y   S   Y   M   H   W   Y   Q   Q   K   P   G   Q   P   P
                            3E10 Vk CDR2
AAA CTC CTC ATC AAG TAT GCA TCC TAC CTA GAA TCT GGG GTT CCT
 K   L   L   I   K   Y   A   S   Y   L   E   S   G   V   P GCC AGG TTC AGT GGC AGT GGG TCT GGG ACA GAC TTC ACC CTC AAC
 A   R   F   S   G   S   G   S   G   T   D   F   T   L   N ATC CAT CCT GTG GAG GAG GAT GCT GCA ACA TAT TAC TGT CAG
 I   H   P   V   E   E   D   A   A   T   Y   Y   C   Q
                            3E10 Vk CDR3
CAC AGT AGG GAG TTT CCG TGG ACG TTC GGT GGA GGC ACC AAG CTG
 H   S   R   E   F   P   W   T   F   G   G   G   T   K   L
```

Figure 7:
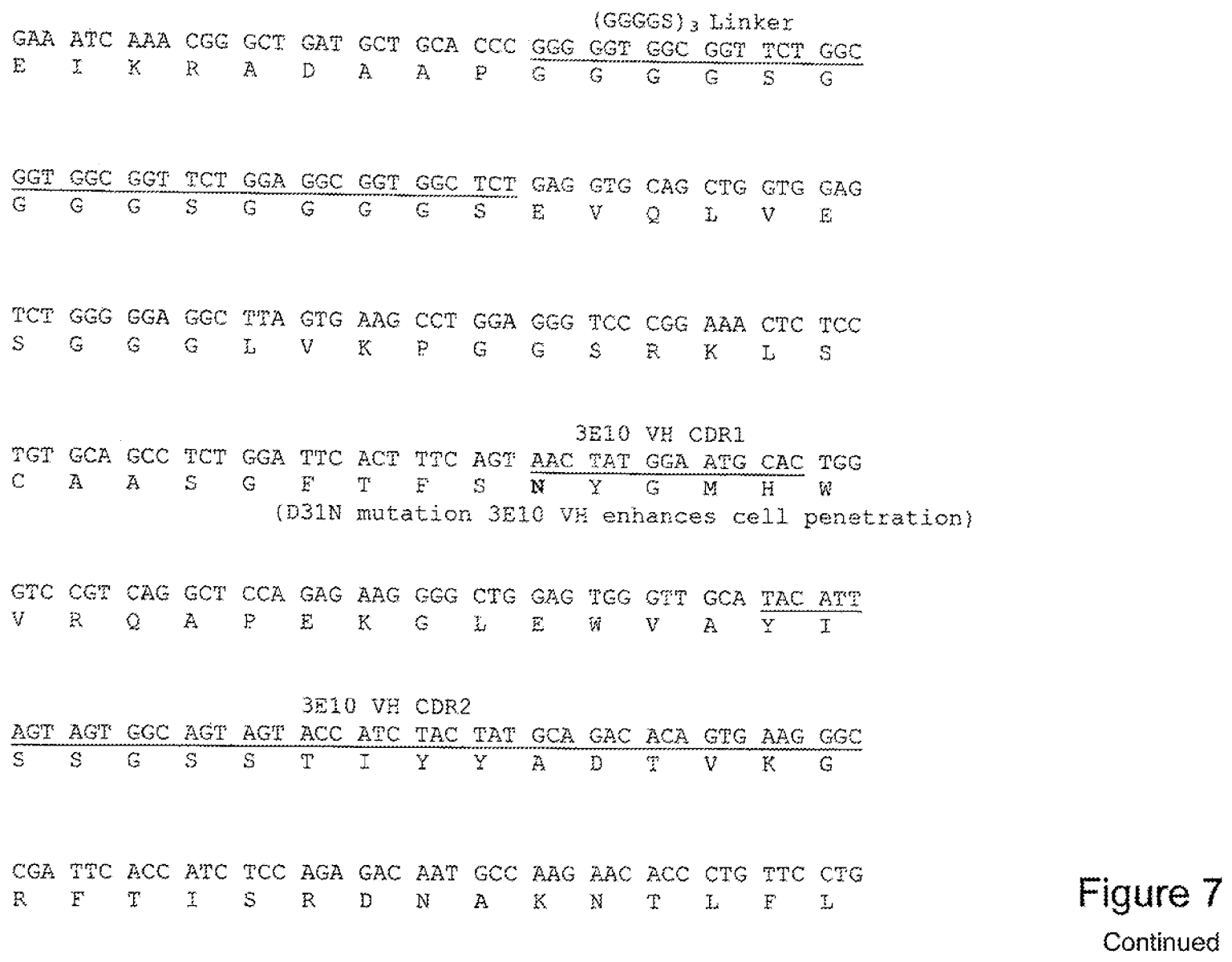

```
                                        (GGGGS)3 Linker
GAA ATC AAA CGG GCT GAT GCT GCA CCC GGG GGT GGC GGT TCT GGC
 E   I   K   R   A   D   A   A   P   G   G   G   G   S   G GGT GGC GGT TCT GGA GGC GGT GGC TCT GAG GTG CAG CTG GTG GAG
 G   G   G   S   G   G   G   G   S   E   V   Q   L   V   E TCT GGG GGA GGC TTA GTG AAG CCT GGA GGG TCC CGG AAA CTC TCC
 S   G   G   G   L   V   K   P   G   G   S   R   K   L   S 3E10 VH CDR1
TGT GCA GCC TCT GGA TTC ACT TTC AGT AAC TAT GGA ATG CAC TGG
 C   A   A   S   G   F   T   F   S   N   Y   G   M   H   W
              (D31N mutation 3E10 VH enhances cell penetration)

GTC CGT CAG GCT CCA GAG AAG GGG CTG GAG TGG GTT GCA TAC ATT
 V   R   Q   A   P   E   K   G   L   E   W   V   A   Y   I

3E10 VH CDR2
AGT AGT GGC AGT AGT ACC ATC TAC TAT GCA GAC AAT GCC AAG GGC
 S   S   G   S   S   T   I   Y   Y   A   D   N   A   K   G

CGA TTC ACC ATC TCC AGA GAC AAT GCC AAG AAC ACC CTG TTC CTG
 R   F   T   I   S   R   D   N   A   K   N   T   L   F   L
```

```
                                                    3E10 VH CDR3
CAA ATG ACC AGT CTA AGG TCT GAG GAC ACA GCC ATG CGG GGG TTA
 Q   M   T   S   L   R   S   E   D   T   A   M   R   G   L

End 3E10 Fv →
CTA CTT GAC TAC TGG GGC CAA GGC ACC ACT CTC ACA GTC TCC TCA
 L   L   D   Y   W   G   Q   G   T   T   L   T   V   S   S

Myc tag
CTA GAA CAA AAA CTC ATC TCA GAA GAG GAT CTG AAT AGC GCC GTC
 L   E   Q   K   L   I   S   E   E   D   L   N   S   A   V →Human CH1 Linker
GAC GCT TCC ACC AAG GGC CCA TCC GTC TTC CCC CTG GCG CCC
 D   A   S   T   K   G   P   S   V   F   P   L   A   P →Swivel Seq
CTG GAG TCT TCC GGA TCC
 L   E   S   S   G   S →Begin Human HSP90
ATG CCT GAG GAA ACC CAG ACC CAA GAC CAA CCG ATG GAG GAG GAG
 M   P   E   E   T   Q   T   Q   D   Q   P   M   E   E   E GAG GTT GAG ACG TTC GCC TTT CAG GCA GAA ATT GCC CAG TTG ATG
 E   V   E   T   F   A   F   Q   A   E   I   A   Q   L   M TCA TTG ATC ATC AAT ACT TTC TAC TCG AAC AAA GAG ATC TTT CTG
 S   L   I   I   N   T   F   Y   S   N   K   E   I   F   L
```

```
AGA GAG CTC ATT TCA AAT TCA GAT GCA TTG GAC AAA ATC CGG
 R   E   L   I   S   N   S   D   A   L   D   K   I   R

TAT GAA AGC TTG ACA GAT CCC AGT AAA TTA GAC TCT GGG AAA GAG
 Y   E   S   L   T   D   P   S   K   L   D   S   G   K   E

CTG CAT ATT AAC CTT ATA CCG AAC CAA AAA GAT CGA ACT CTC ACT
 L   H   I   N   L   I   P   N   Q   K   D   R   T   L   T

ATT GTG GAT ACT GGA ATT GGA ATG ACC AAG GCT GAC TTG ATC AAT
 I   V   D   T   G   I   G   M   T   K   A   D   L   I   N

AAC CTT GGT ACT ATC GCC AAG TCT GGG ACC AAA GCG TTC ATG GAA
 N   L   G   T   I   A   K   S   G   T   K   A   F   M   E

GCT TTG CAG GCT GGT GCA GAT ATC TCT ATG ATT GGC CAG TTC GGT
 A   L   Q   A   G   A   D   I   S   M   I   G   Q   F   G

GTT GGT TTT TAT TCT GCT TAT TTG GTT GCT GAG AAA GTA ACT GTG
 V   G   F   Y   S   A   Y   L   V   A   E   K   V   T   V

ATC ACC AAA CAT AAC GAT GAG CAG TAC GCT TGG GAG TCC TCA
 I   T   K   H   N   D   E   Q   Y   A   W   E   S   S
```

```
GCA GGG GGA TCA TTC ACA GTG AGG ACA GAC ACA GGT GAA CCT ATG
 A   G   G   S   F   T   V   R   T   D   T   G   E   P   M

GGT CGT GGA ACA AAA GTT ATC CTA CAC CTG AAA GAA GAC CAA ACT
 G   R   G   T   K   V   I   L   H   L   K   E   D   Q   T

GAG TAC TTG GAG GAA CGA ATA AAG GAG ATT GTG AAG AAA CAT
 E   Y   L   E   E   R   I   K   E   I   V   K   K   H

TCT CAG TTT ATT GGA TAT CCC ATT ACT CTT TTT GTG GAG AAG GAA
 S   Q   F   I   G   Y   P   I   T   L   F   V   E   K   E

CGT GAT AAA GAA GTA AGC GAT GAG GCT GAA GAA AAG GAA GAC
 R   D   K   E   V   S   D   E   A   E   E   K   E   D

AAA GAA GAA AAA GAA AAA GAG TCG GAA GAC AAA
 K   E   E   K   E   K   E   S   E   D   K

CCT GAA ATT GAA GAT GTT GGT TCT GAT GAG GAA GAA AAG AAG
 P   E   I   E   D   V   G   S   D   E   E   E   K   K

GAT GGT GAC AAG AAG AAG ATT AAG GAA AAG TAC ATC
 D   G   D   K   K   K   I   K   E   K   Y   I
```

Figure 7
Continued

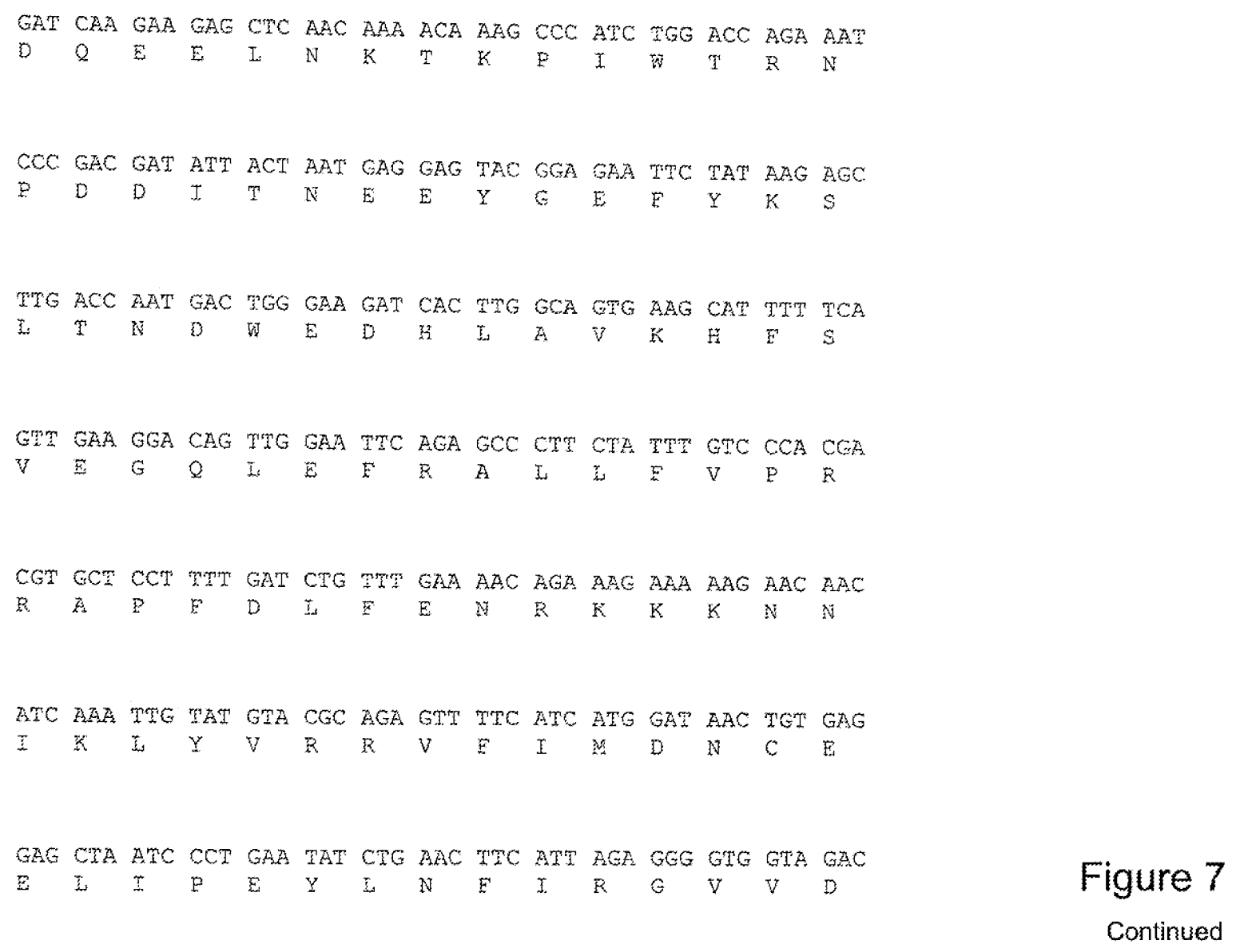

```
GAT CAA GAA GAG CTC AAC AAA ACA AAG CCC ATC TGG ACC AGA AAT
 D   Q   E   E   L   N   K   T   K   P   I   W   T   R   N

CCC GAC GAT ATT ACT AAT GAG GAG TAC GGA GAA TTC TAT AAG AGC
 P   D   D   I   T   N   E   E   Y   G   E   F   Y   K   S

TTG ACC AAT GAC TGG GAA GAT CAC TTG GCA GTG AAG CAT TTT TCA
 L   T   N   D   W   E   D   H   L   A   V   K   H   F   S

GTT GAA GGA CAG TTG GAA TTC AGA GCC CTT CTA TTT GTC CCA CGA
 V   E   G   Q   L   E   F   R   A   L   L   F   V   P   R

CGT GCT CCT TTT GAT CTG TTT GAA AAC AGA AAG AAA AAG AAC AAC
 R   A   P   F   D   L   F   E   N   R   K   K   K   N   N

ATC AAA TTG TAT GTA CGC AGA GTT TTC ATC ATG GAT AAC TGT GAG
 I   K   L   Y   V   R   R   V   F   I   M   D   N   C   E

GAG CTA ATC CCT GAA TAT CTG AAC TTC ATT AGA GGG GTG GTA GAC
 E   L   I   P   E   Y   L   N   F   I   R   G   V   V   D
```

Figure 7
Continued

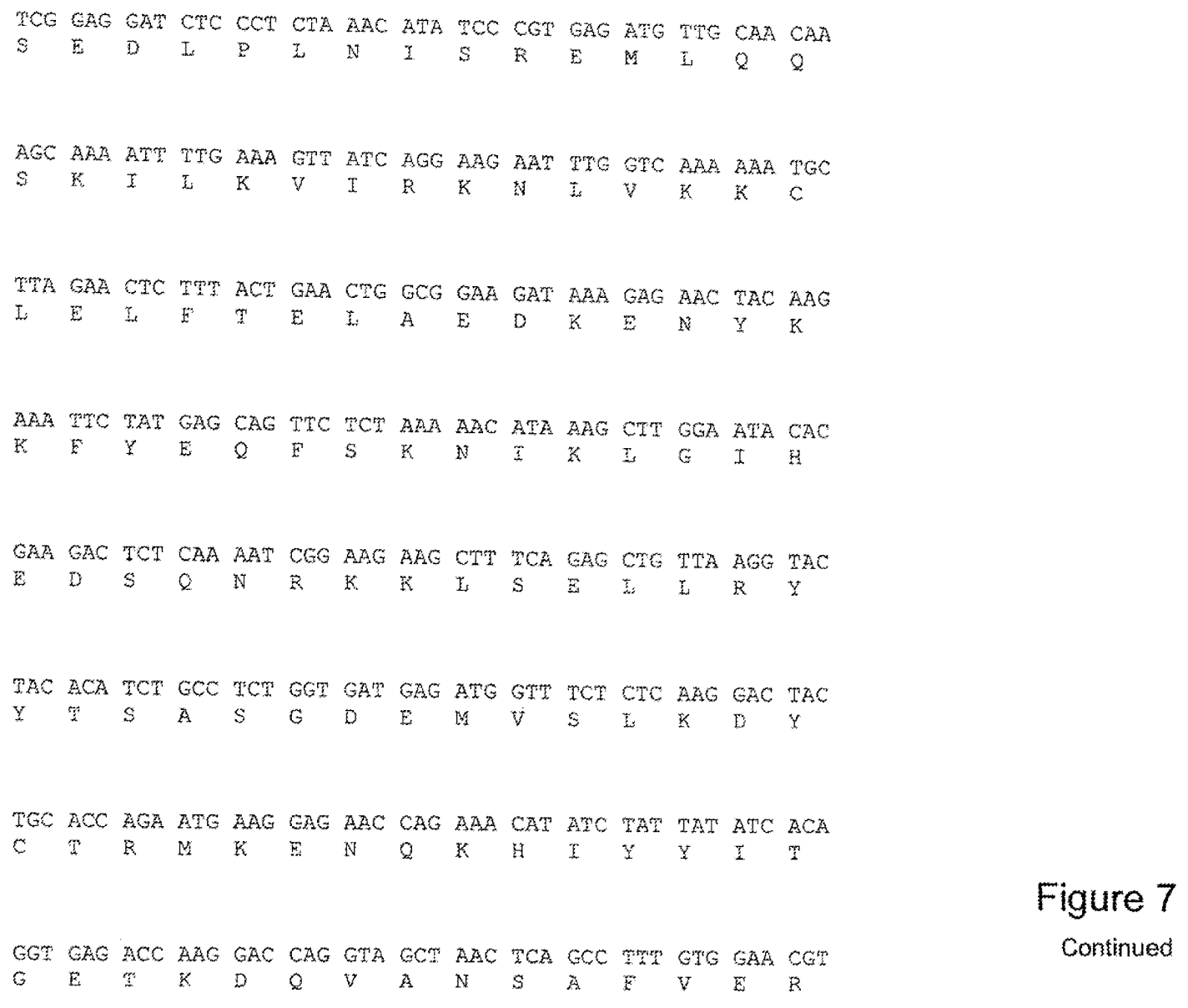

```
TCG GAG GAT CTC CCT CTA AAC ATA TCC CGT GAG ATG TTG CAA CAA
S   E   D   L   P   L   N   I   S   R   E   M   L   Q   Q

AGC AAA ATT TTG AAA GTT ATC AGG AAG AAT TTG GTC AAA AAA TGC
S   K   I   L   K   V   I   R   K   N   L   V   K   K   C

TTA GAA CTC TTT ACT GAA CTG GCG GAA GAT AAA GAG AAC TAC AAG
L   E   L   F   T   E   L   A   E   D   K   E   N   Y   K

AAA TTC TAT GAG CAG TTC TCT AAA AAC ATA AAG CTT GGA ATA CAC
K   F   Y   E   Q   F   S   K   N   I   K   L   G   I   H

GAA GAC TCT CAA AAT CGG AAG AAG CTT TCA GAG CTG TTA AGG TAC
E   D   S   Q   N   R   K   K   L   S   E   L   L   R   Y

TAC ACA TCT GCC TCT GGT GAT GAG ATG GTT TCT CTC AAG GAC TAC
Y   T   S   A   S   G   D   E   M   V   S   L   K   D   Y

TGC ACC AGA ATG AAG GAG AAC CAG AAA CAT ATC TAT TAT ATC ACA
C   T   R   M   K   E   N   Q   K   H   I   Y   Y   I   T

GGT GAG ACC AAG GAC CAG GTA GCT AAC TCA GCC TTT GTG GAA CGT
G   E   T   K   D   Q   V   A   N   S   A   F   V   E   R
```

```
CTT CGG AAA CAT GGC TTA GAA GTG ATC TAT ATG ATT GAG CCC ATT
 L   R   K   H   G   L   E   V   I   Y   M   I   E   P   I

GAT GAG TAC TGT GTC CAA CAG CTG AAG GAA TTT GAG GGG AAG ACT
 D   E   Y   C   V   Q   Q   L   K   E   F   E   G   K   T

TTA GTG TCA ACC AAA GAA GGC CTG GAA CTT CCA GAG GAT GAA
 L   V   S   T   K   E   G   L   E   L   P   E   D   E

GAA GAG AAA AAG AAG CAG GAA GAG AAA ACA AAG TTT GAG AAC
 E   E   K   K   K   Q   E   E   K   T   K   F   E   N

CTC TGC AAA ATC ATG AAA GAC ATA TTG GAG AAA AAA GTT GAA AAG
 L   C   K   I   M   K   D   I   L   E   K   K   V   E   K

GTG GTT TCA AAC CGA TTG GTG ACA TCT CCA TGC TGT ATT GTC
 V   V   S   N   R   L   V   T   S   P   C   C   I   V

ACA AGC ACA TAT GGC TGG ACA GCA AAC ATG GAG AGA ATC ATG AAA
 T   S   T   Y   G   W   T   A   N   M   E   R   I   M   K

GCT CAA GCC CTA AGA GAC AAC TCA ACA ATG GGT TAC ATG GCA GCA
 A   Q   A   L   R   D   N   S   T   M   G   Y   M   A   A
```

Figure 7
Continued

Figure 7:
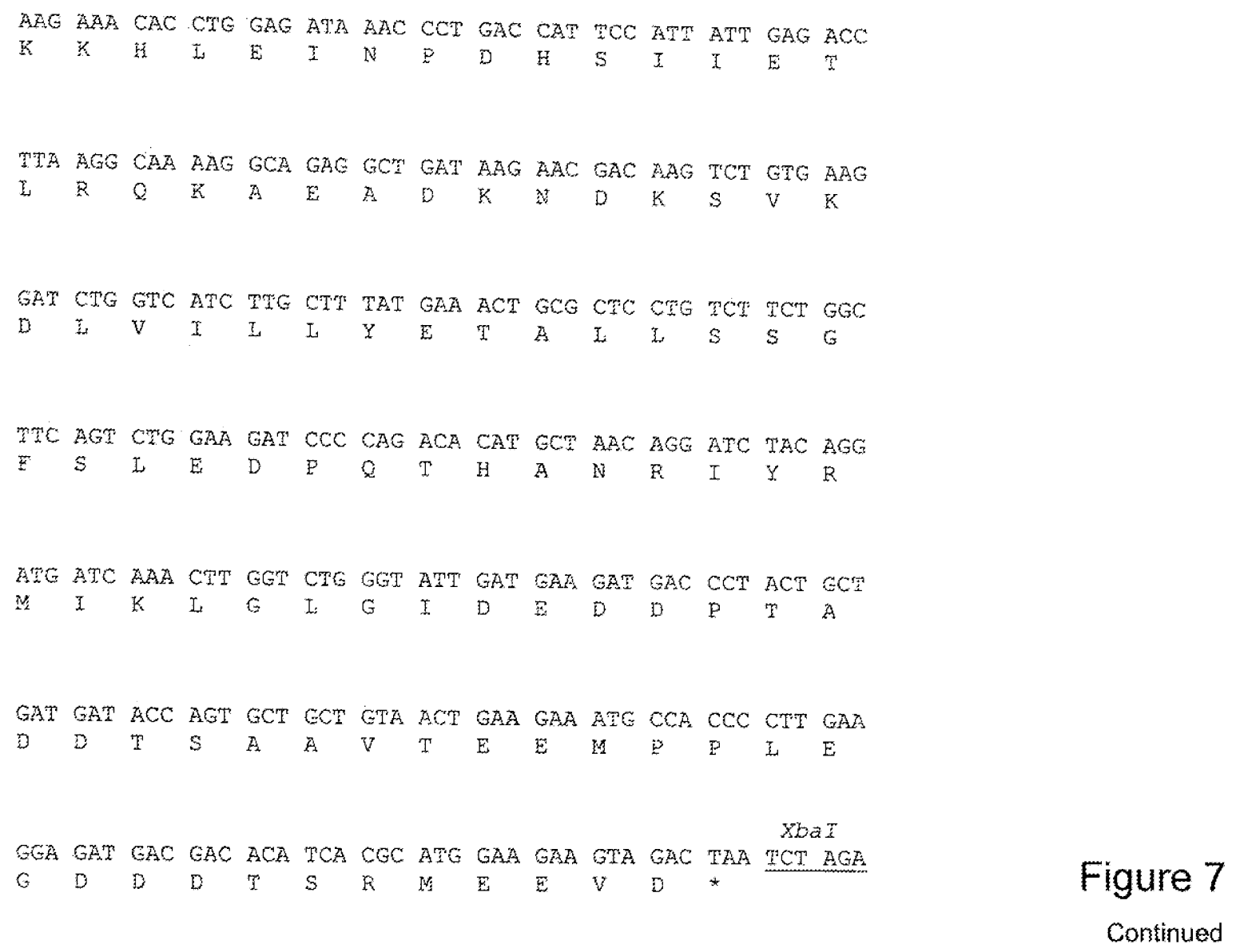

```
AAG AAA CAC CTG GAG ATA AAC CCT GAC CAT TCC ATT ATT GAG ACC
 K   K   H   L   E   I   N   P   D   H   S   I   I   E   T

TTA AGG CAA AAG GCA GAG GCT GAT AAG AAC GAC AAG TCT GTG AAG
 L   R   Q   K   A   E   A   D   K   N   D   K   S   V   K

GAT CTG GTC ATC TTG CTT TAT GAA ACT GCG CTC CTG TCT TCT GGC
 D   L   V   I   L   L   Y   E   T   A   L   L   S   S   G

TTC AGT CTG GAA GAT CCC CAG ACA CAT GCT AAC AGG ATC TAC AGG
 F   S   L   E   D   P   Q   T   H   A   N   R   I   Y   R

ATG ATC AAA CTT GGT CTG ATT GAT GAA GAT GAC CCT ACT GCT
 M   I   K   L   G   L   I   D   E   D   D   P   T   A

GAT GAT ACC AGT GCT GCT ACT GAA GAA ATG CCA CCC CTT GAA
 D   D   T   S   A   A   T   E   E   M   P   P   L   E

XbaI
GGA GAT GAC ACA TCA CGC ATG GAA GTA GAC TAA         TCT AGA
 G   D   D   T   S   R   M   E   V   D   *
```

3E10-Fv-HSP27 in pPiczαA (Mouse linker)

↓Begin pPiczαA signal sequence
```
ATG AGA TTT CCT TCA CTT TTT ACT GCT GTT TTA TTC GCA GCA TCC
 M   R   F   P   S   L   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ACT ATT GCC AGC ATT GCT GCT
 N   G   L   L   F   I   N   T   T   I   A   S   I   A   A
```

Kex2 signal cleavage    End signal seg

```
AAA GAA GGG GTA TCT CTC GAG AAA AGA GAG GCT GAA GCT
 K   E   G   V   S   L   E   K   R   E   A   E   A
```

Ste13 signal cleavage

```
EcoRI     HIS6 tag                         ↑solubility   ↓Begin Fv
GAA TTC CAT CAC CAT CAC CAT CAC GCA GGG ATT CAC GAC ATT GTC
 E   F   H   H   H   H   H   H   A   G   I   H   D   I   V CTG ACA CAG TCT CCT GCT TCC TTA GCT GTA TCT CTG GGG CAG AGG
 L   T   Q   S   P   A   S   L   A   V   S   L   G   Q   R GCC ACC ATC TCC TGC AGG GCC AGC AAA AGT GTC AGT ACA TCT AGC
 A   T   I   S   C   R   A   S   K   S   V   S   T   S   S
         3E10 Vk CDR1
TAT AGT TAC ATG CAC TGG TAC CAA CAG AAA CCA GGA CAG CCA CCC
 Y   S   Y   M   H   W   Y   Q   Q   K   P   G   Q   P   P 3E10 Vk CDR2
AAA CTC CTC ATC AAG TAT GCA TCC TAC CTA GAA TCT GGG GTT CCT
 K   L   L   I   K   Y   A   S   Y   L   E   S   G   V   P GCC AGG TTC AGT GGC AGT GGG TCT GGG ACA GAC TTC ACC CTC AAC
 A   R   F   S   G   S   G   S   G   T   D   F   T   L   N ATC CAT CCT GTG GAG GAG GAT GCT GCA ACA TAT TAC TGT CAG
 I   H   P   V   E   E   D   A   A   T   Y   Y   C   Q
         3E10 Vk CDR3
CAC AGT AGG GAG TTT CCG TGG ACG TTC GGT GGA GGC ACC AAG CTG
 H   S   R   E   F   P   W   T   F   G   G   G   T   K   L
```

Figure 8
Continued

Figure 8:
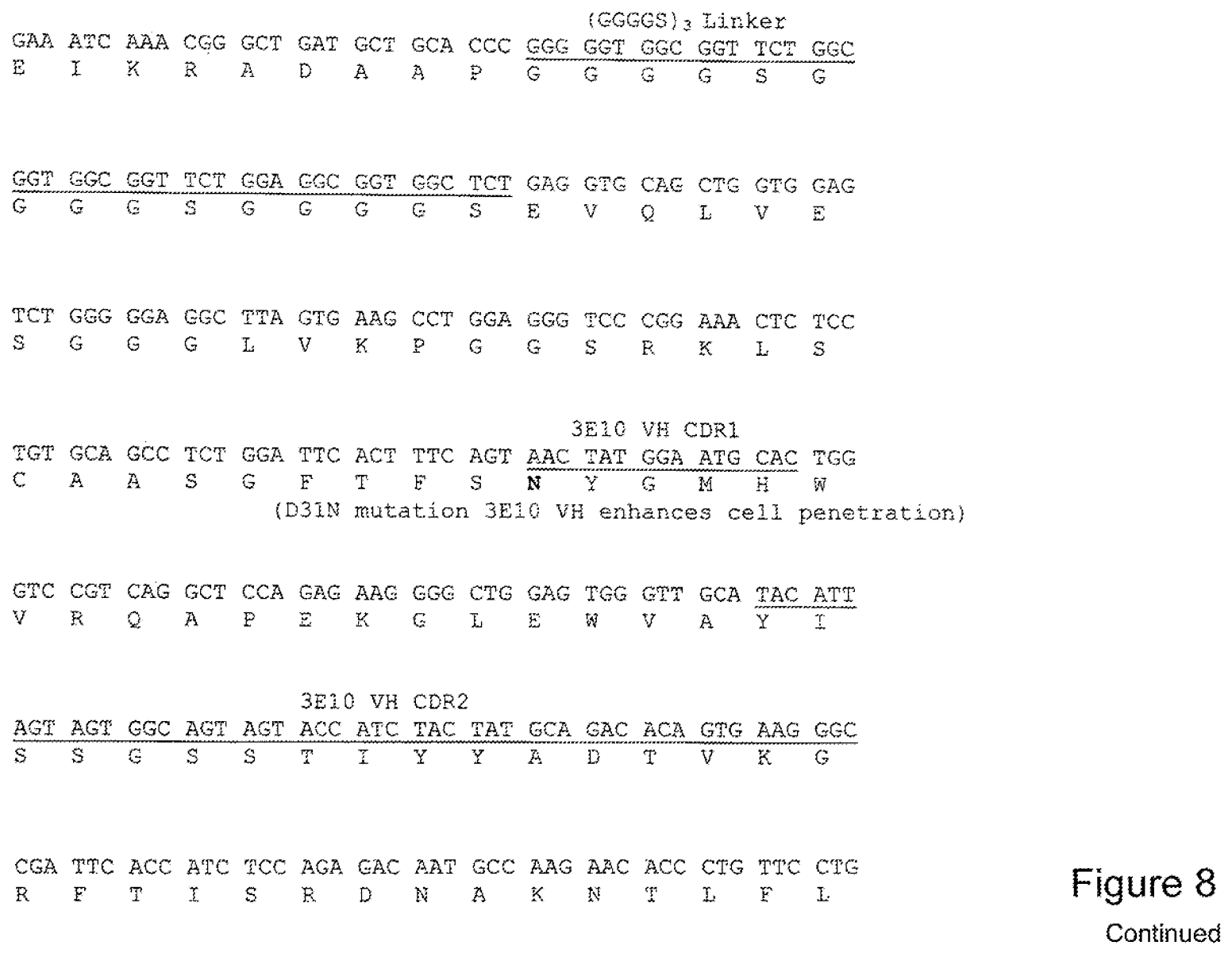

```
                                              (GGGGS)3 Linker
GAA ATC AAA CGG GCT GAT GCT GCA CCC GGG GGT GGC GGT TCT GGC
 E   I   K   R   A   D   A   A   P   G   G   G   G   S   G GGT GGC GGT TCT GGA GGC GGT GGC TCT GAG GTG CAG CTG GTG GAG
 G   G   G   S   G   G   G   G   S   E   V   Q   L   V   E TCT GGG GGA GGC TTA GTG AAG CCT GGA GGG TCC CGG AAA CTC TCC
 S   G   G   G   L   V   K   P   G   G   S   R   K   L   S 3E10 VH CDR1
TGT GCA GCC TCT GGA TTC ACT TTC AGT AAC TAT GGA ATG CAC TGG
 C   A   A   S   G   F   T   F   S   N   Y   G   M   H   W
              (D31N mutation 3E10 VH enhances cell penetration)

GTC CGT CAG GCT CCA GAG AAG GGG CTG GAG TGG GTT GCA TAC ATT
 V   R   Q   A   P   E   K   G   L   E   W   V   A   Y   I

3E10 VH CDR2
AGT AGT GGC AGT AGT ACC ATC TAC TAT GCA GAC ACA GTG AAG GGC
 S   S   G   S   S   T   I   Y   Y   A   D   T   V   K   G

CGA TTC ACC ATC TCC AGA GAC AAT GCC AAG AAC ACC CTG TTC CTG
 R   F   T   I   S   R   D   N   A   K   N   T   L   F   L
```

3E10 VH CDR3
```
CAA ATG ACC AGT CTA AGG TCT GAG GAC ACA GCC ATG CGG GGG TTA
 Q   M   T   S   L   R   S   E   D   T   A   M   R   G   L
```

End 3E10 Fv →
```
CTA CTT GAC TAC TGG GGC CAA GGC ACC ACT CTC ACA GTC TCC TCA
 L   L   D   Y   W   G   Q   G   T   T   L   T   V   S   S
```

Myc tag
```
CTA GAA CAA AAA CTC ATC TCA GAA GAG GAT CTG AAT AGC GCC GTC
 L   E   Q   K   L   I   S   E   E   D   L   N   S   A   V
```

↓mouse CH1 linker
```
GAC GCC AAA ACA ACA GCC CCA TCG GTC TAT CCA CTG GCC CCT GTA
 D   A   K   T   T   A   P   S   V   Y   P   L   A   P   V
```

↓Swivel seq      ↓Begin Human HSP27
```
CTG GAG TCT TCC GGA TCC ATG ACC GAG CGC CGC GTC CCC TTC TCG
 L   E   S   S   G   S   M   T   E   R   R   V   P   F   S
```

```
CTC CTG CGG GGC CCC AGC TGG GAC CCC TTC CGC GAC TGG TAC CCG
 L   L   R   G   P   S   W   D   P   F   R   D   W   Y   P
```

```
CAT AGC CGC CTC TTC GAC CAG GCC TTC GGG CTG CCC CGG CTG CCG
 H   S   R   L   F   D   Q   A   F   G   L   P   R   L   P
```

```
GAG GAG TGG TCG CAG TGG TTA GGC GGC AGC TGG CCA GGC TAC
 E   E   W   S   Q   W   L   G   G   S   W   P   G   Y
```

Figure 8
Continued

```
GTG CGC CCC CTG CCC CCC GCC ATC GAG AGC CCC GCA GTG GCC
 V   R   P   L   P   P   A   I   E   S   P   A   V   A

GCG CCC TAC AGC CGC GCG CTC AGC CGG CAA CTC AGC AGC GGG
 A   P   Y   S   R   A   L   S   R   Q   L   S   S   G

GTC TCG GAG ATC CGG CAC ACT GCG GAC CGC TGG CGC GTG TCC CTG
 V   S   E   I   R   H   T   A   D   R   W   R   V   S   L

GAT GTC AAC CAC TTC GCC CCG GAC GAG CTG ACG GTC AAG ACC AAG
 D   V   N   H   F   A   P   D   E   L   T   V   K   T   K

GAT GGC GTG GTG GAG ATC ACC GGC AAG CAC GAG GAG CGG CAG GAC
 D   G   V   V   E   I   T   G   K   H   E   E   R   Q   D

GAG CAT GGC TAC ATC TCC CGG TGC TTC ACG CGG AAA TAC ACG CTG
 E   H   G   Y   I   S   R   C   F   T   R   K   Y   T   L

CCC CCC GGT GTG GAC ACC CAA GTT TCC TCC TCC CTG TCC CCT
 P   P   G   V   D   T   Q   V   S   S   S   L   S   P

GAG GGC ACA CTG ACC GTG GAG GCC CCC ATG CCC AAG CTA GCC ACG
 E   G   T   L   T   V   E   A   P   M   P   K   L   A   T
```

```
CAG TCC AAC GAG ATC ACC ATC CCA GTC ACC TTC GAG TCG CGG GCC
 Q   S   N   E   I   T   I   P   V   T   F   E   S   R   A

CAG CTT GGG GGC CCA GAA GCT GCA AAA TCC GAT GAG ACT GCC GCC
 Q   L   G   G   P   E   A   A   K   S   D   E   T   A   A

XbaI
AAG TAA TCT AGA
 K   *   S   R
```

Figure 9:
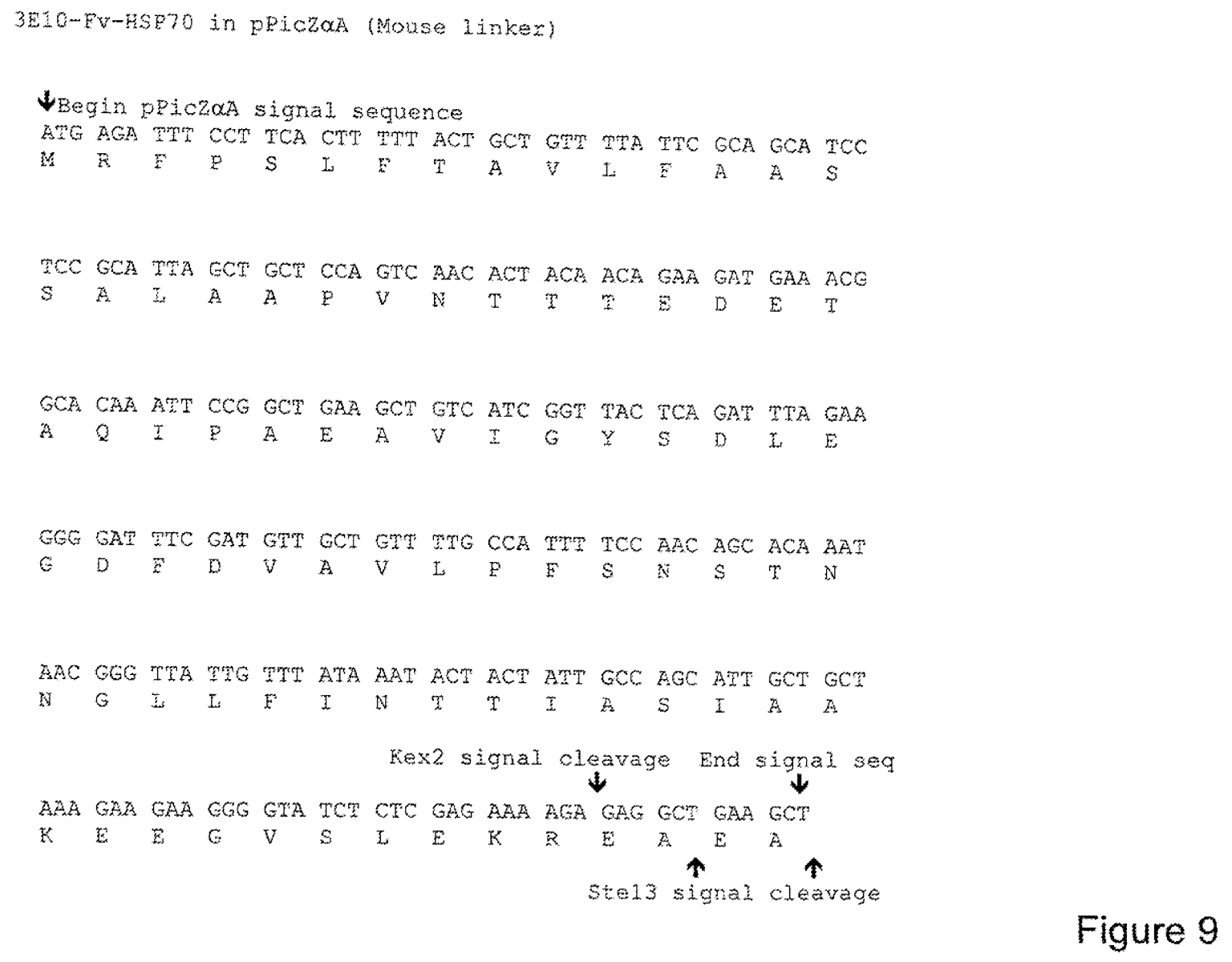

3E10-Fv-HSP70 in pPicZαA (Mouse linker)

↓Begin pPicZαA signal sequence

```
ATG AGA TTT CCT TCA CTT TTT ACT GCT GTT TTA TTC GCA GCA TCC
M   R   F   P   S   L   F   T   A   V   L   F   A   A   S

TCC GCA TTA GCT GCT CCA GTC AAC ACT ACA GAA GAT GAA ACG
S   A   L   A   A   P   V   N   T   T   E   D   E   T

GCA CAA ATT CCG GCT GAA GCT GTC ATC GGT TAC TCA GAT TTA GAA
A   Q   I   P   A   E   A   V   I   G   Y   S   D   L   E

GGG GAT TTC GAT GTT GCT GTT TTG CCA TTT TCC AAC AGC ACA AAT
G   D   F   D   V   A   V   L   P   F   S   N   S   T   N

AAC GGG TTA TTG TTT ATA AAT ACT ACT ATT GCC AGC ATT GCT GCT
N   G   L   L   F   I   N   T   T   I   A   S   I   A   A
                              Kex2 signal cleavage  End signal seq
                                           →             →

AAA GAA GGG GTA TCT CTC GAG AAA AGA GAG GCT GAA GCT
K   E   G   V   S   L   E   K   R   E   A   E   A
                                 ←      ←
                              Ste13 signal cleavage
```

EcoRI　　HIS6 tag　　↑solubility　↓Begin Fv

```
       EcoRI   HIS6 tag                      ↑solubility  ↓Begin Fv
       GAA TTC CAT CAC CAT CAC CAT CAC GCA GGG ATT CAC GAC ATT GTC
       E   F   H   H   H   H   H   H   A   G   I   H   D   I   V CTG ACA CAG TCT CCT GCT TCC TTA GCT GTA TCT CTG GGG CAG AGG
       L   T   Q   S   P   A   S   L   A   V   S   L   G   Q   R GCC ACC ATC TCC TGC AGG GCC AGC AAA AGT GTC AGT ACA TCT AGC
       A   T   I   S   C   R   A   S   K   S   V   S   T   S   S 3E10 Vk CDR1
       TAT AGT TAC ATG CAC TGG TAC CAA CAG AAA CCA GGA CAG CCA CCC
       Y   S   Y   M   H   W   Y   Q   Q   K   P   G   Q   P   P 3E10 Vk CDR2
       AAA CTC CTC ATC AAG TAT GCA TCC TAC CTA GAA TCT GGG GTT CCT
       K   L   L   I   K   Y   A   S   Y   L   E   S   G   V   P GCC AGG TTC AGT GGC AGT GGG TCT GGG ACA GAC TTC ACC CTC AAC
       A   R   F   S   G   S   G   S   G   T   D   F   T   L   N 3E10 Vk CDR3
       ATC CAT CCT GTG GAG GAG GAT GCT GCA ACA TAT TAC TGT CAG
       I   H   P   V   E   E   D   A   A   T   Y   Y   C   Q CAC AGT AGG GAG TTT CCG TGG ACG TTC GGT GGA GGC ACC AAG CTG
       H   S   R   E   F   P   W   T   F   G   G   G   T   K   L
```

Figure 9
Continued

Figure 9:
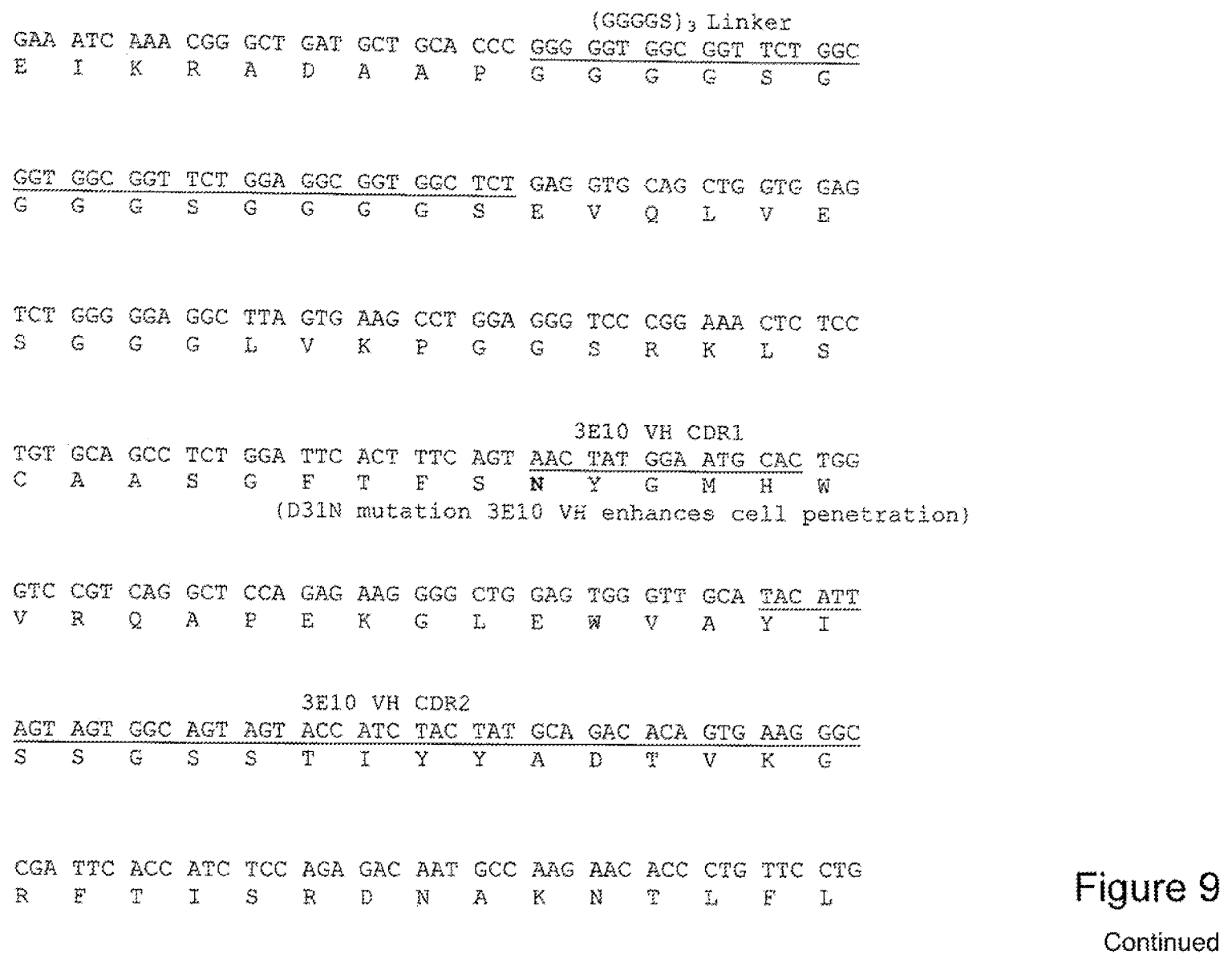

```
GAA ATC AAA CGG GCT GAT GCA CCC GGG GGT GGC GGT TCT GGC
 E   I   K   R   A   D   A   P   G   G   G   G   S   G
                                    (GGGGS)3 Linker GGC GGT TCT GGA GGC GGT GGC TCT GAG GTG CAG CTG GTG GAG
 G   G   S   G   G   G   S   E   V   Q   L   V   E TCT GGG GGA GGC TTA GTG AAG CCT GGA GGG TCC CGG AAA CTC TCC
 S   G   G   G   L   V   K   P   G   G   S   R   K   L   S 3E10 VH CDR1
TGT GCA GCC TCT GGA TTC ACT TTC AGT AAC TAT GGA ATG CAC TGG
 C   A   A   S   G   F   T   F   S   N   Y   G   M   H   W
         (D31N mutation 3E10 VH enhances cell penetration)

GTC CGT CAG GCT CCA GAG AAG GGG CTG GAG TGG GTT GCA TAC ATT
 V   R   Q   A   P   E   K   G   L   E   W   V   A   Y   I
                     3E10 VH CDR2
AGT AGT GGC AGT AGT ACC ATC TAC TAT GCA GAC ACA GTG AAG GGC
 S   S   G   S   S   T   I   Y   Y   A   D   T   V   K   G

CGA TTC ACC ATC TCC AGA GAC AAT GCC AAG AAC ACC CTG TTC CTG
 R   F   T   I   S   R   D   N   A   K   N   T   L   F   L
```

```
                                                          3E10 VH CDR3
CAA ATG ACC AGT CTA AGG TCT GAG GAC ACA GCC ATG CGG GGG TTA
 Q   M   T   S   L   R   S   E   D   T   A   M   R   G   L

End 3E10 Fv  ↓
CTA CTT GAC TAC TGG GGC CAA GGC ACC ACT CTC ACA GTC TCC TCA
 L   L   D   Y   W   G   Q   G   T   T   L   T   V   S   S

Myc tag
CTA GAA CAA AAA CTC ATC TCA GAA GAG GAT CTG AAT AGC GCC GTC
 L   E   Q   K   L   I   S   E   E   D   L   N   S   A   V ↓mouse CH1 Linker
GAC GCC AAA ACA ACA GCC CCA TCG GTC TAT CCA CTG GCC CCT GTA
 D   A   K   T   T   A   P   S   V   Y   P   L   A   P   V ↓Swivel sequence
CTG GAG TCT TCC GGA TCC
 L   E   S   S   G   S ↓Begin Human HSP70
ATG GCC AAA GCC GCG GCG ATC GGC ATC GAC CTG GGC ACC ACC TAC
 M   A   K   A   A   A   I   G   I   D   L   G   T   T   Y TCC TGC GTG GGG GTG TTC CAA CAC GGC AAG GTG GAG ATC ATC GCC
 S   C   V   G   V   F   Q   H   G   K   V   E   I   I   A AAC GAC CAG GGC AAC CGC ACC ACC CCC AGC TAC GTG GCC TTC ACG
 N   D   Q   G   N   R   T   T   P   S   Y   V   A   F   T
```

Figure 9:
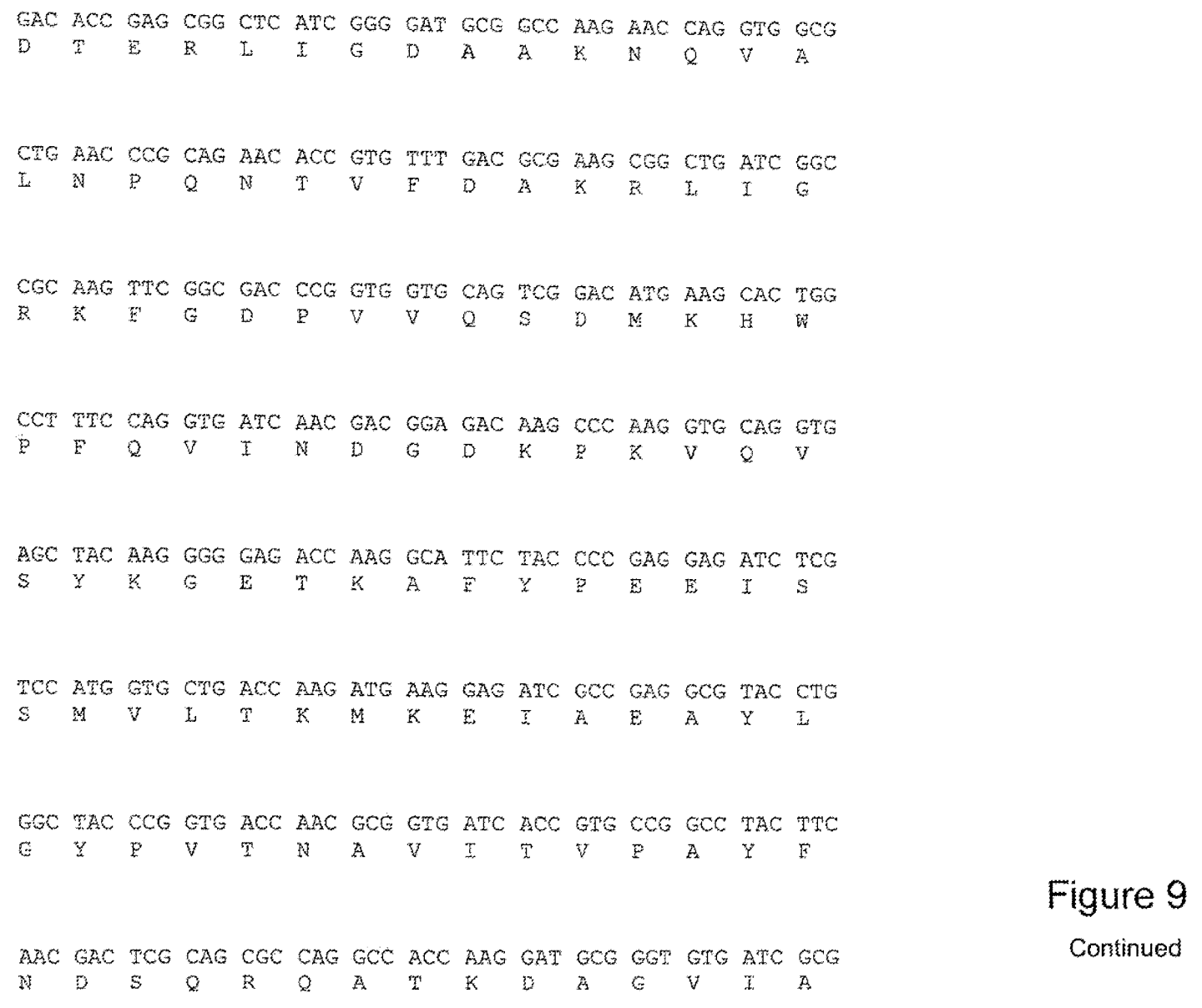

GAC ACC GAG CGG CTC ATC GGG GAT GCC GCC AAG AAC CAG GTG GCG
 D   T   E   R   L   I   G   D   A   A   K   N   Q   V   A

CTG AAC CCG CAG AAC ACC GTG TTT GAC GCG AAG CGG CTG ATC GGC
 L   N   P   Q   N   T   V   F   D   A   K   R   L   I   G

CGC AAG TTC GGC GAC CCG GTG GTG CAG TCG GAC ATC AAG CAC TGG
 R   K   F   G   D   P   V   V   Q   S   D   M   K   H   W

CCT TTC CAG GTG ATC AAC GAC GGA AAG GAC CCC AAG GTG CAG GTG
 P   F   Q   V   I   N   D   G   K   D   P   K   V   Q   V

AGC TAC AAG GGG GAG ACC AAG GCA TTC TAC CCC GAG ATC TCG
 S   Y   K   G   E   T   K   A   F   Y   P   E   I   S

TCC ATG GTG CTG ACC AAG ATG AAG GAG ATC GCC GAG GCG TAC CTG
 S   M   V   L   T   K   M   K   E   I   A   E   A   Y   L

GGC TAC CCG GTG ACC AAC GCG GTG ATC ACC GTG CCG GCC TAC TTC
 G   Y   P   V   T   N   A   V   I   T   V   P   A   Y   F

AAC GAC TCG CAG CGC CAG GCC ACC AAG GAT GCG GGT GTG ATC GCG
 N   D   S   Q   R   Q   A   T   K   D   A   G   V   I   A

```
GGG CTC AAC GTG CTG CGG ATC ATC AAC GAG CCC ACG GCC GCC GCC
 G   L   N   V   L   R   I   I   N   E   P   T   A   A   A

ATC GCC TAC GGC CTG GAC AGA ACG GGC AAG GGG GAG CGC AAC GTG
 I   A   Y   G   L   D   R   T   G   K   G   E   R   N   V

CTC ATC TTT GAC CTG GGC GGG GGC ACC TTC GAC GTG TCC ATC CTG
 L   I   F   D   L   G   G   G   T   F   D   V   S   I   L

ACG ATC GAC GAC GGC ATC TTC GAG GTG AAG GCC ACG GGG GAC
 T   I   D   D   G   I   F   E   V   K   A   T   G   D

ACC CAC CTG GGT GGG GAG GAC TTT GAC AAC AGG CTG GTG AAC CAC
 T   H   L   G   G   E   D   F   D   N   R   L   V   N   H

TTC GTG GAG GAG TTC AAG AGA AAA CAC AAG AAG GAC ATC AGC CAG
 F   V   E   E   F   K   R   K   H   K   K   D   I   S   Q

AAC AAG CGA GCC GTG AGG CGG CTG CGC ACC GCC TGC GAG AGG GCC
 N   K   R   A   V   R   R   L   R   T   A   C   E   R   A

AAG AGG ACC CTG TCG TCC AGC ACC CAG GCC AGC CTG GAG ATC GAC
 K   R   T   L   S   S   S   T   Q   A   S   L   E   I   D
```

```
TCC CTG TTT GAG GGC ATC GAC TTC TAC ACG TCC ATC ACC AGG GCG
 S   L   F   E   G   I   D   F   Y   T   S   I   T   R   A

AGG TTC GAG GAG CTG TGC TCC GAC CTG TTC CGA AGC ACC CTG GAG
 R   F   E   E   L   C   S   D   L   F   R   S   T   L   E

CCC GTG GAG AAG GCT CTG CGC GAC GCC AAG CTG GAC AAG GCC CAG
 P   V   E   K   A   L   R   D   A   K   L   D   K   A   Q

ATT CAC GAC CTG GTC CTG GGG TCC ACC CGC ATC CCC AAG
 I   H   D   L   V   L   G   S   T   R   I   P   K

GTG CAG AAG CTG CAG GAC TTC AAC GGG CGC GAC CTG AAC
 V   Q   K   L   Q   D   F   N   G   R   D   L   N

AAG AGC ATC AAC CCC GAC GAG GCT GTG GCC TAC GGG GCG GCG GTG
 K   S   I   N   P   D   E   A   V   A   Y   G   A   A   V

CAG GCG GCC ATC CTG ATG GGG GAC AAG TCC GAG AAC GTG CAG GAC
 Q   A   A   I   L   M   G   D   K   S   E   N   V   Q   D
```

```
CTG CTG CTG GAC GTG GCT CCC CTG TCG CTG GGG CTG GAG ACG
 L   L   L   D   V   A   P   L   S   L   G   L   E   T

GCC GGA GGC GTG ATG ACT GCC CTG ATC AAG CGC AAC TCC ACC ATC
 A   G   G   V   M   T   A   L   I   K   R   N   S   T   I

CCC ACC AAG CAG ACG CAG ATC TTC ACC TAC TCC GAC AAC CAA
 P   T   K   Q   T   Q   I   F   T   Y   S   D   N   Q

CCC GGG GTG CTG ATC CAG TAC GAG GGC GAG AGG GCC ATG ACG
 P   G   V   L   I   Q   Y   E   G   E   R   A   M   T

AAA GAC AAC AAT CTG TTG GGG CGC TTC GAG CTG AGC ATC CCT
 K   D   N   N   L   L   G   R   F   E   L   S   I   P

CCG GCC CCC AGG GGC GTG CCC CAG ATC GAG GTG ACC TTC GAC ATC
 P   A   P   R   G   V   P   Q   I   E   V   T   F   D   I

GAT CCC AAC GGC ATC CTG AAC GTC ACG GCC GAC AAG AGC ACC
 D   P   N   G   I   L   N   V   T   A   D   K   S   T

GGC AAG GCC AAC AAG ATC ACC ATC AAC GAC AAG GGC CGC CTG
 G   K   A   N   K   I   T   I   N   D   K   G   R   L
```

```
AGC AAG GAG GAG ATC GAG CGC ATG GTG CAG GAG GCG GAG AAG TAC
 S   K   E   E   I   E   R   M   V   Q   E   A   E   K   Y

AAA GCG GAG GAG GAC GTG GAG CAG CGC GAG AGG GTG TCA GCC AAG AAC
 K   A   E   E   D   V   E   Q   R   E   R   V   S   A   K   N

GCC CTG GAG TCC TAC GCC TTC AAC ATG AAG AGC GCC GTG GAG GAT
 A   L   E   S   Y   A   F   N   M   K   S   A   V   E   D

GAG GGG CTC AAG GGC AAG ATC AGC GAG GCG GAC AAG AAG GTT
 E   G   L   K   G   K   I   S   E   A   D   K   K   V

CTG GAC AAG TGT CAA GAG GTC ATC TCG TGG CTG GAC GCC AAC ACC
 L   D   K   C   Q   E   V   I   S   W   L   D   A   N   T

TTG GCC GAG AAG GAC GAG TTT GAG CAC AAG AAG AGG GAG CTG GAG
 L   A   E   K   D   E   F   E   H   K   R   K   E   L   E

CAG GTG TGT AAC CCC ATC ATC AGC GGA CTG TAC CAG GGT GCC GGT
 Q   V   C   N   P   I   I   S   G   L   Y   Q   A   G

GGT CCC GGG CCT GGC TTC GGG GCT CAG GGT CCC AAG GGA GGG
 G   P   G   P   G   F   G   A   Q   G   P   K   G   G
```

TCT GGG TCA GGC CCT ACC ATT GAG GAG GTG GAT TAG
S   G   S   G   P   T   I   E   E   V   D   *

Figure 9
Continued

Figure 10:
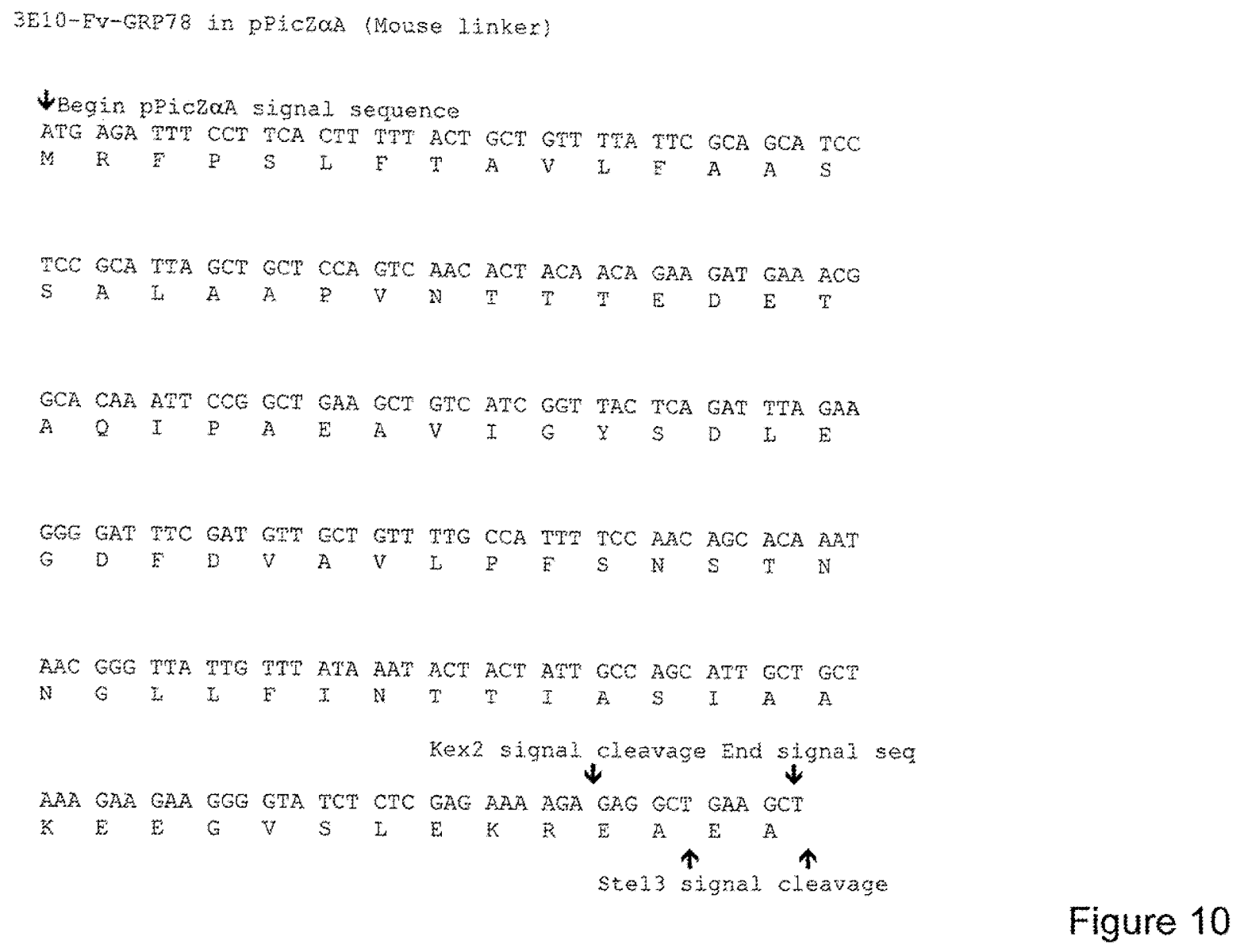

3E10-Fv-GRP78 in pPicZαA (Mouse linker)

↓Begin pPicZαA signal sequence
ATG AGA TTT CCT TCA CTT TTT ACT GCT GTT TTA TTC GCA GCA TCC
 M   R   F   P   S   L   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ACT ATT GCC AGC ATT GCT GCT
 N   G   L   L   F   I   N   T   T   I   A   S   I   A   A Kex2 signal cleavage End signal seq
                                              ↓              ↓
AAA GAA GAA GGG GTA TCT CTC GAG AAA AGA GAG GCT GAA GCT
 K   E   E   G   V   S   L   E   K   R   E   A   E   A
                                              ↑       ↑
                                    Ste13 signal cleavage

```
EcoRI   HIS6 tag                      solubility   Begin Fv
GAA TTC CAT CAC CAT CAC CAT CAC GCA GGG ATT CAC GAC ATT GTC
 E   F   H   H   H   H   H   H   A   G   I   H   D   I   V CTG ACA CAG TCT CCT GCT TCC TTA GCT GTA TCT CTG GGG CAG AGG
 L   T   Q   S   P   A   S   L   A   V   S   L   G   Q   R GCC ACC ATC TCC TGC AGG GCC AGC AAA AGT GTC AGT ACA TCT AGC
 A   T   I   S   C   R   A   S   K   S   V   S   T   S   S
                3E10 Vk CDR1

TAT AGT TAC ATG CAC TGG TAC CAA CAG AAA CCA GGA CAG CCA CCC
 Y   S   Y   M   H   W   Y   Q   Q   K   P   G   Q   P   P
                        3E10 Vk CDR2

AAA CTC CTC ATC AAG TAT GCA TCC TAC CTA GAA TCT GGG GTT CCT
 K   L   L   I   K   Y   A   S   Y   L   E   S   G   V   P

GCC AGG TTC AGT GGC AGT GGG TCT GGG ACA GAC TTC ACC CTC AAC
 A   R   F   S   G   S   G   S   G   T   D   F   T   L   N

ATC CAT CCT GTG GAG GAG GAT GCT GCA ACA TAT TAC TGT CAG
 I   H   P   V   E   E   D   A   A   T   Y   Y   C   Q
                3E10 Vk CDR3

CAC AGT AGG GAG TTT CCG TGG ACG TTC GGT GGA GGC ACC AAG CTG
 H   S   R   E   F   P   W   T   F   G   G   G   T   K   L
```

```
                                                    (GGGGS)3 Linker
GAA ATC AAA CGG GCT GAT GCT GCA CCC GGG GGT GGC GGT TCT GGC
 E   I   K   R   A   D   A   A   P   G   G   G   G   S   G GGT GGC GGT TCT GGA GGC GGT GGC TCT GAG GTG CAG CTG GTG GAG
 G   G   G   S   G   G   G   G   S   E   V   Q   L   V   E TCT GGG GGA GGC TTA GTG AAG CCT GGA GGG TCC CGG AAA CTC TCC
 S   G   G   G   L   V   K   P   G   G   S   R   K   L   S 3E10 VH CDR1
TGT GCA GCC TCT GGA TTC ACT TTC AGT AAC TAT GGA ATG CAC TGG
 C   A   A   S   G   F   T   F   S   N   Y   G   M   H   W
             (D31N mutation 3E10 VH enhances cell penetration)

GTC CGT CAG GCT CCA GAG AAG GGG CTG GAG TGG GTT GCA TAC ATT
 V   R   Q   A   P   E   K   G   L   E   W   V   A   Y   I

3E10 VH CDR2
AGT AGT GGC AGT AGT ACC ATC TAC TAT GCA GAC ACA GTG AAG GGC
 S   S   G   S   S   T   I   Y   Y   A   D   T   V   K   G

CGA TTC ACC ATC TCC AGA GAC AAT GCC AAG AAC ACC CTG TTC CTG
 R   F   T   I   S   R   D   N   A   K   N   T   L   F   L
```

Figure 10:
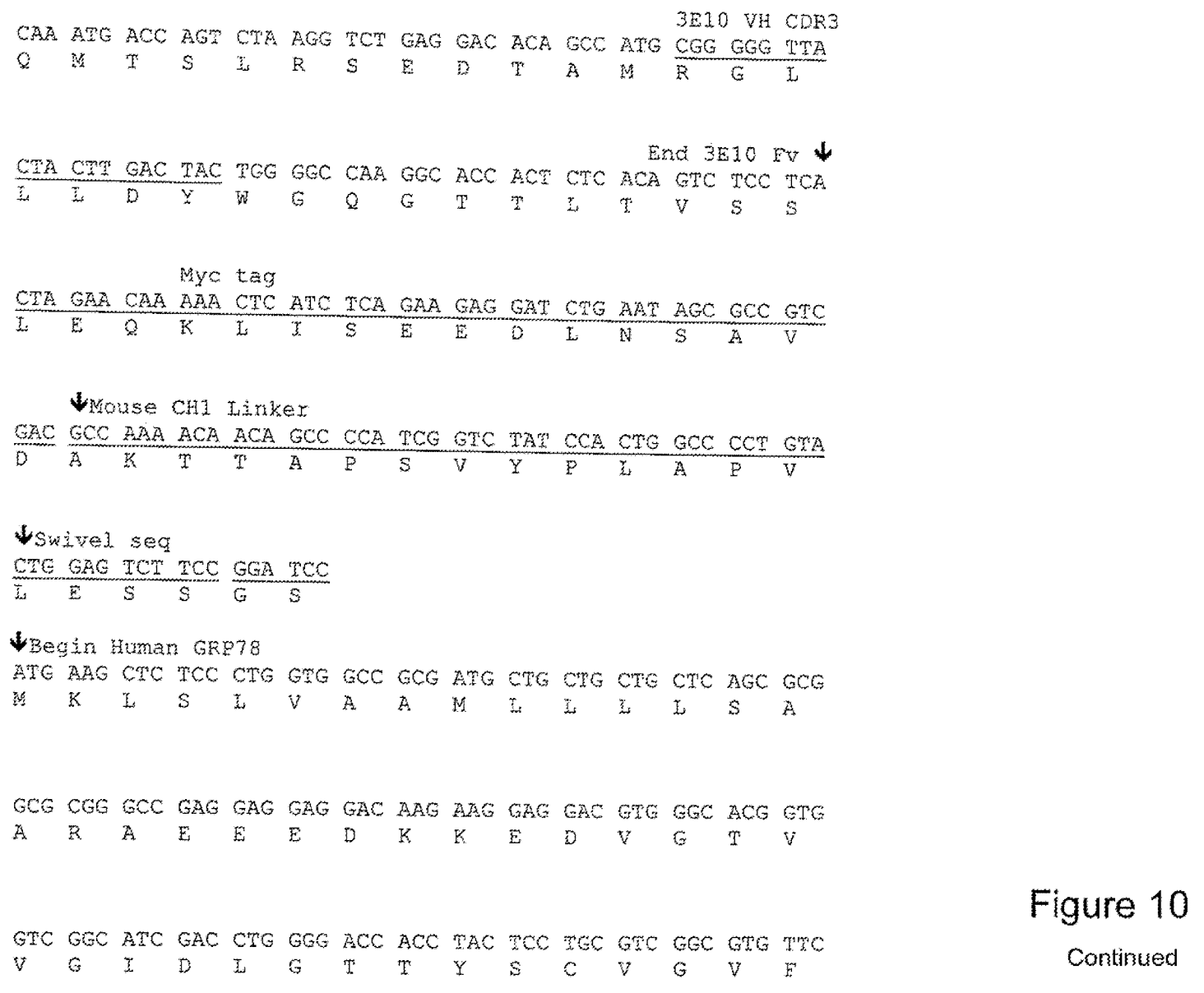

```
                                                        3E10 VH CDR3
CAA ATG ACC AGT CTA AGG TCT GAG GAC ACA GCC ATG CGG GGG TTA
 Q   M   T   S   L   R   S   E   D   T   A   M   R   G   L

End 3E10 Fv →
CTA CTT GAC TAC TGG GGC CAA GGC ACC ACT CTC ACA GTC TCC TCA
 L   L   D   Y   W   G   Q   G   T   T   L   T   V   S   S

Myc tag
CTA GAA CAA AAA CTC ATC TCA GAA GAG GAT CTG AAT AGC GCC GTC
 L   E   Q   K   L   I   S   E   E   D   L   N   S   A   V ↓Mouse CH1 Linker
GAC GCC AAA ACA ACA GCC CCA TCG GTC TAT CCA CTG GCC CCT GTA
 D   A   K   T   T   A   P   S   V   Y   P   L   A   P   V ↓Swivel seq
CTG GAG TCT TCC GGA TCC
 L   E   S   S   G   S ↓Begin Human GRP78
ATG AAG CTC TCC CTG GTG GCC GCG ATG CTG CTG CTC AGC GCG
 M   K   L   S   L   V   A   A   M   L   L   L   S   A GCG CGG GCC GAG GAG GAG GAC AAG AAG GAG GAC GTG GGC ACG GTG
 A   R   A   E   E   E   D   K   K   E   D   V   G   T   V GTC GGC ATC GAC CTG GGG ACC ACC TAC TCC TGC GTC GGC GTG TTC
 V   G   I   D   L   G   T   T   Y   S   C   V   G   V   F
```

```
AAG AAC GGC CGC GTG GAG ATC ATC GCC AAC GAT CAG GGC AAC CGC
 K   N   G   R   V   E   I   I   A   N   D   Q   G   N   R

ATC ACG CCG TCC TAT GTC GCC TTC ACT CCT GAA GGG GAA CGT CTG
 I   T   P   S   Y   V   A   F   T   P   E   G   E   R   L

ATT GGC GAT GCC GCC AAG AAC CAG CTC ACC TCC AAC CCC GAG AAC
 I   G   D   A   A   K   N   Q   L   T   S   N   P   E   N

ACG GTC TTT GAC AAG GCC CGG CTC ATC GGC CGC ACG TGG AAT GAC
 T   V   F   D   A   K   R   L   I   G   R   T   W   N   D

CCG TCT GTG CAG CAG GAC ATC AAG TTC TTG CCG TTC AAG GTG GTT
 P   S   V   Q   Q   D   I   K   F   L   P   F   K   V   V

GAA AAG AAA ACT AAA CCA TAC ATT CAA GTT GAT ATT GGA GGT GGG
 E   K   K   T   K   P   Y   I   Q   V   D   I   G   G   G

CAA ACA AAG ACA TTT GCT CCT GAA GAA ATT TCT GCC ATG GTT CTC
 Q   T   K   T   F   A   P   E   E   I   S   A   M   V   L

ACT AAA ATG AAA GAA ACC GCT GAG GCT TAT TTG GGA AAG AAG GTT
 T   K   M   K   E   T   A   E   A   Y   L   G   K   K   V
```

Figure 10:
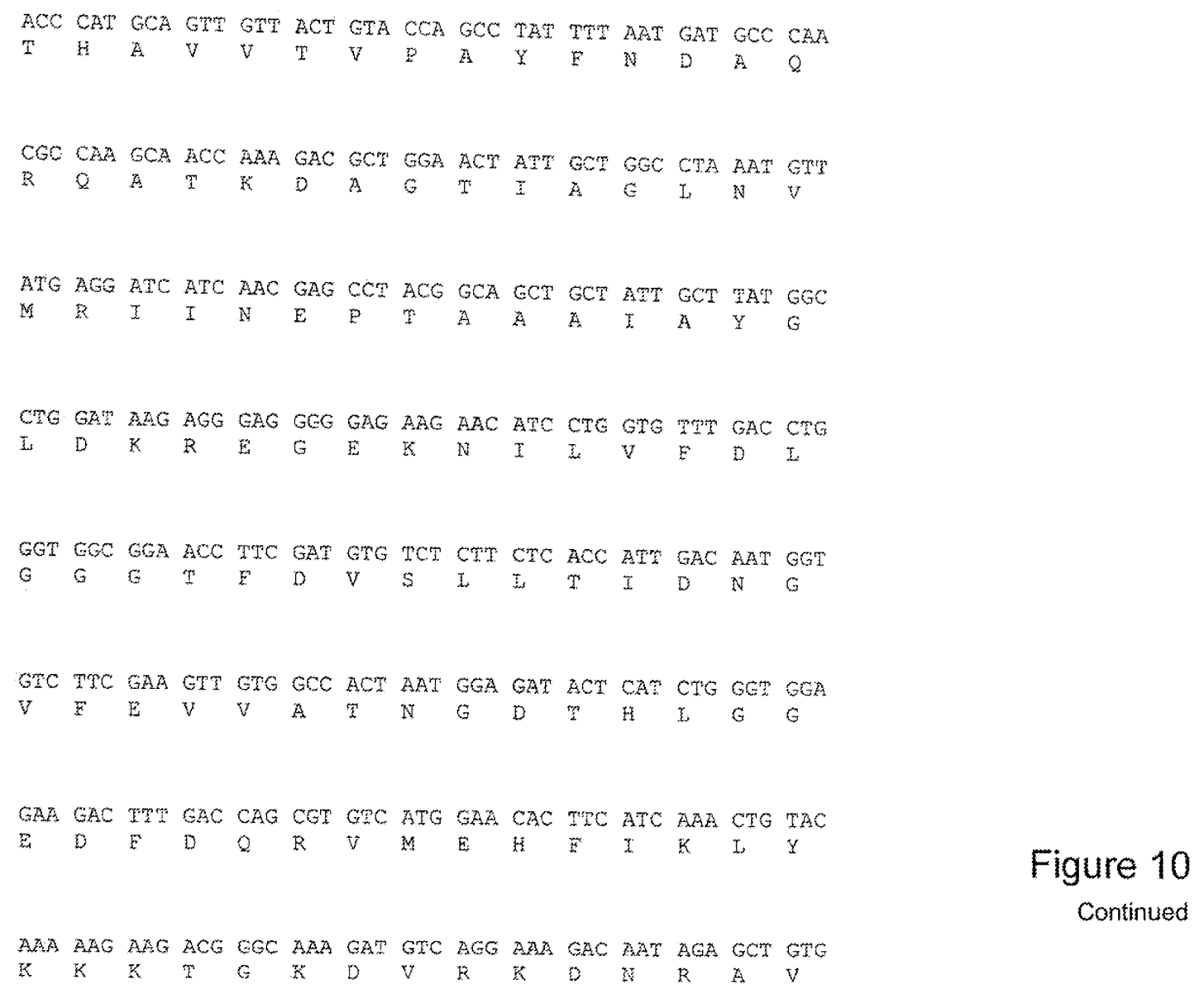

```
ACC CAT GCA GTT GTT ACT GTA CCA GCC TAT TTT AAT GAT GCC CAA
 T   H   A   V   V   T   V   P   A   Y   F   N   D   A   Q

CGC CAA GCA ACC AAA GAC GCT GGA ACT ATT GCT GGC CTA AAT GTT
 R   Q   A   T   K   D   A   G   T   I   A   G   L   N   V

ATG AGG ATC ATC AAC GAG CCT ACG GCA GCT GCT ATT GCT TAT GGC
 M   R   I   I   N   E   P   T   A   A   A   I   A   Y   G

CTG GAT AAG AGG GAG GGG GAG AAG AAC ATC CTG GTG TTT GAC CTG
 L   D   K   R   E   G   E   K   N   I   L   V   F   D   L

GGT GGC GGA ACC TTC GAT GTG TCT CTT CTC ACC ATT GAC AAT GGT
 G   G   G   T   F   D   V   S   L   L   T   I   D   N   G

GTC TTC GAA GTT GTG GCC ACT AAT GGA GAT ACT CAT CTG GCT GGA
 V   F   E   V   V   A   T   N   G   D   T   H   L   G   G

GAA GAC TTT GAC CAG CGT GTC ATG GAA CAC TTC ATC AAA CTG TAC
 E   D   F   D   Q   R   V   M   E   H   F   I   K   L   Y

AAA AAG ACG GGC AAA GAT GTC AGG AAA GAC AAT AGA GCT GTG
 K   K   T   G   K   D   V   R   K   D   N   R   A   V
```

Figure 10:
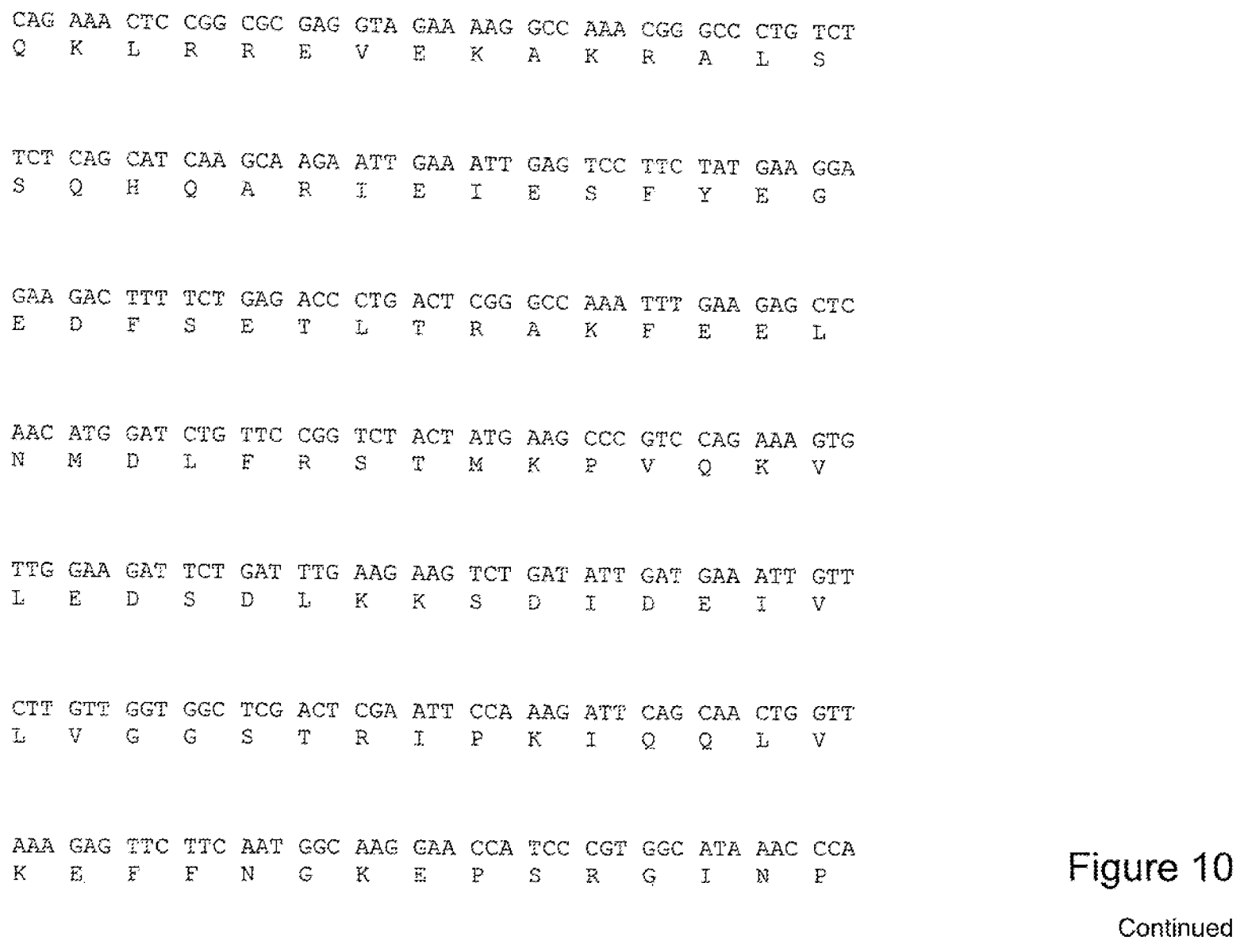

```
CAG AAA CTC CGG CGC GAG GTA GAA AAG GCC AAA CGG GCC CTG TCT
 Q   K   L   R   R   E   V   E   K   A   K   R   A   L   S

TCT CAG CAT CAA GCA AGA ATT GAA ATT GAG TCC TTC TAT GAA GGA
 S   Q   H   Q   A   R   I   E   I   E   S   F   Y   E   G

GAA GAC TTT TCT GAG ACC CTG ACT CGG GCC AAA TTT GAA GAG CTC
 E   D   F   S   E   T   L   T   R   A   K   F   E   E   L

AAC ATG GAT CTG TTC CGG TCT ACT ATG AAG CCC GTC CAG AAA GTG
 N   M   D   L   F   R   S   T   M   K   P   V   Q   K   V

TTG GAA GAT TCT GAT TTG AAG AAG TCT GAT ATT GAT GAA ATT GTT
 L   E   D   S   D   L   K   K   S   D   I   D   E   I   V

CTT GTT GGT GGC TCG ACT CGA ATT CCA AAG ATT CAG CAA CTG GTT
 L   V   G   G   S   T   R   I   P   K   I   Q   Q   L   V

AAA GAG TTC AAT GGC AAG GAA CCA TCC CGT GGC ATA AAC CCA
 K   E   F   N   G   K   E   P   S   R   G   I   N   P
```

Figure 10
Continued

```
GAT GAA GCT GTA GCG TAT GGT GCT GCT GTC CAG GCT GGT GTG CTC
 D   E   A   V   A   Y   G   A   A   V   Q   A   G   V   L

TCT GGT GAT CAA GAT ACA GGT GAC CTG GTA CTG CTT GAT GTA TGT
 S   G   D   Q   D   T   G   D   L   V   L   L   D   V   C

CCC CTT ACA CTT GGT ATT GAA ACT GTG GGA GGT GTC ATG ACC AAA
 P   L   T   L   G   I   E   T   V   G   G   V   M   T   K

CTG ATT CCA AGG AAC ACA GTG GTG CCT ACC AAG AAG TCT CAG ATC
 L   I   P   R   N   T   V   V   P   T   K   K   S   Q   I

TTT TCT ACA GCT TCT GAT AAT CAA CCA ACT GTT ACA ATC AAG GTC
 F   S   T   A   S   D   N   Q   P   T   V   T   I   K   V

TAT GAA GGT GAA AGA CCC CTG ACA AAA GAC AAT CAT CTT CTG GGT
 Y   E   G   E   R   P   L   T   K   D   N   H   L   L   G

ACA TTT GAT CTG ACT GGA ATT CCT CCT GCT CCT CGT GGG GTC CCA
 T   F   D   L   T   G   I   P   P   A   P   R   G   V   P

CAG ATT GAA GTC ACC TTT GAG ATA GAT GTG AAT GGT AAT CTT CGA
 Q   I   E   V   T   F   E   I   D   V   N   G   I   L   R
```

Figure 10
Continued

```
GTG ACA GCT GAA GAC AAG GGT ACA GGG AAC AAA AAT AAG ATC ACA
 V   T   A   E   D   K   G   T   G   N   K   N   K   I   T

ATC ACC AAT GAC CAG AAT CGC CTG ACA CCT GAA GAA ATC GAA AGG
 I   T   N   D   Q   N   R   L   T   P   E   E   I   E   R

ATG GTT AAT GAT GCT GAG AAG TTT GCT GAG GAA GAC AAA AAG CTC
 M   V   N   D   A   E   K   F   A   E   E   D   K   L

AAG GAG CGC ATT GAT ACT AGA AAT GAG TTG GAA AGC TAT GCC TAT
 K   E   R   I   D   T   R   N   E   L   E   S   Y   A   Y

TCT CTA AAG AAT CAG ATT GGA GAT AAA GAA AAG CTG GGA GGT AAA
 S   L   K   N   Q   I   G   D   K   E   K   L   G   G   K

CTT TCC TCT GAA GAT AAG GAG ACC ATG GAA AAA GCT GTA GAA GAA
 L   S   S   E   D   K   E   T   M   E   K   A   V   E   E

AAG ATT GAA TGG CTG GAA AAG AAG GAT ATT GAC ATT GAA GAC
 K   I   E   W   L   E   K   K   D   I   D   I   E   D

TTC AAA GCT AAG AAG GAA CTG GAA GAA ATT GTT CAA CCA ATT
 F   K   A   K   K   E   L   E   E   I   V   Q   P   I
```

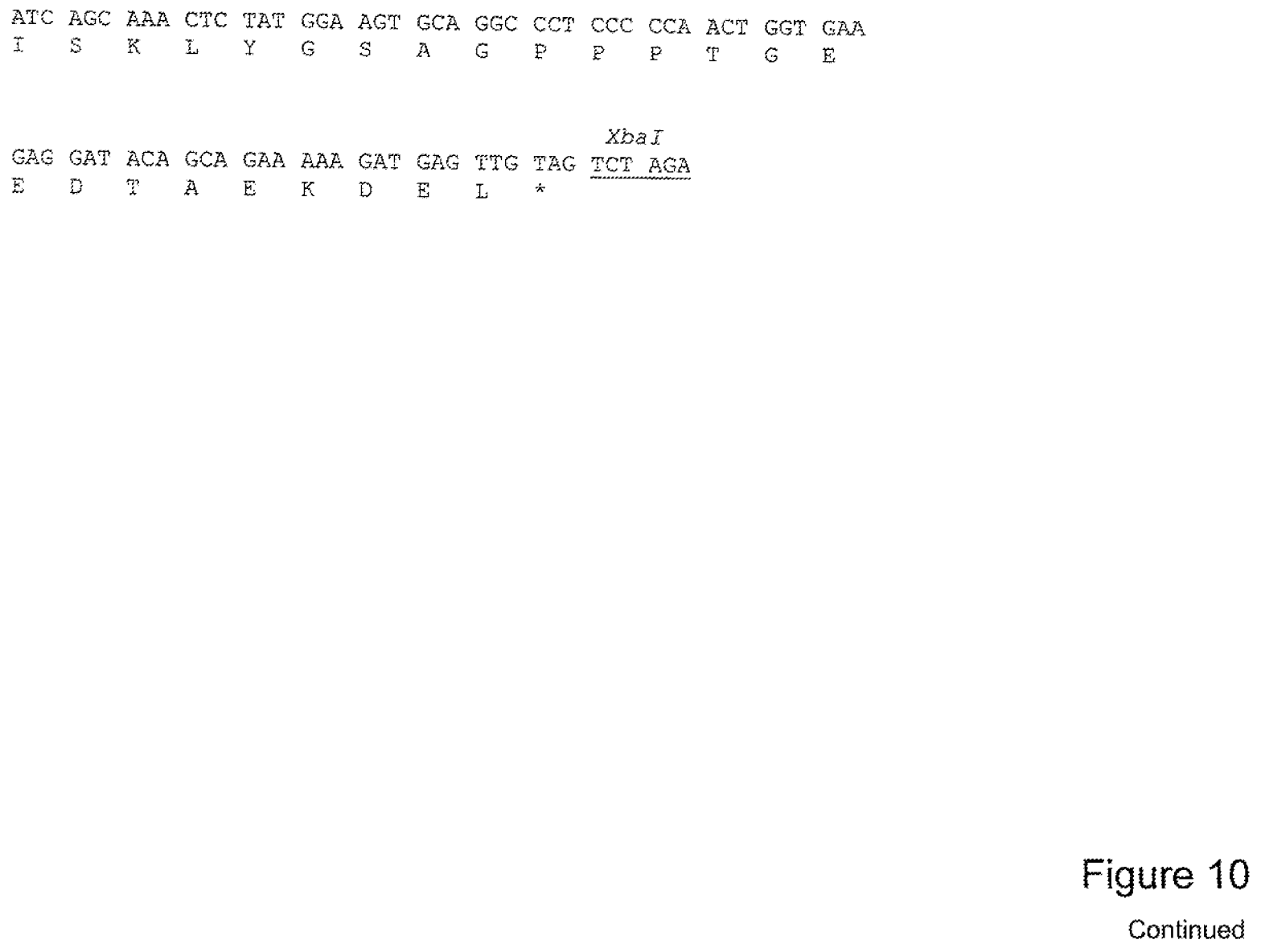

ATC AGC AAA CTC TAT GGA AGT GCA GGC CCT CCC CCA ACT GGT GAA
 I   S   K   L   Y   G   S   A   G   P   P   P   T   G   E

XbaI
GAG GAT ACA GCA GAA AAA GAT GAG TTG TAG TCT AGA
 E   D   T   A   E   K   D   E   L   *

Figure 10
Continued

3E10-Ev-HSP90 in pPiczαA (Mouse linker)

↓Begin pPiczαA signal sequence
```
ATG AGA TTT CCT TCA CTT TTT ACT GCT GTT TTA TTC GCA GCA TCC
 M   R   F   P   S   L   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ACT ATT GCC AGC ATT GCT GCT
 N   G   L   L   F   I   N   T   T   I   A   S   I   A   A
```

Kex2 signal cleavage    End signal seq →

```
AAA GAA GGG GTA TCT CTC GAG AAA AGA GAG GCT GAA GCT
 K   E   G   V   S   L   E   K   R   E   A   E   A
```

Ste13 signal cleavage

```
        EcoRI       HIS6 tag                      ↑solubility    ↓Begin Fv
        GAA TTC CAT CAC CAT CAC CAT CAC GCA GGG ATT CAC GAC ATT GTC
        E   F   H   H   H   H   H   H   A   G   I   H   D   I   V CTG ACA CAG TCT CCT GCT TCC TTA GCT GTA TCT CTG GGG CAG AGG
        L   T   Q   S   P   A   S   L   A   V   S   L   G   Q   R GCC ACC ATC TCC TGC AGG GCC AGC AAA AGT GTC AGT ACA TCT AGC
        A   T   I   S   C   R   A   S   K   S   V   S   T   S   S
                        3E10 Vk CDR1
        TAT AGT TAC ATG CAC TGG TAC CAA CAG AAA CCA GGA CAG CCA CCC
        Y   S   Y   M   H   W   Y   Q   Q   K   P   G   Q   P   P
                                3E10 Vk CDR2
        AAA CTC CTC ATC AAG TAT GCA TCC TAC CTA GAA TCT GGG GTT CCT
        K   L   L   I   K   Y   A   S   Y   L   E   S   G   V   P GCC AGG TTC AGT GGC AGT GGG TCT GGG ACA GAC TTC ACC CTC AAC
        A   R   F   S   G   S   G   S   G   T   D   F   T   L   N ATC CAT CCT GTG GAG GAG GAG GAT GCT GCA ACA TAT TAC TGT CAG
        I   H   P   V   E   E   E   D   A   A   T   Y   Y   C   Q
                        3E10 Vk CDR3
        CAC AGT AGG AGG GAG TTT CCG TGG ACG TTC GGT GGA GGC ACC AAG CTG
        H   S   R   R   E   F   P   W   T   F   G   G   G   T   K   L
```

Figure 11
Continued

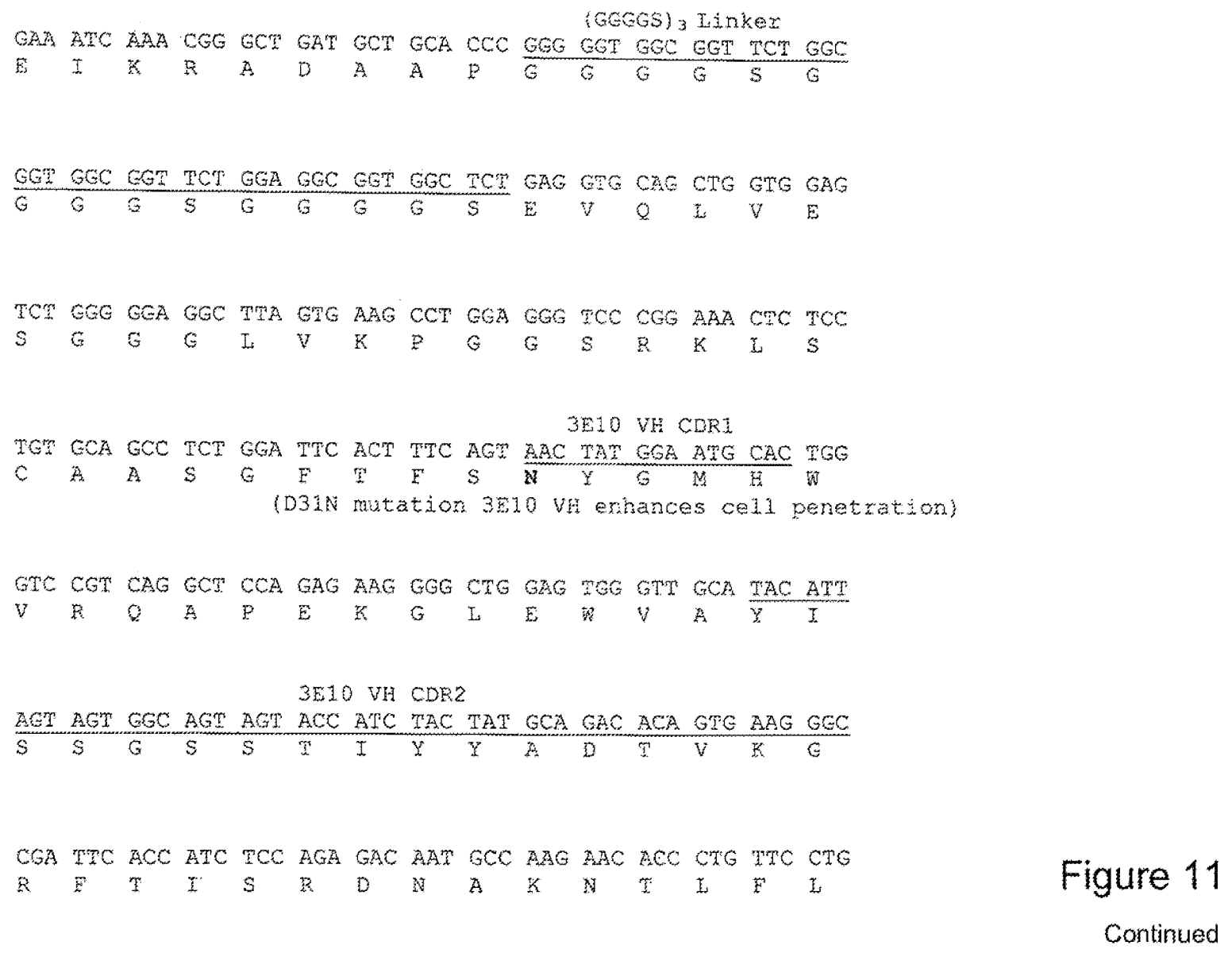

```
                                     (GGGGS)3 Linker
GAA ATC AAA CGG GCT GAT GCT GCA CCC GGG GGT GGC GGT TCT GGC
 E   I   K   R   A   D   A   A   P   G   G   G   G   S   G GGT GGC GGT TCT GGA GGC GGT GGC TCT GAG GTG CAG CTG GTG GAG
 G   G   G   S   G   G   G   G   S   E   V   Q   L   V   E TCT GGG GGA GGC TTA GTG AAG CCT GGA GGG TCC CGG AAA CTC TCC
 S   G   G   G   L   V   K   P   G   G   S   R   K   L   S 3E10 VH CDR1
TGT GCA GCC TCT GGA TTC ACT TTC AGT AAC TAT GGA ATG CAC TGG
 C   A   A   S   G   F   T   F   S   N   Y   G   M   H   W
                  (D31N mutation 3E10 VH enhances cell penetration)

GTC CGT CAG GCT CCA GAG AAG GGG CTG GAG TGG GTT GCA TAC ATT
 V   R   Q   A   P   E   K   G   L   E   W   V   A   Y   I

3E10 VH CDR2
AGT AGT GGC AGT AGT ACC ATC TAC TAT GCA GAC ACA GTG AAG GGC
 S   S   G   S   S   T   I   Y   Y   A   D   T   V   K   G

CGA TTC ACC ATC TCC AGA GAC AAT GCC AAG AAC ACC CTG TTC CTG
 R   F   T   I   S   R   D   N   A   K   N   T   L   F   L
```

Figure 11:
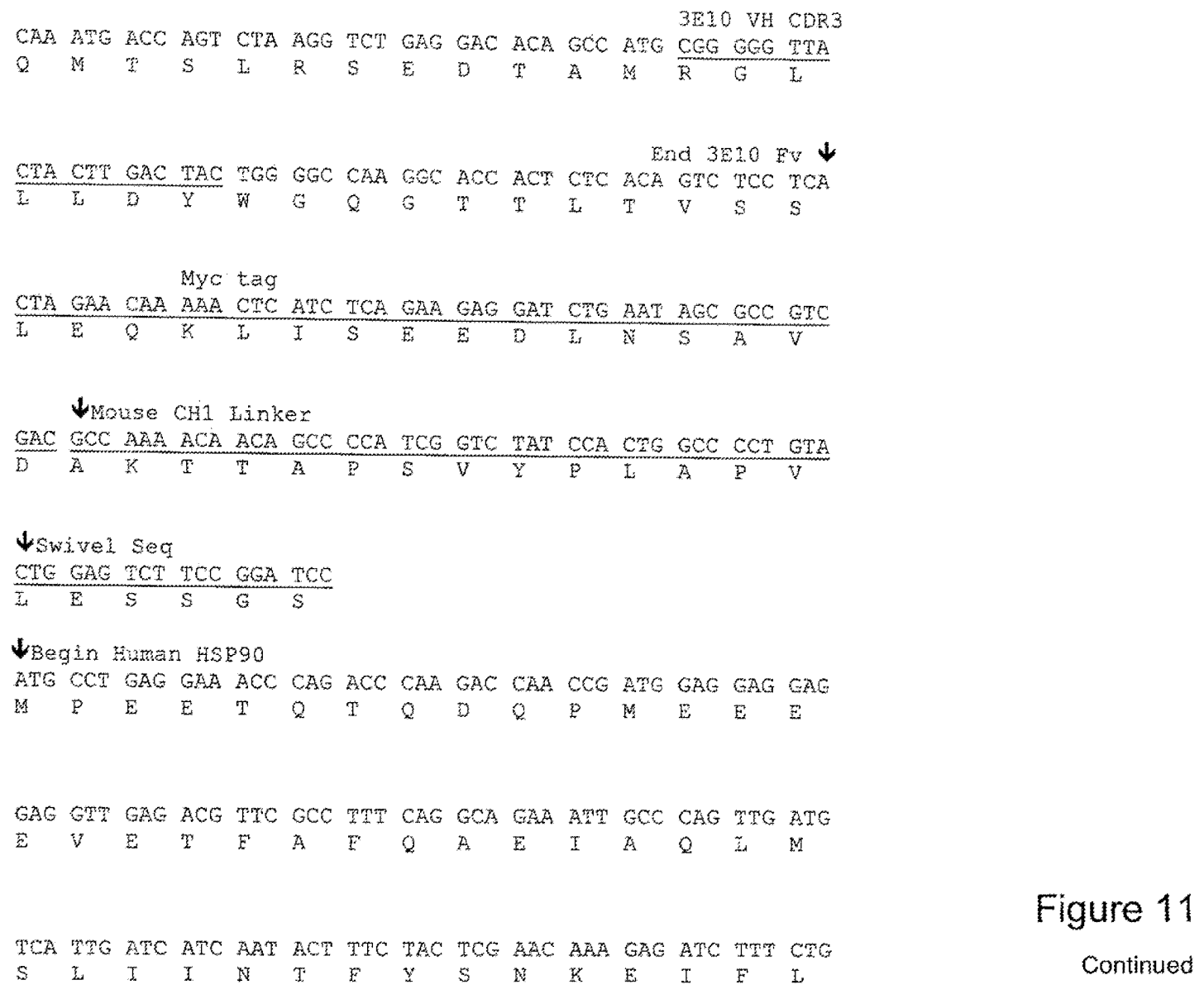

3E10 VH CDR3

CAA ATG ACC AGT CTA AGG TCT GAG GAC ACA GCC ATG CGG GGG TTA
Q   M   T   S   L   R   S   E   D   T   A   M   R   G   L

End 3E10 Fv →

CTA CTT GAC TAC TGG GGC CAA GGC ACC ACT CTC ACA GTC TCC TCA
L   L   D   Y   W   G   Q   G   T   T   L   T   V   S   S

Myc tag

CTA GAA CAA AAA CTC ATC TCA GAA GAG GAT CTG AAT AGC GCC GTC
L   E   Q   K   L   I   S   E   E   D   L   N   S   A   V

↓Mouse CH1 Linker

GAC GCC AAA ACA ACA GCC CCA TCG GTC TAT CCA CTG GCC CCT GTA
D   A   K   T   T   A   P   S   V   Y   P   L   A   P   V

↓Swivel Seq

CTG GAG TCT TCC GGA TCC
L   E   S   S   G   S

↓Begin Human HSP90

ATG CCT GAG GAA ACC CAG ACC CAA GAC CAA CCG ATG GAG GAG GAG
M   P   E   E   T   Q   T   Q   D   Q   P   M   E   E   E

GAG GTT GAG ACG TTC GCC TTT CAG GCA GAA ATT GCC CAG TTG ATG
E   V   E   T   F   A   F   Q   A   E   I   A   Q   L   M

TCA TTG ATC ATC AAT ACT TTC TAC TCG AAC AAA GAG ATC TTT CTG
S   L   I   I   N   T   F   Y   S   N   K   E   I   F   L

```
AGA GAG CTC ATT TCA AAT TCA GAT GCA TTG GAC AAA ATC CGG
 R   E   L   I   S   N   S   D   A   L   D   K   I   R

TAT GAA AGC TTG ACA GAT CCC AGT AAA TTA GAC TCT GGG AAA GAG
 Y   E   S   L   T   D   P   S   K   L   D   S   G   K   E

CTG CAT ATT AAC CTT ATA CCG AAC AAA CAA GAT CGA ACT CTC ACT
 L   H   I   N   L   I   P   N   K   Q   D   R   T   L   T

ATT GTG GAT ACT GGA ATT GGA ATG ACC AAG GCT GAC TTG ATC AAT
 I   V   D   T   G   I   G   M   T   K   A   D   L   I   N

AAC CTT GGT ACT ATC GCC AAG TCT GGG ACC AAA GCG TTC ATG GAA
 N   L   G   T   I   A   K   S   G   T   K   A   F   M   E

GCT TTG CAG GCT GGT GCA GAT ATC TCT ATG ATT GGC CAG TTC GGT
 A   L   Q   A   G   A   D   I   S   M   I   G   Q   F   G

GTT GGT TTT TAT TCT GCT TAT TTG GTT GCT GAG AAA GTA ACT GTG
 V   G   F   Y   S   A   Y   L   V   A   E   K   V   T   V

ATC ACC AAA CAT AAC GAT GAG CAG TAC GCT TGG GAG TCC TCA
 I   T   K   H   N   D   E   Q   Y   A   W   E   S   S
```

Figure 11
Continued

```
GCA GGG GGA TCA TTC ACA GTG AGG ACA GAC ACA GGT GAA CCT ATG
 A   G   G   S   F   T   V   R   T   D   T   G   E   P   M

GGT CGT GGA ACA AAA GTT ATC CTA CAC CTG AAA GAA GAC CAA ACT
 G   R   G   T   K   V   I   L   H   L   K   E   D   Q   T

GAG TAC TTG GAG GAA CGA AGA ATA AAG GAG ATT GTG AAG AAA CAT
 E   Y   L   E   E   R   R   I   K   E   I   V   K   K   H

TCT CAG TTT ATT GGA TAT CCC ATT ACT CTT TTT GTG GAG AAG GAA
 S   Q   F   I   G   Y   P   I   T   L   F   V   E   K   E

CGT GAT AAA GAA GTA AGC GAT GAG GCT GAA AAG GAA GAA GAC
 R   D   K   E   V   S   D   E   A   E   K   E   E   D

AAA GAA GAA AAA GAA GAG AAA GAA GAG TCG GAA GAC AAA
 K   E   E   K   E   E   K   E   E   S   E   D   K

CCT GAA ATT GAA GAT GTT GGT TCT GAT GAG GAA AAG AAG
 P   E   I   E   D   V   G   S   D   E   E   K   K

GAT GGT GAC AAG AAG AAG AAG ATT AAG GAA GAA AAG TAC ATC
 D   G   D   K   K   K   K   I   K   E   E   K   Y   I
```

Figure 11
Continued

```
GAT CAA GAA GAG CTC AAC AAA ACA AAG CCC ATC TGG ACC AGA AAT
 D   Q   E   E   L   N   K   T   K   P   I   W   T   R   N

CCC GAC GAT ATT ACT AAT GAG GAG TAC GGA GAA TTC TAT AAG AGC
 P   D   D   I   T   N   E   E   Y   G   E   F   Y   K   S

TTG ACC AAT GAC TGG GAA GAT CAC TTG GCA GTG AAG CAT TTT TCA
 L   T   N   D   W   E   D   H   L   A   V   K   H   F   S

GTT GAA GGA CAG TTG GAA TTC AGA GCC CTT CTA TTT GTC CCA CGA
 V   E   G   Q   L   E   F   R   A   L   L   F   V   P   R

CGT GCT CCT TTT GAT CTG TTT GAA AAC AGA AAG AAA AAG AAC AAC
 R   A   P   F   D   L   F   E   N   R   K   K   K   N   N

ATC AAA TTG TAT GTA CGC AGA GTT TTC ATC ATG GAT AAC TGT GAG
 I   K   L   Y   V   R   R   V   F   I   M   D   N   C   E

GAG CTA ATC CCT GAA TAT CTG AAC TTC ATT AGA GGG GTG GTA GAC
 E   L   I   P   E   Y   L   N   F   I   R   G   V   V   D
```

Figure 11
Continued

```
TCG GAG GAT CTC CCT CTA AAC ATA TCC CGT GAG ATG TTG CAA CAA
 S   E   D   L   P   L   N   I   S   R   E   M   L   Q   Q

AGC AAA ATT TTG AAA GTT ATC AGG AAG AAT TTG GTC AAA AAA TGC
 S   K   I   L   K   V   I   R   K   N   L   V   K   K   C

TTA GAA CTC TTT ACT GAA CTG GCG GAA GAT AAA GAG AAC TAC AAG
 L   E   L   F   T   E   L   A   E   D   K   E   N   Y   K

AAA TTC TAT GAG CAG TTC TCT AAA AAC ATA AAG CTT GGA ATA CAC
 K   F   Y   E   Q   F   S   K   N   I   K   L   G   I   H

GAA GAC TCT CAA AAT CGG AAG AAG CTT TCA GAG CTG TTA AGG TAC
 E   D   S   Q   N   R   K   K   L   S   E   L   L   R   Y

TAC ACA TCT GCC TCT GGT GAT GAG ATG GTT TCT CTC AAG GAC TAC
 Y   T   S   A   S   G   D   E   M   V   S   L   K   D   Y

TGC ACC AGA ATG AAG GAG AAC CAG AAA CAT ATC TAT TAT ATC ACA
 C   T   R   M   K   E   N   Q   K   H   I   Y   Y   I   T

GGT GAG ACC AAG GAC CAG GTA GCT AAC TCA GCC TTT GTG GAA CGT
 G   E   T   K   D   Q   V   A   N   S   A   F   V   E   R
```

```
CTT CGG AAA CAT GGC TTA GAA GTG ATC TAT ATG ATT GAG CCC ATT
 L   R   K   H   G   L   E   V   I   Y   M   I   E   P   I

GAT GAG TAC TGT GTC CAA CAG CTG AAG GAA TTT GAG GGG AAG ACT
 D   E   Y   C   V   Q   Q   L   K   E   F   E   G   K   T

TTA GTG TCA GTC ACC AAA GAA GGC CTG GAA CTT CCA GAG GAT GAA
 L   V   S   V   T   K   E   G   L   E   L   P   E   D   E

GAA GAG AAA AAG AAG CAG GAA GAG AAA AAA ACA AAG TTT GAG AAC
 E   E   K   K   K   Q   E   E   K   K   T   K   F   E   N

CTC TGC AAA ATC ATG AAA GAC ATA TTG GAG AAA GTT GAA AAG
 L   C   K   I   M   K   D   I   L   E   K   V   E   K

GTG GTT GTG TCA AAC CGA TTG GTG ACA TCT CCA TGC TGT ATT GTC
 V   V   V   S   N   R   L   V   T   S   P   C   C   I   V

ACA AGC ACA TAT GGC TGG ACA GCA AAC ATG GAG AGA ATC ATG AAA
 T   S   T   Y   G   W   T   A   N   M   E   R   I   M   K

GCT CAA GCC CTA AGA GAC AAC TCA ACA ATG GGT TAC ATG GCA GCA
 A   Q   A   L   R   D   N   S   T   M   G   Y   M   A   A
```

```
AAG AAA CAC CTG GAG ATA AAC CCT GAC CAT TCC ATT ATT GAG ACC
 K   K   H   L   E   I   N   P   D   H   S   I   I   E   T

TTA AGG CAA AAG GCA GAG GCT GAT AAG AAC GAC AAG TCT GTG AAG
 L   R   Q   K   A   E   A   D   K   N   D   K   S   V   K

GAT CTG GTC ATC TTG CTT TAT GAA ACT GCG CTC CTG TCT TCT GGC
 D   L   V   I   L   L   Y   E   T   A   L   L   S   S   G

TTC AGT CTG GAA GAT CCC CAG ACA CAT GCT AAC AGG ATC TAC AGG
 F   S   L   E   D   P   Q   T   H   A   N   R   I   Y   R

ATG ATC AAA CTT GGT CTG GGT ATT GAT GAA GAT GAC CCT ACT GCT
 M   I   K   L   G   L   G   I   D   E   D   D   P   T   A

GAT GAT ACC AGT GCT GCT GTA ACT GAA GAA ATG CCA CCC CTT GAA
 D   D   T   S   A   A   V   T   E   E   M   P   P   L   E

XbaI
GGA GAT GAC GAC ACA TCA CGC ATG GAA GAA GTA GAC TAA TCT AGA
 G   D   D   D   T   S   R   M   E   E   V   D   *
```

Schematic of Constructs in Pichia

5′ (His)₆ AGIH Fv myc an HSP (HSP70, HSP27, HSP90), GRP 78, or other polypeptides 3′

ANTIBODY-MEDIATED TRANSDUCTION OF HEAT SHOCK PROTEINS INTO LIVING CELLS

CROSS REFERENCE TO RELATED APPLICATIONS

This patent application is a continuation of U.S. application Ser. No. 15/650,752, filed on Jul. 14, 2017, which is a division of U.S. application Ser. No. 13/815,829, filed Mar. 15, 2013, and which claims priority to U.S. Provisional Application No. 61/618,594, filed Mar. 30, 2012, each of which are herein incorporated by reference in their entirety.

REFERENCE TO SEQUENCE LISTING

The Sequence Listing submitted May 27, 2020 as a text file named "37759_0133U3_Sequence_Listing.txt," created on May 27, 2020, and having a size of 299,253 bytes is hereby incorporated by reference pursuant to 37 C.F.R. § 1.52(e)(5).

Throughout this application various publications are referenced. The disclosures of these publications in their entireties are hereby incorporated by reference into this application in order to more fully describe the state of the art to which this invention pertains.

STATEMENT REGARDING FEDERALLY SPONSORED RESEARCH

This invention was made with government support under Grant No. FRS (NS054652) awarded by NIH/NINDS. The government has certain rights in the invention.

BACKGROUND OF THE INVENTION

Current therapies are limited to small molecules because cells are impervious to large molecules such as proteins. We developed a method to transport proteins into cells as molecular fusion proteins including a fragment or portion of a mAb 3E10, a cell-penetrating antibody. mAb 3E10 is unique and distinguishable from other cell-penetrating peptides (CPPs) or protein transduction domains (PTDs) by its use of hENT2 nucleoside salvage pathway for entry into cells. We also developed single chain variable fragments of 3E10 antibody (3E10 scFv), including conservative variants thereof joined to e.g. heat shock proteins and glucose regulated proteins (e.g., GRP78 (glucose-regulated-protein 78 kDa). The full 3E10 antibody has been previously described (Weisbart R H, et al. J Immunol. 1990 144 (7): 2653-2658; ATCC Accession No. PTA 2439 hybridoma). Our results demonstrate the feasibility of transporting proteins and other large molecules into cells using the fusion proteins of the invention.

SUMMARY OF THE INVENTION

The invention provides a 3E10 Fv attached to a heat shock protein (Hsp). Examples of heat shock proteins include but are not limited to, human Hsp-70 (Hunt and Morimoto PNAS Vol, 82, pp. 64-55-6459, FIGS. 2 and 3); HspA (e.g., HspA1A, HspA1B, HspA1L, HspA2, HspA5, HspA6, HspA7, HspA8, HspA9, HspA 12A, HspA 12B, HspA13, HspA14); HspH (e.g., HspH1, HspH2, HspH3, and HspH4); Hsp40 (e.g., DnaJA (e.g. DNAJA1, DNAJA2, DNAJA3, and DNAJA4), DnaJB (e.g., DNAJB1, DNAJB2, DNAJB3, DNAJB4, DNAJB5, DNAJB6, DNAJB7, DNAJB8, DNAJB9, DNAJB11, DNAJB12, DNAJB13, and DNAJB14), DnaJC (e.g., DNAJC1, DNAJC2, DNAJC3, DNAJC4, DNAJC5B, DNAJC5G, DNAJC6, DNAJC7, DNAJC8, DNAJC9, DNAJC10, DNAJC11, DNAJC12, DNAJC13, DNAJC14, DNAJC15, DNAJC16, DNAJC17, DNAJC18, DNAJC19, DNAJC20, DNAJC21, DNAJC22, DNAJC23, DNAJC24, DNAJC25, DNAJC26, DNAJC27, DNAJC28, and DNAJC30) and HSPB (HSPB1, HSPB2, HSPB3, HSPB4, HSPB5, HSPB6, HSPB7, HSPB8, HSPB9, HSPB10 and HSPB11) (Kampinga et al., Cell Stress and Chaperones (2009) 14:105-111).

The 3E10 Fv's of the invention may further comprise one or more amino acid sequence comprising Ala-Gly-Ile-His (AGIH) (SEQ ID NO:37) at its amino terminus.

The invention provides a 3E10 Fv attached to a Hsp-70 or portion thereof, the 3E10 Fv comprising an amino acid sequence AGIH at its amino terminus and pharmaceutical compositions and uses thereof.

The invention also provides a 3E10 Fv attached to Hsp-27 or portion thereof, the 3E10 Fv comprising an amino acid sequence AGIH at its amino terminus and pharmaceutical compositions and uses thereof.

The invention further provides a 3E10 Fv attached to a Hsp-90 or portion thereof, the 3E10 Fv comprising an amino acid sequence AGIH at its amino terminus and pharmaceutical compositions and uses thereof.

The invention further provides a 3E10 Fv attached to glucose regulated protein 78 kDa (GRP78) or portion thereof, the 3E10 Fv comprising an amino acid sequence AGIH at its amino terminus and pharmaceutical compositions and uses thereof.

The 3E10 Fv's of the invention may be joined or attached to localizing signals to direct the scFvs to intracellular compartments such as endoplasmic reticulum and mitochondria. Further, the 3E10 Fv's of the invention may incorporate enzyme cleavage sites to separate the scFvs once they are transported into cells.

The invention provides a fusion protein comprising a 3E10 Fv joined to a Hsp-70 or portion thereof, and optionally, the 3E10 Fv comprising an amino acid sequence AGIH at its amino terminus.

The invention also provides a fusion protein comprising a 3E10 Fv joined to Hsp-27 or portion thereof, and optionally, the 3E10 Fv comprising an amino acid sequence AGIH at its amino terminus.

The invention also provides a fusion protein comprising a 3E10 Fv attached/joined to a Hsp-90 or portion thereof, and optionally, the 3E10 Fv comprising an amino acid sequence AGIH at its amino terminus.

The invention also provides a fusion protein comprising a 3E10 Fv attached/joined to GRP78 or portion thereof, and optionally, the 3E10 Fv comprising an amino acid sequence AGIH at its amino terminus.

The invention also provides a 3E10 Fv attached to a Hsp-70 or portion thereof, the 3E10 Fv comprising an amino acid sequence AGIH at its amino terminus.

The invention also provides a 3E10 Fv attached to Hsp-27 or portion thereof, the 3E10 Fv comprising an amino acid sequence AGM at its amino terminus.

The invention also provides a 3E10 Fv attached to a Hsp-90 or portion thereof, the 3E10 Fv comprising an amino acid sequence AGIH at its amino terminus.

The invention also provides a 3E10 Fv attached to glucose regulated protein 78 kDa (GRP78) or portion thereof, the 3E10 Fv comprising an amino acid sequence AGIH at its amino terminus.

BRIEF DESCRIPTION OF THE FIGURES

FIG. 1 shows that FvHsp27 protects cells significantly at two concentrations of H2O2.

FIG. 4 shows the sequence of 3E10-Fv-HSP27 in pPicZαA (Human linker).

Figure 5:
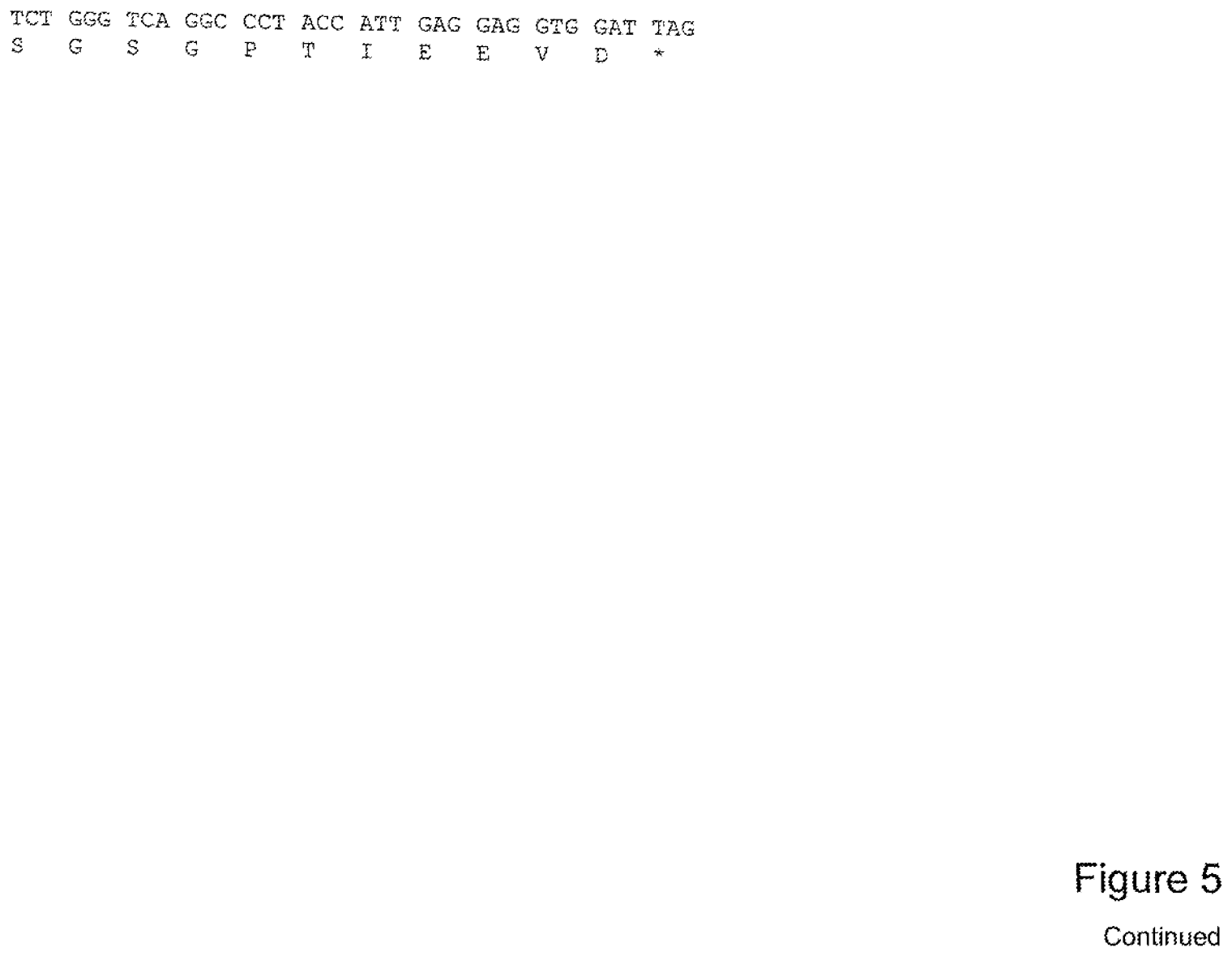

FIG. 5 shows the sequence of 3E10-Fv-HSP70 in pPicZαA (Human linker).

FIG. 6 shows the sequence of 3E10-Fv-GRP78 in pPicZαA (Human linker).

FIG. 7 shows the sequence of 3E10-Fv-HSP90 in pPicZαA (Human linker).

FIG. 8 shows the sequence of 3E10-Fv-HSP27 in pPicZαA (Mouse linker).

Figure 9:
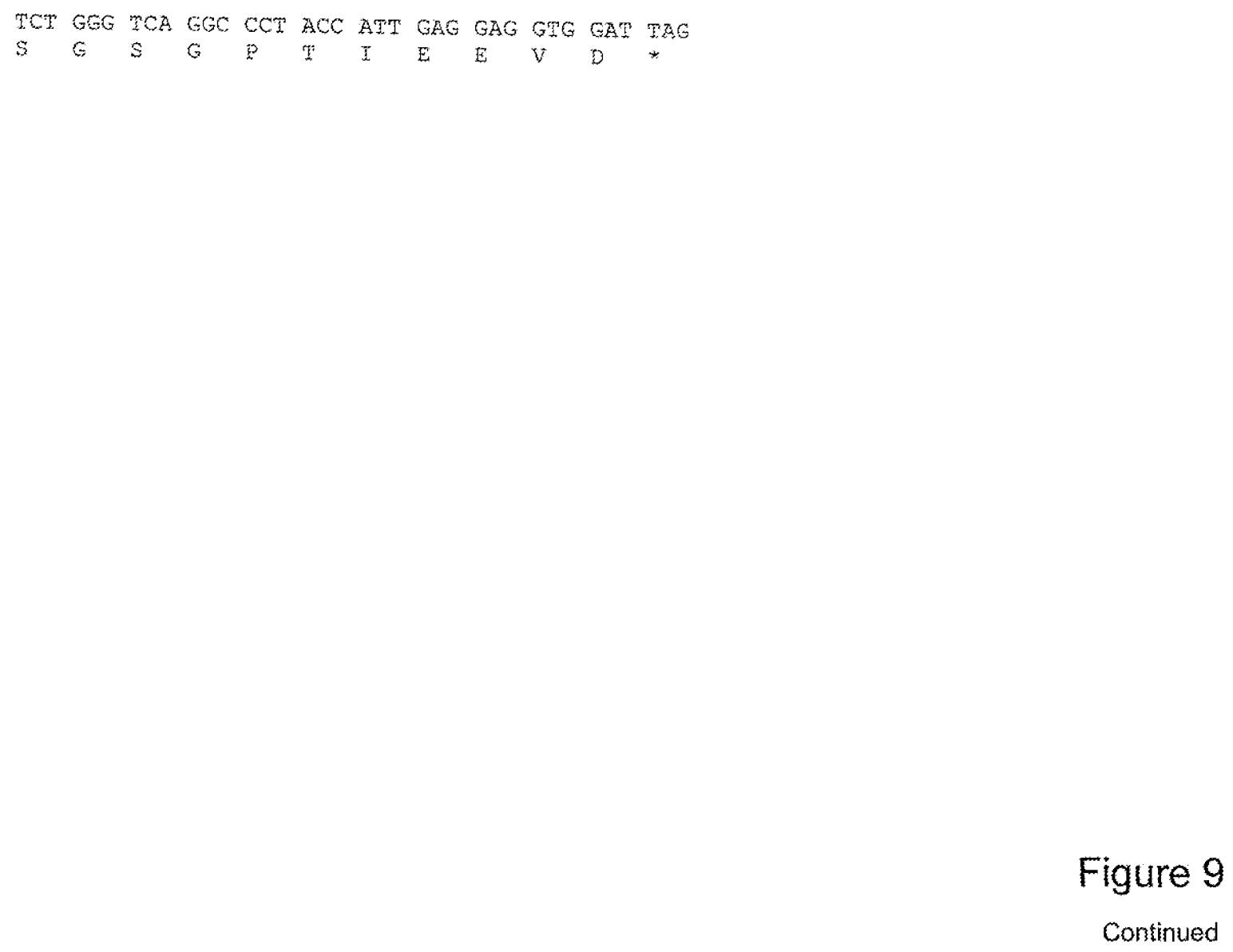

FIG. 9 shows the sequence of 3E10-Fv-HSP70 in pPicZαA (Mouse linker).

FIG. 10 shows the sequence of 3E10-Fv-GRP78 in pPicZαA (Mouse linker).

FIG. 11 shows the sequence of 3E10-Fv-HSP90 in pPicZαA (Mouse linker).

Figure 1:
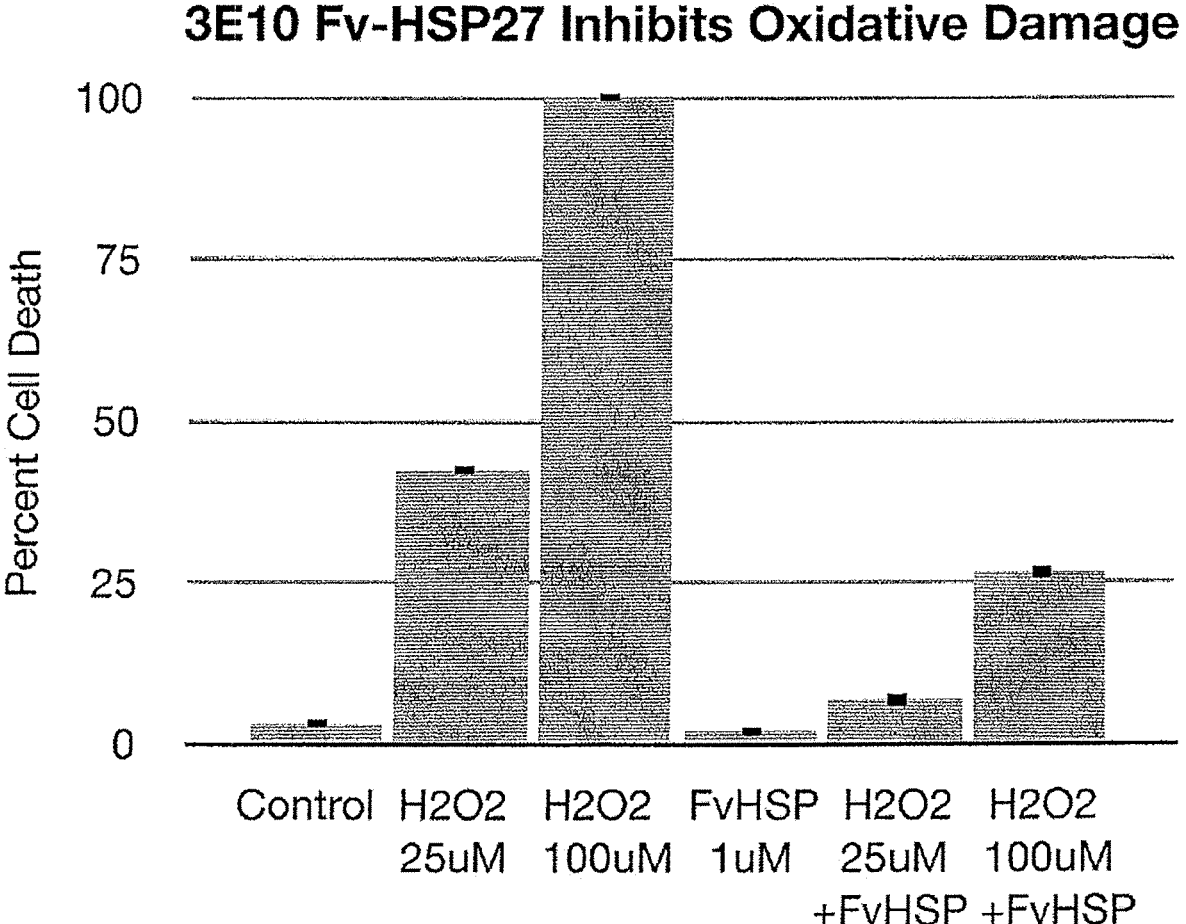
FIG. 1. Fv-Hsp27 protects human neuroblastoma cells (SHSY 5Y) from oxidative injury induced by H2O2. SHSY 5y cells were plated in 12 well culture plates and grown to 80% confluence in medium (DMEM:F12, 1:1) with 5% calf serum. Prior to the addition of H2O2, medium was replaced with DMEM:F12 without serum. Fv-Hsp27 was added to the cutures at 1 uM concentration 30 minutes prior to the addition of H2O2. After the addition of H2O2, the cultures were incubated at 37° C. overnight and cell counts were obtained by the addition of propidium iodide, 1 ug/ml medium.

| Summary Table of SEQ ID NO and Description | |
| --- | --- |
| SEQ ID NO | DESCRIPTION |
| 1 | 3E10 Fv-Hsp27 Mouse Linker annotated nucleic acid |
| 2 | 3E10 Fv-Hsp27 Mouse Linker translation |
| 3 | 3E10 Fv-Hsp27 Mouse Linker annotated protein |
| 4 | 3E10 Fv-Hsp70 Mouse Linker annotated nucleic acid |
| 5 | 3E10 Fv-Hsp70 Mouse Linker translation |
| 6 | 3E10 Fv-Hsp70 Mouse Linker annotated protein |
| 7 | 3E10 Fv-GRP78 Mouse Linker annotated nucleic acid |
| 8 | 3E10 Fv-GRP78 Mouse Linker translation |
| 9 | 3E10 Fv-GRP78 Mouse Linker annotated protein |
| 10 | 3E10 Fv-Hsp90 Mouse Linker annotated nucleic acid |
| 11 | 3E10 Fv-Hsp90 Mouse Linker translation |
| 12 | 3E10 Fv-Hsp90 Mouse Linker annotated protein |
| 13 | 3E10 Vk CDR1 nucleic acid |
| 14 | 3E10 Vk CDR1 protein |
| 15 | 3E10 Vk CDR2 nucleic acid |
| 16 | 3E10 Vk CDR2 protein |
| 17 | 3E10 Vk CDR3 nucleic acid |
| 18 | 3E10 Vk CDR3 protein |
| 19 | 3E10 VH CDR1 with D31N nucleic acid |
| 20 | 3E10 VH CDR1 with D31N protein |
| 21 | 3E10 VH CDR2 nucleic acid |
| 22 | 3E10 VH CDR2 protein |
| 23 | 3E10 VH CDR3 nucleic acid |
| 24 | 3E10 VH CDR3 protein |
| 25 | 3E10 Fv-Hsp27 Human Linker annotated nucleic acid |
| 26 | 3E10 Fv-Hsp27 Human Linker translation |
| 27 | 3E10 Fv-Hsp27 Human Linker annotated protein |
| 28 | 3E10 Fv-Hsp70 Human Linker annotated nucleic acid |
| 29 | 3E10 Fv-Hsp70 Human Linker translation |

-continued

| Summary Table of SEQ ID NO and Description | |
| --- | --- |
| SEQ ID NO | DESCRIPTION |
| 30 | 3E10 Fv-Hsp70 Human Linker annotated protein |
| 31 | 3E10 Fv-GRP78 Human Linker annotated nucleic acid |
| 32 | 3E10 Fv-GRP78 Human Linker translation |
| 33 | 3E10 Fv-GRP78 Human Linker annotated protein |
| 34 | 3E10 Fv-Hsp90 Human Linker annotated nucleic acid |
| 35 | 3E10 Fv-Hsp90 Human Linker translation |
| 36 | 3E10 Fv-Hsp90 Human Linker annotated protein |

DETAILED DESCRIPTION OF THE INVENTION

Definitions

To facilitate understanding of the invention, a number of terms are defined below.

As used herein, "anti-DNA monoclonal antibody 3E10" (also referred to herein as 3E10 antibody or mAb 3E10) refers to an antibody produced by ATCC PTA 2439 or a functional fragment or variant thereof or an antibody having the specificity of mAb 3E10.

As used herein recombinant variable regions of immunoglobulin molecules refers to variable regions of Ig molecules which are produced by molecular biological means. Sequences encoding variable domain of the heavy and light chains may be isolated from T-cells, B-cells, leukemic cells, lymphoma cells, or immunoglobulin gene expressing cells, cloned into expression vector systems, and introduced into a host cell to produce "recombinant variable regions of immunoglobulin molecules." Alternatively, the sequences may be recombinantly produced or obtained from genomic DNA. Recombinant antibodies produced in this manner consists of an antibody or antibody fragment with the antigen binding specificity dependent on the variable region, comprising framework sequences and CDRs. Such recombinant antibodies may be formed from a polypeptide chain containing a variable region from a light chain and a polypeptide chain containing a variable region from a heavy chain or alternatively both the light chain and heavy chain variable regions could be found within a polypeptide in which a linker is used to link by recombinant DNA methods the coding sequences for the two variable chain regions, such as in the case of single chain Fv fragment (scFv).

When "recombinant variable regions of immunoglobulin molecules" are formed from two separate polypeptides, one for the light chain variable region and other for the heavy chain variable region, the recombinant Ig molecules may be an intact antibody as is normally produced by an organism from which the coding sequences were isolated or it could be a fragment. Antibody fragments could be produced either by recombinant DNA methods allowing tailored antibodies not dependent on specific protease cleavage sites or by proteolytic cleavage of the recombinant antibodies such as by IdeS, pepsin, or papain to produce Fab, F(ab') or F(ab')2 fragments. The "recombinant variable regions of immunoglobulin molecules" may include the entire constant region or a portion of the constant region. In addition, the constant region of one antibody may be replaced by recombinant DNA method with the constant region of a different antibody if desired.

"Single-chain antibodies" or "Fv" consist of an antibody light chain variable domain or region ("$V_L$") and heavy chain variable region ("V$_H$") connected by a short peptide linker. The peptide linker allows the structure to assume a conformation which is capable of binding to antigen [Bird et al., (1988) Science 242:423 and Huston et al. (1988) Proc. Natl. Acad. Sci. USA 85:5879].

Compositions of the Invention

Figure 12:
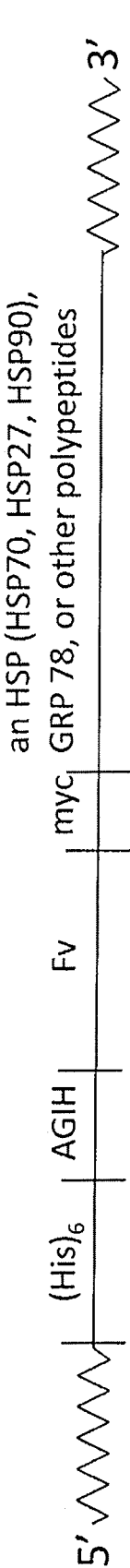
FIG. 12 shows the schematic diagram of constructs in Pichia.

The invention provides fusion proteins comprising a 3E10 Fv joined or attached to a Hsp-70 or portion thereof, and optionally, the 3E10 Fv comprising an amino acid sequence alanine, glycine, isoleucine, and histidine (AGIH) at its amino terminus. For example, FIG. 12 shows a construct of a fusion protein of the invention, His6-AGIH-Fv-myc-Hsp70 (FIG. 12; SEQ ID NOS:4, 5, 6, 28, 29, or 30).

The invention also provides for fusion proteins comprising a 3E10 Fv joined to Hsp-27 or portion thereof, and optionally, the 3E10 Fv comprising an amino acid sequence AGIH at its amino terminus. For example, FIG. 12 shows a construct of a fusion protein of the invention, His6-AGIH-Fv-myc-Hsp27 (FIG. 12; SEQ ID NOS:1, 2, 3, 25, 26, or 27).

In another embodiment, the fusion protein of the invention comprises a 3E10 Fv derived from monoclonal antibody 3E10.

The invention further provides for a fusion protein comprising a 3E10 Fv attached or joined to a Hsp-90 or portion thereof, and optionally, an 3E10 Fv comprising an amino acid sequence AGIH at its amino terminus. For example, FIG. 12 shows a construct of a fusion protein of the invention, His6-AGIH-Fv-myc-Hsp90 (FIG. 12; SEQ ID NOS:10, 11, 12, 34, 35, or 36).

The invention further provides for a fusion protein comprising a 3E10 Fv attached or joined to GRP78 or portion thereof, and optionally, the 3E10 Fv comprising an amino acid sequence AGIH at its amino terminus. For example, FIG. 12 shows a construct of a fusion protein of the invention, His6-AGIH-Fv-myc-GRP78 (FIG. 12; SEQ ID NOS:7, 8, 9, 31, 32, or 33).

In one embodiment, the 3E10 Fv is a derivative of monoclonal antibody 3E10 from 3E10 hybridoma (ATCC Accession No. PTA 2439 hybridoma) or an antibody that competes with monoclonal antibody 3E10. For example, the derivative of monoclonal antibody 3E10 may contain a part or all of a light chain CDR1, light chain CR2, light chain CDR3, heavy chain CDR1, heavy chain CDR2, or heavy chain CDR3 of 3E10 antibody. The part or all of a light chain CDR1, light chain CR2, light chain CDR3, heavy chain CDR1, heavy chain CDR2, or heavy chain CDR3 of 3E10 antibody is shown in SEQ ID NO:14, SEQ ID NO:16, SEQ ID NO:18, SEQ ID NO:20, SEQ ID NO:22, or SEQ ID NO:24, respectively.

In another embodiment, the derivative of an antibody that competes with monoclonal antibody 3E10 or fragment thereof competes with the ENT2-dependent cell penetrating property and epitope recognition of monoclonal antibody 3E10. For example, the derivative may be obtained by using any of the sequences of a light chain CDR1, light chain CR2, light chain CDR3, heavy chain CDR1, heavy chain CDR2, or heavy chain CDR3 of 3E10 antibody as shown in SEQ ID NO:14, SEQ ID NO:16, SEQ ID NO:18, SEQ ID NO:20, SEQ ID NO:22, or SEQ ID NO:24, respectively in antibody phage display screen.

In one embodiment, the derivative may be encoded by a part of the nucleic acid sequences for 3E10 Fv protein sequence, as provided in SEQ ID NO:1 from nucleotide position 304 to 1032, corresponding to amino acid position 102 to 344.

In another embodiment, the fusion protein of the invention may be joined to a therapeutic or diagnostic agent. In one embodiment, the therapeutic agent may be a cytotoxic agent. In a further embodiment, the diagnostic agent is a detectable marker.

Examples of cytotoxic agents include but are not limited to ricin, ricin A-chain, doxorubicin, daunorubicin, taxol, ethiduim bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, arbrin A chain, modeccin A chain, alpha-sarcin, gelonin, mitogellin, restrictocin, phenomycin, enomycin, curacin, crotin, calicheamicin, sapaonaria officinalis inhibitor, maytansinoids, and glucocorticoidricin.

Examples of detectable marker include but are not limited to an enzyme, biotin, a fluorophore, a chromophore, a heavy metal, a paramagnetic isotope, or a radioisotope.

In a further embodiment, the fusion protein of the invention may have the sequence as shown in FIGS. 3, 4, 5, 6, 7, 8, 9, 10 or 11.

In another embodiment, the bispecific antibody or fragment thereof which specifically binds an Hsp protein and comprises first and second variable regions. The first variable region and the second variable region comprises an 3E10 Fv of the fusion protein of the invention and that the first and second variable regions are not the same.

In one embodiment, the Fv may be a recombinant Fv, a chimeric Fv, a humanized Fv or a human Fv.

In another embodiment, the 3E10 Fv may be replaced with a non 3E10 Fv which competes with the binding of 3E10 to its epitope.

In an embodiment, the invention provides a nucleic acid molecule encoding the bispecific compositions of the invention. The nucleic acid molecule may encode the bispecific or fusion protein composition of the invention.

The nucleic acids of the invention may comprise nucleotide sequences and polypeptides encoding amino acid sequences which are at least about 70% identical, preferably at least about 80% identical, more preferably at least about 90% identical and most preferably at least about 95% identical (e.g., 95%, 96%, 97%, 98%, 99%, 100%) to the reference nucleotide and amino acid sequences of the present invention (i.e., see examples herein) when the comparison is performed by a BLAST algorithm wherein the parameters of the algorithm are selected to give the largest match between the respective sequences over the entire length of the respective reference sequences. Polypeptides comprising amino acid sequences which are at least about 70% similar, preferably at least about 80% similar, more preferably at least about 90% similar and most preferably at least about 95% similar (e.g., 95%, 96%, 97%, 98%, 99%, 100%) to the reference amino acid sequences of the present invention when the comparison is performed with a BLAST algorithm wherein the parameters of the algorithm are selected to give the largest match between the respective sequences over the entire length of the respective reference sequences, are also included in the present invention.

The nucleic acid molecule may be a DNA molecule (e.g., cDNA) encoding the bispecific composition of the invention. For example, the invention provides for a DNA construct comprising a vector that expresses the bispecific composition of the invention.

Additionally, the invention provides a vector which comprises the nucleic acid molecule of the invention. The host vector system comprises the vector of the invention in a suitable host cell. Examples of suitable host cells include but are not limited to bacterial cell and eukaryotic cells.

In one embodiment, the invention provides for a composition comprising the fusion protein of the invention in an effective amount and a suitable carrier.

In one embodiment, the composition may consist essentially of an 3E10 Fv attached to a Hsp-27 and pharmaceutically acceptable carriers, binders, diluents, adjuvants, excipients, and/or vehicles.

In another embodiment, the composition may consist essentially of an 3E10 Fv attached to a Hsp-70 and pharmaceutically acceptable carriers, binders, diluents, adjuvants, excipients, and/or vehicles.

In yet another embodiment, the composition may consist essentially of an 3E10 Fv attached to a Hsp-90 and pharmaceutically acceptable carriers, binders, diluents, adjuvants, excipients, and/or vehicles.

In another embodiment, the composition may consist essentially of an 3E10 Fv attached to a Hsp-GRP78 and pharmaceutically acceptable carriers, binders, diluents, adjuvants, excipients, and/or vehicles.

In one embodiment, the disease or disorder comprising the fusion protein of the invention may be associated with hydrogen peroxide toxicity or reactive oxygen species (ROS) toxicity. The disease or disorder may be a brain injury, heart injury, skin injury, or radiation injury and may be an acute injury. Examples of brain injury include but are not limited to brain trauma, spinal cord injury, peripheral nerve injury, or stroke. A heart injury may include but not limited to a myocardial infarction. Examples of skin injury include but are not limited to wound, burn, or decubitus ulcer. A radiation injury may include but not limited to burn or poison.

In another embodiment, the disease or disorder may be acute renal failure, acute organ failure, liver injury, bowel infarction, peripheral vascular disease, pulmonary failure, or a cancer.

In one embodiment, the pharmaceutical composition for inhibiting a disease or disorder associated with hydrogen peroxide toxicity or reactive oxygen species (ROS) comprising the fusion protein of the invention and pharmaceutically acceptable carriers, binders, diluents, adjuvants, excipients, and/or vehicles. Examples of reactive oxygen species (ROS) include but are not limited to peroxides, oxygen ions, superoxides, hypochlorited, hydroxyl radicals, hydroxyl ions, and hydroperoyls. In one embodiment, the reactive oxygen species (ROS) may be generated by ionizing radiation or ultraviolet light.

In a further embodiment, the pharmaceutical composition may be the fusion protein comprising a 3E10 Fv joined to a Hsp-70 or portion thereof, a 3E10 Fv joined to Hsp-27 or portion thereof, a 3E10 Fv attached/joined to a Hsp-90 or portion thereof or a 3E10 Fv attached/joined to GRP78 or portion thereof.

According to one aspect of the invention there are provided pharmaceutical compositions comprising effective amounts of the compositions of the invention by mucosal membrane administration in the treatment.

One embodiment of the current invention is a novel nasal formulation of the compositions of the invention. The nasal dosing route is easily accessible in an emergency situation, especially in children. Nasal formulations of the present invention is useful for self-administration outside of a medical setting by patients or their non-medical caregivers.

For the administration to mucosal membranes, in particular the nasal mucosal membranes, the compositions according to the invention may be conveniently delivered by conventional means (e.g. in the form of a single dose or multiple dose manual pump nasal spray). The compositions may also be delivered to the lungs by direct inhalation by numerous delivery methods well known to those skilled in the art.

Nasal spray compositions may, for example, be formulated as pH neutral and isotonic aqueous solutions or suspensions and may be administered by a nebulizer. Aerosol spray formulations, for example in which the active ingredients are suspended, optionally together with one or more stabilizers, using a non-halogenated hydrocarbon propellant, including air, nitrogen, or other gases, or manual pump action may also be employed, or by numerous other delivery methods well known to those skilled in the art. An another embodiment, the pH of the intranasal formulation can be acidic, for example in the range of e.g. pH 3 to pH 6.

Alternatively, for administration by inhalation or insufflation, the composition according to the invention may take the form of a dry powder composition, for example a powder mix of the active ingredients and a suitable carrier such as lactose. The powder compositions may be presented in a unit dosage form in, for example, capsules, cartridges, or blister packs from which the powder may be administered with the aid of an Dry Powder Inhaler (DPI), or by numerous other delivery methods well known to those skilled in the art.

In another embodiment, the compositions of the invention are provided through intramuscular or sublingual routes of administration.

Administration of a composition of the invention may be conducted generally by injection over a suitable time period and with use of a suitable adjuvant, as is generally understood in the art. During the immunization schedule, titers of antibodies can be taken to determine adequacy of antibody formation.

For example, one way to apply the compositions of the invention clinically is to administer them in unmodified form, using fusion proteins of the invention which display, e.g., internalizing ability in vitro and/or in animal models (see, e.g. Hellstrom et al., *Proc. Natl. Acad. Sci. USA* 82:1499-1502 (1985).

In one embodiment, the compositions of the invention further comprises a therapeutic agent admixed with the bispecific composition. The therapeutic agent may be an anti-cancer agent which may be lenalidomide, ipilimumab, rituximab, alemtuzumab, ofatumumab, flavopiridol, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; amino glutethimide; amsacrine; anastrozole; anthramycin; asparaginase; asperlin; azacitidine; azetepa; azotomycin; batimastat; benzodepa; bicalutamide; bisantrene hydrochloride; bizelesin; bleomycin sulfate; brequinar sodium; bropirimine; busulfan; cactinomycin; calusterone; caracemide; carbetimer; carboplatin; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfmer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfm; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

In another embodiment, the compositions of the invention further comprises a therapeutic agent admixed with the fusion protein composition and the therapeutic agent may be an alkylating agent which includes but are not limited to nitrogen mustards (e.g., bendamustine, mechloroethamine, cyclophosphamide, chlorambucil, melphalan), ethylenimine and methylmelamines (e.g., hexamethlymelamine, thiotepa), alkyl sulfonates (e.g., busulfan), nitrosoureas (e.g., carmustine, lomustine, semustine, streptozocin), or triazenes (decarbazine).

Kits of the Invention

According to another aspect of the invention, kits are provided. Kits according to the invention include package(s) comprising composition of the invention.

The phrase "package" means any vessel containing compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes (including pre-filled syringes), bottles, and any packaging material suitable for a selected formulation and intended mode of administration and treatment.

The kit can also contain items that are not contained within the package but are attached to the outside of the package, for example, pipettes.

Kits may optionally contain instructions for administering compositions of the present invention to a subject having a condition in need of treatment. Kits may also comprise instructions for approved uses of components of the composition herein by regulatory agencies, such as the United States Food and Drug Administration. Kits may optionally contain labeling or product inserts for the present compositions. The package(s) and/or any product insert(s) may themselves be approved by regulatory agencies. The kits can include compositions in the solid phase or in a liquid phase (such as buffers provided) in a package. The kits also can include buffers for preparing solutions for conducting the methods, and pipettes for transferring liquids from one container to another.

The kit may optionally also contain one or more other compositions for use in combination therapies as described herein. In certain embodiments, the package(s) is a container for intravenous administration. In other embodiments, compositions are provided in an inhaler. In still other embodiments compositions are provided in a polymeric matrix or in the form of a liposome.

Methods of the Invention

The invention also provides methods for inhibiting a disease or disorder by promoting hydrogen peroxide or reactive oxygen species (ROS) cytoprotection comprising administering the pharmaceutical composition of the invention.

In one embodiment, the fusion protein may be the fusion protein comprising a 3E10 Fv joined to a Hsp-70 or portion thereof, a 3E10 Fv joined to Hsp-27 or portion thereof, a 3E10 Fv attached/joined to a Hsp-90 or portion thereof or a 3E10 Fv attached/joined to GRP78 or portion thereof.

The invention further provides for a method for inhibiting or treating a subject suffering a disease or disorder comprising administering a suitable amount of the the pharmaceutical composition of the invention to the subject.

In one embodiment, the disease or disorder may be acute renal failure, acute organ failure, liver injury, bowel infarction, peripheral vascular disease, pulmonary failure, or a cancer. In another embodiment, the disease or disorder may be a brain injury, heart injury, skin injury or radiation injury.

Examples of brain injury include but are not limited to a brain trauma, spinal cord injury, peripheral nerve injury, or stroke. A heart injury may include but not limited to a myocardial infarction. Examples of skin injury may include but are not limited to a wound, burn, or decubitus ulcer. A radiation injury may include but not limited to burn or poison.

The methods of the invention contemplate the administration of the compositions of the invention as well as combinations, or "cocktails, of different individual Fv's such as those recognizing different epitopes. Such antibody cocktails may have certain advantages inasmuch as they contain antibodies which bind to different epitopes and/or exploit different effector mechanisms or combine directly cytotoxic mAbs with mAbs that rely on immune effector functionality. Such antibodies in combination may exhibit synergistic therapeutic effects.

In addition, the administration of the fusion proteins of the invention may be combined with other therapeutic agents, including but not limited to various chemotherapeutic agents, androgen-blockers, and immune modulators (e.g., IL-2, GM-CSF). The fusion proteins of the invention may be administered in their "naked" or unconjugated form, or may have therapeutic agents conjugated to them.

The fusion proteins of the invention used in the practice of the method of the invention may be formulated into pharmaceutical compositions comprising a carrier suitable for the desired delivery method. Suitable carriers include any material which when combined with the fusion proteins of the invention retains the heat shock protein of the antibody and is non-reactive with the subject's immune systems. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

The fusion protein formulations may be administered via any route capable of delivering the antibodies to the tumor site. Potentially effective routes of administration include, but are not limited to, intravenous, intraperitoneal, intramuscular, intratumor, intradermal, intranasal (e.g., by mucosal membrane administration) and the like. A suitable formulation for intravenous injection comprises the fusion proteins of the invention in a solution of preserved bacteriostatic water, sterile unpreserved water, and/or diluted in polyvinylchloride or polyethylene bags containing 0.9% sterile Sodium Chloride for Injection, USP. The fusion protein preparation may be lyophilized and stored as a sterile powder, preferably under vacuum, and then reconstituted in bacteriostatic water containing, for example, benzyl alcohol preservative, or in sterile water prior to injection. Treatment will generally involve the repeated administration of the fusion protein preparation via an acceptable route of administration such as intravenous injection (IV), at an effective dose.

Dosages will depend upon various factors generally appreciated by those of skill in the art, including without limitation the type of disease or disorder and the severity, grade, or stage of the disease or disorder, the binding affinity and half life of the fusion proteins used, the desired steady-state antibody concentration level, frequency of treatment, and the influence of chemotherapeutic agents used in combination with the treatment method of the invention.

Typical daily doses may range from about 0.1 to 100 mg/kg. Doses in the range of 10-500 mg mAb per week may be effective and well tolerated, although even higher weekly doses may be appropriate and/or well tolerated. The principal determining factor in defining the appropriate dose is the amount of a particular antibody necessary to be therapeutically effective in a particular context. Repeated administrations may be required in order to achieve tumor inhibition or regression. Initial loading doses may be higher. The initial loading dose may be administered as an infusion. Periodic maintenance doses may be administered similarly, provided the initial dose is well tolerated.

The invention further provides for method for producing a fusion protein comprising culturing the host vector system under suitable culture conditions so as to produce the fusion protein in the host and recovering the fusion protein so produced.

The invention also provides for method for inhibiting a disease or disorder comprising administering the pharmaceutical compositions of the invention.

In one embodiment, the disease or disorder may be an acute renal failure, acute organ failure, liver injury, bowel infarction, peripheral vascular disease, pulmonary failure, or a cancer. The disease or disorder may be a brain injury, heart injury, or skin injury.

Examples of brain injury include but are not limited to brain trauma, spinal cord injury, peripheral nerve injury, or stroke.

Example of heart injury includes but is not limited to myocardial infarction.

Examples of skin injury include but are not limited to wound, burn, or decubitus ulcer.

The following examples are presented to illustrate the present invention and to assist one of ordinary skill in making and using the same. The examples are not intended in any way to otherwise limit the scope of the invention.

EXAMPLES

Example 1

Materials and Methods

Expression of Fv-Hsp70 Recombinant Protein in *Pichia pastoris*

Figure 2:
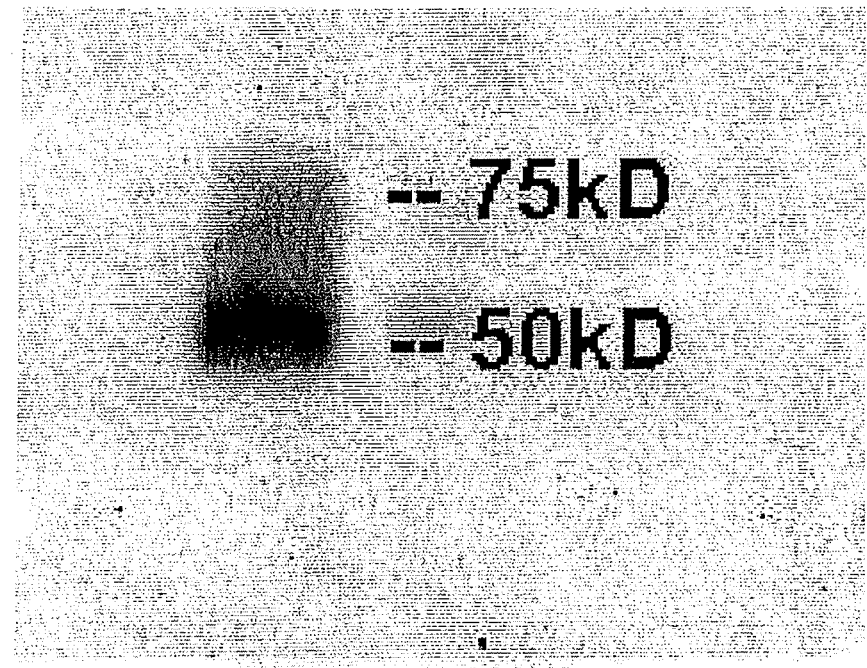
FIG. 2. Western blot of purified Fv-Hsp27 produced in Pichia. The recombinant protein is approximately 60 kDa.
Figure 3:
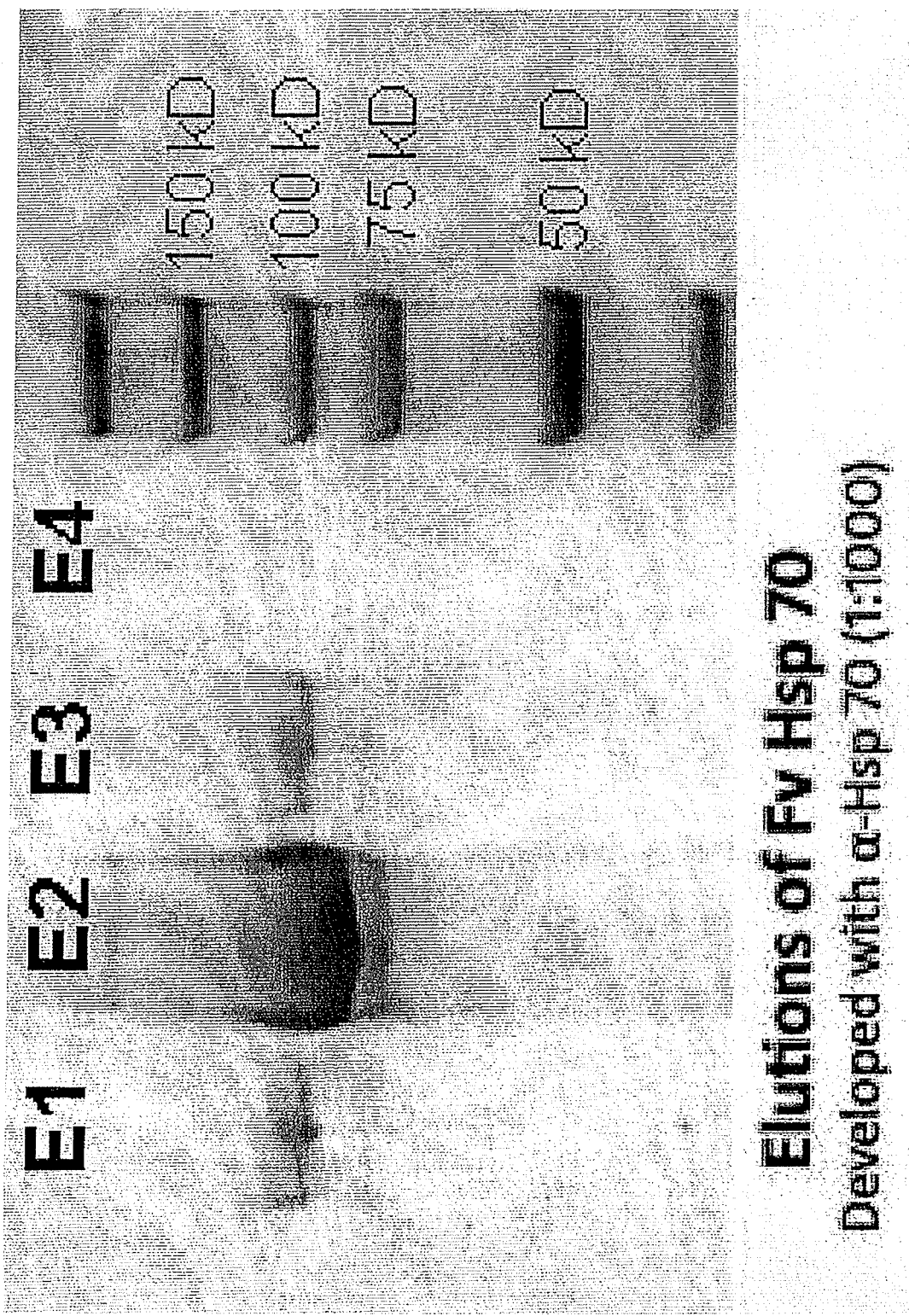
FIG. 3. Western blot of purified Fv-Hsp70 produced in Pichia. The recombinant protein is primarily in elution 2 from the Ni-agarose column.

Single-chain Fv antibody was derived from mAB 3E10. cDNA for the Fv fragment was ligated into the plasmid pPICZαA as previously described. Briefly, human Hsp70 cDNA was ligated into the Fv containing pPICZαA separated by Myc and His$_6$ tags. The subsequent construct was electroporated into the X-33 methyolotropic yeast strain *Pichia pastoris* (Invitrogen, Carlsbad, Calif.). Fv-Hsp70 construct includes 4 amino acids, AGIH, added to the amino-terminal portion of the construct. Recombinant protein was purified from the medium using Ni-NTA agarose beads (Qiagen, Valencia, Calif.) under sterile conditions. Protein was eluted from the column with elution buffer (50 mmol/L NaH$_2$PO$_4$, 300 mmol/L NaCl, 500 mmol/L imidazole, pH 8.0) in 5 1.5.-mL aliquots. Aliquots were then exchanged-dialyzed with Dulbecco phosphate-buffered saline (Mediatech, Manassas, Va.) to remove the imidazole (with a final concentration of imidazole less than 2 mmol/L). Final sample volume was 1 to 3 mL with an Fv-Hsp70 concentration of approximately 0.5 mg/mL. Fv-Hsp70 protein was stored at 4° C. and used within 24 hours. This enables greater purity and greater amounts of protein being produced than from the previous construct. FIG. 2 shows new construct on SDS gel.

Hsp27 construct: The procedure for making Fv-Hsp27 is identical to the procedure above in connection with Fv-Hsp70 except that the Hsp27 was cloned from human cells and inserted into the yeast vector, pPICZαA (Invitrogen, Carlsbad, Calif.), which includes the addition of AGIH to the amino-terminus of the protein.

Example 2

Construction of Fv-Hsp27

The human Hsp27 gene was cloned from human cell using primers from the known human hsp27 sequence. Once isolated the gene was sequenced by Seqwright DNA Sequencing, Houston, Tex.

The hsp27 gene was subcloned into PCR2.1 (bacterial plasmid, Invitrogen)) and grown in transformed competent TOP10 bacteria (invitrogen).

The amplified gene—sequence was isolated with a miniprep (Qiagen). The isolated gene was ligated into the multiple cloning site of pPicZalphaA (yeast cloning plasmid). The pPicZalphaA plasmid contains a 6-His selection gene on the 5' end of the Fv-Hsp27 construct. The final construct consisted of 6-His, AGIH (amino acids), Fv, myc tag, and Hsp27 ligated into the BamHI and XbaI sites added to the 5' and 3' ends, respectively.

The pPicZalphaA-FvHsp27 was then transfected into and grown in *Pichia pastoris* and harvested by isolation from yeast medium as a secretory protein.

Isolation of the protein from medium was performed using the Ni-agarose beads from Qiagen by their protocol.

An alternative method for making the Fv-Hsp27 was also used in bacteria. The whole construct from the 6-His to the Hsp27 was removed from the yeast plasmid and cloned into the bacterial plasmid PQE30 (Clontech). This plasmid was transfected into M-15 competent bacteria and grown and isolated using a bacterial lysis buffer (B-Per, Pierce). The 6-His tagged protein was isolated from the bacterial lysate using the Ni-beads from Qiagen by manufacturers' protocol.

REFERENCES

An J J, Lee Y P, Kim S Y, Lee S H, Lee M J, Jeong M S, Kim D W, Jang S H, Yoo K-Y, Won M H, Kang T-C, et al. (2008) Transduced human PEP-1-heat shock protein 27 efficiently protects against brain ischemic insult. *FEBS J.* 275:1296-1308.

Arrigo A-P, Landry J. (1994) Expression and function of the low-molecular weight heat shock proteins. In: Morimoto R I, Tissieres A, Georgopoulos C (eds.) *The Biology of Heat Shock Proteins and Molecular Chaperones,* Cold Spring Harbor Laboratory Press, Cold Spring Harbor, N.Y. pp. 335-373.

Arrigo A-P, Firdaus W J, Mellier G, Moulin M, Paul C, Diaz-Latoud C, Kretz-Remy C. (2005) Cytotoxic effects induced by oxidative stress in cultured mammalian cells and protection provided by Hsp27 expression. *Methods.* 35, 126-138.

Arrigo A-P. (2011) Structure-Function of HspB1 (Hsp27). In *Mol. Chaperones: Methods and Protocols, Methods in Mol. Biol.* Vol 787, pp 105-119.

Bellyei S, Szigeti A, Pozsgai E, Boronkai A, Gomori E, Hocsak E, Farkas R, Sumegi B, Gallyas F. (2007) Preventing apoptotic cell death by a novel small heat shock protein. *Eur. J. Cell Biol.* 86, 161-171.

Lee G J, Roseman A M, Saibil H R, Vierling E. (1997) A small heat shock protein stably binds heat-denatured model substrates and can maintain a substrate in a folding-competent state. *EMBO J.* 16, 221-229.

Liu J P, Schlosser R, Ma W Y, Dong Z, Feng H, Liu L, Huang X Q, Liu Y, Li D W. (2004) Human alphaA- and alphaB-crystallins prevent UVA-induced apoptosis through regulation of PKCalpha, RAF/MEK/ERK and AKT signaling pathways. *Exp. Eye Res.* 79, 393-403.

Martin J L, Mestril R, Hilal-Dandan R, Brunton L L, Dillmann W H. (1997) Small heat shock proteins and protection against ischemic injury in cardiac myocytes. *Circulation* 96:4343-4348.

Martin-Ventura J L, Duran M C, Blanco-Colio L M, Meilhac O, Leclercq A, Michel J B, Jensen O N, Hernandez-Merida S. Tuñón J, Vivanco F, Egido J. (2004) Identification by a differential proteomic approach of heat shock protein 27 as a potential marker of atherosclerosis. *Circulation* 110: 2216-2219

Mehlen P, Carole K-R, Preville X, Arrigo A-P. (1996) Human hsp27, Drosophila hsp27 and human alphabeta-crystallin expression-mediated increase in glutathione is essential for the protective activity of these proteins against TNFalpha-induced cell death. *EMBO J.* 15, 2695-2706.

Nicholl I D, Quinlan R A. (1994) Chaperone activity of alpha-crystallins modulates intermediate filament assembly. *EMBO J.* 13, 945-953.

Rane M J, Pan Y, Singh, Poell D, Wu R, Cummins T, Chen Q, McLeish K R, Klein J B. (2003) Heat shock protein 27 controls apoptosis by regulating Akt activation. *J. Biol. Chem.* 279, 27828-27835.

Stetler R A Signore A P, Gao Y, Cao G, Chen J. (2009) Hsp27: Mechanisms of cellular protection against neuronal injury. *Curr. Mol. Med.* 9:863-872.

van der Weerd L Akbar M T, Badin R A, Vanentim L M, Thomas D L, Wells D J, Latchman D S, Gadian D G, Lythgoe M F, de Belleroche J S. (2010) Overexpression of heat shock protein 27 reduces cortical damage after cerebral ischemia. *J. Cereb. Blood Flow Metab.* 30:849-856.

Tsaytler P A Krijgsveld J Goerdayal S S Rudiger S, Egmond M R. (2009) Novel Hsp90 partners discovered using complementary proteomic approaches. *Cell Stress Chaperones* 4:629-638.

Wang W, Peng Y, Wang Y, Zhao X, Yuan Z. (2009) Anti-apoptotic effect of heat shock protein 90 on hypoxia-mediated cardiomyocyte damage is mediated via the phosphatidylinositol 3-kinase/AKT pathway. *Clin. Exp. Pharmacol. Physiol.* 36:899-903.

Ni M, Zhang Y, and Lee A S, (2011) Beyond the endoplasmic reticulum: atypical GRP78 in cell viability, signaling and therapeutic targeting, *Biochemical J.* 434 (2): 181-188. Review Amin V, Cumming D V, Latchman D S. (1996) Overexpression of heat shcok protein 70 protects neuronal cells against both thermal and ischaemic stress but with different efficiencies. *Neurosci. Lett.* 206 (1):45-48.

Beckman R P, Mizzen L E, Welch W J. (1990) Interaction of Hsp70 with newly synthesized proteins: implication for protein folding and assembly. *Science* 248 (4957:850-854.

Beere H M, Wolf B B, Cain K, Mosser D D, Mahboubi A, Kuwana T, Tailor P, Morimoto R I, Cohen G M, Green D R. (2000) Heat shock protein 70 inhibits apoptosis by preventing recruitment of procaspase-9 to the Apaf-1 apoptosome. *Nat. Cell. Biol.* 2 (8):469-475.

Brar B K, Stephanou A, Wagstaff M J, Coffin R L, Marber M S, Engelmann G, Latchman D S. (1999) Heat shock proteins delivered with a virus vector can protect cardiac cells against apoptosis as well as against thermal or hypoxic stress. *J. Mol. Cell. Cardiol.* 31 (1):135-146.

Bruey J M, Ducasse C, Bonniaud P, Ravagnan L, Susin S A, Diaz-Latoud C, Gurbuxani S, Arrigo A-P, Kroemer G, Solary E, et al. (2000) Hsp27 negatively regulates cell death by interacting with cytochrome c. *Nat. Cell Biol.* 2 (9):645-652.

Cheetham M E, Anderton B H, Jackson A P. (1996) Inhibition of hsc70-catalysed clathrin uncoating by HSJ1 proteins. *Biochem J* 319 (Pt1):103-108.

Chen J, Graham S H, Zhu R L, Simon R P. (1996) Stress proteins and tolerance to focal cerebral ischemia. *J. Cereb. Blood Flow Metab.* 16 (4)566-577.

Demand J, Luders J, Hohfeld J. (1998) The carboxy-terminal domain of Hsc70 provides binding sites for a distinct set of chaperone cofactors. *Mol. Cell. Biol.* 18 (4):2023-2028.

Gabai V L, Merlin A B, Mosser D D, Caron A W, Rits S, Shifrin V I, Sherman M Y. (1997) Hsp70 prevents activation of stress kinases. A novel pathway of cellular thermotolerance. *J Biol. Chem.* 272 (29):18033-18037.

Gebauer M, Zeiner M., Gehring U. (1997) Proteins interacting with the molecular chaperone hsp70/hsc70: physical associations and effects on refolding activity. *FEBS Lett.* 417 (1):109-113.

Hansen J E, Sohn W, Kim C, Chang S S, Huang N C, Santos D G, Chan G, Weisbart R H, Nishimura R N. (2006) Antibody-mediated Hsp70 protein therapy. *Brain Res.* 1088: 187-196.

Lee J E, Yenari M A, Sun G H Xu L, Emond M R, Cheng D, Steinberg G K, Giffard R G. (2001) Differential neuroprotection from human heat shock protein 70 overexpression in in-vitro and in-vivo models of ischemia and ischemia-like conditions. *Exp. Neurol.* 170 (1):129-139.

Lindquist S. (1992) Heat shock proteins and stress tolerance in microorganisms. *Curr. Opin. Genet. Dev.* 2 (5):748-755.

Pandey P, Saleh A, Nakazawa A, Kumar S, Srinivasula S M, Kumar V, Weichselbaum R, Nalin C, Alnemri E S, Kufe D, et al. (2000) Negative regulation of cytochrome c-mediated oligomerization of Apaf-1 and activation of pro-caspase-9 by heat shock protein 90. *EMBO J.* 19 (16):4310-4322.

Samali A and Orrenius S. (1998) Heat shock proteins: regulators of stress response and apoptosis. *Cell Stress Chaperones* 3 (4):228-236.

Schumacher R J, Hansen W J, Freeman B C, Alnemri E, Litwack G, Toft D O. (1996) Cooperative action of Hsp70, Hsp90, and DnaJ proteins in protein renaturation. *Biochem.* 35 (7):14889-14898.

Shi Y, Mosser D D, Morimoto R I. (1998) Molecular chaperones as HSF1 specific transcriptional repressors. *Genes Dev.* 12 (5):654-666.

Stevens F J, Argon Y. (1999) Protein folding in the ER. *Semin. Cell. Dev. Biol.* 10 (5):443-454.

Welch W J, Brown C R. (1996) Influence of molecular and chemical chaperones on protein folding. *Cell Stress Chaperones* 1 (2):109-115

Yenari M A, Fink S L, Sun G H, Chang L K, Patel M K, Kunis D M, Olney D, Ho D Y, Sapolsky R M, Steinberg G K. (1998) Gene therapy with HSP72 is neuroprotective in rat models of stroke and epilepsy. *Ann. Neurol.* 44 (4): 584-591.

Zhan X, Ander B P, Liao I H, Hansen J E, Kim C, Clements D, Weisbart R H, Nishimura R N, Sharp F R. (2010) Recombinant Fv-Hsp70 protein mediates neuroprotection after focal cerebral ischemia in rats. *Stroke* 41:538-541

Zou J, Guo Y, Guettouche T, Smith D F, Voellmy R. (1998) Repression of heat shock transcription factor HSF1 activation by HSP90 (HSP90 complex) that forms a stress-sensitive complex with HSF1. *Cell* 94:471-480.

What is claimed is:

1. A method of treating of subject having a disease or disorder associated with hydrogen peroxide toxicity or ROS toxicity comprising administering to the subject a pharmaceutical composition comprising a fusion protein comprising a 3E10 Fv joined to a HSP-70, a peptide linker comprising an immunoglobulin heavy chain constant domain CH1 or a portion thereof; and a swivel sequence, wherein the swivel sequence comprises a peptide sequence located between the 3E10 Fv and the HSP-70 and permits the 3E10 Fv and the HSP-70 to swivel, wherein the swivel sequence consists of the amino acid sequence of residues 375 through 380 of SEQ ID NO:2.

2. The method of claim 1, wherein the disease or disorder associated with hydrogen peroxide toxicity or ROS toxicity is a brain injury, heart injury, skin injury, radiation injury, acute renal failure, acute organ failure, liver injury, bowel infarction, peripheral vascular disease, pulmonary failure, or cancer.

3. The method of claim 1, wherein the fusion protein has an arrangement of functional peptide sequence from amino- to carboxyl terminus, AGIH (SEQ ID NO:37)-3E10 Fv-CH1-swivel sequence-Hsp70.

4. The method of claim 1, wherein the 3E10 Fv is a derivative of monoclonal antibody 3E10 from 3E10 hybridoma (ATCC Accession No. PTA 2439 hybridoma), wherein the derivative of monoclonal antibody 3E10 comprises a light chain CDR1, light chain CDR2, light chain CDR3, heavy chain CDR1, heavy chain CDR2, and heavy chain CDR3 of 3E10 antibody and wherein the derivative competes with the monoclonal antibody 3E10.

5. The method of claim 4, wherein the derivative of monoclonal antibody 3E10 comprises a light chain CDR1, light chain CDR2, light chain CDR3, heavy chain CDR1, heavy chain CDR2, and heavy chain CDR3 of 3E10 antibody as shown in SEQ ID NO:14, SEQ ID NO:16, SEQ ID NO: 18, SEQ ID NO:20, SEQ ID NO:22, and SEQ ID NO:24, respectively.

6. The method of claim 4, wherein the antibody that competes with the monoclonal antibody 3E10 is an antibody that competes with the ENT2-dependent cell penetrating property and epitope recognition of the monoclonal antibody 3E10.

7. The method of claim 4, wherein the derivative is obtained by using any of the sequences of a light chain CDR1, light chain CDR2, light chain CDR3, heavy chain CDR1, heavy chain CDR2, or heavy chain CDR3 of 3E10 antibody as shown in SEQ ID NO:14, SEQ ID NO: 16, SEQ ID NO:18, SEQ ID NO:20, SEQ ID NO:22, or SEQ ID NO:24, respectively, in an antibody phage display screen.

8. The method of claim 1, wherein the portion of the immunoglobulin heavy chain constant domain CHI comprises a sequence of amino acids starting from position 361 and ending with position 374 of SEQ ID NO: 6 or a sequence of amino acid starting from position 361 and ending with position 373 of SEQ ID NO:30 and wherein the swivel sequence comprises a sequence of amino acids starting from position 375 and ending with position 380 of SEQ ID NO:6.

9. The method of claim 1, wherein fusion protein further comprises a therapeutic agent.

10. The method of claim 1, wherein the peptide linker is selected from a group consisting of a sequence of amino acids starting from position 361 and ending with position 380 of SEQ ID NO:6 and a sequence of amino acids starting from position 361 and ending with position 379 of SEQ ID NO: 30.

11. The method of claim 4, wherein the light chain CDR1, light chain CDR2, light chain CDR3, heavy chain CDR1, heavy chain CDR2, or heavy chain CDR3 of 3E10 antibody is encoded by nucleic acid sequence shown in SEQ ID NO:13, SEQ ID NO:15, SEQ ID NO: 17, SEQ ID NO:19, SEQ ID NO: 21, or SEQ ID NO:23, respectively.

12. The method of claim 1, wherein the 3E10 Fv sequence is a recombinant 3E10 Fv, a chimeric 3E10 Fv, a humanized 3E10 Fv or a human 3E10 Fv.

13. The method of claim 1, wherein the swivel sequence is attached to the C-terminus of the immunoglobulin heavy chain constant domain CHI sequence or the portion thereof sequence.

14. The method of claim 1, wherein the 3E10 Fv comprises the amino acid sequence AGIH, at its amino terminus.

* * * * *

SEQUENCE LISTING

```
<160> NUMBER OF SEQ ID NOS: 36

<210> SEQ ID NO 1
<211> LENGTH: 1764
<212> TYPE: DNA
<213> ORGANISM: Artificial Sequence
<220> FEATURE:
<223> OTHER INFORMATION: 3E10 Fv-Hsp27 nucleotide sequence encoding a
      chimeric protein comprising a single chain Fv antibody fragment
      derived from Mus musculus 3E10 hybridoma and Hsp27 from Homo
      sapiens joined by mouse CH1 linker and swivel sequence
<220> FEATURE:
<221> NAME/KEY: CDS
<222> LOCATION: (1)..(1758)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Mus musculus CH1 linker, swivel sequence, epitope tags, and Homo
      sapiens Hsp27 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
<221> NAME/KEY: misc_feature
<222> LOCATION: (274)..(291)
<223> OTHER INFORMATION: Coding sequence: His6 tag
<220> FEATURE:
```

-continued

```
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
<223> OTHER INFORMATION: Begin of coding sequence for Mus musculus 3E10
      immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
      first codon of CDR1 resulting in a D31N change for 3E10 VH chain
      and enhanced cell penetration of the 3E10 monoclonal antibody and
      3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
      immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1122)
<223> OTHER INFORMATION: Coding sequence: Mus musculus immunoglobulin
      heavy chain constant domain, CH1, linker
<220> FEATURE:
<221> NAME/KEY: misc_feature
<222> LOCATION: (1123)..(1140)
<223> OTHER INFORMATION: Coding sequence: swivel sequence
<220> FEATURE:
<221> NAME/KEY: misc_feature
<222> LOCATION: (1135)..(1140)
<223> OTHER INFORMATION: BamHI restriction enzyme site
<220> FEATURE:
<221> NAME/KEY: misc_feature
<222> LOCATION: (1141)..(1758)
<223> OTHER INFORMATION: Coding sequence: Homo sapiens Hsp27 sequence
<220> FEATURE:
<221> NAME/KEY: misc_feature
<222> LOCATION: (1756)..(1758)
```

<223> OTHER INFORMATION: Stop codon
<220> FEATURE:
<221> NAME/KEY: misc_feature
<222> LOCATION: (1759)..(1764)
<223> OTHER INFORMATION: XbaI restriction enzyme site

<400> SEQUENCE: 1

```
atg aga ttt cct tca ctt ttt act gct gtt tta ttc gca gca tcc tcc        48
Met Arg Phe Pro Ser Leu Phe Thr Ala Val Leu Phe Ala Ala Ser Ser
1               5                   10                  15 gca tta gct gct cca gtc aac act aca aca gaa gat gaa acg gca caa        96
Ala Leu Ala Ala Pro Val Asn Thr Thr Thr Glu Asp Glu Thr Ala Gln
                20                  25                  30 att ccg gct gaa gct gtc atc ggt tac tca gat tta gaa ggg gat ttc       144
Ile Pro Ala Glu Ala Val Ile Gly Tyr Ser Asp Leu Glu Gly Asp Phe
            35                  40                  45 gat gtt gct gtt ttg cca ttt tcc aac agc aca aat aac ggg tta ttg       192
Asp Val Ala Val Leu Pro Phe Ser Asn Ser Thr Asn Asn Gly Leu Leu
        50                  55                  60 ttt ata aat act act att gcc agc att gct gct aaa gaa gaa ggg gta       240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat       288
Ser Leu Glu Lys Arg Glu Ala Glu Ala Glu Phe His His His His His
                85                  90                  95 cac gca ggg att cac gac att gtc ctg aca cag tct cct gct tcc tta       336
His Ala Gly Ile His Asp Ile Val Leu Thr Gln Ser Pro Ala Ser Leu
            100                 105                 110 gct gta tct ctg ggg cag agg gcc acc atc tcc tgc agg gcc agc aaa       384
Ala Val Ser Leu Gly Gln Arg Ala Thr Ile Ser Cys Arg Ala Ser Lys
        115                 120                 125 agt gtc agt aca tct agc tat agt tac atg cac tgg tac caa cag aaa       432
Ser Val Ser Thr Ser Ser Tyr Ser Tyr Met His Trp Tyr Gln Gln Lys
        130                 135                 140 cca gga cag cca ccc aaa ctc ctc atc aag tat gca tcc tac cta gaa       480
Pro Gly Gln Pro Pro Lys Leu Leu Ile Lys Tyr Ala Ser Tyr Leu Glu
145                 150                 155                 160 tct ggg gtt cct gcc agg ttc agt ggc agt ggg tct ggg aca gac ttc       528
Ser Gly Val Pro Ala Arg Phe Ser Gly Ser Gly Ser Gly Thr Asp Phe
                165                 170                 175 acc ctc aac atc cat cct gtg gag gag gag gat gct gca aca tat tac       576
Thr Leu Asn Ile His Pro Val Glu Glu Glu Asp Ala Ala Thr Tyr Tyr
            180                 185                 190 tgt cag cac agt agg gag ttt ccg tgg acg ttc ggt gga ggc acc aag       624
Cys Gln His Ser Arg Glu Phe Pro Trp Thr Phe Gly Gly Gly Thr Lys
            195                 200                 205 ctg gaa atc aaa cgg gct gat gct gca ccc ggg ggt ggc ggt tct ggc       672
Leu Glu Ile Lys Arg Ala Asp Ala Ala Pro Gly Gly Gly Gly Ser Gly
        210                 215                 220 ggt ggc ggt tct gga ggc ggt ggc tct gag gtg cag ctg gtg gag tct       720
Gly Gly Gly Ser Gly Gly Gly Gly Ser Glu Val Gln Leu Val Glu Ser
225                 230                 235                 240 ggg gga ggc tta gtg aag cct gga ggg tcc cgg aaa ctc tcc tgt gca       768
Gly Gly Gly Leu Val Lys Pro Gly Gly Ser Arg Lys Leu Ser Cys Ala
            245                 250                 255 gcc tct gga ttc act ttc agt aac tat gga atg cac tgg gtc cgt cag       816
Ala Ser Gly Phe Thr Phe Ser Asn Tyr Gly Met His Trp Val Arg Gln
            260                 265                 270 gct cca gag aag ggg ctg gag tgg gtt gca tac att agt agt ggc agt       864
Ala Pro Glu Lys Gly Leu Glu Trp Val Ala Tyr Ile Ser Ser Gly Ser
            275                 280                 285
```

-continued

```
agt acc atc tac tat gca gac aca gtg aag ggc cga ttc acc atc tcc      912
Ser Thr Ile Tyr Tyr Ala Asp Thr Val Lys Gly Arg Phe Thr Ile Ser
    290             295                 300 aga gac aat gcc aag aac acc ctg ttc ctg caa atg acc agt cta agg      960
Arg Asp Asn Ala Lys Asn Thr Leu Phe Leu Gln Met Thr Ser Leu Arg
305             310                 315                 320 tct gag gac aca gcc atg cgg ggg tta cta ctt gac tac tgg ggc caa     1008
Ser Glu Asp Thr Ala Met Arg Gly Leu Leu Leu Asp Tyr Trp Gly Gln
                325                 330                 335 ggc acc act ctc aca gtc tcc tca cta gaa caa aaa ctc atc tca gaa     1056
Gly Thr Thr Leu Thr Val Ser Ser Leu Glu Gln Lys Leu Ile Ser Glu
            340                 345                 350 gag gat ctg aat agc gcc gtc gac gcc aaa aca aca gcc cca tcg gtc     1104
Glu Asp Leu Asn Ser Ala Val Asp Ala Lys Thr Thr Ala Pro Ser Val
            355                 360                 365 tat cca ctg gcc cct gta ctg gag tct tcc gga tcc atg acc gag cgc     1152
Tyr Pro Leu Ala Pro Val Leu Glu Ser Ser Gly Ser Met Thr Glu Arg
        370                 375                 380 cgc gtc ccc ttc tcg ctc ctg cgg ggc ccc agc tgg gac ccc ttc cgc     1200
Arg Val Pro Phe Ser Leu Leu Arg Gly Pro Ser Trp Asp Pro Phe Arg
385             390                 395                 400 gac tgg tac ccg cat agc cgc ctc ttc gac cag gcc ttc ggg ctg ccc     1248
Asp Trp Tyr Pro His Ser Arg Leu Phe Asp Gln Ala Phe Gly Leu Pro
                405                 410                 415 cgg ctg ccg gag gag tgg tcg cag tgg tta ggc ggc agc agc tgg cca     1296
Arg Leu Pro Glu Glu Trp Ser Gln Trp Leu Gly Gly Ser Ser Trp Pro
                420                 425                 430 ggc tac gtg cgc ccc ctg ccc ccc gcc gcc atc gag agc ccc gca gtg     1344
Gly Tyr Val Arg Pro Leu Pro Pro Ala Ala Ile Glu Ser Pro Ala Val
            435                 440                 445 gcc gcg ccc gcc tac agc cgc gcg ctc agc cgg caa ctc agc agc ggg     1392
Ala Ala Pro Ala Tyr Ser Arg Ala Leu Ser Arg Gln Leu Ser Ser Gly
        450                 455                 460 gtc tcg gag atc cgg cac act gcg gac cgc tgg cgc gtg tcc ctg gat     1440
Val Ser Glu Ile Arg His Thr Ala Asp Arg Trp Arg Val Ser Leu Asp
465             470                 475                 480 gtc aac cac ttc gcc ccg gac gag ctg acg gtc aag acc aag gat ggc     1488
Val Asn His Phe Ala Pro Asp Glu Leu Thr Val Lys Thr Lys Asp Gly
                485                 490                 495 gtg gtg gag atc acc ggc aag cac gag gag cgg cag gac gag cat ggc     1536
Val Val Glu Ile Thr Gly Lys His Glu Glu Arg Gln Asp Glu His Gly
                500                 505                 510 tac atc tcc cgg tgc ttc acg cgg aaa tac acg ctg ccc ccc ggt gtg     1584
Tyr Ile Ser Arg Cys Phe Thr Arg Lys Tyr Thr Leu Pro Pro Gly Val
            515                 520                 525 gac ccc acc caa gtt tcc tcc tcc ctg tcc cct gag ggc aca ctg acc     1632
Asp Pro Thr Gln Val Ser Ser Ser Leu Ser Pro Glu Gly Thr Leu Thr
        530                 535                 540 gtg gag gcc ccc atg ccc aag cta gcc acg cag tcc aac gag atc acc     1680
Val Glu Ala Pro Met Pro Lys Leu Ala Thr Gln Ser Asn Glu Ile Thr
545             550                 555                 560 atc cca gtc acc ttc gag tcg cgg gcc cag ctt ggg ggc cca gaa gct     1728
Ile Pro Val Thr Phe Glu Ser Arg Ala Gln Leu Gly Gly Pro Glu Ala
                565                 570                 575 gca aaa tcc gat gag act gcc gcc aag taa tctaga                       1764
Ala Lys Ser Asp Glu Thr Ala Ala Lys
                580                 585
```

<210> SEQ ID NO 2

-continued

```
<211> LENGTH: 585
<212> TYPE: PRT
<213> ORGANISM: Artificial Sequence
<220> FEATURE:
<223> OTHER INFORMATION: Synthetic Construct

<400> SEQUENCE: 2

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
            195                 200                 205

Leu Glu Ile Lys Arg Ala Asp Ala Ala Pro Gly Gly Gly Gly Ser Gly
        210                 215                 220

Gly Gly Gly Ser Gly Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
                260                 265                 270

Ala Pro Glu Lys Gly Leu Glu Trp Val Ala Tyr Ile Ser Ser Gly Ser
            275                 280                 285

Ser Thr Ile Tyr Tyr Ala Asp Thr Val Lys Gly Arg Phe Thr Ile Ser
    290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
            340                 345                 350

Glu Asp Leu Asn Ser Ala Val Asp Ala Lys Thr Thr Ala Pro Ser Val
            355                 360                 365

Tyr Pro Leu Ala Pro Val Leu Glu Ser Ser Gly Ser Met Thr Glu Arg
    370                 375                 380
```

```
Arg Val Pro Phe Ser Leu Leu Arg Gly Pro Ser Trp Asp Pro Phe Arg
385                 390                 395                 400

Asp Trp Tyr Pro His Ser Arg Leu Phe Asp Gln Ala Phe Gly Leu Pro
                405                 410                 415

Arg Leu Pro Glu Glu Trp Ser Gln Trp Leu Gly Gly Ser Ser Trp Pro
                420                 425                 430

Gly Tyr Val Arg Pro Leu Pro Pro Ala Ala Ile Glu Ser Pro Ala Val
            435                 440                 445

Ala Ala Pro Ala Tyr Ser Arg Ala Leu Ser Arg Gln Leu Ser Ser Gly
        450                 455                 460

Val Ser Glu Ile Arg His Thr Ala Asp Arg Trp Arg Val Ser Leu Asp
465                 470                 475                 480

Val Asn His Phe Ala Pro Asp Glu Leu Thr Val Lys Thr Lys Asp Gly
                485                 490                 495

Val Val Glu Ile Thr Gly Lys His Glu Glu Arg Gln Asp Glu His Gly
            500                 505                 510

Tyr Ile Ser Arg Cys Phe Thr Arg Lys Tyr Thr Leu Pro Pro Gly Val
            515                 520                 525

Asp Pro Thr Gln Val Ser Ser Ser Leu Ser Pro Glu Gly Thr Leu Thr
        530                 535                 540

Val Glu Ala Pro Met Pro Lys Leu Ala Thr Gln Ser Asn Glu Ile Thr
545                 550                 555                 560

Ile Pro Val Thr Phe Glu Ser Arg Ala Gln Leu Gly Gly Pro Glu Ala
                565                 570                 575

Ala Lys Ser Asp Glu Thr Ala Ala Lys
            580                 585
```

<210> SEQ ID NO 3
<211> LENGTH: 585
<212> TYPE: PRT
<213> ORGANISM: Artificial Sequence
<220> FEATURE:
<223> OTHER INFORMATION: 3E10 Fv-Hsp27 amino acid sequence for a
     chimeric protein comprising a single chain Fv antibody fragment
     derived from Mus musculus 3E10 hybridoma and Hsp27 from Homo
     sapiens joined by Mus musculus CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
     signal sequence for secretion of fusion protein, provided by
     pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
     removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
     removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
     removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility

```
<220> FEATURE:
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting
      in enhanced cell penetration of the 3E10 monoclonal antibody and
      3E10 Fv antibody fragment
<220> FEATURE:
<221> NAME/KEY: MISC_FEATURE
<222> LOCATION: (264)..(264)
<223> OTHER INFORMATION: Asparagine (N) in place of aspartic acid in
      3E10 variable heavy chain, VH, conferring enhanced cell
      penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
      chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(374)
<223> OTHER INFORMATION: Mus musculus immunoglobulin heavy chain
      constant domain, CH1, linker
<220> FEATURE:
<221> NAME/KEY: MISC_FEATURE
<222> LOCATION: (375)..(380)
<223> OTHER INFORMATION: Swivel sequence
<220> FEATURE:
<221> NAME/KEY: MISC_FEATURE
<222> LOCATION: (381)..(585)
<223> OTHER INFORMATION: Homo sapiens Hsp27 sequence

<400> SEQUENCE: 3

Met Arg Phe Pro Ser Leu Phe Thr Ala Val Leu Phe Ala Ala Ser Ser
1               5                   10                  15
```

```
Ala Leu Ala Ala Pro Val Asn Thr Thr Thr Glu Asp Glu Thr Ala Gln
         20              25              30

Ile Pro Ala Glu Ala Val Ile Gly Tyr Ser Asp Leu Glu Gly Asp Phe
         35              40              45

Asp Val Ala Val Leu Pro Phe Ser Asn Ser Thr Asn Asn Gly Leu Leu
     50              55              60

Phe Ile Asn Thr Thr Ile Ala Ser Ile Ala Ala Lys Glu Glu Gly Val
 65              70              75              80

Ser Leu Glu Lys Arg Glu Ala Glu Ala Glu Phe His His His His His
             85              90              95

His Ala Gly Ile His Asp Ile Val Leu Thr Gln Ser Pro Ala Ser Leu
         100             105             110

Ala Val Ser Leu Gly Gln Arg Ala Thr Ile Ser Cys Arg Ala Ser Lys
         115             120             125

Ser Val Ser Thr Ser Ser Tyr Ser Tyr Met His Trp Tyr Gln Gln Lys
     130             135             140

Pro Gly Gln Pro Pro Lys Leu Leu Ile Lys Tyr Ala Ser Tyr Leu Glu
145             150             155             160

Ser Gly Val Pro Ala Arg Phe Ser Gly Ser Gly Ser Gly Thr Asp Phe
             165             170             175

Thr Leu Asn Ile His Pro Val Glu Glu Glu Asp Ala Ala Thr Tyr Tyr
         180             185             190

Cys Gln His Ser Arg Glu Phe Pro Trp Thr Phe Gly Gly Gly Thr Lys
         195             200             205

Leu Glu Ile Lys Arg Ala Asp Ala Ala Pro Gly Gly Gly Gly Ser Gly
         210             215             220

Gly Gly Gly Ser Gly Gly Gly Ser Glu Val Gln Leu Val Glu Ser
225             230             235             240

Gly Gly Gly Leu Val Lys Pro Gly Gly Ser Arg Lys Leu Ser Cys Ala
             245             250             255

Ala Ser Gly Phe Thr Phe Ser Asn Tyr Gly Met His Trp Val Arg Gln
         260             265             270

Ala Pro Glu Lys Gly Leu Glu Trp Val Ala Tyr Ile Ser Ser Gly Ser
         275             280             285

Ser Thr Ile Tyr Tyr Ala Asp Thr Val Lys Gly Arg Phe Thr Ile Ser
     290             295             300

Arg Asp Asn Ala Lys Asn Thr Leu Phe Leu Gln Met Thr Ser Leu Arg
305             310             315             320

Ser Glu Asp Thr Ala Met Arg Gly Leu Leu Leu Asp Tyr Trp Gly Gln
             325             330             335

Gly Thr Thr Leu Thr Val Ser Ser Leu Glu Gln Lys Leu Ile Ser Glu
             340             345             350

Glu Asp Leu Asn Ser Ala Val Asp Ala Lys Thr Thr Ala Pro Ser Val
         355             360             365

Tyr Pro Leu Ala Pro Val Leu Glu Ser Ser Gly Ser Met Thr Glu Arg
     370             375             380

Arg Val Pro Phe Ser Leu Leu Arg Gly Pro Ser Trp Asp Pro Phe Arg
385             390             395             400

Asp Trp Tyr Pro His Ser Arg Leu Phe Asp Gln Ala Phe Gly Leu Pro
             405             410             415

Arg Leu Pro Glu Glu Trp Ser Gln Trp Leu Gly Gly Ser Ser Trp Pro
         420             425             430
```

-continued

```
Gly Tyr Val Arg Pro Leu Pro Pro Ala Ala Ile Glu Ser Pro Ala Val
        435             440             445

Ala Ala Pro Ala Tyr Ser Arg Ala Leu Ser Arg Gln Leu Ser Ser Gly
    450             455             460

Val Ser Glu Ile Arg His Thr Ala Asp Arg Trp Arg Val Ser Leu Asp
465             470             475             480

Val Asn His Phe Ala Pro Asp Glu Leu Thr Val Lys Thr Lys Asp Gly
            485             490             495

Val Val Glu Ile Thr Gly Lys His Glu Glu Arg Gln Asp Glu His Gly
        500             505             510

Tyr Ile Ser Arg Cys Phe Thr Arg Lys Tyr Thr Leu Pro Pro Gly Val
        515             520             525

Asp Pro Thr Gln Val Ser Ser Ser Leu Ser Pro Glu Gly Thr Leu Thr
    530             535             540

Val Glu Ala Pro Met Pro Lys Leu Ala Thr Gln Ser Asn Glu Ile Thr
545             550             555             560

Ile Pro Val Thr Phe Glu Ser Arg Ala Gln Leu Gly Gly Pro Glu Ala
            565             570             575

Ala Lys Ser Asp Glu Thr Ala Ala Lys
        580             585

<210> SEQ ID NO 4
<211> LENGTH: 3072
<212> TYPE: DNA
<213> ORGANISM: Artificial Sequence
<220> FEATURE:
<223> OTHER INFORMATION: 3E10 Fv-Hsp70 nucleotide sequence encoding a
      chimeric protein comprising a single chain Fv antibody fragment
      derived from Mus musculus 3E10 hybridoma and Hsp70 from Homo
      sapiens joined by mouse CH1 linker and swivel sequence
<220> FEATURE:
<221> NAME/KEY: CDS
<222> LOCATION: (1)..(3066)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Mus musculus CH1 linker, swivel sequence, epitope tags, and Homo
      sapiens Hsp70 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
<221> NAME/KEY: misc_feature
<222> LOCATION: (274)..(291)
```

```
<223> OTHER INFORMATION: Coding sequence: His6 epitope tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
<223> OTHER INFORMATION: Begin of coding sequence for Mus musculus 3E10
      immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
      first codon of CDR1 resulting in a D31N change for 3E10 VH chain
      and enhanced cell penetration of the 3E10 monoclonal antibody and
      3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
      immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1122)
<223> OTHER INFORMATION: Coding sequence: Mus musculus immunoglobulin
      heavy chain constant domain, CH1, linker
<220> FEATURE:
<221> NAME/KEY: misc_feature
<222> LOCATION: (1123)..(1140)
<223> OTHER INFORMATION: Coding sequence: swivel sequence
<220> FEATURE:
<221> NAME/KEY: misc_feature
<222> LOCATION: (1135)..(1140)
<223> OTHER INFORMATION: BamHI restriction enzyme site
<220> FEATURE:
<221> NAME/KEY: misc_feature
<222> LOCATION: (1141)..(3066)
<223> OTHER INFORMATION: Coding sequence: Homo sapiens Hsp70 sequence
<220> FEATURE:
```

-continued

```
<221> NAME/KEY: misc_feature
<222> LOCATION: (3064)..(3066)
<223> OTHER INFORMATION: Stop codon
<220> FEATURE:
<221> NAME/KEY: misc_feature
<222> LOCATION: (3067)..(3072)
<223> OTHER INFORMATION: XbaI restriction enzyme site

<400> SEQUENCE: 4 atg aga ttt cct tca ctt ttt act gct gtt tta ttc gca gca tcc tcc        48
Met Arg Phe Pro Ser Leu Phe Thr Ala Val Leu Phe Ala Ala Ser Ser
1               5                   10                  15 gca tta gct gct cca gtc aac act aca aca gaa gat gaa acg gca caa        96
Ala Leu Ala Ala Pro Val Asn Thr Thr Thr Glu Asp Glu Thr Ala Gln
                20                  25                  30 att ccg gct gaa gct gtc atc ggt tac tca gat tta gaa ggg gat ttc        144
Ile Pro Ala Glu Ala Val Ile Gly Tyr Ser Asp Leu Glu Gly Asp Phe
            35                  40                  45 gat gtt gct gtt ttg cca ttt tcc aac agc aca aat aac ggg tta ttg        192
Asp Val Ala Val Leu Pro Phe Ser Asn Ser Thr Asn Asn Gly Leu Leu
        50                  55                  60 ttt ata aat act act att gcc agc att gct gct aaa gaa gaa ggg gta        240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat        288
Ser Leu Glu Lys Arg Glu Ala Glu Ala Glu Phe His His His His His
                85                  90                  95 cac gca ggg att cac gac att gtc ctg aca cag tct cct gct tcc tta        336
His Ala Gly Ile His Asp Ile Val Leu Thr Gln Ser Pro Ala Ser Leu
            100                 105                 110 gct gta tct ctg ggg cag agg gcc acc atc tcc tgc agg gcc agc aaa        384
Ala Val Ser Leu Gly Gln Arg Ala Thr Ile Ser Cys Arg Ala Ser Lys
        115                 120                 125 agt gtc agt aca tct agc tat agt tac atg cac tgg tac caa cag aaa        432
Ser Val Ser Thr Ser Ser Tyr Ser Tyr Met His Trp Tyr Gln Gln Lys
    130                 135                 140 cca gga cag cca ccc aaa ctc ctc atc aag tat gca tcc tac cta gaa        480
Pro Gly Gln Pro Pro Lys Leu Leu Ile Lys Tyr Ala Ser Tyr Leu Glu
145                 150                 155                 160 tct ggg gtt cct gcc agg ttc agt ggc agt ggg tct ggg aca gac ttc        528
Ser Gly Val Pro Ala Arg Phe Ser Gly Ser Gly Ser Gly Thr Asp Phe
                165                 170                 175 acc ctc aac atc cat cct gtg gag gag gag gat gct gca aca tat tac        576
Thr Leu Asn Ile His Pro Val Glu Glu Glu Asp Ala Ala Thr Tyr Tyr
            180                 185                 190 tgt cag cac agt agg gag ttt ccg tgg acg ttc ggt gga ggc acc aag        624
Cys Gln His Ser Arg Glu Phe Pro Trp Thr Phe Gly Gly Gly Thr Lys
        195                 200                 205 ctg gaa atc aaa cgg gct gat gct gca ccc ggg ggt ggc ggt tct ggc        672
Leu Glu Ile Lys Arg Ala Asp Ala Ala Pro Gly Gly Gly Gly Ser Gly
    210                 215                 220 ggt ggc ggt tct gga ggc ggt ggc tct gag gtg cag ctg gtg gag tct        720
Gly Gly Gly Ser Gly Gly Gly Gly Ser Glu Val Gln Leu Val Glu Ser
225                 230                 235                 240 ggg gga ggc tta gtg aag cct gga ggg tcc cgg aaa ctc tcc tgt gca        768
Gly Gly Gly Leu Val Lys Pro Gly Gly Ser Arg Lys Leu Ser Cys Ala
                245                 250                 255 gcc tct gga ttc act ttc agt aac tat gga atg cac tgg gtc cgt cag        816
Ala Ser Gly Phe Thr Phe Ser Asn Tyr Gly Met His Trp Val Arg Gln
            260                 265                 270 gct cca gag aag ggg ctg gag tgg gtt gca tac att agt agt ggc agt        864
```

-continued

```
Ala Pro Glu Lys Gly Leu Glu Trp Val Ala Tyr Ile Ser Ser Gly Ser
        275                 280                 285 agt acc atc tac tat gca gac aca gtg aag ggc cga ttc acc atc tcc        912
Ser Thr Ile Tyr Tyr Ala Asp Thr Val Lys Gly Arg Phe Thr Ile Ser
    290                 295                 300 aga gac aat gcc aag aac acc ctg ttc ctg caa atg acc agt cta agg        960
Arg Asp Asn Ala Lys Asn Thr Leu Phe Leu Gln Met Thr Ser Leu Arg
305                 310                 315                 320 tct gag gac aca gcc atg cgg ggg tta cta ctt gac tac tgg ggc caa       1008
Ser Glu Asp Thr Ala Met Arg Gly Leu Leu Leu Asp Tyr Trp Gly Gln
                325                 330                 335 ggc acc act ctc aca gtc tcc tca cta gaa caa aaa ctc atc tca gaa       1056
Gly Thr Thr Leu Thr Val Ser Ser Leu Glu Gln Lys Leu Ile Ser Glu
            340                 345                 350 gag gat ctg aat agc gcc gtc gac gcc aaa aca aca gcc cca tcg gtc       1104
Glu Asp Leu Asn Ser Ala Val Asp Ala Lys Thr Thr Ala Pro Ser Val
            355                 360                 365 tat cca ctg gcc cct gta ctg gag tct tcc gga tcc atg gcc aaa gcc       1152
Tyr Pro Leu Ala Pro Val Leu Glu Ser Ser Gly Ser Met Ala Lys Ala
    370                 375                 380 gcg gcg atc ggc atc gac ctg ggc acc acc tac tcc tgc gtg ggg gtg       1200
Ala Ala Ile Gly Ile Asp Leu Gly Thr Thr Tyr Ser Cys Val Gly Val
385                 390                 395                 400 ttc caa cac ggc aag gtg gag atc atc gcc aac gac cag ggc aac cgc       1248
Phe Gln His Gly Lys Val Glu Ile Ile Ala Asn Asp Gln Gly Asn Arg
                405                 410                 415 acc acc ccc agc tac gtg gcc ttc acg gac acc gag cgg ctc atc ggg       1296
Thr Thr Pro Ser Tyr Val Ala Phe Thr Asp Thr Glu Arg Leu Ile Gly
            420                 425                 430 gat gcg gcc aag aac cag gtg gcg ctg aac ccg cag aac acc gtg ttt       1344
Asp Ala Ala Lys Asn Gln Val Ala Leu Asn Pro Gln Asn Thr Val Phe
            435                 440                 445 gac gcg aag cgg ctg atc ggc cgc aag ttc ggc gac ccg gtg gtg cag       1392
Asp Ala Lys Arg Leu Ile Gly Arg Lys Phe Gly Asp Pro Val Val Gln
    450                 455                 460 tcg gac atg aag cac tgg cct ttc cag gtg atc aac gac gga gac aag       1440
Ser Asp Met Lys His Trp Pro Phe Gln Val Ile Asn Asp Gly Asp Lys
465                 470                 475                 480 ccc aag gtg cag gtg agc tac aag ggg gag acc aag gca ttc tac ccc       1488
Pro Lys Val Gln Val Ser Tyr Lys Gly Glu Thr Lys Ala Phe Tyr Pro
                485                 490                 495 gag gag atc tcg tcc atg gtg ctg acc aag atg aag gag atc gcc gag       1536
Glu Glu Ile Ser Ser Met Val Leu Thr Lys Met Lys Glu Ile Ala Glu
            500                 505                 510 gcg tac ctg ggc tac ccg gtg acc aac gcg gtg atc acc gtg ccg gcc       1584
Ala Tyr Leu Gly Tyr Pro Val Thr Asn Ala Val Ile Thr Val Pro Ala
            515                 520                 525 tac ttc aac gac tcg cag cgc cag gcc acc aag gat gcg ggt gtg atc       1632
Tyr Phe Asn Asp Ser Gln Arg Gln Ala Thr Lys Asp Ala Gly Val Ile
    530                 535                 540 gcg ggg ctc aac gtg ctg cgg atc atc aac gag ccc acg gcc gcc gcc       1680
Ala Gly Leu Asn Val Leu Arg Ile Ile Asn Glu Pro Thr Ala Ala Ala
545                 550                 555                 560 atc gcc tac ggc ctg gac aga acg ggc aag ggg gag cgc aac gtg ctc       1728
Ile Ala Tyr Gly Leu Asp Arg Thr Gly Lys Gly Glu Arg Asn Val Leu
                565                 570                 575 atc ttt gac ctg ggc ggg ggc acc ttc gac gtg tcc atc ctg acg atc       1776
Ile Phe Asp Leu Gly Gly Gly Thr Phe Asp Val Ser Ile Leu Thr Ile
                580                 585                 590
```

-continued

```
gac gac ggc atc ttc gag gtg aag gcc acg gcc ggg gac acc cac ctg    1824
Asp Asp Gly Ile Phe Glu Val Lys Ala Thr Ala Gly Asp Thr His Leu
        595                 600                 605 ggt ggg gag gac ttt gac aac agg ctg gtg aac cac ttc gtg gag gag    1872
Gly Gly Glu Asp Phe Asp Asn Arg Leu Val Asn His Phe Val Glu Glu
    610                 615                 620 ttc aag aga aaa cac aag aag gac atc agc cag aac aag cga gcc gtg    1920
Phe Lys Arg Lys His Lys Lys Asp Ile Ser Gln Asn Lys Arg Ala Val
625                 630                 635                 640 agg cgg ctg cgc acc gcc tgc gag agg gcc aag agg acc ctg tcg tcc    1968
Arg Arg Leu Arg Thr Ala Cys Glu Arg Ala Lys Arg Thr Leu Ser Ser
                645                 650                 655 agc acc cag gcc agc ctg gag atc gac tcc ctg ttt gag ggc atc gac    2016
Ser Thr Gln Ala Ser Leu Glu Ile Asp Ser Leu Phe Glu Gly Ile Asp
            660                 665                 670 ttc tac acg tcc atc acc agg gcg agg ttc gag gag ctg tgc tcc gac    2064
Phe Tyr Thr Ser Ile Thr Arg Ala Arg Phe Glu Glu Leu Cys Ser Asp
            675                 680                 685 ctg ttc cga agc acc ctg gag ccc gtg gag aag gct ctg cgc gac gcc    2112
Leu Phe Arg Ser Thr Leu Glu Pro Val Glu Lys Ala Leu Arg Asp Ala
        690                 695                 700 aag ctg gac aag gcc cag att cac gac ctg gtc ctg gtc ggg ggc tcc    2160
Lys Leu Asp Lys Ala Gln Ile His Asp Leu Val Leu Val Gly Gly Ser
705                 710                 715                 720 acc cgc atc ccc aag gtg cag aag ctg ctg cag gac ttc ttc aac ggg    2208
Thr Arg Ile Pro Lys Val Gln Lys Leu Leu Gln Asp Phe Phe Asn Gly
                725                 730                 735 cgc gac ctg aac aag agc atc aac ccc gac gag gct gtg gcc tac ggg    2256
Arg Asp Leu Asn Lys Ser Ile Asn Pro Asp Glu Ala Val Ala Tyr Gly
            740                 745                 750 gcg gcg gtg cag gcg gcc atc ctg atg ggg gac aag tcc gag aac gtg    2304
Ala Ala Val Gln Ala Ala Ile Leu Met Gly Asp Lys Ser Glu Asn Val
            755                 760                 765 cag gac ctg ctg ctg ctg gac gtg gct ccc ctg tcg ctg ggg ctg gag    2352
Gln Asp Leu Leu Leu Leu Asp Val Ala Pro Leu Ser Leu Gly Leu Glu
        770                 775                 780 acg gcc gga ggc gtg atg act gcc ctg atc aag cgc aac tcc acc atc    2400
Thr Ala Gly Gly Val Met Thr Ala Leu Ile Lys Arg Asn Ser Thr Ile
785                 790                 795                 800 ccc acc aag cag acg cag atc ttc acc acc tac tcc gac aac caa ccc    2448
Pro Thr Lys Gln Thr Gln Ile Phe Thr Thr Tyr Ser Asp Asn Gln Pro
                805                 810                 815 ggg gtg ctg atc cag gtg tac gag ggc gag agg gcc atg acg aaa gac    2496
Gly Val Leu Ile Gln Val Tyr Glu Gly Glu Arg Ala Met Thr Lys Asp
            820                 825                 830 aac aat ctg ttg ggg cgc ttc gag ctg agc ggc atc cct ccg gcc ccc    2544
Asn Asn Leu Leu Gly Arg Phe Glu Leu Ser Gly Ile Pro Pro Ala Pro
            835                 840                 845 agg ggc gtg ccc cag atc gag gtg acc ttc gac atc gat gcc aac ggc    2592
Arg Gly Val Pro Gln Ile Glu Val Thr Phe Asp Ile Asp Ala Asn Gly
        850                 855                 860 atc ctg aac gtc acg gcc acg gac aag agc acc ggc aag gcc aac aag    2640
Ile Leu Asn Val Thr Ala Thr Asp Lys Ser Thr Gly Lys Ala Asn Lys
865                 870                 875                 880 atc acc atc acc aac gac aag ggc cgc ctg agc aag gag gag atc gag    2688
Ile Thr Ile Thr Asn Asp Lys Gly Arg Leu Ser Lys Glu Glu Ile Glu
                885                 890                 895 cgc atg gtg cag gag gcg gag aag tac aaa gcg gag gac gag gtg cag    2736
Arg Met Val Gln Glu Ala Glu Lys Tyr Lys Ala Glu Asp Glu Val Gln
            900                 905                 910
```

```
cgc gag agg gtg tca gcc aag aac gcc ctg gag tcc tac gcc ttc aac     2784
Arg Glu Arg Val Ser Ala Lys Asn Ala Leu Glu Ser Tyr Ala Phe Asn
        915                 920                 925 atg aag agc gcc gtg gag gat gag ggg ctc aag ggc aag atc agc gag     2832
Met Lys Ser Ala Val Glu Asp Glu Gly Leu Lys Gly Lys Ile Ser Glu
        930                 935                 940 gcg gac aag aag aag gtt ctg gac aag tgt caa gag gtc atc tcg tgg     2880
Ala Asp Lys Lys Lys Val Leu Asp Lys Cys Gln Glu Val Ile Ser Trp
945                 950                 955                 960 ctg gac gcc aac acc ttg gcc gag aag gac gag ttt gag cac aag agg     2928
Leu Asp Ala Asn Thr Leu Ala Glu Lys Asp Glu Phe Glu His Lys Arg
                965                 970                 975 aag gag ctg gag cag gtg tgt aac ccc atc atc agc gga ctg tac cag     2976
Lys Glu Leu Glu Gln Val Cys Asn Pro Ile Ile Ser Gly Leu Tyr Gln
            980                 985                 990 ggt gcc ggt ggt ccc ggg cct ggc  ggc ttc ggg gct cag  ggt ccc aag   3024
Gly Ala Gly Gly Pro Gly Pro Gly  Gly Phe Gly Ala Gln  Gly Pro Lys
        995                 1000                1005 gga ggg tct ggg tca ggc cct  acc att gag gag gtg  gat tag tctaga     3072
Gly Gly Ser Gly Ser Gly Pro  Thr Ile Glu Glu Val  Asp
        1010                1015                1020
```

```
<210> SEQ ID NO 5
<211> LENGTH: 1021
<212> TYPE: PRT
<213> ORGANISM: Artificial Sequence
<220> FEATURE:
<223> OTHER INFORMATION: Synthetic Construct

<400> SEQUENCE: 5

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
            85                  90                  95

His Ala Gly Ile His Asp Ile Val Leu Thr Gln Ser Pro Ala Ser Leu
        100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
        130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
            165                 170                 175

Thr Leu Asn Ile His Pro Val Glu Glu Glu Asp Ala Ala Thr Tyr Tyr
        180                 185                 190

Cys Gln His Ser Arg Glu Phe Pro Trp Thr Phe Gly Gly Gly Thr Lys
        195                 200                 205

Leu Glu Ile Lys Arg Ala Asp Ala Ala Pro Gly Gly Gly Gly Ser Gly
```

-continued

```
           210                 215                 220

Gly Gly Gly Ser Gly Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
                260                 265                 270

Ala Pro Glu Lys Gly Leu Glu Trp Val Ala Tyr Ile Ser Ser Gly Ser
                275                 280                 285

Ser Thr Ile Tyr Tyr Ala Asp Thr Val Lys Gly Arg Phe Thr Ile Ser
                290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
                340                 345                 350

Glu Asp Leu Asn Ser Ala Val Asp Ala Lys Thr Thr Ala Pro Ser Val
                355                 360                 365

Tyr Pro Leu Ala Pro Val Leu Glu Ser Ser Gly Ser Met Ala Lys Ala
                370                 375                 380

Ala Ala Ile Gly Ile Asp Leu Gly Thr Thr Tyr Ser Cys Val Gly Val
385                 390                 395                 400

Phe Gln His Gly Lys Val Glu Ile Ile Ala Asn Asp Gln Gly Asn Arg
                405                 410                 415

Thr Thr Pro Ser Tyr Val Ala Phe Thr Asp Thr Glu Arg Leu Ile Gly
                420                 425                 430

Asp Ala Ala Lys Asn Gln Val Ala Leu Asn Pro Gln Asn Thr Val Phe
                435                 440                 445

Asp Ala Lys Arg Leu Ile Gly Arg Lys Phe Gly Asp Pro Val Val Gln
                450                 455                 460

Ser Asp Met Lys His Trp Pro Phe Gln Val Ile Asn Asp Gly Asp Lys
465                 470                 475                 480

Pro Lys Val Gln Val Ser Tyr Lys Gly Glu Thr Lys Ala Phe Tyr Pro
                485                 490                 495

Glu Glu Ile Ser Ser Met Val Leu Thr Lys Met Lys Glu Ile Ala Glu
                500                 505                 510

Ala Tyr Leu Gly Tyr Pro Val Thr Asn Ala Val Ile Thr Val Pro Ala
                515                 520                 525

Tyr Phe Asn Asp Ser Gln Arg Gln Ala Thr Lys Asp Ala Gly Val Ile
                530                 535                 540

Ala Gly Leu Asn Val Leu Arg Ile Ile Asn Glu Pro Thr Ala Ala Ala
545                 550                 555                 560

Ile Ala Tyr Gly Leu Asp Arg Thr Gly Lys Gly Glu Arg Asn Val Leu
                565                 570                 575

Ile Phe Asp Leu Gly Gly Gly Thr Phe Asp Val Ser Ile Leu Thr Ile
                580                 585                 590

Asp Asp Gly Ile Phe Glu Val Lys Ala Thr Ala Gly Asp Thr His Leu
                595                 600                 605

Gly Gly Glu Asp Phe Asp Asn Arg Leu Val Asn His Phe Val Glu Glu
                610                 615                 620

Phe Lys Arg Lys His Lys Lys Asp Ile Ser Gln Asn Lys Arg Ala Val
625                 630                 635                 640
```

-continued

```
Arg Arg Leu Arg Thr Ala Cys Glu Arg Ala Lys Arg Thr Leu Ser Ser
            645                 650                 655

Ser Thr Gln Ala Ser Leu Glu Ile Asp Ser Leu Phe Glu Gly Ile Asp
            660                 665                 670

Phe Tyr Thr Ser Ile Thr Arg Ala Arg Phe Glu Glu Leu Cys Ser Asp
            675                 680                 685

Leu Phe Arg Ser Thr Leu Glu Pro Val Glu Lys Ala Leu Arg Asp Ala
        690                 695                 700

Lys Leu Asp Lys Ala Gln Ile His Asp Leu Val Leu Val Gly Gly Ser
705                 710                 715                 720

Thr Arg Ile Pro Lys Val Gln Lys Leu Leu Gln Asp Phe Phe Asn Gly
                725                 730                 735

Arg Asp Leu Asn Lys Ser Ile Asn Pro Asp Glu Ala Val Ala Tyr Gly
            740                 745                 750

Ala Ala Val Gln Ala Ala Ile Leu Met Gly Asp Lys Ser Glu Asn Val
            755                 760                 765

Gln Asp Leu Leu Leu Leu Asp Val Ala Pro Leu Ser Leu Gly Leu Glu
        770                 775                 780

Thr Ala Gly Gly Val Met Thr Ala Leu Ile Lys Arg Asn Ser Thr Ile
785                 790                 795                 800

Pro Thr Lys Gln Thr Gln Ile Phe Thr Thr Tyr Ser Asp Asn Gln Pro
                805                 810                 815

Gly Val Leu Ile Gln Val Tyr Glu Gly Glu Arg Ala Met Thr Lys Asp
            820                 825                 830

Asn Asn Leu Leu Gly Arg Phe Glu Leu Ser Gly Ile Pro Pro Ala Pro
            835                 840                 845

Arg Gly Val Pro Gln Ile Glu Val Thr Phe Asp Ile Asp Ala Asn Gly
        850                 855                 860

Ile Leu Asn Val Thr Ala Thr Asp Lys Ser Thr Gly Lys Ala Asn Lys
865                 870                 875                 880

Ile Thr Ile Thr Asn Asp Lys Gly Arg Leu Ser Lys Glu Glu Ile Glu
                885                 890                 895

Arg Met Val Gln Glu Ala Glu Lys Tyr Lys Ala Glu Asp Glu Val Gln
            900                 905                 910

Arg Glu Arg Val Ser Ala Lys Asn Ala Leu Glu Ser Tyr Ala Phe Asn
            915                 920                 925

Met Lys Ser Ala Val Glu Asp Glu Gly Leu Lys Gly Lys Ile Ser Glu
        930                 935                 940

Ala Asp Lys Lys Lys Val Leu Asp Lys Cys Gln Glu Val Ile Ser Trp
945                 950                 955                 960

Leu Asp Ala Asn Thr Leu Ala Glu Lys Asp Glu Phe Glu His Lys Arg
                965                 970                 975

Lys Glu Leu Glu Gln Val Cys Asn Pro Ile Ile Ser Gly Leu Tyr Gln
            980                 985                 990

Gly Ala Gly Gly Pro Gly Pro Gly  Gly Phe Gly Ala Gln  Gly Pro Lys
            995                 1000                1005

Gly Gly  Ser Gly Ser Gly Pro  Thr Ile Glu Glu Val  Asp
    1010                1015                1020
```

<210> SEQ ID NO 6
<211> LENGTH: 1021
<212> TYPE: PRT
<213> ORGANISM: Artificial Sequence
<220> FEATURE:

-continued

```
<223> OTHER INFORMATION: 3E10 Fv-Hsp70 amino acid sequence for a
      chimeric protein comprising a single chain Fv antibody fragment
      derived from Mus musculus 3E10 hybridoma and Hsp70 from Homo
      sapiens joined by mouse CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
      signal sequence for secretion of fusion protein, provided by
      pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
      removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility
<220> FEATURE:
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting
      in enhanced cell penetration of the 3E10 monoclonal antibody and
      3E10 Fv antibody fragment
<220> FEATURE:
<221> NAME/KEY: MISC_FEATURE
<222> LOCATION: (264)..(264)
<223> OTHER INFORMATION: Asparagine (N) in place of aspartic acid in
      3E10 variable heavy chain, VH, conferring enhanced cell
      penetration; D31N mutation in CDR1 of 3E10 VH chain
<220> FEATURE:
<221> NAME/KEY: MISC_FEATURE
```

<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
      chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(374)
<223> OTHER INFORMATION: Mus musculus immunoglobulin heavy chain
      constant domain, CH1, linker
<220> FEATURE:
<221> NAME/KEY: MISC_FEATURE
<222> LOCATION: (375)..(380)
<223> OTHER INFORMATION: Swivel sequence
<220> FEATURE:
<221> NAME/KEY: MISC_FEATURE
<222> LOCATION: (381)..(1021)
<223> OTHER INFORMATION: Homo sapiens Hsp70 sequence

<400> SEQUENCE: 6

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
            195                 200                 205

Leu Glu Ile Lys Arg Ala Asp Ala Ala Pro Gly Gly Gly Gly Ser Gly
    210                 215                 220

Gly Gly Gly Ser Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

-continued

```
Ala Ser Gly Phe Thr Phe Ser Asn Tyr Gly Met His Trp Val Arg Gln
            260                 265                 270

Ala Pro Glu Lys Gly Leu Glu Trp Val Ala Tyr Ile Ser Ser Gly Ser
            275                 280                 285

Ser Thr Ile Tyr Tyr Ala Asp Thr Val Lys Gly Arg Phe Thr Ile Ser
            290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
            340                 345                 350

Glu Asp Leu Asn Ser Ala Val Asp Ala Lys Thr Thr Ala Pro Ser Val
            355                 360                 365

Tyr Pro Leu Ala Pro Val Leu Glu Ser Ser Gly Ser Met Ala Lys Ala
            370                 375                 380

Ala Ala Ile Gly Ile Asp Leu Gly Thr Thr Tyr Ser Cys Val Gly Val
385                 390                 395                 400

Phe Gln His Gly Lys Val Glu Ile Ile Ala Asn Asp Gln Gly Asn Arg
                405                 410                 415

Thr Thr Pro Ser Tyr Val Ala Phe Thr Asp Thr Glu Arg Leu Ile Gly
                420                 425                 430

Asp Ala Ala Lys Asn Gln Val Ala Leu Asn Pro Gln Asn Thr Val Phe
            435                 440                 445

Asp Ala Lys Arg Leu Ile Gly Arg Lys Phe Gly Asp Pro Val Val Gln
            450                 455                 460

Ser Asp Met Lys His Trp Pro Phe Gln Val Ile Asn Asp Gly Asp Lys
465                 470                 475                 480

Pro Lys Val Gln Val Ser Tyr Lys Gly Glu Thr Lys Ala Phe Tyr Pro
                485                 490                 495

Glu Glu Ile Ser Ser Met Val Leu Thr Lys Met Lys Glu Ile Ala Glu
                500                 505                 510

Ala Tyr Leu Gly Tyr Pro Val Thr Asn Ala Val Ile Thr Val Pro Ala
            515                 520                 525

Tyr Phe Asn Asp Ser Gln Arg Gln Ala Thr Lys Asp Ala Gly Val Ile
            530                 535                 540

Ala Gly Leu Asn Val Leu Arg Ile Ile Asn Glu Pro Thr Ala Ala Ala
545                 550                 555                 560

Ile Ala Tyr Gly Leu Asp Arg Thr Gly Lys Gly Glu Arg Asn Val Leu
                565                 570                 575

Ile Phe Asp Leu Gly Gly Gly Thr Phe Asp Val Ser Ile Leu Thr Ile
                580                 585                 590

Asp Asp Gly Ile Phe Glu Val Lys Ala Thr Ala Gly Asp Thr His Leu
            595                 600                 605

Gly Gly Glu Asp Phe Asp Asn Arg Leu Val Asn His Phe Val Glu Glu
            610                 615                 620

Phe Lys Arg Lys His Lys Lys Asp Ile Ser Gln Asn Lys Arg Ala Val
625                 630                 635                 640

Arg Arg Leu Arg Thr Ala Cys Glu Arg Ala Lys Arg Thr Leu Ser Ser
                645                 650                 655

Ser Thr Gln Ala Ser Leu Glu Ile Asp Ser Leu Phe Glu Gly Ile Asp
            660                 665                 670

Phe Tyr Thr Ser Ile Thr Arg Ala Arg Phe Glu Glu Leu Cys Ser Asp
```

-continued

```
                  675               680               685

Leu Phe Arg Ser Thr Leu Glu Pro Val Glu Lys Ala Leu Arg Asp Ala
    690               695               700

Lys Leu Asp Lys Ala Gln Ile His Asp Leu Val Leu Val Gly Gly Ser
705               710               715               720

Thr Arg Ile Pro Lys Val Gln Lys Leu Leu Gln Asp Phe Phe Asn Gly
              725               730               735

Arg Asp Leu Asn Lys Ser Ile Asn Pro Asp Glu Ala Val Ala Tyr Gly
          740               745               750

Ala Ala Val Gln Ala Ala Ile Leu Met Gly Asp Lys Ser Glu Asn Val
          755               760               765

Gln Asp Leu Leu Leu Leu Asp Val Ala Pro Leu Ser Leu Gly Leu Glu
    770               775               780

Thr Ala Gly Gly Val Met Thr Ala Leu Ile Lys Arg Asn Ser Thr Ile
785               790               795               800

Pro Thr Lys Gln Thr Gln Ile Phe Thr Thr Tyr Ser Asp Asn Gln Pro
              805               810               815

Gly Val Leu Ile Gln Val Tyr Glu Gly Glu Arg Ala Met Thr Lys Asp
          820               825               830

Asn Asn Leu Leu Gly Arg Phe Glu Leu Ser Gly Ile Pro Pro Ala Pro
          835               840               845

Arg Gly Val Pro Gln Ile Glu Val Thr Phe Asp Ile Asp Ala Asn Gly
    850               855               860

Ile Leu Asn Val Thr Ala Thr Asp Lys Ser Thr Gly Lys Ala Asn Lys
865               870               875               880

Ile Thr Ile Thr Asn Asp Lys Gly Arg Leu Ser Lys Glu Glu Ile Glu
              885               890               895

Arg Met Val Gln Glu Ala Glu Lys Tyr Lys Ala Glu Asp Glu Val Gln
          900               905               910

Arg Glu Arg Val Ser Ala Lys Asn Ala Leu Glu Ser Tyr Ala Phe Asn
          915               920               925

Met Lys Ser Ala Val Glu Asp Glu Gly Leu Lys Gly Lys Ile Ser Glu
    930               935               940

Ala Asp Lys Lys Lys Val Leu Asp Lys Cys Gln Glu Val Ile Ser Trp
945               950               955               960

Leu Asp Ala Asn Thr Leu Ala Glu Lys Asp Glu Phe Glu His Lys Arg
              965               970               975

Lys Glu Leu Glu Gln Val Cys Asn Pro Ile Ile Ser Gly Leu Tyr Gln
              980               985               990

Gly Ala Gly Gly Pro Gly Pro Gly  Gly Phe Gly Ala Gln  Gly Pro Lys
          995               1000               1005

Gly Gly  Ser Gly Ser Gly Pro  Thr Ile Glu Glu Val  Asp
    1010               1015               1020
```

<210> SEQ ID NO 7
<211> LENGTH: 3111
<212> TYPE: DNA
<213> ORGANISM: Artificial Sequence
<220> FEATURE:
<223> OTHER INFORMATION: 3E10 Fv-GRP78 nucleotide sequence encoding a
      chimeric protein comprising a single chain Fv antibody fragment
      derived from Mus musculus 3E10 hybridoma and GRP78 from Homo
      sapiens joined by mouse CH1 linker and swivel sequence
<220> FEATURE:
<221> NAME/KEY: CDS
<222> LOCATION: (1)..(3105)
<223> OTHER INFORMATION: Coding sequence for a chimeric protein containing Saccharomyces cerevisiae alpha-factor secretory signal
sequence, AGIH peptide, Mus musculus 3E10 Fv antibody fragment,
Mus musculus CH1 linker, swivel sequence, epitope tags, and Homo
sapiens GRP78 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
<221> NAME/KEY: misc_feature
<222> LOCATION: (274)..(291)
<223> OTHER INFORMATION: Coding sequence: His6 tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
<223> OTHER INFORMATION: Begin of coding sequence for Mus musculus 3E10
      immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
      first codon of CDR1 resulting in a D31N change for 3E10 VH chain
      and enhanced cell penetration of the 3E10 monoclonal antibody and
      3E10 Fv antibody fragment -continued

```
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
      immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1122)
<223> OTHER INFORMATION: Coding sequence: Mus musculus immunoglobulin
      heavy chain constant domain, CH1, linker
<220> FEATURE:
<221> NAME/KEY: misc_feature
<222> LOCATION: (1123)..(1140)
<223> OTHER INFORMATION: Coding sequence: swivel sequence
<220> FEATURE:
<221> NAME/KEY: misc_feature
<222> LOCATION: (1135)..(1140)
<223> OTHER INFORMATION: BamHI restriction enzyme site
<220> FEATURE:
<221> NAME/KEY: misc_feature
<222> LOCATION: (1141)..(3105)
<223> OTHER INFORMATION: Coding sequence: Homo sapiens GRP78 sequence
<220> FEATURE:
<221> NAME/KEY: misc_feature
<222> LOCATION: (3103)..(3105)
<223> OTHER INFORMATION: Stop codon
<220> FEATURE:
<221> NAME/KEY: misc_feature
<222> LOCATION: (3106)..(3111)
<223> OTHER INFORMATION: XbaI restriction enzyme site

<400> SEQUENCE: 7 atg aga ttt cct tca ctt ttt act gct gtt tta ttc gca gca tcc tcc        48
Met Arg Phe Pro Ser Leu Phe Thr Ala Val Leu Phe Ala Ala Ser Ser
1               5                   10                  15 gca tta gct gct cca gtc aac act aca aca gaa gat gaa acg gca caa        96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc       144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg       192
Asp Val Ala Val Leu Pro Phe Ser Asn Ser Thr Asn Asn Gly Leu Leu
    50                  55                  60 ttt ata aat act act att gcc agc att gct gct aaa gaa gaa ggg gta       240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat       288
Ser Leu Glu Lys Arg Glu Ala Glu Ala Glu Phe His His His His His
                85                  90                  95 cac gca ggg att cac gac att gtc ctg aca cag tct cct gct tcc tta       336
His Ala Gly Ile His Asp Ile Val Leu Thr Gln Ser Pro Ala Ser Leu
            100                 105                 110 gct gta tct ctg ggg cag agg gcc acc atc tcc tgc agg gcc agc aaa       384
Ala Val Ser Leu Gly Gln Arg Ala Thr Ile Ser Cys Arg Ala Ser Lys
        115                 120                 125 agt gtc agt aca tct agc tat agt tac atg cac tgg tac caa cag aaa       432
Ser Val Ser Thr Ser Ser Tyr Ser Tyr Met His Trp Tyr Gln Gln Lys
```

-continued

```
            130                 135                 140
cca gga cag cca ccc aaa ctc ctc atc aag tat gca tcc tac cta gaa      480
Pro Gly Gln Pro Pro Lys Leu Leu Ile Lys Tyr Ala Ser Tyr Leu Glu
145                 150                 155                 160 tct ggg gtt cct gcc agg ttc agt ggc agt ggg tct ggg aca gac ttc      528
Ser Gly Val Pro Ala Arg Phe Ser Gly Ser Gly Ser Gly Thr Asp Phe
                165                 170                 175 acc ctc aac atc cat cct gtg gag gag gag gat gct gca aca tat tac      576
Thr Leu Asn Ile His Pro Val Glu Glu Glu Asp Ala Ala Thr Tyr Tyr
            180                 185                 190 tgt cag cac agt agg gag ttt ccg tgg acg ttc ggt gga ggc acc aag      624
Cys Gln His Ser Arg Glu Phe Pro Trp Thr Phe Gly Gly Gly Thr Lys
            195                 200                 205 ctg gaa atc aaa cgg gct gat gct gca ccc ggg ggt ggc ggt tct ggc      672
Leu Glu Ile Lys Arg Ala Asp Ala Ala Pro Gly Gly Gly Gly Ser Gly
            210                 215                 220 ggt ggc ggt tct gga ggc ggt ggc tct gag gtg cag ctg gtg gag tct      720
Gly Gly Gly Ser Gly Gly Gly Gly Ser Glu Val Gln Leu Val Glu Ser
225                 230                 235                 240 ggg gga ggc tta gtg aag cct gga ggg tcc cgg aaa ctc tcc tgt gca      768
Gly Gly Gly Leu Val Lys Pro Gly Gly Ser Arg Lys Leu Ser Cys Ala
                245                 250                 255 gcc tct gga ttc act ttc agt aac tat gga atg cac tgg gtc cgt cag      816
Ala Ser Gly Phe Thr Phe Ser Asn Tyr Gly Met His Trp Val Arg Gln
                260                 265                 270 gct cca gag aag ggg ctg gag tgg gtt gca tac att agt agt ggc agt      864
Ala Pro Glu Lys Gly Leu Glu Trp Val Ala Tyr Ile Ser Ser Gly Ser
            275                 280                 285 agt acc atc tac tat gca gac aca gtg aag ggc cga ttc acc atc tcc      912
Ser Thr Ile Tyr Tyr Ala Asp Thr Val Lys Gly Arg Phe Thr Ile Ser
            290                 295                 300 aga gac aat gcc aag aac acc ctg ttc ctg caa atg acc agt cta agg      960
Arg Asp Asn Ala Lys Asn Thr Leu Phe Leu Gln Met Thr Ser Leu Arg
305                 310                 315                 320 tct gag gac aca gcc atg cgg ggg tta cta ctt gac tac tgg ggc caa     1008
Ser Glu Asp Thr Ala Met Arg Gly Leu Leu Leu Asp Tyr Trp Gly Gln
                325                 330                 335 ggc acc act ctc aca gtc tcc tca cta gaa caa aaa ctc atc tca gaa     1056
Gly Thr Thr Leu Thr Val Ser Ser Leu Glu Gln Lys Leu Ile Ser Glu
                340                 345                 350 gag gat ctg aat agc gcc gtc gac gcc aaa aca aca gcc cca tcg gtc     1104
Glu Asp Leu Asn Ser Ala Val Asp Ala Lys Thr Thr Ala Pro Ser Val
            355                 360                 365 tat cca ctg gcc cct gta ctg gag tct tcc gga tcc atg aag ctc tcc     1152
Tyr Pro Leu Ala Pro Val Leu Glu Ser Ser Gly Ser Met Lys Leu Ser
            370                 375                 380 ctg gtg gcc gcg atg ctg ctg ctc agc gcg gcg cgg gcc gag gag     1200
Leu Val Ala Ala Met Leu Leu Leu Ser Ala Ala Arg Ala Glu Glu
385                 390                 395                 400 gag gac aag aag gag gac gtg ggc acg gtg gtc ggc atc gac ctg ggg     1248
Glu Asp Lys Lys Glu Asp Val Gly Thr Val Val Gly Ile Asp Leu Gly
                405                 410                 415 acc acc tac tcc tgc gtc ggc gtg ttc aag aac ggc cgc gtg gag atc     1296
Thr Thr Tyr Ser Cys Val Gly Val Phe Lys Asn Gly Arg Val Glu Ile
                420                 425                 430 atc gcc aac gat cag ggc aac cgc atc acg ccg tcc tat gtc gcc ttc     1344
Ile Ala Asn Asp Gln Gly Asn Arg Ile Thr Pro Ser Tyr Val Ala Phe
            435                 440                 445 act cct gaa ggg gaa cgt ctg att ggc gat gcc gcc aag aac cag ctc     1392
```

-continued

```
Thr Pro Glu Gly Glu Arg Leu Ile Gly Asp Ala Ala Lys Asn Gln Leu
    450             455             460 acc tcc aac ccc gag aac acg gtc ttt gac gcc aag cgg ctc atc ggc     1440
Thr Ser Asn Pro Glu Asn Thr Val Phe Asp Ala Lys Arg Leu Ile Gly
465             470             475             480 cgc acg tgg aat gac ccg tct gtg cag cag gac atc aag ttc ttg ccg     1488
Arg Thr Trp Asn Asp Pro Ser Val Gln Gln Asp Ile Lys Phe Leu Pro
                485             490             495 ttc aag gtg gtt gaa aag aaa act aaa cca tac att caa gtt gat att     1536
Phe Lys Val Val Glu Lys Lys Thr Lys Pro Tyr Ile Gln Val Asp Ile
            500             505             510 gga ggt ggg caa aca aag aca ttt gct cct gaa gaa att tct gcc atg     1584
Gly Gly Gly Gln Thr Lys Thr Phe Ala Pro Glu Glu Ile Ser Ala Met
            515             520             525 gtt ctc act aaa atg aaa gaa acc gct gag gct tat ttg gga aag aag     1632
Val Leu Thr Lys Met Lys Glu Thr Ala Glu Ala Tyr Leu Gly Lys Lys
    530             535             540 gtt acc cat gca gtt gtt act gta cca gcc tat ttt aat gat gcc caa     1680
Val Thr His Ala Val Val Thr Val Pro Ala Tyr Phe Asn Asp Ala Gln
545             550             555             560 cgc caa gca acc aaa gac gct gga act att gct ggc cta aat gtt atg     1728
Arg Gln Ala Thr Lys Asp Ala Gly Thr Ile Ala Gly Leu Asn Val Met
            565             570             575 agg atc atc aac gag cct acg gca gct gct att gct tat ggc ctg gat     1776
Arg Ile Ile Asn Glu Pro Thr Ala Ala Ala Ile Ala Tyr Gly Leu Asp
            580             585             590 aag agg gag ggg gag aag aac atc ctg gtg ttt gac ctg ggt ggc gga     1824
Lys Arg Glu Gly Glu Lys Asn Ile Leu Val Phe Asp Leu Gly Gly Gly
            595             600             605 acc ttc gat gtg tct ctt ctc acc att gac aat ggt gtc ttc gaa gtt     1872
Thr Phe Asp Val Ser Leu Leu Thr Ile Asp Asn Gly Val Phe Glu Val
    610             615             620 gtg gcc act aat gga gat act cat ctg ggt gga gaa gac ttt gac cag     1920
Val Ala Thr Asn Gly Asp Thr His Leu Gly Gly Glu Asp Phe Asp Gln
625             630             635             640 cgt gtc atg gaa cac ttc atc aaa ctg tac aaa aag aag acg ggc aaa     1968
Arg Val Met Glu His Phe Ile Lys Leu Tyr Lys Lys Lys Thr Gly Lys
            645             650             655 gat gtc agg aaa gac aat aga gct gtg cag aaa ctc cgg cgc gag gta     2016
Asp Val Arg Lys Asp Asn Arg Ala Val Gln Lys Leu Arg Arg Glu Val
            660             665             670 gaa aag gcc aaa cgg gcc ctg tct tct cag cat caa gca aga att gaa     2064
Glu Lys Ala Lys Arg Ala Leu Ser Ser Gln His Gln Ala Arg Ile Glu
            675             680             685 att gag tcc ttc tat gaa gga gaa gac ttt tct gag acc ctg act cgg     2112
Ile Glu Ser Phe Tyr Glu Gly Glu Asp Phe Ser Glu Thr Leu Thr Arg
            690             695             700 gcc aaa ttt gaa gag ctc aac atg gat ctg ttc cgg tct act atg aag     2160
Ala Lys Phe Glu Glu Leu Asn Met Asp Leu Phe Arg Ser Thr Met Lys
705             710             715             720 ccc gtc cag aaa gtg ttg gaa gat tct gat ttg aag aag tct gat att     2208
Pro Val Gln Lys Val Leu Glu Asp Ser Asp Leu Lys Lys Ser Asp Ile
            725             730             735 gat gaa att gtt ctt gtt ggt ggc tcg act cga att cca aag att cag     2256
Asp Glu Ile Val Leu Val Gly Gly Ser Thr Arg Ile Pro Lys Ile Gln
            740             745             750 caa ctg gtt aaa gag ttc ttc aat ggc aag gaa cca tcc cgt ggc ata     2304
Gln Leu Val Lys Glu Phe Phe Asn Gly Lys Glu Pro Ser Arg Gly Ile
            755             760             765
```

-continued

```
aac cca gat gaa gct gta gcg tat ggt gct gct gtc cag gct ggt gtg          2352
Asn Pro Asp Glu Ala Val Ala Tyr Gly Ala Ala Val Gln Ala Gly Val
    770             775                 780 ctc tct ggt gat caa gat aca ggt gac ctg gta ctg ctt gat gta tgt          2400
Leu Ser Gly Asp Gln Asp Thr Gly Asp Leu Val Leu Leu Asp Val Cys
785             790                 795                 800 ccc ctt aca ctt ggt att gaa act gtg gga ggt gtc atg acc aaa ctg          2448
Pro Leu Thr Leu Gly Ile Glu Thr Val Gly Gly Val Met Thr Lys Leu
                805                 810                 815 att cca agg aac aca gtg gtg cct acc aag aag tct cag atc ttt tct          2496
Ile Pro Arg Asn Thr Val Val Pro Thr Lys Lys Ser Gln Ile Phe Ser
            820                 825                 830 aca gct tct gat aat caa cca act gtt aca atc aag gtc tat gaa ggt          2544
Thr Ala Ser Asp Asn Gln Pro Thr Val Thr Ile Lys Val Tyr Glu Gly
            835                 840                 845 gaa aga ccc ctg aca aaa gac aat cat ctt ctg ggt aca ttt gat ctg          2592
Glu Arg Pro Leu Thr Lys Asp Asn His Leu Leu Gly Thr Phe Asp Leu
    850                 855                 860 act gga att cct cct gct cct cgt ggg gtc cca cag att gaa gtc acc          2640
Thr Gly Ile Pro Pro Ala Pro Arg Gly Val Pro Gln Ile Glu Val Thr
865                 870                 875                 880 ttt gag ata gat gtg aat ggt att ctt cga gtg aca gct gaa gac aag          2688
Phe Glu Ile Asp Val Asn Gly Ile Leu Arg Val Thr Ala Glu Asp Lys
                885                 890                 895 ggt aca ggg aac aaa aat aag atc aca atc acc aat gac cag aat cgc          2736
Gly Thr Gly Asn Lys Asn Lys Ile Thr Ile Thr Asn Asp Gln Asn Arg
                900                 905                 910 ctg aca cct gaa gaa atc gaa agg atg gtt aat gat gct gag aag ttt          2784
Leu Thr Pro Glu Glu Ile Glu Arg Met Val Asn Asp Ala Glu Lys Phe
            915                 920                 925 gct gag gaa gac aaa aag ctc aag gag cgc att gat act aga aat gag          2832
Ala Glu Glu Asp Lys Lys Leu Lys Glu Arg Ile Asp Thr Arg Asn Glu
    930                 935                 940 ttg gaa agc tat gcc tat tct cta aag aat cag att gga gat aaa gaa          2880
Leu Glu Ser Tyr Ala Tyr Ser Leu Lys Asn Gln Ile Gly Asp Lys Glu
945                 950                 955                 960 aag ctg gga ggt aaa ctt tcc tct gaa gat aag gag acc atg gaa aaa          2928
Lys Leu Gly Gly Lys Leu Ser Ser Glu Asp Lys Glu Thr Met Glu Lys
                965                 970                 975 gct gta gaa gaa aag att gaa tgg ctg gaa agc cac caa gat gct gac          2976
Ala Val Glu Glu Lys Ile Glu Trp Leu Glu Ser His Gln Asp Ala Asp
                980                 985                 990 att gaa gac ttc aaa gct aag aag  aag gaa ctg gaa gaa  att gtt caa       3024
Ile Glu Asp Phe Lys Ala Lys Lys  Lys Glu Leu Glu Glu  Ile Val Gln
            995                 1000                1005 cca att  atc agc aaa ctc tat  gga agt gca ggc cct  ccc cca act          3069
Pro Ile  Ile Ser Lys Leu Tyr  Gly Ser Ala Gly Pro  Pro Pro Thr
    1010                1015                1020 ggt gaa  gag gat aca gca gaa  aaa gat gag ttg tag tctaga                 3111
Gly Glu  Glu Asp Thr Ala Glu  Lys Asp Glu Leu
    1025                1030
```

<210> SEQ ID NO 8
<211> LENGTH: 1034
<212> TYPE: PRT
<213> ORGANISM: Artificial Sequence
<220> FEATURE:
<223> OTHER INFORMATION: Synthetic Construct

<400> SEQUENCE: 8

Met Arg Phe Pro Ser Leu Phe Thr Ala Val Leu Phe Ala Ala Ser Ser

-continued

```
 1                5                   10                  15
Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
             35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His
             85                  90                  95

His Ala Gly Ile His Asp Ile Val Leu Thr Gln Ser Pro Ala Ser Leu
             100                 105                 110

Ala Val Ser Leu Gly Gln Arg Ala Thr Ile Ser Cys Arg Ala Ser Lys
             115                 120                 125

Ser Val Ser Thr Ser Ser Tyr Ser Tyr Met His Trp Tyr Gln Gln Lys
     130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
             165                 170                 175

Thr Leu Asn Ile His Pro Val Glu Glu Glu Asp Ala Ala Thr Tyr Tyr
             180                 185                 190

Cys Gln His Ser Arg Glu Phe Pro Trp Thr Phe Gly Gly Gly Thr Lys
             195                 200                 205

Leu Glu Ile Lys Arg Ala Asp Ala Ala Pro Gly Gly Gly Ser Gly
     210                 215                 220

Gly Gly Gly Ser Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
             245                 250                 255

Ala Ser Gly Phe Thr Phe Ser Asn Tyr Gly Met His Trp Val Arg Gln
             260                 265                 270

Ala Pro Glu Lys Gly Leu Glu Trp Val Ala Tyr Ile Ser Ser Gly Ser
             275                 280                 285

Ser Thr Ile Tyr Tyr Ala Asp Thr Val Lys Gly Arg Phe Thr Ile Ser
     290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
             325                 330                 335

Gly Thr Thr Leu Thr Val Ser Ser Leu Glu Gln Lys Leu Ile Ser Glu
             340                 345                 350

Glu Asp Leu Asn Ser Ala Val Asp Ala Lys Thr Thr Ala Pro Ser Val
             355                 360                 365

Tyr Pro Leu Ala Pro Val Leu Glu Ser Ser Gly Ser Met Lys Leu Ser
     370                 375                 380

Leu Val Ala Ala Met Leu Leu Leu Ser Ala Ala Arg Ala Glu Glu
385                 390                 395                 400

Glu Asp Lys Lys Glu Asp Val Gly Thr Val Val Gly Ile Asp Leu Gly
             405                 410                 415

Thr Thr Tyr Ser Cys Val Gly Val Phe Lys Asn Gly Arg Val Glu Ile
             420                 425                 430
```

-continued

```
Ile Ala Asn Asp Gln Gly Asn Arg Ile Thr Pro Ser Tyr Val Ala Phe
        435             440             445

Thr Pro Glu Gly Glu Arg Leu Ile Gly Asp Ala Ala Lys Asn Gln Leu
        450             455             460

Thr Ser Asn Pro Glu Asn Thr Val Phe Asp Ala Lys Arg Leu Ile Gly
465             470             475             480

Arg Thr Trp Asn Asp Pro Ser Val Gln Gln Asp Ile Lys Phe Leu Pro
                485             490             495

Phe Lys Val Val Glu Lys Lys Thr Lys Pro Tyr Ile Gln Val Asp Ile
                500             505             510

Gly Gly Gly Gln Thr Lys Thr Phe Ala Pro Glu Glu Ile Ser Ala Met
        515             520             525

Val Leu Thr Lys Met Lys Glu Thr Ala Glu Ala Tyr Leu Gly Lys Lys
        530             535             540

Val Thr His Ala Val Val Thr Val Pro Ala Tyr Phe Asn Asp Ala Gln
545             550             555             560

Arg Gln Ala Thr Lys Asp Ala Gly Thr Ile Ala Gly Leu Asn Val Met
                565             570             575

Arg Ile Ile Asn Glu Pro Thr Ala Ala Ala Ile Ala Tyr Gly Leu Asp
                580             585             590

Lys Arg Glu Gly Glu Lys Asn Ile Leu Val Phe Asp Leu Gly Gly Gly
        595             600             605

Thr Phe Asp Val Ser Leu Leu Thr Ile Asp Asn Gly Val Phe Glu Val
        610             615             620

Val Ala Thr Asn Gly Asp Thr His Leu Gly Gly Glu Asp Phe Asp Gln
625             630             635             640

Arg Val Met Glu His Phe Ile Lys Leu Tyr Lys Lys Lys Thr Gly Lys
                645             650             655

Asp Val Arg Lys Asp Asn Arg Ala Val Gln Lys Leu Arg Arg Glu Val
                660             665             670

Glu Lys Ala Lys Arg Ala Leu Ser Ser Gln His Gln Ala Arg Ile Glu
        675             680             685

Ile Glu Ser Phe Tyr Glu Gly Glu Asp Phe Ser Glu Thr Leu Thr Arg
        690             695             700

Ala Lys Phe Glu Glu Leu Asn Met Asp Leu Phe Arg Ser Thr Met Lys
705             710             715             720

Pro Val Gln Lys Val Leu Glu Asp Ser Asp Leu Lys Lys Ser Asp Ile
                725             730             735

Asp Glu Ile Val Leu Val Gly Gly Ser Thr Arg Ile Pro Lys Ile Gln
                740             745             750

Gln Leu Val Lys Glu Phe Phe Asn Gly Lys Glu Pro Ser Arg Gly Ile
        755             760             765

Asn Pro Asp Glu Ala Val Ala Tyr Gly Ala Ala Val Gln Ala Gly Val
        770             775             780

Leu Ser Gly Asp Gln Asp Thr Gly Asp Leu Val Leu Leu Asp Val Cys
785             790             795             800

Pro Leu Thr Leu Gly Ile Glu Thr Val Gly Gly Val Met Thr Lys Leu
                805             810             815

Ile Pro Arg Asn Thr Val Val Pro Thr Lys Lys Ser Gln Ile Phe Ser
                820             825             830

Thr Ala Ser Asp Asn Gln Pro Thr Val Thr Ile Lys Val Tyr Glu Gly
        835             840             845
```

```
Glu Arg Pro Leu Thr Lys Asp Asn His Leu Leu Gly Thr Phe Asp Leu
    850             855             860

Thr Gly Ile Pro Pro Ala Pro Arg Gly Val Pro Gln Ile Glu Val Thr
865             870             875             880

Phe Glu Ile Asp Val Asn Gly Ile Leu Arg Val Thr Ala Glu Asp Lys
            885             890             895

Gly Thr Gly Asn Lys Asn Lys Ile Thr Ile Thr Asn Asp Gln Asn Arg
            900             905             910

Leu Thr Pro Glu Glu Ile Glu Arg Met Val Asn Asp Ala Glu Lys Phe
            915             920             925

Ala Glu Glu Asp Lys Lys Leu Lys Glu Arg Ile Asp Thr Arg Asn Glu
    930             935             940

Leu Glu Ser Tyr Ala Tyr Ser Leu Lys Asn Gln Ile Gly Asp Lys Glu
945             950             955             960

Lys Leu Gly Gly Lys Leu Ser Ser Glu Asp Lys Glu Thr Met Glu Lys
            965             970             975

Ala Val Glu Glu Lys Ile Glu Trp Leu Glu Ser His Gln Asp Ala Asp
            980             985             990

Ile Glu Asp Phe Lys Ala Lys Lys  Lys Glu Leu Glu Glu  Ile Val Gln
            995             1000             1005

Pro Ile  Ile Ser Lys Leu Tyr  Gly Ser Ala Gly Pro  Pro Pro Thr
    1010             1015             1020

Gly Glu  Glu Asp Thr Ala Glu  Lys Asp Glu Leu
    1025             1030
```

<210> SEQ ID NO 9
<211> LENGTH: 1034
<212> TYPE: PRT
<213> ORGANISM: Artificial Sequence
<220> FEATURE:
<223> OTHER INFORMATION: 3E10 Fv-GRP78 amino acid sequence for a
      chimeric protein comprising a single chain Fv antibody fragment
      derived from Mus musculus 3E10 hybridoma and GRP78 from Homo
      sapiens joined by mouse CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
      signal sequence for secretion of fusion protein, provided by
      pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
      removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility
<220> FEATURE:
<221> NAME/KEY: MISC_FEATURE
<222> LOCATION: (102)..(102)
<223> OTHER INFORMATION: Begin Mus musculus 3E10 immunoglobulin variable -continued

```
light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting
      in enhanced cell penetration of the 3E10 monoclonal antibody and
      3E10 Fv antibody fragment
<220> FEATURE:
<221> NAME/KEY: MISC_FEATURE
<222> LOCATION: (264)..(264)
<223> OTHER INFORMATION: Asparagine (N) in place of aspartic acid in
      3E10 variable heavy chain, VH, conferring enhanced cell
      penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
      chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(374)
<223> OTHER INFORMATION: Mus musculus immunoglobulin heavy chain
      constant domain, CH1, linker
<220> FEATURE:
<221> NAME/KEY: MISC_FEATURE
<222> LOCATION: (375)..(380)
<223> OTHER INFORMATION: Swivel sequence
<220> FEATURE:
<221> NAME/KEY: MISC_FEATURE
<222> LOCATION: (381)..(1034)
<223> OTHER INFORMATION: Homo sapiens GRP78 sequence

<400> SEQUENCE: 9

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30
```

-continued

```
Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
                85                  90                  95

His Ala Gly Ile His Asp Ile Val Leu Thr Gln Ser Pro Ala Ser Leu
                100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
        195                 200                 205

Leu Glu Ile Lys Arg Ala Asp Ala Ala Pro Gly Gly Gly Gly Ser Gly
        210                 215                 220

Gly Gly Gly Ser Gly Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
        260                 265                 270

Ala Pro Glu Lys Gly Leu Glu Trp Val Ala Tyr Ile Ser Ser Gly Ser
        275                 280                 285

Ser Thr Ile Tyr Tyr Ala Asp Thr Val Lys Gly Arg Phe Thr Ile Ser
    290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
            340                 345                 350

Glu Asp Leu Asn Ser Ala Val Asp Ala Lys Thr Thr Ala Pro Ser Val
        355                 360                 365

Tyr Pro Leu Ala Pro Val Leu Glu Ser Ser Gly Ser Met Lys Leu Ser
    370                 375                 380

Leu Val Ala Ala Met Leu Leu Leu Leu Ser Ala Ala Arg Ala Glu Glu
385                 390                 395                 400

Glu Asp Lys Lys Glu Asp Val Gly Thr Val Val Gly Ile Asp Leu Gly
                405                 410                 415

Thr Thr Tyr Ser Cys Val Gly Val Phe Lys Asn Gly Arg Val Glu Ile
            420                 425                 430

Ile Ala Asn Asp Gln Gly Asn Arg Ile Thr Pro Ser Tyr Val Ala Phe
        435                 440                 445

Thr Pro Glu Gly Glu Arg Leu Ile Gly Asp Ala Ala Lys Asn Gln Leu
```

```
            450             455             460

Thr Ser Asn Pro Glu Asn Thr Val Phe Asp Ala Lys Arg Leu Ile Gly
465             470             475             480

Arg Thr Trp Asn Asp Pro Ser Val Gln Gln Asp Ile Lys Phe Leu Pro
            485             490             495

Phe Lys Val Val Glu Lys Lys Thr Lys Pro Tyr Ile Gln Val Asp Ile
            500             505             510

Gly Gly Gly Gln Thr Lys Thr Phe Ala Pro Glu Glu Ile Ser Ala Met
            515             520             525

Val Leu Thr Lys Met Lys Glu Thr Ala Glu Ala Tyr Leu Gly Lys Lys
            530             535             540

Val Thr His Ala Val Val Thr Val Pro Ala Tyr Phe Asn Asp Ala Gln
545             550             555             560

Arg Gln Ala Thr Lys Asp Ala Gly Thr Ile Ala Gly Leu Asn Val Met
            565             570             575

Arg Ile Ile Asn Glu Pro Thr Ala Ala Ala Ile Ala Tyr Gly Leu Asp
            580             585             590

Lys Arg Glu Gly Glu Lys Asn Ile Leu Val Phe Asp Leu Gly Gly Gly
            595             600             605

Thr Phe Asp Val Ser Leu Leu Thr Ile Asp Asn Gly Val Phe Glu Val
            610             615             620

Val Ala Thr Asn Gly Asp Thr His Leu Gly Gly Glu Asp Phe Asp Gln
625             630             635             640

Arg Val Met Glu His Phe Ile Lys Leu Tyr Lys Lys Lys Thr Gly Lys
            645             650             655

Asp Val Arg Lys Asp Asn Arg Ala Val Gln Lys Leu Arg Arg Glu Val
            660             665             670

Glu Lys Ala Lys Arg Ala Leu Ser Ser Gln His Gln Ala Arg Ile Glu
            675             680             685

Ile Glu Ser Phe Tyr Glu Gly Glu Asp Phe Ser Glu Thr Leu Thr Arg
            690             695             700

Ala Lys Phe Glu Glu Leu Asn Met Asp Leu Phe Arg Ser Thr Met Lys
705             710             715             720

Pro Val Gln Lys Val Leu Glu Asp Ser Asp Leu Lys Lys Ser Asp Ile
            725             730             735

Asp Glu Ile Val Leu Val Gly Gly Ser Thr Arg Ile Pro Lys Ile Gln
            740             745             750

Gln Leu Val Lys Glu Phe Phe Asn Gly Lys Glu Pro Ser Arg Gly Ile
            755             760             765

Asn Pro Asp Glu Ala Val Ala Tyr Gly Ala Ala Val Gln Ala Gly Val
            770             775             780

Leu Ser Gly Asp Gln Asp Thr Gly Asp Leu Val Leu Leu Asp Val Cys
785             790             795             800

Pro Leu Thr Leu Gly Ile Glu Thr Val Gly Gly Val Met Thr Lys Leu
            805             810             815

Ile Pro Arg Asn Thr Val Val Pro Thr Lys Lys Ser Gln Ile Phe Ser
            820             825             830

Thr Ala Ser Asp Asn Gln Pro Thr Val Thr Ile Lys Val Tyr Glu Gly
            835             840             845

Glu Arg Pro Leu Thr Lys Asp Asn His Leu Leu Gly Thr Phe Asp Leu
            850             855             860

Thr Gly Ile Pro Pro Ala Pro Arg Gly Val Pro Gln Ile Glu Val Thr
865             870             875             880
```

-continued

```
Phe Glu Ile Asp Val Asn Gly Ile Leu Arg Val Thr Ala Glu Asp Lys
            885               890               895

Gly Thr Gly Asn Lys Asn Lys Ile Thr Ile Thr Asn Asp Gln Asn Arg
            900               905               910

Leu Thr Pro Glu Glu Ile Glu Arg Met Val Asn Asp Ala Glu Lys Phe
        915               920               925

Ala Glu Glu Asp Lys Lys Leu Lys Glu Arg Ile Asp Thr Arg Asn Glu
    930               935               940

Leu Glu Ser Tyr Ala Tyr Ser Leu Lys Asn Gln Ile Gly Asp Lys Glu
945               950               955               960

Lys Leu Gly Gly Lys Leu Ser Ser Glu Asp Lys Glu Thr Met Glu Lys
            965               970               975

Ala Val Glu Glu Lys Ile Glu Trp Leu Glu Ser His Gln Asp Ala Asp
            980               985               990

Ile Glu Asp Phe Lys Ala Lys Lys  Lys Glu Leu Glu Glu  Ile Val Gln
        995               1000               1005

Pro Ile  Ile Ser Lys Leu Tyr  Gly Ser Ala Gly Pro  Pro Pro Thr
    1010               1015               1020

Gly Glu  Glu Asp Thr Ala Glu  Lys Asp Glu Leu
    1025               1030
```

```
<210> SEQ ID NO 10
<211> LENGTH: 3345
<212> TYPE: DNA
<213> ORGANISM: Artificial Sequence
<220> FEATURE:
<223> OTHER INFORMATION: 3E10 Fv-Hsp90 nucleotide sequence encoding a
      chimeric protein comprising a single chain Fv antibody fragment
      derived from Mus musculus 3E10 hybridoma and Hsp90 from Homo
      sapiens joined by mouse CH1 linker and swivel sequence
<220> FEATURE:
<221> NAME/KEY: CDS
<222> LOCATION: (1)..(3339)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Mus musculus CH1 linker, swivel sequence, epitope tags, and Homo
      sapiens Hsp90 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
<221> NAME/KEY: misc_feature
```

```
<222> LOCATION: (274)..(291)
<223> OTHER INFORMATION: His6 tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
<223> OTHER INFORMATION: Begin of coding sequence for Mus musculus 3E10
      immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
      first codon of CDR1 resulting in a D31N change for 3E10 VH chain
      and enhanced cell penetration of the 3E10 monoclonal antibody and
      3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
      immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1122)
<223> OTHER INFORMATION: Coding sequence: Mus musculus immunoglobulin
      heavy chain constant domain, CH1, linker
<220> FEATURE:
<221> NAME/KEY: misc_feature
<222> LOCATION: (1123)..(1140)
<223> OTHER INFORMATION: Coding sequence: swivel sequence
<220> FEATURE:
<221> NAME/KEY: misc_feature
<222> LOCATION: (1135)..(1140)
<223> OTHER INFORMATION: BamHI restriction enzyme site
<220> FEATURE:
<221> NAME/KEY: misc_feature
<222> LOCATION: (1141)..(3339)
<223> OTHER INFORMATION: Coding sequence: Homo sapiens Hsp90 sequence
```

```
<220> FEATURE:
<221> NAME/KEY: misc_feature
<222> LOCATION: (3337)..(3339)
<223> OTHER INFORMATION: Stop codon
<220> FEATURE:
<221> NAME/KEY: misc_feature
<222> LOCATION: (3340)..(3345)
<223> OTHER INFORMATION: XbaI restriction enzyme site

<400> SEQUENCE: 10 atg aga ttt cct tca ctt ttt act gct gtt tta ttc gca gca tcc tcc      48
Met Arg Phe Pro Ser Leu Phe Thr Ala Val Leu Phe Ala Ala Ser Ser
1               5                   10                  15 gca tta gct gct cca gtc aac act aca aca gaa gat gaa acg gca caa      96
Ala Leu Ala Ala Pro Val Asn Thr Thr Thr Glu Asp Glu Thr Ala Gln
                20                  25                  30 att ccg gct gaa gct gtc atc ggt tac tca gat tta gaa ggg gat ttc     144
Ile Pro Ala Glu Ala Val Ile Gly Tyr Ser Asp Leu Glu Gly Asp Phe
            35                  40                  45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu
        50                  55                  60 ttt ata aat act act att gcc agc att gct gct aaa gaa gaa ggg gta     240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat     288
Ser Leu Glu Lys Arg Glu Ala Glu Ala Glu Phe His His His His His
                85                  90                  95 cac gca ggg att cac gac att gtc ctg aca cag tct cct gct tcc tta     336
His Ala Gly Ile His Asp Ile Val Leu Thr Gln Ser Pro Ala Ser Leu
            100                 105                 110 gct gta tct ctg ggg cag agg gcc acc atc tcc tgc agg gcc agc aaa     384
Ala Val Ser Leu Gly Gln Arg Ala Thr Ile Ser Cys Arg Ala Ser Lys
        115                 120                 125 agt gtc agt aca tct agc tat agt tac atg cac tgg tac caa cag aaa     432
Ser Val Ser Thr Ser Ser Tyr Ser Tyr Met His Trp Tyr Gln Gln Lys
    130                 135                 140 cca gga cag cca ccc aaa ctc ctc atc aag tat gca tcc tac cta gaa     480
Pro Gly Gln Pro Pro Lys Leu Leu Ile Lys Tyr Ala Ser Tyr Leu Glu
145                 150                 155                 160 tct ggg gtt cct gcc agg ttc agt ggc agt ggg tct ggg aca gac ttc     528
Ser Gly Val Pro Ala Arg Phe Ser Gly Ser Gly Ser Gly Thr Asp Phe
                165                 170                 175 acc ctc aac atc cat cct gtg gag gag gag gat gct gca aca tat tac     576
Thr Leu Asn Ile His Pro Val Glu Glu Glu Asp Ala Ala Thr Tyr Tyr
            180                 185                 190 tgt cag cac agt agg gag ttt ccg tgg acg ttc ggt gga ggc acc aag     624
Cys Gln His Ser Arg Glu Phe Pro Trp Thr Phe Gly Gly Gly Thr Lys
        195                 200                 205 ctg gaa atc aaa cgg gct gat gct gca ccc ggg ggt ggc ggt tct ggc     672
Leu Glu Ile Lys Arg Ala Asp Ala Ala Pro Gly Gly Gly Gly Ser Gly
    210                 215                 220 ggt ggc ggt tct gga ggc ggt ggc tct gag gtg cag ctg gtg gag tct     720
Gly Gly Gly Ser Gly Gly Gly Gly Ser Glu Val Gln Leu Val Glu Ser
225                 230                 235                 240 ggg gga ggc tta gtg aag cct gga ggg tcc cgg aaa ctc tcc tgt gca     768
Gly Gly Gly Leu Val Lys Pro Gly Gly Ser Arg Lys Leu Ser Cys Ala
                245                 250                 255 gcc tct gga ttc act ttc agt aac tat gga atg cac tgg gtc cgt cag     816
Ala Ser Gly Phe Thr Phe Ser Asn Tyr Gly Met His Trp Val Arg Gln
            260                 265                 270
```

-continued

```
gct cca gag aag ggg ctg gag tgg gtt gca tac att agt agt ggc agt      864
Ala Pro Glu Lys Gly Leu Glu Trp Val Ala Tyr Ile Ser Ser Gly Ser
        275                 280                 285 agt acc atc tac tat gca gac aca gtg aag ggc cga ttc acc atc tcc      912
Ser Thr Ile Tyr Tyr Ala Asp Thr Val Lys Gly Arg Phe Thr Ile Ser
    290                 295                 300 aga gac aat gcc aag aac acc ctg ttc ctg caa atg acc agt cta agg      960
Arg Asp Asn Ala Lys Asn Thr Leu Phe Leu Gln Met Thr Ser Leu Arg
305                 310                 315                 320 tct gag gac aca gcc atg cgg ggg tta cta ctt gac tac tgg ggc caa     1008
Ser Glu Asp Thr Ala Met Arg Gly Leu Leu Leu Asp Tyr Trp Gly Gln
                325                 330                 335 ggc acc act ctc aca gtc tcc tca cta gaa caa aaa ctc atc tca gaa     1056
Gly Thr Thr Leu Thr Val Ser Ser Leu Glu Gln Lys Leu Ile Ser Glu
            340                 345                 350 gag gat ctg aat agc gcc gtc gac gcc aaa aca aca gcc cca tcg gtc     1104
Glu Asp Leu Asn Ser Ala Val Asp Ala Lys Thr Thr Ala Pro Ser Val
        355                 360                 365 tat cca ctg gcc cct gta ctg gag tct tcc gga tcc atg cct gag gaa     1152
Tyr Pro Leu Ala Pro Val Leu Glu Ser Ser Gly Ser Met Pro Glu Glu
    370                 375                 380 acc cag acc caa gac caa ccg atg gag gag gag gag gtt gag acg ttc     1200
Thr Gln Thr Gln Asp Gln Pro Met Glu Glu Glu Glu Val Glu Thr Phe
385                 390                 395                 400 gcc ttt cag gca gaa att gcc cag ttg atg tca ttg atc atc aat act     1248
Ala Phe Gln Ala Glu Ile Ala Gln Leu Met Ser Leu Ile Ile Asn Thr
                405                 410                 415 ttc tac tcg aac aaa gag atc ttt ctg aga gag ctc att tca aat tca     1296
Phe Tyr Ser Asn Lys Glu Ile Phe Leu Arg Glu Leu Ile Ser Asn Ser
                420                 425                 430 tca gat gca ttg gac aaa atc cgg tat gaa agc ttg aca gat ccc agt     1344
Ser Asp Ala Leu Asp Lys Ile Arg Tyr Glu Ser Leu Thr Asp Pro Ser
        435                 440                 445 aaa tta gac tct ggg aaa gag ctg cat att aac ctt ata ccg aac aaa     1392
Lys Leu Asp Ser Gly Lys Glu Leu His Ile Asn Leu Ile Pro Asn Lys
    450                 455                 460 caa gat cga act ctc act att gtg gat act gga att gga atg acc aag     1440
Gln Asp Arg Thr Leu Thr Ile Val Asp Thr Gly Ile Gly Met Thr Lys
465                 470                 475                 480 gct gac ttg atc aat aac ctt ggt act atc gcc aag tct ggg acc aaa     1488
Ala Asp Leu Ile Asn Asn Leu Gly Thr Ile Ala Lys Ser Gly Thr Lys
                485                 490                 495 gcg ttc atg gaa gct ttg cag gct ggt gca gat atc tct atg att ggc     1536
Ala Phe Met Glu Ala Leu Gln Ala Gly Ala Asp Ile Ser Met Ile Gly
                500                 505                 510 cag ttc ggt gtt ggt ttt tat tct gct tat ttg gtt gct gag aaa gta     1584
Gln Phe Gly Val Gly Phe Tyr Ser Ala Tyr Leu Val Ala Glu Lys Val
        515                 520                 525 act gtg atc acc aaa cat aac gat gat gag cag tac gct tgg gag tcc     1632
Thr Val Ile Thr Lys His Asn Asp Asp Glu Gln Tyr Ala Trp Glu Ser
    530                 535                 540 tca gca ggg gga tca ttc aca gtg agg aca gac aca ggt gaa cct atg     1680
Ser Ala Gly Gly Ser Phe Thr Val Arg Thr Asp Thr Gly Glu Pro Met
545                 550                 555                 560 ggt cgt gga aca aaa gtt atc cta cac ctg aaa gaa gac caa act gag     1728
Gly Arg Gly Thr Lys Val Ile Leu His Leu Lys Glu Asp Gln Thr Glu
                565                 570                 575 tac ttg gag gaa cga aga ata aag gag att gtg aag aaa cat tct cag     1776
Tyr Leu Glu Glu Arg Arg Ile Lys Glu Ile Val Lys Lys His Ser Gln
                580                 585                 590
```

-continued

```
ttt att gga tat ccc att act ctt ttt gtg gag aag gaa cgt gat aaa    1824
Phe Ile Gly Tyr Pro Ile Thr Leu Phe Val Glu Lys Glu Arg Asp Lys
        595             600             605 gaa gta agc gat gat gag gct gaa gaa aag gaa gac aaa gaa gaa gaa    1872
Glu Val Ser Asp Asp Glu Ala Glu Glu Lys Glu Asp Lys Glu Glu Glu
610             615             620 aaa gaa aaa gaa gag aaa gag tcg gaa gac aaa cct gaa att gaa gat    1920
Lys Glu Lys Glu Glu Lys Glu Ser Glu Asp Lys Pro Glu Ile Glu Asp
625             630             635             640 gtt ggt tct gat gag gaa gaa gaa aag aag gat ggt gac aag aag aag    1968
Val Gly Ser Asp Glu Glu Glu Glu Lys Lys Asp Gly Asp Lys Lys Lys
            645             650             655 aag aag aag att aag gaa aag tac atc gat caa gaa gag ctc aac aaa    2016
Lys Lys Lys Ile Lys Glu Lys Tyr Ile Asp Gln Glu Glu Leu Asn Lys
            660             665             670 aca aag ccc atc tgg acc aga aat ccc gac gat att act aat gag gag    2064
Thr Lys Pro Ile Trp Thr Arg Asn Pro Asp Asp Ile Thr Asn Glu Glu
            675             680             685 tac gga gaa ttc tat aag agc ttg acc aat gac tgg gaa gat cac ttg    2112
Tyr Gly Glu Phe Tyr Lys Ser Leu Thr Asn Asp Trp Glu Asp His Leu
            690             695             700 gca gtg aag cat ttt tca gtt gaa gga cag ttg gaa ttc aga gcc ctt    2160
Ala Val Lys His Phe Ser Val Glu Gly Gln Leu Glu Phe Arg Ala Leu
705             710             715             720 cta ttt gtc cca cga cgt gct cct ttt gat ctg ttt gaa aac aga aag    2208
Leu Phe Val Pro Arg Arg Ala Pro Phe Asp Leu Phe Glu Asn Arg Lys
                725             730             735 aaa aag aac aac atc aaa ttg tat gta cgc aga gtt ttc atc atg gat    2256
Lys Lys Asn Asn Ile Lys Leu Tyr Val Arg Arg Val Phe Ile Met Asp
            740             745             750 aac tgt gag gag cta atc cct gaa tat ctg aac ttc att aga ggg gtg    2304
Asn Cys Glu Glu Leu Ile Pro Glu Tyr Leu Asn Phe Ile Arg Gly Val
            755             760             765 gta gac tcg gag gat ctc cct cta aac ata tcc cgt gag atg ttg caa    2352
Val Asp Ser Glu Asp Leu Pro Leu Asn Ile Ser Arg Glu Met Leu Gln
770             775             780 caa agc aaa att ttg aaa gtt atc agg aag aat ttg gtc aaa aaa tgc    2400
Gln Ser Lys Ile Leu Lys Val Ile Arg Lys Asn Leu Val Lys Lys Cys
785             790             795             800 tta gaa ctc ttt act gaa ctg gcg gaa gat aaa gag aac tac aag aaa    2448
Leu Glu Leu Phe Thr Glu Leu Ala Glu Asp Lys Glu Asn Tyr Lys Lys
                805             810             815 ttc tat gag cag ttc tct aaa aac ata aag ctt gga ata cac gaa gac    2496
Phe Tyr Glu Gln Phe Ser Lys Asn Ile Lys Leu Gly Ile His Glu Asp
            820             825             830 tct caa aat cgg aag aag ctt tca gag ctg tta agg tac tac aca tct    2544
Ser Gln Asn Arg Lys Lys Leu Ser Glu Leu Leu Arg Tyr Tyr Thr Ser
            835             840             845 gcc tct ggt gat gag atg gtt tct ctc aag gac tac tgc acc aga atg    2592
Ala Ser Gly Asp Glu Met Val Ser Leu Lys Asp Tyr Cys Thr Arg Met
            850             855             860 aag gag aac cag aaa cat atc tat tat atc aca ggt gag acc aag gac    2640
Lys Glu Asn Gln Lys His Ile Tyr Tyr Ile Thr Gly Glu Thr Lys Asp
865             870             875             880 cag gta gct aac tca gcc ttt gtg gaa cgt ctt cgg aaa cat ggc tta    2688
Gln Val Ala Asn Ser Ala Phe Val Glu Arg Leu Arg Lys His Gly Leu
                885             890             895 gaa gtg atc tat atg att gag ccc att gat gag tac tgt gtc caa cag    2736
Glu Val Ile Tyr Met Ile Glu Pro Ile Asp Glu Tyr Cys Val Gln Gln
```

```
              900              905              910 ctg aag gaa ttt gag ggg aag act tta gtg tca gtc acc aaa gaa ggc    2784
Leu Lys Glu Phe Glu Gly Lys Thr Leu Val Ser Val Thr Lys Glu Gly
        915              920              925 ctg gaa ctt cca gag gat gaa gaa gag aaa aag aag cag gaa gag aaa    2832
Leu Glu Leu Pro Glu Asp Glu Glu Glu Lys Lys Lys Gln Glu Glu Lys
        930              935              940 aaa aca aag ttt gag aac ctc tgc aaa atc atg aaa gac ata ttg gag    2880
Lys Thr Lys Phe Glu Asn Leu Cys Lys Ile Met Lys Asp Ile Leu Glu
945              950              955              960 aaa aaa gtt gaa aag gtg gtt gtg tca aac cga ttg gtg aca tct cca    2928
Lys Lys Val Glu Lys Val Val Val Ser Asn Arg Leu Val Thr Ser Pro
                965              970              975 tgc tgt att gtc aca agc aca tat ggc tgg aca gca aac atg gag aga    2976
Cys Cys Ile Val Thr Ser Thr Tyr Gly Trp Thr Ala Asn Met Glu Arg
                980              985              990 atc atg aaa gct caa gcc cta aga  gac aac tca aca atg  ggt tac atg    3024
Ile Met Lys Ala Gln Ala Leu Arg  Asp Asn Ser Thr Met  Gly Tyr Met
        995              1000              1005 gca gca  aag aaa cac ctg gag  ata aac cct gac cat  tcc att att       3069
Ala Ala  Lys Lys His Leu Glu  Ile Asn Pro Asp His  Ser Ile Ile
        1010              1015              1020 gag acc  tta agg caa aag gca  gag gct gat aag aac  gac aag tct       3114
Glu Thr  Leu Arg Gln Lys Ala  Glu Ala Asp Lys Asn  Asp Lys Ser
        1025              1030              1035 gtg aag  gat ctg gtc atc ttg  ctt tat gaa act gcg  ctc ctg tct       3159
Val Lys  Asp Leu Val Ile Leu  Leu Tyr Glu Thr Ala  Leu Leu Ser
        1040              1045              1050 tct ggc  ttc agt ctg gaa gat  ccc cag aca cat gct  aac agg atc       3204
Ser Gly  Phe Ser Leu Glu Asp  Pro Gln Thr His Ala  Asn Arg Ile
        1055              1060              1065 tac agg  atg atc aaa ctt ggt  ctg ggt att gat gaa  gat gac cct       3249
Tyr Arg  Met Ile Lys Leu Gly  Leu Gly Ile Asp Glu  Asp Asp Pro
        1070              1075              1080 act gct  gat gat acc agt gct  gct gta act gaa gaa  atg cca ccc       3294
Thr Ala  Asp Asp Thr Ser Ala  Ala Val Thr Glu Glu  Met Pro Pro
        1085              1090              1095 ctt gaa  gga gat gac gac aca  tca cgc atg gaa gaa  gta gac taa       3339
Leu Glu  Gly Asp Asp Asp Thr  Ser Arg Met Glu Glu  Val Asp
        1100              1105              1110 tctaga                                                              3345
```

```
<210> SEQ ID NO 11
<211> LENGTH: 1112
<212> TYPE: PRT
<213> ORGANISM: Artificial Sequence
<220> FEATURE:
<223> OTHER INFORMATION: Synthetic Construct

<400> SEQUENCE: 11

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
```

```
65                    70                   75                   80

Ser Leu Glu Lys Arg Glu Ala Glu Ala Glu Phe His His His His
                85                   90                   95

His Ala Gly Ile His Asp Ile Val Leu Thr Gln Ser Pro Ala Ser Leu
                100                  105                  110

Ala Val Ser Leu Gly Gln Arg Ala Thr Ile Ser Cys Arg Ala Ser Lys
                115                  120                  125

Ser Val Ser Thr Ser Ser Tyr Ser Tyr Met His Trp Tyr Gln Gln Lys
                130                  135                  140

Pro Gly Gln Pro Pro Lys Leu Leu Ile Lys Tyr Ala Ser Tyr Leu Glu
145                  150                  155                  160

Ser Gly Val Pro Ala Arg Phe Ser Gly Ser Gly Ser Gly Thr Asp Phe
                165                  170                  175

Thr Leu Asn Ile His Pro Val Glu Glu Glu Asp Ala Ala Thr Tyr Tyr
                180                  185                  190

Cys Gln His Ser Arg Glu Phe Pro Trp Thr Phe Gly Gly Gly Thr Lys
                195                  200                  205

Leu Glu Ile Lys Arg Ala Asp Ala Ala Pro Gly Gly Gly Gly Ser Gly
                210                  215                  220

Gly Gly Gly Ser Gly Gly Gly Ser Glu Val Gln Leu Val Glu Ser
225                  230                  235                  240

Gly Gly Gly Leu Val Lys Pro Gly Gly Ser Arg Lys Leu Ser Cys Ala
                245                  250                  255

Ala Ser Gly Phe Thr Phe Ser Asn Tyr Gly Met His Trp Val Arg Gln
                260                  265                  270

Ala Pro Glu Lys Gly Leu Glu Trp Val Ala Tyr Ile Ser Ser Gly Ser
                275                  280                  285

Ser Thr Ile Tyr Tyr Ala Asp Thr Val Lys Gly Arg Phe Thr Ile Ser
                290                  295                  300

Arg Asp Asn Ala Lys Asn Thr Leu Phe Leu Gln Met Thr Ser Leu Arg
305                  310                  315                  320

Ser Glu Asp Thr Ala Met Arg Gly Leu Leu Leu Asp Tyr Trp Gly Gln
                325                  330                  335

Gly Thr Thr Leu Thr Val Ser Ser Leu Glu Gln Lys Leu Ile Ser Glu
                340                  345                  350

Glu Asp Leu Asn Ser Ala Val Asp Ala Lys Thr Thr Ala Pro Ser Val
                355                  360                  365

Tyr Pro Leu Ala Pro Val Leu Glu Ser Ser Gly Ser Met Pro Glu Glu
                370                  375                  380

Thr Gln Thr Gln Asp Gln Pro Met Glu Glu Glu Glu Val Glu Thr Phe
385                  390                  395                  400

Ala Phe Gln Ala Glu Ile Ala Gln Leu Met Ser Leu Ile Ile Asn Thr
                405                  410                  415

Phe Tyr Ser Asn Lys Glu Ile Phe Leu Arg Glu Leu Ile Ser Asn Ser
                420                  425                  430

Ser Asp Ala Leu Asp Lys Ile Arg Tyr Glu Ser Leu Thr Asp Pro Ser
                435                  440                  445

Lys Leu Asp Ser Gly Lys Glu Leu His Ile Asn Leu Ile Pro Asn Lys
                450                  455                  460

Gln Asp Arg Thr Leu Thr Ile Val Asp Thr Gly Ile Gly Met Thr Lys
465                  470                  475                  480

Ala Asp Leu Ile Asn Asn Leu Gly Thr Ile Ala Lys Ser Gly Thr Lys
                485                  490                  495
```

```
Ala Phe Met Glu Ala Leu Gln Ala Gly Ala Asp Ile Ser Met Ile Gly
            500                 505                 510

Gln Phe Gly Val Gly Phe Tyr Ser Ala Tyr Leu Val Ala Glu Lys Val
            515                 520                 525

Thr Val Ile Thr Lys His Asn Asp Asp Glu Gln Tyr Ala Trp Glu Ser
            530                 535                 540

Ser Ala Gly Gly Ser Phe Thr Val Arg Thr Asp Thr Gly Glu Pro Met
545                 550                 555                 560

Gly Arg Gly Thr Lys Val Ile Leu His Leu Lys Glu Asp Gln Thr Glu
                565                 570                 575

Tyr Leu Glu Glu Arg Arg Ile Lys Glu Ile Val Lys Lys His Ser Gln
            580                 585                 590

Phe Ile Gly Tyr Pro Ile Thr Leu Phe Val Glu Lys Glu Arg Asp Lys
            595                 600                 605

Glu Val Ser Asp Asp Glu Ala Glu Glu Lys Glu Asp Lys Glu Glu Glu
            610                 615                 620

Lys Glu Lys Glu Glu Lys Glu Ser Glu Asp Lys Pro Glu Ile Glu Asp
625                 630                 635                 640

Val Gly Ser Asp Glu Glu Glu Glu Lys Lys Asp Gly Asp Lys Lys Lys
                645                 650                 655

Lys Lys Lys Ile Lys Glu Lys Tyr Ile Asp Gln Glu Glu Leu Asn Lys
                660                 665                 670

Thr Lys Pro Ile Trp Thr Arg Asn Pro Asp Asp Ile Thr Asn Glu Glu
            675                 680                 685

Tyr Gly Glu Phe Tyr Lys Ser Leu Thr Asn Asp Trp Glu Asp His Leu
            690                 695                 700

Ala Val Lys His Phe Ser Val Glu Gly Gln Leu Glu Phe Arg Ala Leu
705                 710                 715                 720

Leu Phe Val Pro Arg Arg Ala Pro Phe Asp Leu Phe Glu Asn Arg Lys
                725                 730                 735

Lys Lys Asn Asn Ile Lys Leu Tyr Val Arg Arg Val Phe Ile Met Asp
                740                 745                 750

Asn Cys Glu Glu Leu Ile Pro Glu Tyr Leu Asn Phe Ile Arg Gly Val
            755                 760                 765

Val Asp Ser Glu Asp Leu Pro Leu Asn Ile Ser Arg Glu Met Leu Gln
            770                 775                 780

Gln Ser Lys Ile Leu Lys Val Ile Arg Lys Asn Leu Val Lys Lys Cys
785                 790                 795                 800

Leu Glu Leu Phe Thr Glu Leu Ala Glu Asp Lys Glu Asn Tyr Lys Lys
                805                 810                 815

Phe Tyr Glu Gln Phe Ser Lys Asn Ile Lys Leu Gly Ile His Glu Asp
            820                 825                 830

Ser Gln Asn Arg Lys Lys Leu Ser Glu Leu Leu Arg Tyr Tyr Thr Ser
            835                 840                 845

Ala Ser Gly Asp Glu Met Val Ser Leu Lys Asp Tyr Cys Thr Arg Met
            850                 855                 860

Lys Glu Asn Gln Lys His Ile Tyr Tyr Ile Thr Gly Glu Thr Lys Asp
865                 870                 875                 880

Gln Val Ala Asn Ser Ala Phe Val Glu Arg Leu Arg Lys His Gly Leu
                885                 890                 895

Glu Val Ile Tyr Met Ile Glu Pro Ile Asp Glu Tyr Cys Val Gln Gln
            900                 905                 910
```

-continued

```
Leu Lys Glu Phe Glu Gly Lys Thr Leu Val Ser Val Thr Lys Glu Gly
        915                 920             925

Leu Glu Leu Pro Glu Asp Glu Glu Glu Lys Lys Lys Gln Glu Glu Lys
        930                 935             940

Lys Thr Lys Phe Glu Asn Leu Cys Lys Ile Met Lys Asp Ile Leu Glu
945                 950             955                 960

Lys Lys Val Glu Lys Val Val Val Ser Asn Arg Leu Val Thr Ser Pro
                965             970             975

Cys Cys Ile Val Thr Ser Thr Tyr Gly Trp Thr Ala Asn Met Glu Arg
            980             985             990

Ile Met Lys Ala Gln Ala Leu Arg  Asp Asn Ser Thr Met  Gly Tyr Met
        995             1000             1005

Ala Ala  Lys Lys His Leu Glu  Ile Asn Pro Asp His  Ser Ile Ile
    1010             1015             1020

Glu Thr  Leu Arg Gln Lys Ala  Glu Ala Asp Lys Asn  Asp Lys Ser
    1025             1030             1035

Val Lys  Asp Leu Val Ile Leu  Leu Tyr Glu Thr Ala  Leu Leu Ser
    1040             1045             1050

Ser Gly  Phe Ser Leu Glu Asp  Pro Gln Thr His Ala  Asn Arg Ile
    1055             1060             1065

Tyr Arg  Met Ile Lys Leu Gly  Leu Gly Ile Asp Glu  Asp Asp Pro
    1070             1075             1080

Thr Ala  Asp Asp Thr Ser Ala  Ala Val Thr Glu Glu  Met Pro Pro
    1085             1090             1095

Leu Glu  Gly Asp Asp Asp Thr  Ser Arg Met Glu Glu  Val Asp
    1100             1105             1110
```

<210> SEQ ID NO 12
<211> LENGTH: 1112
<212> TYPE: PRT
<213> ORGANISM: Artificial Sequence
<220> FEATURE:
<223> OTHER INFORMATION: 3E10 Fv-Hsp90 amino acid sequence for a
     chimeric protein comprising a single chain Fv antibody fragment
     derived from Mus musculus 3E10 hybridoma and Hsp90 from Homo
     sapiens joined by mouse CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
     signal sequence for secretion of fusion protein, provided by
     pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
     removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
     removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
     removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility
<220> FEATURE:

-continued

```
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting
      in enhanced cell penetration of the 3E10 monoclonal antibody and
      3E10 Fv antibody fragment
<220> FEATURE:
<221> NAME/KEY: MISC_FEATURE
<222> LOCATION: (264)..(264)
<223> OTHER INFORMATION: Asparagine (N) in place of aspartic acid in
      3E10 variable heavy chain, VH, conferring enhanced cell
      penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
      chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(374)
<223> OTHER INFORMATION: Mus musculus immunoglobulin heavy chain
      constant domain, CH1, linker
<220> FEATURE:
<221> NAME/KEY: MISC_FEATURE
<222> LOCATION: (375)..(380)
<223> OTHER INFORMATION: Swivel sequence
<220> FEATURE:
<221> NAME/KEY: MISC_FEATURE
<222> LOCATION: (381)..(1112)
<223> OTHER INFORMATION: Homo sapiens Hsp90 sequence

<400> SEQUENCE: 12

Met Arg Phe Pro Ser Leu Phe Thr Ala Val Leu Phe Ala Ala Ser Ser
1               5                   10                  15
```

-continued

```
Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
            115                 120                 125

Ser Val Ser Thr Ser Ser Tyr Ser Tyr Met His Trp Tyr Gln Gln Lys
        130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
            195                 200                 205

Leu Glu Ile Lys Arg Ala Asp Ala Ala Pro Gly Gly Gly Gly Ser Gly
        210                 215                 220

Gly Gly Gly Ser Gly Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
            260                 265                 270

Ala Pro Glu Lys Gly Leu Glu Trp Val Ala Tyr Ile Ser Ser Gly Ser
            275                 280                 285

Ser Thr Ile Tyr Tyr Ala Asp Thr Val Lys Gly Arg Phe Thr Ile Ser
        290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
            340                 345                 350

Glu Asp Leu Asn Ser Ala Val Asp Ala Lys Thr Thr Ala Pro Ser Val
            355                 360                 365

Tyr Pro Leu Ala Pro Val Leu Glu Ser Ser Gly Ser Met Pro Glu Glu
        370                 375                 380

Thr Gln Thr Gln Asp Gln Pro Met Glu Glu Glu Glu Val Glu Thr Phe
385                 390                 395                 400

Ala Phe Gln Ala Glu Ile Ala Gln Leu Met Ser Leu Ile Ile Asn Thr
                405                 410                 415

Phe Tyr Ser Asn Lys Glu Ile Phe Leu Arg Glu Leu Ile Ser Asn Ser
            420                 425                 430

Ser Asp Ala Leu Asp Lys Ile Arg Tyr Glu Ser Leu Thr Asp Pro Ser
```

-continued

```
              435                    440                    445
Lys Leu Asp Ser Gly Lys Glu Leu His Ile Asn Leu Ile Pro Asn Lys
    450                    455                    460
Gln Asp Arg Thr Leu Thr Ile Val Asp Thr Gly Ile Gly Met Thr Lys
465                    470                    475                    480
Ala Asp Leu Ile Asn Asn Leu Gly Thr Ile Ala Lys Ser Gly Thr Lys
                    485                    490                    495
Ala Phe Met Glu Ala Leu Gln Ala Gly Ala Asp Ile Ser Met Ile Gly
                500                    505                    510
Gln Phe Gly Val Gly Phe Tyr Ser Ala Tyr Leu Val Ala Glu Lys Val
            515                    520                    525
Thr Val Ile Thr Lys His Asn Asp Asp Glu Gln Tyr Ala Trp Glu Ser
    530                    535                    540
Ser Ala Gly Gly Ser Phe Thr Val Arg Thr Asp Thr Gly Glu Pro Met
545                    550                    555                    560
Gly Arg Gly Thr Lys Val Ile Leu His Leu Lys Glu Asp Gln Thr Glu
                565                    570                    575
Tyr Leu Glu Glu Arg Arg Ile Lys Glu Ile Val Lys Lys His Ser Gln
            580                    585                    590
Phe Ile Gly Tyr Pro Ile Thr Leu Phe Val Glu Lys Glu Arg Asp Lys
        595                    600                    605
Glu Val Ser Asp Asp Glu Ala Glu Glu Lys Glu Asp Lys Glu Glu Glu
    610                    615                    620
Lys Glu Lys Glu Glu Lys Glu Ser Glu Asp Lys Pro Glu Ile Glu Asp
625                    630                    635                    640
Val Gly Ser Asp Glu Glu Glu Glu Lys Lys Asp Gly Asp Lys Lys Lys
                645                    650                    655
Lys Lys Lys Ile Lys Glu Lys Tyr Ile Asp Gln Glu Glu Leu Asn Lys
                660                    665                    670
Thr Lys Pro Ile Trp Thr Arg Asn Pro Asp Asp Ile Thr Asn Glu Glu
            675                    680                    685
Tyr Gly Glu Phe Tyr Lys Ser Leu Thr Asn Asp Trp Glu Asp His Leu
    690                    695                    700
Ala Val Lys His Phe Ser Val Glu Gly Gln Leu Glu Phe Arg Ala Leu
705                    710                    715                    720
Leu Phe Val Pro Arg Arg Ala Pro Phe Asp Leu Phe Glu Asn Arg Lys
                725                    730                    735
Lys Lys Asn Asn Ile Lys Leu Tyr Val Arg Arg Val Phe Ile Met Asp
            740                    745                    750
Asn Cys Glu Glu Leu Ile Pro Glu Tyr Leu Asn Phe Ile Arg Gly Val
            755                    760                    765
Val Asp Ser Glu Asp Leu Pro Leu Asn Ile Ser Arg Glu Met Leu Gln
    770                    775                    780
Gln Ser Lys Ile Leu Lys Val Ile Arg Lys Asn Leu Val Lys Lys Cys
785                    790                    795                    800
Leu Glu Leu Phe Thr Glu Leu Ala Glu Asp Lys Glu Asn Tyr Lys Lys
                805                    810                    815
Phe Tyr Glu Gln Phe Ser Lys Asn Ile Lys Leu Gly Ile His Glu Asp
            820                    825                    830
Ser Gln Asn Arg Lys Lys Leu Ser Glu Leu Leu Arg Tyr Tyr Thr Ser
        835                    840                    845
Ala Ser Gly Asp Glu Met Val Ser Leu Lys Asp Tyr Cys Thr Arg Met
    850                    855                    860
```

```
Lys Glu Asn Gln Lys His Ile Tyr Tyr Ile Thr Gly Glu Thr Lys Asp
865                 870                 875                 880

Gln Val Ala Asn Ser Ala Phe Val Glu Arg Leu Arg Lys His Gly Leu
                885                 890                 895

Glu Val Ile Tyr Met Ile Glu Pro Ile Asp Glu Tyr Cys Val Gln Gln
                900                 905                 910

Leu Lys Glu Phe Glu Gly Lys Thr Leu Val Ser Val Thr Lys Glu Gly
        915                 920                 925

Leu Glu Leu Pro Glu Asp Glu Glu Gly Lys Lys Lys Gln Glu Glu Lys
        930                 935                 940

Lys Thr Lys Phe Glu Asn Leu Cys Lys Ile Met Lys Asp Ile Leu Glu
945                 950                 955                 960

Lys Lys Val Glu Lys Val Val Val Ser Asn Arg Leu Val Thr Ser Pro
                965                 970                 975

Cys Cys Ile Val Thr Ser Thr Tyr Gly Trp Thr Ala Asn Met Glu Arg
                980                 985                 990

Ile Met Lys Ala Gln Ala Leu Arg  Asp Asn Ser Thr Met  Gly Tyr Met
        995                 1000                1005

Ala Ala  Lys Lys His Leu Glu  Ile Asn Pro Asp His  Ser Ile Ile
    1010                1015                1020

Glu Thr  Leu Arg Gln Lys Ala  Glu Ala Asp Lys Asn  Asp Lys Ser
    1025                1030                1035

Val Lys  Asp Leu Val Ile Leu  Leu Tyr Glu Thr Ala  Leu Leu Ser
    1040                1045                1050

Ser Gly  Phe Ser Leu Glu Asp  Pro Gln Thr His Ala  Asn Arg Ile
    1055                1060                1065

Tyr Arg  Met Ile Lys Leu Gly  Leu Gly Ile Asp Glu  Asp Asp Pro
    1070                1075                1080

Thr Ala  Asp Asp Thr Ser Ala  Ala Val Thr Glu Glu  Met Pro Pro
    1085                1090                1095

Leu Glu  Gly Asp Asp Asp Thr  Ser Arg Met Glu Glu  Val Asp
    1100                1105                1110
```

<210> SEQ ID NO 13
<211> LENGTH: 12
<212> TYPE: DNA
<213> ORGANISM: Mus musculus
<220> FEATURE:
<221> NAME/KEY: CDS
<222> LOCATION: (1)..(12)
<223> OTHER INFORMATION: anti-DNA monoclonal antibody 3E10 kappa light
    (Vk) chain complementarity determining region 1 (CDR1) coding
    sequence

<400> SEQUENCE: 13 agt tac atg cac                                                                   12
Ser Tyr Met His
1

<210> SEQ ID NO 14
<211> LENGTH: 4
<212> TYPE: PRT
<213> ORGANISM: Mus musculus

<400> SEQUENCE: 14

Ser Tyr Met His
1

-continued

<210> SEQ ID NO 15
<211> LENGTH: 18
<212> TYPE: DNA
<213> ORGANISM: Mus musculus
<220> FEATURE:
<221> NAME/KEY: CDS
<222> LOCATION: (1)..(18)
<223> OTHER INFORMATION: anti-DNA monoclonal antibody 3E10 kappa light
      (Vk) chain complementarity determining region 2 (CDR2) coding
      sequence

<400> SEQUENCE: 15 gca tcc tac cta gaa tct                                                                 18
Ala Ser Tyr Leu Glu Ser
1               5

<210> SEQ ID NO 16
<211> LENGTH: 6
<212> TYPE: PRT
<213> ORGANISM: Mus musculus

<400> SEQUENCE: 16

Ala Ser Tyr Leu Glu Ser
1               5

<210> SEQ ID NO 17
<211> LENGTH: 27
<212> TYPE: DNA
<213> ORGANISM: Mus musculus
<220> FEATURE:
<221> NAME/KEY: CDS
<222> LOCATION: (1)..(27)
<223> OTHER INFORMATION: anti-DNA monoclonal antibody 3E10 kappa light
      (Vk) chain complementarity determining region 3 (CDR3) coding
      sequence

<400> SEQUENCE: 17 cag cac agt agg gag ttt ccg tgg acg                                                     27
Gln His Ser Arg Glu Phe Pro Trp Thr
1               5

<210> SEQ ID NO 18
<211> LENGTH: 9
<212> TYPE: PRT
<213> ORGANISM: Mus musculus

<400> SEQUENCE: 18

Gln His Ser Arg Glu Phe Pro Trp Thr
1               5

<210> SEQ ID NO 19
<211> LENGTH: 15
<212> TYPE: DNA
<213> ORGANISM: Mus musculus
<220> FEATURE:
<221> NAME/KEY: CDS
<222> LOCATION: (1)..(15)
<223> OTHER INFORMATION: anti-DNA monoclonal antibody 3E10 variable
      heavy (VH) chain complementarity determining region 1 (CDR1)
      coding sequence with D31N mutation at the first amino acid
      position of CDR1 for enhanced cell penetration

<400> SEQUENCE: 19 aac tat gga atg cac                                                                     15
Asn Tyr Gly Met His
1               5

<210> SEQ ID NO 20
<211> LENGTH: 5

-continued

```
<212> TYPE: PRT
<213> ORGANISM: Mus musculus

<400> SEQUENCE: 20

Asn Tyr Gly Met His
1               5

<210> SEQ ID NO 21
<211> LENGTH: 51
<212> TYPE: DNA
<213> ORGANISM: Mus musculus
<220> FEATURE:
<221> NAME/KEY: CDS
<222> LOCATION: (1)..(51)
<223> OTHER INFORMATION: anti-DNA monoclonal antibody 3E10 variable
      heavy (VH) chain complementarity determining region 2 (CDR2)
      coding sequence

<400> SEQUENCE: 21 tac att agt agt ggc agt agt acc atc tac tat gca gac aca gtg aag          48
Tyr Ile Ser Ser Gly Ser Ser Thr Ile Tyr Tyr Ala Asp Thr Val Lys
1               5                   10                  15 ggc                                                                      51
Gly

<210> SEQ ID NO 22
<211> LENGTH: 17
<212> TYPE: PRT
<213> ORGANISM: Mus musculus

<400> SEQUENCE: 22

Tyr Ile Ser Ser Gly Ser Ser Thr Ile Tyr Tyr Ala Asp Thr Val Lys
1               5                   10                  15

Gly

<210> SEQ ID NO 23
<211> LENGTH: 21
<212> TYPE: DNA
<213> ORGANISM: Mus musculus
<220> FEATURE:
<221> NAME/KEY: CDS
<222> LOCATION: (1)..(21)
<223> OTHER INFORMATION: anti-DNA monoclonal antibody 3E10 variable
      heavy (VH) chain complementarity determining region 3 (CDR3)
      coding sequence

<400> SEQUENCE: 23 cgg ggg tta cta ctt gac tac                                              21
Arg Gly Leu Leu Leu Asp Tyr
1               5

<210> SEQ ID NO 24
<211> LENGTH: 7
<212> TYPE: PRT
<213> ORGANISM: Mus musculus

<400> SEQUENCE: 24

Arg Gly Leu Leu Leu Asp Tyr
1               5

<210> SEQ ID NO 25
<211> LENGTH: 1761
<212> TYPE: DNA
<213> ORGANISM: Artificial Sequence
<220> FEATURE:
<223> OTHER INFORMATION: 3E10 Fv-Hsp27 nucleotide sequence encoding a
      chimeric protein comprising a single chain Fv antibody fragment
```

```
        derived from Mus musculus 3E10 hybridoma and Hsp27 from Homo
        sapiens joined by human CH1 linker and swivel sequence
<220> FEATURE:
<221> NAME/KEY: CDS
<222> LOCATION: (1)..(1755)
<223> OTHER INFORMATION: Coding sequence for a chimeric protein
        containing Saccharomyces cerevisiae alpha-factor secretory signal
        sequence, AGIH peptide, Mus musculus 3E10 Fv antibody fragment,
        Homo sapiens CH1 linker, swivel sequence, epitope tags, and Homo
        sapiens Hsp27 protein
<220> FEATURE:
<221> NAME/KEY: misc_feature
<222> LOCATION: (1)..(267)
<223> OTHER INFORMATION: Coding sequence: Saccharomyces cerevisiae
        alpha-factor secretory signal sequence for secretion of fusion
        protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
        encoded by nucleotide positions 253-258 for removing Saccharomyces
        cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
        encoded by nucleotide positions 259-264 for removing Saccharomyces
        cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
        encoded by nucleotide positions 265-270 for removing Saccharomyces
        cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
<221> NAME/KEY: misc_feature
<222> LOCATION: (274)..(291)
<223> OTHER INFORMATION: Coding sequence: His6 tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
        immunoglobulin variable light chain kappa (Vk); begin 3E10 Fv
        antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
        variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
<223> OTHER INFORMATION: Begin of coding sequence for Mus musculus 3E10
        immunoglobulin variable heavy chain (VH)
<220> FEATURE:
```

```
<221> NAME/KEY: misc_feature
<222> LOCATION: (790)..(804)
<223> OTHER INFORMATION: Coding sequence: CDR1 VH with mutation in the
      first codon of CDR1 resulting in a D31N change for 3E10 VH chain
      and enhanced cell penetration of the 3E10 monoclonal antibody and
      3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
      immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1119)
<223> OTHER INFORMATION: Coding sequence: Homo sapiens immunoglobulin
      heavy chain constant domain, CH1, linker
<220> FEATURE:
<221> NAME/KEY: misc_feature
<222> LOCATION: (1120)..(1137)
<223> OTHER INFORMATION: Coding sequence: swivel sequence
<220> FEATURE:
<221> NAME/KEY: misc_feature
<222> LOCATION: (1132)..(1137)
<223> OTHER INFORMATION: BamHI restriction enzyme site
<220> FEATURE:
<221> NAME/KEY: misc_feature
<222> LOCATION: (1138)..(1755)
<223> OTHER INFORMATION: Coding sequence: Homo sapiens Hsp27 sequence
<220> FEATURE:
<221> NAME/KEY: misc_feature
<222> LOCATION: (1753)..(1755)
<223> OTHER INFORMATION: Stop codon
<220> FEATURE:
<221> NAME/KEY: misc_feature
<222> LOCATION: (1756)..(1761)
<223> OTHER INFORMATION: XbaI restriction enzyme site

<400> SEQUENCE: 25 atg aga ttt cct tca ctt ttt act gct gtt tta ttc gca gca tcc tcc        48
Met Arg Phe Pro Ser Leu Phe Thr Ala Val Leu Phe Ala Ala Ser Ser
1               5                   10                  15 gca tta gct gct cca gtc aac act aca aca gaa gat gaa acg gca caa        96
Ala Leu Ala Ala Pro Val Asn Thr Thr Thr Glu Asp Glu Thr Ala Gln
                20                  25                  30 att ccg gct gaa gct gtc atc ggt tac tca gat tta gaa ggg gat ttc       144
Ile Pro Ala Glu Ala Val Ile Gly Tyr Ser Asp Leu Glu Gly Asp Phe
            35                  40                  45 gat gtt gct gtt ttg cca ttt tcc aac agc aca aat aac ggg tta ttg       192
Asp Val Ala Val Leu Pro Phe Ser Asn Ser Thr Asn Asn Gly Leu Leu
        50                  55                  60 ttt ata aat act act att gcc agc att gct gct aaa gaa gaa ggg gta       240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat       288
Ser Leu Glu Lys Arg Glu Ala Glu Ala Glu Phe His His His His His
                85                  90                  95 cac gca ggg att cac gac att gtc ctg aca cag tct cct gct tcc tta       336
His Ala Gly Ile His Asp Ile Val Leu Thr Gln Ser Pro Ala Ser Leu
            100                 105                 110
```

```
gct gta tct ctg ggg cag agg gcc acc atc tcc tgc agg gcc agc aaa        384
Ala Val Ser Leu Gly Gln Arg Ala Thr Ile Ser Cys Arg Ala Ser Lys
        115             120             125 agt gtc agt aca tct agc tat agt tac atg cac tgg tac caa cag aaa        432
Ser Val Ser Thr Ser Ser Tyr Ser Tyr Met His Trp Tyr Gln Gln Lys
        130             135             140 cca gga cag cca ccc aaa ctc ctc atc aag tat gca tcc tac cta gaa        480
Pro Gly Gln Pro Pro Lys Leu Leu Ile Lys Tyr Ala Ser Tyr Leu Glu
145             150             155             160 tct ggg gtt cct gcc agg ttc agt ggc agt ggg tct ggg aca gac ttc        528
Ser Gly Val Pro Ala Arg Phe Ser Gly Ser Gly Ser Gly Thr Asp Phe
                165             170             175 acc ctc aac atc cat cct gtg gag gag gag gat gct gca aca tat tac        576
Thr Leu Asn Ile His Pro Val Glu Glu Glu Asp Ala Ala Thr Tyr Tyr
            180             185             190 tgt cag cac agt agg gag ttt ccg tgg acg ttc ggt gga ggc acc aag        624
Cys Gln His Ser Arg Glu Phe Pro Trp Thr Phe Gly Gly Gly Thr Lys
        195             200             205 ctg gaa atc aaa cgg gct gat gct gca ccc ggg ggt ggc ggt tct ggc        672
Leu Glu Ile Lys Arg Ala Asp Ala Ala Pro Gly Gly Gly Gly Ser Gly
        210             215             220 ggt ggc ggt tct gga ggc ggt ggc tct gag gtg cag ctg gtg gag tct        720
Gly Gly Gly Ser Gly Gly Gly Gly Ser Glu Val Gln Leu Val Glu Ser
225             230             235             240 ggg gga ggc tta gtg aag cct gga ggg tcc cgg aaa ctc tcc tgt gca        768
Gly Gly Gly Leu Val Lys Pro Gly Gly Ser Arg Lys Leu Ser Cys Ala
                245             250             255 gcc tct gga ttc act ttc agt aac tat gga atg cac tgg gtc cgt cag        816
Ala Ser Gly Phe Thr Phe Ser Asn Tyr Gly Met His Trp Val Arg Gln
                260             265             270 gct cca gag aag ggg ctg gag tgg gtt gca tac att agt agt ggc agt        864
Ala Pro Glu Lys Gly Leu Glu Trp Val Ala Tyr Ile Ser Ser Gly Ser
        275             280             285 agt acc atc tac tat gca gac aca gtg aag ggc cga ttc acc atc tcc        912
Ser Thr Ile Tyr Tyr Ala Asp Thr Val Lys Gly Arg Phe Thr Ile Ser
        290             295             300 aga gac aat gcc aag aac acc ctg ttc ctg caa atg acc agt cta agg        960
Arg Asp Asn Ala Lys Asn Thr Leu Phe Leu Gln Met Thr Ser Leu Arg
305             310             315             320 tct gag gac aca gcc atg cgg ggg tta cta ctt gac tac tgg ggc caa       1008
Ser Glu Asp Thr Ala Met Arg Gly Leu Leu Leu Asp Tyr Trp Gly Gln
                325             330             335 ggc acc act ctc aca gtc tcc tca cta gaa caa aaa ctc atc tca gaa       1056
Gly Thr Thr Leu Thr Val Ser Ser Leu Glu Gln Lys Leu Ile Ser Glu
                340             345             350 gag gat ctg aat agc gcc gtc gac gct tcc acc aag ggc cca tcc gtc       1104
Glu Asp Leu Asn Ser Ala Val Asp Ala Ser Thr Lys Gly Pro Ser Val
        355             360             365 ttc ccc ctg gcg ccc ctg gag tct tcc gga tcc atg acc gag cgc cgc       1152
Phe Pro Leu Ala Pro Leu Glu Ser Ser Gly Ser Met Thr Glu Arg Arg
        370             375             380 gtc ccc ttc tcg ctc ctg cgg ggc ccc agc tgg gac ccc ttc cgc gac       1200
Val Pro Phe Ser Leu Leu Arg Gly Pro Ser Trp Asp Pro Phe Arg Asp
385             390             395             400 tgg tac ccg cat agc cgc ctc ttc gac cag gcc ttc ggg ctg ccc cgg       1248
Trp Tyr Pro His Ser Arg Leu Phe Asp Gln Ala Phe Gly Leu Pro Arg
                405             410             415 ctg ccg gag gag tgg tcg cag tgg tta ggc ggc agc agc tgg cca ggc       1296
Leu Pro Glu Glu Trp Ser Gln Trp Leu Gly Gly Ser Ser Trp Pro Gly
        420             425             430
```

-continued

```
tac gtg cgc ccc ctg ccc ccc gcc gcc atc gag agc ccc gca gtg gcc        1344
Tyr Val Arg Pro Leu Pro Pro Ala Ala Ile Glu Ser Pro Ala Val Ala
        435             440             445 gcg ccc gcc tac agc cgc gcg ctc agc cgg caa ctc agc agc ggg gtc        1392
Ala Pro Ala Tyr Ser Arg Ala Leu Ser Arg Gln Leu Ser Ser Gly Val
    450             455             460 tcg gag atc cgg cac act gcg gac cgc tgg cgc gtg tcc ctg gat gtc        1440
Ser Glu Ile Arg His Thr Ala Asp Arg Trp Arg Val Ser Leu Asp Val
465             470             475             480 aac cac ttc gcc ccg gac gag ctg acg gtc aag acc aag gat ggc gtg        1488
Asn His Phe Ala Pro Asp Glu Leu Thr Val Lys Thr Lys Asp Gly Val
                485             490             495 gtg gag atc acc ggc aag cac gag gag cgg cag gac gag cat ggc tac        1536
Val Glu Ile Thr Gly Lys His Glu Glu Arg Gln Asp Glu His Gly Tyr
            500             505             510 atc tcc cgg tgc ttc acg cgg aaa tac acg ctg ccc ccc ggt gtg gac        1584
Ile Ser Arg Cys Phe Thr Arg Lys Tyr Thr Leu Pro Pro Gly Val Asp
            515             520             525 ccc acc caa gtt tcc tcc tcc ctg tcc cct gag ggc aca ctg acc gtg        1632
Pro Thr Gln Val Ser Ser Ser Leu Ser Pro Glu Gly Thr Leu Thr Val
        530             535             540 gag gcc ccc atg ccc aag cta gcc acg cag tcc aac gag atc acc atc        1680
Glu Ala Pro Met Pro Lys Leu Ala Thr Gln Ser Asn Glu Ile Thr Ile
545             550             555             560 cca gtc acc ttc gag tcg cgg gcc cag ctt ggg ggc cca gaa gct gca        1728
Pro Val Thr Phe Glu Ser Arg Ala Gln Leu Gly Gly Pro Glu Ala Ala
                565             570             575 aaa tcc gat gag act gcc gcc aag taa tctaga                             1761
Lys Ser Asp Glu Thr Ala Ala Lys
                580

<210> SEQ ID NO 26
<211> LENGTH: 584
<212> TYPE: PRT
<213> ORGANISM: Artificial Sequence
<220> FEATURE:
<223> OTHER INFORMATION: Synthetic Construct

<400> SEQUENCE: 26

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
            115                 120                 125

Ser Val Ser Thr Ser Ser Tyr Ser Tyr Met His Trp Tyr Gln Gln Lys
        130                 135                 140

Pro Gly Gln Pro Pro Lys Leu Leu Ile Lys Tyr Ala Ser Tyr Leu Glu
```

```
145                150                155                160

Ser Gly Val Pro Ala Arg Phe Ser Gly Ser Gly Ser Gly Thr Asp Phe
            165                170                175

Thr Leu Asn Ile His Pro Val Glu Glu Glu Asp Ala Ala Thr Tyr Tyr
            180                185                190

Cys Gln His Ser Arg Glu Phe Pro Trp Thr Phe Gly Gly Gly Thr Lys
            195                200                205

Leu Glu Ile Lys Arg Ala Asp Ala Ala Pro Gly Gly Gly Gly Ser Gly
    210                215                220

Gly Gly Ser Gly Gly Gly Gly Ser Glu Val Gln Leu Val Glu Ser
225                230                235                240

Gly Gly Gly Leu Val Lys Pro Gly Gly Ser Arg Lys Leu Ser Cys Ala
            245                250                255

Ala Ser Gly Phe Thr Phe Ser Asn Tyr Gly Met His Trp Val Arg Gln
            260                265                270

Ala Pro Glu Lys Gly Leu Glu Trp Val Ala Tyr Ile Ser Ser Gly Ser
            275                280                285

Ser Thr Ile Tyr Tyr Ala Asp Thr Val Lys Gly Arg Phe Thr Ile Ser
            290                295                300

Arg Asp Asn Ala Lys Asn Thr Leu Phe Leu Gln Met Thr Ser Leu Arg
305                310                315                320

Ser Glu Asp Thr Ala Met Arg Gly Leu Leu Leu Asp Tyr Trp Gly Gln
            325                330                335

Gly Thr Thr Leu Thr Val Ser Ser Leu Glu Gln Lys Leu Ile Ser Glu
            340                345                350

Glu Asp Leu Asn Ser Ala Val Asp Ala Ser Thr Lys Gly Pro Ser Val
            355                360                365

Phe Pro Leu Ala Pro Leu Glu Ser Ser Gly Ser Met Thr Glu Arg Arg
    370                375                380

Val Pro Phe Ser Leu Leu Arg Gly Pro Ser Trp Asp Pro Phe Arg Asp
385                390                395                400

Trp Tyr Pro His Ser Arg Leu Phe Asp Gln Ala Phe Gly Leu Pro Arg
            405                410                415

Leu Pro Glu Glu Trp Ser Gln Trp Leu Gly Gly Ser Ser Trp Pro Gly
            420                425                430

Tyr Val Arg Pro Leu Pro Pro Ala Ala Ile Glu Ser Pro Ala Val Ala
            435                440                445

Ala Pro Ala Tyr Ser Arg Ala Leu Ser Arg Gln Leu Ser Ser Gly Val
    450                455                460

Ser Glu Ile Arg His Thr Ala Asp Arg Trp Arg Val Ser Leu Asp Val
465                470                475                480

Asn His Phe Ala Pro Asp Glu Leu Thr Val Lys Thr Lys Asp Gly Val
            485                490                495

Val Glu Ile Thr Gly Lys His Glu Glu Arg Gln Asp Glu His Gly Tyr
            500                505                510

Ile Ser Arg Cys Phe Thr Arg Lys Tyr Thr Leu Pro Pro Gly Val Asp
            515                520                525

Pro Thr Gln Val Ser Ser Ser Leu Ser Pro Glu Gly Thr Leu Thr Val
    530                535                540

Glu Ala Pro Met Pro Lys Leu Ala Thr Gln Ser Asn Glu Ile Thr Ile
545                550                555                560

Pro Val Thr Phe Glu Ser Arg Ala Gln Leu Gly Gly Pro Glu Ala Ala
            565                570                575
```

Lys Ser Asp Glu Thr Ala Ala Lys
            580

<210> SEQ ID NO 27
<211> LENGTH: 584
<212> TYPE: PRT
<213> ORGANISM: Artificial Sequence
<220> FEATURE:
<223> OTHER INFORMATION: 3E10 Fv-Hsp27 amino acid sequence for a
      chimeric protein comprising a single chain Fv antibody fragment
      derived from Mus musculus 3E10 hybridoma and Hsp27 from Homo
      sapiens joined by human CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
      signal sequence for secretion of fusion protein, provided by
      pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
      removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility
<220> FEATURE:
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting -continued

```
    in enhanced cell penetration of the 3E10 monoclonal antibody and
    3E10 Fv antibody fragment
<220> FEATURE:
<221> NAME/KEY: MISC_FEATURE
<222> LOCATION: (264)..(264)
<223> OTHER INFORMATION: Asparagine (N) in place of aspartic acid in
    3E10 variable heavy chain, VH, conferring enhanced cell
    penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
    chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(373)
<223> OTHER INFORMATION: Homo sapiens immunoglobulin heavy chain
    constant domain, CH1, linker
<220> FEATURE:
<221> NAME/KEY: MISC_FEATURE
<222> LOCATION: (374)..(379)
<223> OTHER INFORMATION: Swivel sequence
<220> FEATURE:
<221> NAME/KEY: MISC_FEATURE
<222> LOCATION: (380)..(584)
<223> OTHER INFORMATION: Homo sapiens Hsp27 sequence

<400> SEQUENCE: 27

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
            115                 120                 125

Ser Val Ser Thr Ser Ser Tyr Ser Tyr Met His Trp Tyr Gln Gln Lys
        130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
            195                 200                 205
```

```
Leu Glu Ile Lys Arg Ala Asp Ala Ala Pro Gly Gly Gly Ser Gly
    210             215             220

Gly Gly Gly Ser Gly Gly Gly Gly Ser Glu Val Gln Leu Val Glu Ser
225             230             235             240

Gly Gly Gly Leu Val Lys Pro Gly Gly Ser Arg Lys Leu Ser Cys Ala
            245             250             255

Ala Ser Gly Phe Thr Phe Ser Asn Tyr Gly Met His Trp Val Arg Gln
            260             265             270

Ala Pro Glu Lys Gly Leu Glu Trp Val Ala Tyr Ile Ser Ser Gly Ser
            275             280             285

Ser Thr Ile Tyr Tyr Ala Asp Thr Val Lys Gly Arg Phe Thr Ile Ser
    290             295             300

Arg Asp Asn Ala Lys Asn Thr Leu Phe Leu Gln Met Thr Ser Leu Arg
305             310             315             320

Ser Glu Asp Thr Ala Met Arg Gly Leu Leu Leu Asp Tyr Trp Gly Gln
            325             330             335

Gly Thr Thr Leu Thr Val Ser Ser Leu Glu Gln Lys Leu Ile Ser Glu
            340             345             350

Glu Asp Leu Asn Ser Ala Val Asp Ala Ser Thr Lys Gly Pro Ser Val
            355             360             365

Phe Pro Leu Ala Pro Leu Glu Ser Ser Gly Ser Met Thr Glu Arg Arg
    370             375             380

Val Pro Phe Ser Leu Leu Arg Gly Pro Ser Trp Asp Pro Phe Arg Asp
385             390             395             400

Trp Tyr Pro His Ser Arg Leu Phe Asp Gln Ala Phe Gly Leu Pro Arg
            405             410             415

Leu Pro Glu Glu Trp Ser Gln Trp Leu Gly Gly Ser Ser Trp Pro Gly
            420             425             430

Tyr Val Arg Pro Leu Pro Pro Ala Ala Ile Glu Ser Pro Ala Val Ala
            435             440             445

Ala Pro Ala Tyr Ser Arg Ala Leu Ser Arg Gln Leu Ser Ser Gly Val
    450             455             460

Ser Glu Ile Arg His Thr Ala Asp Arg Trp Arg Val Ser Leu Asp Val
465             470             475             480

Asn His Phe Ala Pro Asp Glu Leu Thr Val Lys Thr Lys Asp Gly Val
            485             490             495

Val Glu Ile Thr Gly Lys His Glu Glu Arg Gln Asp Glu His Gly Tyr
            500             505             510

Ile Ser Arg Cys Phe Thr Arg Lys Tyr Thr Leu Pro Pro Gly Val Asp
            515             520             525

Pro Thr Gln Val Ser Ser Ser Leu Ser Pro Glu Gly Thr Leu Thr Val
    530             535             540

Glu Ala Pro Met Pro Lys Leu Ala Thr Gln Ser Asn Glu Ile Thr Ile
545             550             555             560

Pro Val Thr Phe Glu Ser Arg Ala Gln Leu Gly Gly Pro Glu Ala Ala
            565             570             575

Lys Ser Asp Glu Thr Ala Ala Lys
            580
```

<210> SEQ ID NO 28
<211> LENGTH: 3069
<212> TYPE: DNA
<213> ORGANISM: Artificial Sequence
<220> FEATURE:

```
<223> OTHER INFORMATION: 3E10 Fv-Hsp70 nucleotide sequence encoding a
      chimeric protein comprising a single chain Fv antibody fragment
      derived from Mus musculus 3E10 hybridoma and Hsp70 from Homo
      sapiens joined by human CH1 linker and swivel sequence
<220> FEATURE:
<221> NAME/KEY: CDS
<222> LOCATION: (1)..(3063)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Homo sapiens CH1 linker, swivel sequence, epitope tags, and Homo
      sapiens Hsp70 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
<221> NAME/KEY: misc_feature
<222> LOCATION: (274)..(291)
<223> OTHER INFORMATION: Coding sequence: His6 epitope tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
<223> OTHER INFORMATION: Begin of coding sequence for Mus musculus 3E10
```

-continued

```
            immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
            first codon of CDR1 resulting in a D31N change for 3E10 VH chain
            and enhanced cell penetration of the 3E10 monoclonal antibody and
            3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
            immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1119)
<223> OTHER INFORMATION: Coding sequence: Homo sapiens immunoglobulin
            heavy chain constant domain, CH1, linker
<220> FEATURE:
<221> NAME/KEY: misc_feature
<222> LOCATION: (1120)..(1137)
<223> OTHER INFORMATION: Coding sequence: swivel sequence
<220> FEATURE:
<221> NAME/KEY: misc_feature
<222> LOCATION: (1132)..(1137)
<223> OTHER INFORMATION: BamHI restriction enzyme site
<220> FEATURE:
<221> NAME/KEY: misc_feature
<222> LOCATION: (1138)..(3063)
<223> OTHER INFORMATION: Coding sequence: Homo sapiens Hsp70 sequence
<220> FEATURE:
<221> NAME/KEY: misc_feature
<222> LOCATION: (3061)..(3063)
<223> OTHER INFORMATION: Stop codon
<220> FEATURE:
<221> NAME/KEY: misc_feature
<222> LOCATION: (3064)..(3069)
<223> OTHER INFORMATION: XbaI restriction enzyme site

<400> SEQUENCE: 28 atg aga ttt cct tca ctt ttt act gct gtt tta ttc gca gca tcc tcc      48
Met Arg Phe Pro Ser Leu Phe Thr Ala Val Leu Phe Ala Ala Ser Ser
1               5                   10                  15 gca tta gct gct cca gtc aac act aca aca gaa gat gaa acg gca caa      96
Ala Leu Ala Ala Pro Val Asn Thr Thr Thr Glu Asp Glu Thr Ala Gln
                20                  25                  30 att ccg gct gaa gct gtc atc ggt tac tca gat tta gaa ggg gat ttc     144
Ile Pro Ala Glu Ala Val Ile Gly Tyr Ser Asp Leu Glu Gly Asp Phe
            35                  40                  45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu
        50                  55                  60 ttt ata aat act act att gcc agc att gct gct aaa gaa gaa ggg gta     240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat     288
Ser Leu Glu Lys Arg Glu Ala Glu Ala Glu Phe His His His His His
                85                  90                  95 cac gca ggg att cac gac att gtc ctg aca cag tct cct gct tcc tta     336
His Ala Gly Ile His Asp Ile Val Leu Thr Gln Ser Pro Ala Ser Leu
```

```
                   100                      105                      110
gct gta tct ctg ggg cag agg gcc acc atc tcc tgc agg gcc agc aaa     384
Ala Val Ser Leu Gly Gln Arg Ala Thr Ile Ser Cys Arg Ala Ser Lys
        115                      120                      125 agt gtc agt aca tct agc tat agt tac atg cac tgg tac caa cag aaa     432
Ser Val Ser Thr Ser Ser Tyr Ser Tyr Met His Trp Tyr Gln Gln Lys
    130                      135                      140 cca gga cag cca ccc aaa ctc ctc atc aag tat gca tcc tac cta gaa     480
Pro Gly Gln Pro Pro Lys Leu Leu Ile Lys Tyr Ala Ser Tyr Leu Glu
145                      150                      155                      160 tct ggg gtt cct gcc agg ttc agt ggc agt ggg tct ggg aca gac ttc     528
Ser Gly Val Pro Ala Arg Phe Ser Gly Ser Gly Ser Gly Thr Asp Phe
                165                      170                      175 acc ctc aac atc cat cct gtg gag gag gag gat gct gca aca tat tac     576
Thr Leu Asn Ile His Pro Val Glu Glu Glu Asp Ala Ala Thr Tyr Tyr
            180                      185                      190 tgt cag cac agt agg gag ttt ccg tgg acg ttc ggt gga ggc acc aag     624
Cys Gln His Ser Arg Glu Phe Pro Trp Thr Phe Gly Gly Gly Thr Lys
        195                      200                      205 ctg gaa atc aaa cgg gct gat gct gca ccc ggg ggt ggc ggt tct ggc     672
Leu Glu Ile Lys Arg Ala Asp Ala Ala Pro Gly Gly Gly Gly Ser Gly
    210                      215                      220 ggt ggc ggt tct gga ggc ggt ggc tct gag gtg cag ctg gtg gag tct     720
Gly Gly Gly Ser Gly Gly Gly Ser Glu Val Gln Leu Val Glu Ser
225                      230                      235                      240 ggg gga ggc tta gtg aag cct gga ggg tcc cgg aaa ctc tcc tgt gca     768
Gly Gly Gly Leu Val Lys Pro Gly Gly Ser Arg Lys Leu Ser Cys Ala
            245                      250                      255 gcc tct gga ttc act ttc agt aac tat gga atg cac tgg gtc cgt cag     816
Ala Ser Gly Phe Thr Phe Ser Asn Tyr Gly Met His Trp Val Arg Gln
            260                      265                      270 gct cca gag aag ggg ctg gag tgg gtt gca tac att agt agt ggc agt     864
Ala Pro Glu Lys Gly Leu Glu Trp Val Ala Tyr Ile Ser Ser Gly Ser
        275                      280                      285 agt acc atc tac tat gca gac aca gtg aag ggc cga ttc acc atc tcc     912
Ser Thr Ile Tyr Tyr Ala Asp Thr Val Lys Gly Arg Phe Thr Ile Ser
    290                      295                      300 aga gac aat gcc aag aac acc ctg ttc ctg caa atg acc agt cta agg     960
Arg Asp Asn Ala Lys Asn Thr Leu Phe Leu Gln Met Thr Ser Leu Arg
305                      310                      315                      320 tct gag gac aca gcc atg cgg ggg tta cta ctt gac tac tgg ggc caa    1008
Ser Glu Asp Thr Ala Met Arg Gly Leu Leu Leu Asp Tyr Trp Gly Gln
                325                      330                      335 ggc acc act ctc aca gtc tcc tca cta gaa caa aaa ctc atc tca gaa    1056
Gly Thr Thr Leu Thr Val Ser Ser Leu Glu Gln Lys Leu Ile Ser Glu
            340                      345                      350 gag gat ctg aat agc gcc gtc gac gct tcc acc aag ggc cca tcc gtc    1104
Glu Asp Leu Asn Ser Ala Val Asp Ala Ser Thr Lys Gly Pro Ser Val
        355                      360                      365 ttc ccc ctg gcg ccc ctg gag tct tcc gga tcc atg gcc aaa gcc gcg    1152
Phe Pro Leu Ala Pro Leu Glu Ser Ser Gly Ser Met Ala Lys Ala Ala
    370                      375                      380 gcg atc ggc atc gac ctg ggc acc acc tac tcc tgc gtg ggg gtg ttc    1200
Ala Ile Gly Ile Asp Leu Gly Thr Thr Tyr Ser Cys Val Gly Val Phe
385                      390                      395                      400 caa cac ggc aag gtg gag atc atc gcc aac gac cag ggc aac cgc acc    1248
Gln His Gly Lys Val Glu Ile Ile Ala Asn Asp Gln Gly Asn Arg Thr
                405                      410                      415 acc ccc agc tac gtg gcc ttc acg gac acc gag cgg ctc atc ggg gat    1296
```

-continued

```
Thr Pro Ser Tyr Val Ala Phe Thr Asp Thr Glu Arg Leu Ile Gly Asp
        420             425             430 gcg gcc aag aac cag gtg gcg ctg aac ccg cag aac acc gtg ttt gac      1344
Ala Ala Lys Asn Gln Val Ala Leu Asn Pro Gln Asn Thr Val Phe Asp
        435             440             445 gcg aag cgg ctg atc ggc cgc aag ttc ggc gac ccg gtg gtg cag tcg      1392
Ala Lys Arg Leu Ile Gly Arg Lys Phe Gly Asp Pro Val Val Gln Ser
    450             455             460 gac atg aag cac tgg cct ttc cag gtg atc aac gac gga gac aag ccc      1440
Asp Met Lys His Trp Pro Phe Gln Val Ile Asn Asp Gly Asp Lys Pro
465             470             475             480 aag gtg cag gtg agc tac aag ggg gag acc aag gca ttc tac ccc gag      1488
Lys Val Gln Val Ser Tyr Lys Gly Glu Thr Lys Ala Phe Tyr Pro Glu
            485             490             495 gag atc tcg tcc atg gtg ctg acc aag atg aag gag atc gcc gag gcg      1536
Glu Ile Ser Ser Met Val Leu Thr Lys Met Lys Glu Ile Ala Glu Ala
            500             505             510 tac ctg ggc tac ccg gtg acc aac gcg gtg atc acc gtg ccg gcc tac      1584
Tyr Leu Gly Tyr Pro Val Thr Asn Ala Val Ile Thr Val Pro Ala Tyr
        515             520             525 ttc aac gac tcg cag cgc cag gcc acc aag gat gcg ggt gtg atc gcg      1632
Phe Asn Asp Ser Gln Arg Gln Ala Thr Lys Asp Ala Gly Val Ile Ala
        530             535             540 ggg ctc aac gtg ctg cgg atc atc aac gag ccc acg gcc gcc gcc atc      1680
Gly Leu Asn Val Leu Arg Ile Ile Asn Glu Pro Thr Ala Ala Ala Ile
545             550             555             560 gcc tac ggc ctg gac aga acg ggc aag ggg gag cgc aac gtg ctc atc      1728
Ala Tyr Gly Leu Asp Arg Thr Gly Lys Gly Glu Arg Asn Val Leu Ile
            565             570             575 ttt gac ctg ggc ggg ggc acc ttc gac gtg tcc atc ctg acg atc gac      1776
Phe Asp Leu Gly Gly Gly Thr Phe Asp Val Ser Ile Leu Thr Ile Asp
        580             585             590 gac ggc atc ttc gag gtg aag gcc acg gcc ggg gac acc cac ctg ggt      1824
Asp Gly Ile Phe Glu Val Lys Ala Thr Ala Gly Asp Thr His Leu Gly
        595             600             605 ggg gag gac ttt gac aac agg ctg gtg aac cac ttc gtg gag gag ttc      1872
Gly Glu Asp Phe Asp Asn Arg Leu Val Asn His Phe Val Glu Glu Phe
        610             615             620 aag aga aaa cac aag aag gac atc agc cag aac aag cga gcc gtg agg      1920
Lys Arg Lys His Lys Lys Asp Ile Ser Gln Asn Lys Arg Ala Val Arg
625             630             635             640 cgg ctg cgc acc gcc tgc gag agg gcc aag agg acc ctg tcg tcc agc      1968
Arg Leu Arg Thr Ala Cys Glu Arg Ala Lys Arg Thr Leu Ser Ser Ser
            645             650             655 acc cag gcc agc ctg gag atc gac tcc ctg ttt gag ggc atc gac ttc      2016
Thr Gln Ala Ser Leu Glu Ile Asp Ser Leu Phe Glu Gly Ile Asp Phe
            660             665             670 tac acg tcc atc acc agg gcg agg ttc gag gag ctg tgc tcc gac ctg      2064
Tyr Thr Ser Ile Thr Arg Ala Arg Phe Glu Glu Leu Cys Ser Asp Leu
        675             680             685 ttc cga agc acc ctg gag ccc gtg gag aag gct ctg cgc gac gcc aag      2112
Phe Arg Ser Thr Leu Glu Pro Val Glu Lys Ala Leu Arg Asp Ala Lys
        690             695             700 ctg gac aag gcc cag att cac gac ctg gtc ctg gtc ggg ggc tcc acc      2160
Leu Asp Lys Ala Gln Ile His Asp Leu Val Leu Val Gly Gly Ser Thr
705             710             715             720 cgc atc ccc aag gtg cag aag ctg ctg cag gac ttc ttc aac ggg cgc      2208
Arg Ile Pro Lys Val Gln Lys Leu Leu Gln Asp Phe Phe Asn Gly Arg
            725             730             735
```

```
gac ctg aac aag agc atc aac ccc gac gag gct gtg gcc tac ggg gcg    2256
Asp Leu Asn Lys Ser Ile Asn Pro Asp Glu Ala Val Ala Tyr Gly Ala
            740             745             750 gcg gtg cag gcg gcc atc ctg atg ggg gac aag tcc gag aac gtg cag    2304
Ala Val Gln Ala Ala Ile Leu Met Gly Asp Lys Ser Glu Asn Val Gln
            755             760             765 gac ctg ctg ctg ctg gac gtg gct ccc ctg tcg ctg ggg ctg gag acg    2352
Asp Leu Leu Leu Leu Asp Val Ala Pro Leu Ser Leu Gly Leu Glu Thr
    770             775             780 gcc gga ggc gtg atg act gcc ctg atc aag cgc aac tcc acc atc ccc    2400
Ala Gly Gly Val Met Thr Ala Leu Ile Lys Arg Asn Ser Thr Ile Pro
785             790             795             800 acc aag cag acg cag atc ttc acc acc tac tcc gac aac caa ccc ggg    2448
Thr Lys Gln Thr Gln Ile Phe Thr Thr Tyr Ser Asp Asn Gln Pro Gly
                805             810             815 gtg ctg atc cag gtg tac gag ggc gag agg gcc atg acg aaa gac aac    2496
Val Leu Ile Gln Val Tyr Glu Gly Glu Arg Ala Met Thr Lys Asp Asn
            820             825             830 aat ctg ttg ggg cgc ttc gag ctg agc ggc atc cct ccg gcc ccc agg    2544
Asn Leu Leu Gly Arg Phe Glu Leu Ser Gly Ile Pro Pro Ala Pro Arg
            835             840             845 ggc gtg ccc cag atc gag gtg acc ttc gac atc gat gcc aac ggc atc    2592
Gly Val Pro Gln Ile Glu Val Thr Phe Asp Ile Asp Ala Asn Gly Ile
    850             855             860 ctg aac gtc acg gcc acg gac aag agc acc ggc aag gcc aac aag atc    2640
Leu Asn Val Thr Ala Thr Asp Lys Ser Thr Gly Lys Ala Asn Lys Ile
865             870             875             880 acc atc acc aac gac aag ggc cgc ctg agc aag gag gag atc gag cgc    2688
Thr Ile Thr Asn Asp Lys Gly Arg Leu Ser Lys Glu Glu Ile Glu Arg
                885             890             895 atg gtg cag gag gcg gag aag tac aaa gcg gag gac gag gtg cag cgc    2736
Met Val Gln Glu Ala Glu Lys Tyr Lys Ala Glu Asp Glu Val Gln Arg
            900             905             910 gag agg gtg tca gcc aag aac gcc ctg gag tcc tac gcc ttc aac atg    2784
Glu Arg Val Ser Ala Lys Asn Ala Leu Glu Ser Tyr Ala Phe Asn Met
            915             920             925 aag agc gcc gtg gag gat gag ggg ctc aag ggc aag atc agc gag gcg    2832
Lys Ser Ala Val Glu Asp Glu Gly Leu Lys Gly Lys Ile Ser Glu Ala
    930             935             940 gac aag aag aag gtt ctg gac aag tgt caa gag gtc atc tcg tgg ctg    2880
Asp Lys Lys Lys Val Leu Asp Lys Cys Gln Glu Val Ile Ser Trp Leu
945             950             955             960 gac gcc aac acc ttg gcc gag aag gac gag ttt gag cac aag agg aag    2928
Asp Ala Asn Thr Leu Ala Glu Lys Asp Glu Phe Glu His Lys Arg Lys
                965             970             975 gag ctg gag cag gtg tgt aac ccc atc atc agc gga ctg tac cag ggt    2976
Glu Leu Glu Gln Val Cys Asn Pro Ile Ile Ser Gly Leu Tyr Gln Gly
            980             985             990 gcc ggt ggt ccc ggg cct ggc ggc  ttc ggg gct cag ggt  ccc aag gga  3024
Ala Gly Gly Pro Gly Pro Gly Gly  Phe Gly Ala Gln Gly  Pro Lys Gly
            995             1000            1005 ggg tct  ggg tca ggc cct acc  att gag gag gtg gat  tag tctaga       3069
Gly Ser  Gly Ser Gly Pro Thr  Ile Glu Glu Val Asp
    1010            1015            1020
```

<210> SEQ ID NO 29
<211> LENGTH: 1020
<212> TYPE: PRT
<213> ORGANISM: Artificial Sequence
<220> FEATURE:
<223> OTHER INFORMATION: Synthetic Construct

<400> SEQUENCE: 29

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
            115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
            195                 200                 205

Leu Glu Ile Lys Arg Ala Asp Ala Ala Pro Gly Gly Gly Ser Gly
    210                 215                 220

Gly Gly Gly Ser Gly Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
            260                 265                 270

Ala Pro Glu Lys Gly Leu Glu Trp Val Ala Tyr Ile Ser Ser Gly Ser
            275                 280                 285

Ser Thr Ile Tyr Tyr Ala Asp Thr Val Lys Gly Arg Phe Thr Ile Ser
    290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
            340                 345                 350

Glu Asp Leu Asn Ser Ala Val Asp Ala Ser Thr Lys Gly Pro Ser Val
            355                 360                 365

Phe Pro Leu Ala Pro Leu Glu Ser Ser Gly Ser Met Ala Lys Ala Ala
    370                 375                 380

Ala Ile Gly Ile Asp Leu Gly Thr Thr Tyr Ser Cys Val Gly Val Phe
385                 390                 395                 400

Gln His Gly Lys Val Glu Ile Ile Ala Asn Asp Gln Gly Asn Arg Thr

-continued

```
              405                410                415

Thr Pro Ser Tyr Val Ala Phe Thr Asp Thr Glu Arg Leu Ile Gly Asp
            420                425                430

Ala Ala Lys Asn Gln Val Ala Leu Asn Pro Gln Asn Thr Val Phe Asp
            435                440                445

Ala Lys Arg Leu Ile Gly Arg Lys Phe Gly Asp Pro Val Val Gln Ser
            450                455                460

Asp Met Lys His Trp Pro Phe Gln Val Ile Asn Asp Gly Asp Lys Pro
465                470                475                480

Lys Val Gln Val Ser Tyr Lys Gly Glu Thr Lys Ala Phe Tyr Pro Glu
                485                490                495

Glu Ile Ser Ser Met Val Leu Thr Lys Met Lys Glu Ile Ala Glu Ala
                500                505                510

Tyr Leu Gly Tyr Pro Val Thr Asn Ala Val Ile Thr Val Pro Ala Tyr
            515                520                525

Phe Asn Asp Ser Gln Arg Gln Ala Thr Lys Asp Ala Gly Val Ile Ala
    530                535                540

Gly Leu Asn Val Leu Arg Ile Ile Asn Glu Pro Thr Ala Ala Ala Ile
545                550                555                560

Ala Tyr Gly Leu Asp Arg Thr Gly Lys Gly Glu Arg Asn Val Leu Ile
                565                570                575

Phe Asp Leu Gly Gly Gly Thr Phe Asp Val Ser Ile Leu Thr Ile Asp
            580                585                590

Asp Gly Ile Phe Glu Val Lys Ala Thr Ala Gly Asp Thr His Leu Gly
            595                600                605

Gly Glu Asp Phe Asp Asn Arg Leu Val Asn His Phe Val Glu Glu Phe
    610                615                620

Lys Arg Lys His Lys Lys Asp Ile Ser Gln Asn Lys Arg Ala Val Arg
625                630                635                640

Arg Leu Arg Thr Ala Cys Glu Arg Ala Lys Arg Thr Leu Ser Ser Ser
            645                650                655

Thr Gln Ala Ser Leu Glu Ile Asp Ser Leu Phe Glu Gly Ile Asp Phe
            660                665                670

Tyr Thr Ser Ile Thr Arg Ala Arg Phe Glu Glu Leu Cys Ser Asp Leu
            675                680                685

Phe Arg Ser Thr Leu Glu Pro Val Glu Lys Ala Leu Arg Asp Ala Lys
    690                695                700

Leu Asp Lys Ala Gln Ile His Asp Leu Val Leu Val Gly Gly Ser Thr
705                710                715                720

Arg Ile Pro Lys Val Gln Lys Leu Leu Gln Asp Phe Phe Asn Gly Arg
            725                730                735

Asp Leu Asn Lys Ser Ile Asn Pro Asp Glu Ala Val Ala Tyr Gly Ala
            740                745                750

Ala Val Gln Ala Ala Ile Leu Met Gly Asp Lys Ser Glu Asn Val Gln
            755                760                765

Asp Leu Leu Leu Leu Asp Val Ala Pro Leu Ser Leu Gly Leu Glu Thr
    770                775                780

Ala Gly Gly Val Met Thr Ala Leu Ile Lys Arg Asn Ser Thr Ile Pro
785                790                795                800

Thr Lys Gln Thr Gln Ile Phe Thr Thr Tyr Ser Asp Asn Gln Pro Gly
            805                810                815

Val Leu Ile Gln Val Tyr Glu Gly Glu Arg Ala Met Thr Lys Asp Asn
            820                825                830
```

-continued

```
Asn Leu Leu Gly Arg Phe Glu Leu Ser Gly Ile Pro Pro Ala Pro Arg
        835                 840                 845

Gly Val Pro Gln Ile Glu Val Thr Phe Asp Ile Asp Ala Asn Gly Ile
    850                 855                 860

Leu Asn Val Thr Ala Thr Asp Lys Ser Thr Gly Lys Ala Asn Lys Ile
865                 870                 875                 880

Thr Ile Thr Asn Asp Lys Gly Arg Leu Ser Lys Glu Glu Ile Glu Arg
                885                 890                 895

Met Val Gln Glu Ala Glu Lys Tyr Lys Ala Glu Asp Glu Val Gln Arg
                900                 905                 910

Glu Arg Val Ser Ala Lys Asn Ala Leu Glu Ser Tyr Ala Phe Asn Met
        915                 920                 925

Lys Ser Ala Val Glu Asp Glu Gly Leu Lys Gly Lys Ile Ser Glu Ala
    930                 935                 940

Asp Lys Lys Lys Val Leu Asp Lys Cys Gln Glu Val Ile Ser Trp Leu
945                 950                 955                 960

Asp Ala Asn Thr Leu Ala Glu Lys Asp Glu Phe Glu His Lys Arg Lys
                965                 970                 975

Glu Leu Glu Gln Val Cys Asn Pro Ile Ile Ser Gly Leu Tyr Gln Gly
        980                 985                 990

Ala Gly Gly Pro Gly Pro Gly Gly  Phe Gly Ala Gln Gly  Pro Lys Gly
        995                 1000                1005

Gly Ser  Gly Ser Gly Pro Thr  Ile Glu Glu Val Asp
    1010                1015                1020
```

<210> SEQ ID NO 30
<211> LENGTH: 1020
<212> TYPE: PRT
<213> ORGANISM: Artificial Sequence
<220> FEATURE:
<223> OTHER INFORMATION: 3E10 Fv-Hsp70 amino acid sequence for a
      chimeric protein comprising a single chain Fv antibody fragment
      derived from Mus musculus 3E10 hybridoma and Hsp70 from Homo
      sapiens joined by human CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
      signal sequence for secretion of fusion protein, provided by
      pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
      removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility
<220> FEATURE:
<221> NAME/KEY: MISC_FEATURE
<222> LOCATION: (102)..(102)

-continued

```
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting
      in enhanced cell penetration of the 3E10 monoclonal antibody and
      3E10 Fv antibody fragment
<220> FEATURE:
<221> NAME/KEY: MISC_FEATURE
<222> LOCATION: (264)..(264)
<223> OTHER INFORMATION: Asparagine (N) in place of aspartic acid in
      3E10 variable heavy chain, VH, conferring enhanced cell
      penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
      chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(373)
<223> OTHER INFORMATION: Homo sapiens immunoglobulin heavy chain
      constant domain, CH1, linker
<220> FEATURE:
<221> NAME/KEY: MISC_FEATURE
<222> LOCATION: (374)..(379)
<223> OTHER INFORMATION: Swivel sequence
<220> FEATURE:
<221> NAME/KEY: MISC_FEATURE
<222> LOCATION: (380)..(1020)
<223> OTHER INFORMATION: Homo sapiens Hsp70 sequence

<400> SEQUENCE: 30

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30
```

-continued

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His
                85                  90                  95

His Ala Gly Ile His Asp Ile Val Leu Thr Gln Ser Pro Ala Ser Leu
                100                 105                 110

Ala Val Ser Leu Gly Gln Arg Ala Thr Ile Ser Cys Arg Ala Ser Lys
                115                 120                 125

Ser Val Ser Thr Ser Ser Tyr Ser Tyr Met His Trp Tyr Gln Gln Lys
        130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
        180                 185                 190

Cys Gln His Ser Arg Glu Phe Pro Trp Thr Phe Gly Gly Gly Thr Lys
        195                 200                 205

Leu Glu Ile Lys Arg Ala Asp Ala Ala Pro Gly Gly Gly Gly Ser Gly
        210                 215                 220

Gly Gly Gly Ser Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
                260                 265                 270

Ala Pro Glu Lys Gly Leu Glu Trp Val Ala Tyr Ile Ser Ser Gly Ser
        275                 280                 285

Ser Thr Ile Tyr Tyr Ala Asp Thr Val Lys Gly Arg Phe Thr Ile Ser
        290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
                340                 345                 350

Glu Asp Leu Asn Ser Ala Val Asp Ala Ser Thr Lys Gly Pro Ser Val
        355                 360                 365

Phe Pro Leu Ala Pro Leu Glu Ser Ser Gly Ser Met Ala Lys Ala Ala
        370                 375                 380

Ala Ile Gly Ile Asp Leu Gly Thr Thr Tyr Ser Cys Val Gly Val Phe
385                 390                 395                 400

Gln His Gly Lys Val Glu Ile Ile Ala Asn Asp Gln Gly Asn Arg Thr
                405                 410                 415

Thr Pro Ser Tyr Val Ala Phe Thr Asp Thr Glu Arg Leu Ile Gly Asp
                420                 425                 430

Ala Ala Lys Asn Gln Val Ala Leu Asn Pro Gln Asn Thr Val Phe Asp
        435                 440                 445

-continued

```
Ala Lys Arg Leu Ile Gly Arg Lys Phe Gly Asp Pro Val Val Gln Ser
    450                 455                 460

Asp Met Lys His Trp Pro Phe Gln Val Ile Asn Asp Gly Asp Lys Pro
465                 470                 475                 480

Lys Val Gln Val Ser Tyr Lys Gly Glu Thr Lys Ala Phe Tyr Pro Glu
                485                 490                 495

Glu Ile Ser Ser Met Val Leu Thr Lys Met Lys Glu Ile Ala Glu Ala
                500                 505                 510

Tyr Leu Gly Tyr Pro Val Thr Asn Ala Val Ile Thr Val Pro Ala Tyr
                515                 520                 525

Phe Asn Asp Ser Gln Arg Gln Ala Thr Lys Asp Ala Gly Val Ile Ala
    530                 535                 540

Gly Leu Asn Val Leu Arg Ile Ile Asn Glu Pro Thr Ala Ala Ala Ile
545                 550                 555                 560

Ala Tyr Gly Leu Asp Arg Thr Gly Lys Gly Glu Arg Asn Val Leu Ile
                565                 570                 575

Phe Asp Leu Gly Gly Gly Thr Phe Asp Val Ser Ile Leu Thr Ile Asp
                580                 585                 590

Asp Gly Ile Phe Glu Val Lys Ala Thr Ala Gly Asp Thr His Leu Gly
                595                 600                 605

Gly Glu Asp Phe Asp Asn Arg Leu Val Asn His Phe Val Glu Glu Phe
                610                 615                 620

Lys Arg Lys His Lys Lys Asp Ile Ser Gln Asn Lys Arg Ala Val Arg
625                 630                 635                 640

Arg Leu Arg Thr Ala Cys Glu Arg Ala Lys Arg Thr Leu Ser Ser Ser
                645                 650                 655

Thr Gln Ala Ser Leu Glu Ile Asp Ser Leu Phe Glu Gly Ile Asp Phe
                660                 665                 670

Tyr Thr Ser Ile Thr Arg Ala Arg Phe Glu Glu Leu Cys Ser Asp Leu
                675                 680                 685

Phe Arg Ser Thr Leu Glu Pro Val Glu Lys Ala Leu Arg Asp Ala Lys
    690                 695                 700

Leu Asp Lys Ala Gln Ile His Asp Leu Val Leu Val Gly Gly Ser Thr
705                 710                 715                 720

Arg Ile Pro Lys Val Gln Lys Leu Leu Gln Asp Phe Phe Asn Gly Arg
                725                 730                 735

Asp Leu Asn Lys Ser Ile Asn Pro Asp Glu Ala Val Ala Tyr Gly Ala
                740                 745                 750

Ala Val Gln Ala Ala Ile Leu Met Gly Asp Lys Ser Glu Asn Val Gln
                755                 760                 765

Asp Leu Leu Leu Leu Asp Val Ala Pro Leu Ser Leu Gly Leu Glu Thr
    770                 775                 780

Ala Gly Gly Val Met Thr Ala Leu Ile Lys Arg Asn Ser Thr Ile Pro
785                 790                 795                 800

Thr Lys Gln Thr Gln Ile Phe Thr Thr Tyr Ser Asp Asn Gln Pro Gly
                805                 810                 815

Val Leu Ile Gln Val Tyr Glu Gly Glu Arg Ala Met Thr Lys Asp Asn
                820                 825                 830

Asn Leu Leu Gly Arg Phe Glu Leu Ser Gly Ile Pro Pro Ala Pro Arg
    835                 840                 845

Gly Val Pro Gln Ile Glu Val Thr Phe Asp Ile Asp Ala Asn Gly Ile
    850                 855                 860

Leu Asn Val Thr Ala Thr Asp Lys Ser Thr Gly Lys Ala Asn Lys Ile
```

-continued

```
865              870              875              880

Thr Ile Thr Asn Asp Lys Gly Arg Leu Ser Lys Glu Glu Ile Glu Arg
                885              890              895

Met Val Gln Glu Ala Glu Lys Tyr Lys Ala Glu Asp Glu Val Gln Arg
            900              905              910

Glu Arg Val Ser Ala Lys Asn Ala Leu Glu Ser Tyr Ala Phe Asn Met
         915              920              925

Lys Ser Ala Val Glu Asp Glu Gly Leu Lys Gly Lys Ile Ser Glu Ala
    930              935              940

Asp Lys Lys Lys Val Leu Asp Lys Cys Gln Glu Val Ile Ser Trp Leu
945              950              955              960

Asp Ala Asn Thr Leu Ala Glu Lys Asp Glu Phe Glu His Lys Arg Lys
            965              970              975

Glu Leu Glu Gln Val Cys Asn Pro Ile Ile Ser Gly Leu Tyr Gln Gly
            980              985              990

Ala Gly Gly Pro Gly Pro Gly Gly  Phe Gly Ala Gln Gly  Pro Lys Gly
         995              1000              1005

Gly Ser  Gly Ser Gly Pro Thr  Ile Glu Glu Val Asp
    1010              1015              1020
```

<210> SEQ ID NO 31
<211> LENGTH: 3108
<212> TYPE: DNA
<213> ORGANISM: Artificial Sequence
<220> FEATURE:
<223> OTHER INFORMATION: 3E10 Fv-GRP78 nucleotide sequence encoding a
      chimeric protein comprising a single chain Fv antibody fragment
      derived from Mus musculus 3E10 hybridoma and GRP78 from Homo
      sapiens joined by human CH1 linker and swivel sequence
<220> FEATURE:
<221> NAME/KEY: CDS
<222> LOCATION: (1)..(3102)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Homo sapiens CH1 linker, swivel sequence, epitope tags, and Homo
      sapiens GRP78 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
<221> NAME/KEY: misc_feature
<222> LOCATION: (274)..(291)
<223> OTHER INFORMATION: Coding sequence: His6 tag -continued

```
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
<223> OTHER INFORMATION: Begin of coding sequence for Mus musculus 3E10
      immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
      first codon of CDR1 resulting in a D31N change for 3E10 VH chain
      and enhanced cell penetration of the 3E10 monoclonal antibody and
      3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
      immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1119)
<223> OTHER INFORMATION: Coding sequence: Homo sapiens immunoglobulin
      heavy chain constant domain, CH1, linker
<220> FEATURE:
<221> NAME/KEY: misc_feature
<222> LOCATION: (1120)..(1137)
<223> OTHER INFORMATION: Coding sequence: swivel sequence
<220> FEATURE:
<221> NAME/KEY: misc_feature
<222> LOCATION: (1132)..(1137)
<223> OTHER INFORMATION: BamHI restriction enzyme site
<220> FEATURE:
<221> NAME/KEY: misc_feature
<222> LOCATION: (1138)..(3102)
<223> OTHER INFORMATION: Coding sequence: Homo sapiens GRP78 sequence
<220> FEATURE:
<221> NAME/KEY: misc_feature
```

-continued

```
<222> LOCATION: (3100)..(3102)
<223> OTHER INFORMATION: Stop codon
<220> FEATURE:
<221> NAME/KEY: misc_feature
<222> LOCATION: (3103)..(3108)
<223> OTHER INFORMATION: XbaI restriction enzyme site

<400> SEQUENCE: 31 atg aga ttt cct tca ctt ttt act gct gtt tta ttc gca gca tcc tcc        48
Met Arg Phe Pro Ser Leu Phe Thr Ala Val Leu Phe Ala Ala Ser Ser
1               5                   10                  15 gca tta gct gct cca gtc aac act aca aca gaa gat gaa acg gca caa        96
Ala Leu Ala Ala Pro Val Asn Thr Thr Thr Glu Asp Glu Thr Ala Gln
                20                  25                  30 att ccg gct gaa gct gtc atc ggt tac tca gat tta gaa ggg gat ttc       144
Ile Pro Ala Glu Ala Val Ile Gly Tyr Ser Asp Leu Glu Gly Asp Phe
            35                  40                  45 gat gtt gct gtt ttg cca ttt tcc aac agc aca aat aac ggg tta ttg       192
Asp Val Ala Val Leu Pro Phe Ser Asn Ser Thr Asn Asn Gly Leu Leu
        50                  55                  60 ttt ata aat act act att gcc agc att gct gct aaa gaa gaa ggg gta       240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat       288
Ser Leu Glu Lys Arg Glu Ala Glu Ala Glu Phe His His His His His
                85                  90                  95 cac gca ggg att cac gac att gtc ctg aca cag tct cct gct tcc tta       336
His Ala Gly Ile His Asp Ile Val Leu Thr Gln Ser Pro Ala Ser Leu
            100                 105                 110 gct gta tct ctg ggg cag agg gcc acc atc tcc tgc agg gcc agc aaa       384
Ala Val Ser Leu Gly Gln Arg Ala Thr Ile Ser Cys Arg Ala Ser Lys
        115                 120                 125 agt gtc agt aca tct agc tat agt tac atg cac tgg tac caa cag aaa       432
Ser Val Ser Thr Ser Ser Tyr Ser Tyr Met His Trp Tyr Gln Gln Lys
    130                 135                 140 cca gga cag cca ccc aaa ctc ctc atc aag tat gca tcc tac cta gaa       480
Pro Gly Gln Pro Pro Lys Leu Leu Ile Lys Tyr Ala Ser Tyr Leu Glu
145                 150                 155                 160 tct ggg gtt cct gcc agg ttc agt ggc agt ggg tct ggg aca gac ttc       528
Ser Gly Val Pro Ala Arg Phe Ser Gly Ser Gly Ser Gly Thr Asp Phe
                165                 170                 175 acc ctc aac atc cat cct gtg gag gag gag gat gct gca aca tat tac       576
Thr Leu Asn Ile His Pro Val Glu Glu Glu Asp Ala Ala Thr Tyr Tyr
            180                 185                 190 tgt cag cac agt agg gag ttt ccg tgg acg ttc ggt gga ggc acc aag       624
Cys Gln His Ser Arg Glu Phe Pro Trp Thr Phe Gly Gly Gly Thr Lys
        195                 200                 205 ctg gaa atc aaa cgg gct gat gct gca ccc ggg ggt ggc ggt tct ggc       672
Leu Glu Ile Lys Arg Ala Asp Ala Ala Pro Gly Gly Gly Gly Ser Gly
    210                 215                 220 ggt ggc ggt tct gga ggc ggt ggc tct gag gtg cag ctg gtg gag tct       720
Gly Gly Gly Ser Gly Gly Gly Gly Ser Glu Val Gln Leu Val Glu Ser
225                 230                 235                 240 ggg gga ggc tta gtg aag cct gga ggg tcc cgg aaa ctc tcc tgt gca       768
Gly Gly Gly Leu Val Lys Pro Gly Gly Ser Arg Lys Leu Ser Cys Ala
                245                 250                 255 gcc tct gga ttc act ttc agt aac tat gga atg cac tgg gtc cgt cag       816
Ala Ser Gly Phe Thr Phe Ser Asn Tyr Gly Met His Trp Val Arg Gln
            260                 265                 270 gct cca gag aag ggg ctg gag tgg gtt gca tac att agt agt ggc agt       864
Ala Pro Glu Lys Gly Leu Glu Trp Val Ala Tyr Ile Ser Ser Gly Ser
```

```
                275                    280                    285 agt acc atc tac tat gca gac aca gtg aag ggc cga ttc acc atc tcc      912
Ser Thr Ile Tyr Tyr Ala Asp Thr Val Lys Gly Arg Phe Thr Ile Ser
    290                    295                    300 aga gac aat gcc aag aac acc ctg ttc ctg caa atg acc agt cta agg      960
Arg Asp Asn Ala Lys Asn Thr Leu Phe Leu Gln Met Thr Ser Leu Arg
305                    310                    315                    320 tct gag gac aca gcc atg cgg ggg tta cta ctt gac tac tgg ggc caa     1008
Ser Glu Asp Thr Ala Met Arg Gly Leu Leu Leu Asp Tyr Trp Gly Gln
                325                    330                    335 ggc acc act ctc aca gtc tcc tca cta gaa caa aaa ctc atc tca gaa     1056
Gly Thr Thr Leu Thr Val Ser Ser Leu Glu Gln Lys Leu Ile Ser Glu
                340                    345                    350 gag gat ctg aat agc gcc gtc gac gct tcc acc aag ggc cca tcc gtc     1104
Glu Asp Leu Asn Ser Ala Val Asp Ala Ser Thr Lys Gly Pro Ser Val
                355                    360                    365 ttc ccc ctg gcg ccc ctg gag tct tcc gga tcc atg aag ctc tcc ctg     1152
Phe Pro Leu Ala Pro Leu Glu Ser Ser Gly Ser Met Lys Leu Ser Leu
    370                    375                    380 gtg gcc gcg atg ctg ctg ctc agc gcg gcg cgg gcc gag gag gag     1200
Val Ala Ala Met Leu Leu Leu Leu Ser Ala Ala Arg Ala Glu Glu Glu
385                    390                    395                    400 gac aag aag gag gac gtg ggc acg gtg gtc ggc atc gac ctg ggg acc     1248
Asp Lys Lys Glu Asp Val Gly Thr Val Val Gly Ile Asp Leu Gly Thr
                405                    410                    415 acc tac tcc tgc gtc ggc gtg ttc aag aac ggc cgc gtg gag atc atc     1296
Thr Tyr Ser Cys Val Gly Val Phe Lys Asn Gly Arg Val Glu Ile Ile
                420                    425                    430 gcc aac gat cag ggc aac cgc atc acg ccg tcc tat gtc gcc ttc act     1344
Ala Asn Asp Gln Gly Asn Arg Ile Thr Pro Ser Tyr Val Ala Phe Thr
                435                    440                    445 cct gaa ggg gaa cgt ctg att ggc gat gcc gcc aag aac cag ctc acc     1392
Pro Glu Gly Glu Arg Leu Ile Gly Asp Ala Ala Lys Asn Gln Leu Thr
    450                    455                    460 tcc aac ccc gag aac acg gtc ttt gac gcc aag cgg ctc atc ggc cgc     1440
Ser Asn Pro Glu Asn Thr Val Phe Asp Ala Lys Arg Leu Ile Gly Arg
465                    470                    475                    480 acg tgg aat gac ccg tct gtg cag cag gac atc aag ttc ttg ccg ttc     1488
Thr Trp Asn Asp Pro Ser Val Gln Gln Asp Ile Lys Phe Leu Pro Phe
                485                    490                    495 aag gtg gtt gaa aag aaa act aaa cca tac att caa gtt gat att gga     1536
Lys Val Val Glu Lys Lys Thr Lys Pro Tyr Ile Gln Val Asp Ile Gly
                500                    505                    510 ggt ggg caa aca aag aca ttt gct cct gaa gaa att tct gcc atg gtt     1584
Gly Gly Gln Thr Lys Thr Phe Ala Pro Glu Glu Ile Ser Ala Met Val
                515                    520                    525 ctc act aaa atg aaa gaa acc gct gag gct tat ttg gga aag aag gtt     1632
Leu Thr Lys Met Lys Glu Thr Ala Glu Ala Tyr Leu Gly Lys Lys Val
                530                    535                    540 acc cat gca gtt gtt act gta cca gcc tat ttt aat gat gcc caa cgc     1680
Thr His Ala Val Val Thr Val Pro Ala Tyr Phe Asn Asp Ala Gln Arg
545                    550                    555                    560 caa gca acc aaa gac gct gga act att gct ggc cta aat gtt atg agg     1728
Gln Ala Thr Lys Asp Ala Gly Thr Ile Ala Gly Leu Asn Val Met Arg
                565                    570                    575 atc atc aac gag cct acg gca gct gct att gct tat ggc ctg gat aag     1776
Ile Ile Asn Glu Pro Thr Ala Ala Ala Ile Ala Tyr Gly Leu Asp Lys
                580                    585                    590 agg gag ggg gag aag aac atc ctg gtg ttt gac ctg ggt ggc gga acc     1824
```

-continued

```
             Arg Glu Gly Glu Lys Asn Ile Leu Val Phe Asp Leu Gly Gly Gly Thr
                 595                 600                 605 ttc gat gtg tct ctt ctc acc att gac aat ggt gtc ttc gaa gtt gtg          1872
Phe Asp Val Ser Leu Leu Thr Ile Asp Asn Gly Val Phe Glu Val Val
610                 615                 620 gcc act aat gga gat act cat ctg ggt gga gaa gac ttt gac cag cgt          1920
Ala Thr Asn Gly Asp Thr His Leu Gly Gly Glu Asp Phe Asp Gln Arg
625                 630                 635                 640 gtc atg gaa cac ttc atc aaa ctg tac aaa aag aag acg ggc aaa gat          1968
Val Met Glu His Phe Ile Lys Leu Tyr Lys Lys Lys Thr Gly Lys Asp
                    645                 650                 655 gtc agg aaa gac aat aga gct gtg cag aaa ctc cgg cgc gag gta gaa          2016
Val Arg Lys Asp Asn Arg Ala Val Gln Lys Leu Arg Arg Glu Val Glu
                660                 665                 670 aag gcc aaa cgg gcc ctg tct tct cag cat caa gca aga att gaa att          2064
Lys Ala Lys Arg Ala Leu Ser Ser Gln His Gln Ala Arg Ile Glu Ile
                675                 680                 685 gag tcc ttc tat gaa gga gaa gac ttt tct gag acc ctg act cgg gcc          2112
Glu Ser Phe Tyr Glu Gly Glu Asp Phe Ser Glu Thr Leu Thr Arg Ala
            690                 695                 700 aaa ttt gaa gag ctc aac atg gat ctg ttc cgg tct act atg aag ccc          2160
Lys Phe Glu Glu Leu Asn Met Asp Leu Phe Arg Ser Thr Met Lys Pro
705                 710                 715                 720 gtc cag aaa gtg ttg gaa gat tct gat ttg aag aag tct gat att gat          2208
Val Gln Lys Val Leu Glu Asp Ser Asp Leu Lys Lys Ser Asp Ile Asp
                    725                 730                 735 gaa att gtt ctt gtt ggt ggc tcg act cga att cca aag att cag caa          2256
Glu Ile Val Leu Val Gly Gly Ser Thr Arg Ile Pro Lys Ile Gln Gln
                740                 745                 750 ctg gtt aaa gag ttc ttc aat ggc aag gaa cca tcc cgt ggc ata aac          2304
Leu Val Lys Glu Phe Phe Asn Gly Lys Glu Pro Ser Arg Gly Ile Asn
                755                 760                 765 cca gat gaa gct gta gcg tat ggt gct gct gtc cag gct ggt gtg ctc          2352
Pro Asp Glu Ala Val Ala Tyr Gly Ala Ala Val Gln Ala Gly Val Leu
            770                 775                 780 tct ggt gat caa gat aca ggt gac ctg gta ctg ctt gat gta tgt ccc          2400
Ser Gly Asp Gln Asp Thr Gly Asp Leu Val Leu Leu Asp Val Cys Pro
785                 790                 795                 800 ctt aca ctt ggt att gaa act gtg gga ggt gtc atg acc aaa ctg att          2448
Leu Thr Leu Gly Ile Glu Thr Val Gly Gly Val Met Thr Lys Leu Ile
                    805                 810                 815 cca agg aac aca gtg gtg cct acc aag aag tct cag atc ttt tct aca          2496
Pro Arg Asn Thr Val Val Pro Thr Lys Lys Ser Gln Ile Phe Ser Thr
                820                 825                 830 gct tct gat aat caa cca act gtt aca atc aag gtc tat gaa ggt gaa          2544
Ala Ser Asp Asn Gln Pro Thr Val Thr Ile Lys Val Tyr Glu Gly Glu
                835                 840                 845 aga ccc ctg aca aaa gac aat cat ctt ctg ggt aca ttt gat ctg act          2592
Arg Pro Leu Thr Lys Asp Asn His Leu Leu Gly Thr Phe Asp Leu Thr
            850                 855                 860 gga att cct cct gct cct cgt ggg gtc cca cag att gaa gtc acc ttt          2640
Gly Ile Pro Pro Ala Pro Arg Gly Val Pro Gln Ile Glu Val Thr Phe
865                 870                 875                 880 gag ata gat gtg aat ggt att ctt cga gtg aca gct gaa gac aag ggt          2688
Glu Ile Asp Val Asn Gly Ile Leu Arg Val Thr Ala Glu Asp Lys Gly
                    885                 890                 895 aca ggg aac aaa aat aag atc aca atc acc aat gac cag aat cgc ctg          2736
Thr Gly Asn Lys Asn Lys Ile Thr Ile Thr Asn Asp Gln Asn Arg Leu
                900                 905                 910
```

-continued

```
aca cct gaa gaa atc gaa agg atg gtt aat gat gct gag aag ttt gct       2784
Thr Pro Glu Glu Ile Glu Arg Met Val Asn Asp Ala Glu Lys Phe Ala
        915             920             925 gag gaa gac aaa aag ctc aag gag cgc att gat act aga aat gag ttg       2832
Glu Glu Asp Lys Lys Leu Lys Glu Arg Ile Asp Thr Arg Asn Glu Leu
        930             935             940 gaa agc tat gcc tat tct cta aag aat cag att gga gat aaa gaa aag       2880
Glu Ser Tyr Ala Tyr Ser Leu Lys Asn Gln Ile Gly Asp Lys Glu Lys
945             950             955             960 ctg gga ggt aaa ctt tcc tct gaa gat aag gag acc atg gaa aaa gct       2928
Leu Gly Gly Lys Leu Ser Ser Glu Asp Lys Glu Thr Met Glu Lys Ala
        965             970             975 gta gaa gaa aag att gaa tgg ctg gaa agc cac caa gat gct gac att       2976
Val Glu Glu Lys Ile Glu Trp Leu Glu Ser His Gln Asp Ala Asp Ile
        980             985             990 gaa gac ttc aaa gct aag aag aag  gaa ctg gaa gaa att  gtt caa cca     3024
Glu Asp Phe Lys Ala Lys Lys Lys  Glu Leu Glu Glu Ile  Val Gln Pro
        995             1000            1005 att atc  agc aaa ctc tat gga  agt gca ggc cct ccc  cca act ggt        3069
Ile Ile  Ser Lys Leu Tyr Gly  Ser Ala Gly Pro Pro  Pro Thr Gly
        1010            1015            1020 gaa gag  gat aca gca gaa aaa  gat gag ttg tag tctaga                  3108
Glu Glu  Asp Thr Ala Glu Lys  Asp Glu Leu
        1025            1030
```

```
<210> SEQ ID NO 32
<211> LENGTH: 1033
<212> TYPE: PRT
<213> ORGANISM: Artificial Sequence
<220> FEATURE:
<223> OTHER INFORMATION: Synthetic Construct

<400> SEQUENCE: 32

Met Arg Phe Pro Ser Leu Phe Thr Ala Val Leu Phe Ala Ala Ser Ser
1               5               10              15

Ala Leu Ala Ala Pro Val Asn Thr Thr Thr Glu Asp Glu Thr Ala Gln
        20              25              30

Ile Pro Ala Glu Ala Val Ile Gly Tyr Ser Asp Leu Glu Gly Asp Phe
        35              40              45

Asp Val Ala Val Leu Pro Phe Ser Asn Ser Thr Asn Asn Gly Leu Leu
        50              55              60

Phe Ile Asn Thr Thr Ile Ala Ser Ile Ala Ala Lys Glu Glu Gly Val
65              70              75              80

Ser Leu Glu Lys Arg Glu Ala Glu Ala Glu Phe His His His His His
        85              90              95

His Ala Gly Ile His Asp Ile Val Leu Thr Gln Ser Pro Ala Ser Leu
        100             105             110

Ala Val Ser Leu Gly Gln Arg Ala Thr Ile Ser Cys Arg Ala Ser Lys
        115             120             125

Ser Val Ser Thr Ser Ser Tyr Ser Tyr Met His Trp Tyr Gln Gln Lys
        130             135             140

Pro Gly Gln Pro Pro Lys Leu Leu Ile Lys Tyr Ala Ser Tyr Leu Glu
145             150             155             160

Ser Gly Val Pro Ala Arg Phe Ser Gly Ser Gly Ser Gly Thr Asp Phe
        165             170             175

Thr Leu Asn Ile His Pro Val Glu Glu Glu Asp Ala Ala Thr Tyr Tyr
        180             185             190

Cys Gln His Ser Arg Glu Phe Pro Trp Thr Phe Gly Gly Gly Thr Lys
```

```
                195                  200                  205

Leu Glu Ile Lys Arg Ala Asp Ala Ala Pro Gly Gly Gly Gly Ser Gly
    210                  215                  220

Gly Gly Gly Ser Gly Gly Gly Gly Ser Glu Val Gln Leu Val Glu Ser
225                  230                  235                  240

Gly Gly Gly Leu Val Lys Pro Gly Gly Ser Arg Lys Leu Ser Cys Ala
                245                  250                  255

Ala Ser Gly Phe Thr Phe Ser Asn Tyr Gly Met His Trp Val Arg Gln
                260                  265                  270

Ala Pro Glu Lys Gly Leu Glu Trp Val Ala Tyr Ile Ser Ser Gly Ser
    275                  280                  285

Ser Thr Ile Tyr Tyr Ala Asp Thr Val Lys Gly Arg Phe Thr Ile Ser
    290                  295                  300

Arg Asp Asn Ala Lys Asn Thr Leu Phe Leu Gln Met Thr Ser Leu Arg
305                  310                  315                  320

Ser Glu Asp Thr Ala Met Arg Gly Leu Leu Leu Asp Tyr Trp Gly Gln
                325                  330                  335

Gly Thr Thr Leu Thr Val Ser Ser Leu Glu Gln Lys Leu Ile Ser Glu
                340                  345                  350

Glu Asp Leu Asn Ser Ala Val Asp Ala Ser Thr Lys Gly Pro Ser Val
    355                  360                  365

Phe Pro Leu Ala Pro Leu Glu Ser Ser Gly Ser Met Lys Leu Ser Leu
    370                  375                  380

Val Ala Ala Met Leu Leu Leu Leu Ser Ala Ala Arg Ala Glu Glu Glu
385                  390                  395                  400

Asp Lys Lys Glu Asp Val Gly Thr Val Val Gly Ile Asp Leu Gly Thr
                405                  410                  415

Thr Tyr Ser Cys Val Gly Val Phe Lys Asn Gly Arg Val Glu Ile Ile
                420                  425                  430

Ala Asn Asp Gln Gly Asn Arg Ile Thr Pro Ser Tyr Val Ala Phe Thr
    435                  440                  445

Pro Glu Gly Glu Arg Leu Ile Gly Asp Ala Ala Lys Asn Gln Leu Thr
    450                  455                  460

Ser Asn Pro Glu Asn Thr Val Phe Asp Ala Lys Arg Leu Ile Gly Arg
465                  470                  475                  480

Thr Trp Asn Asp Pro Ser Val Gln Gln Asp Ile Lys Phe Leu Pro Phe
                485                  490                  495

Lys Val Val Glu Lys Lys Thr Lys Pro Tyr Ile Gln Val Asp Ile Gly
                500                  505                  510

Gly Gly Gln Thr Lys Thr Phe Ala Pro Glu Glu Ile Ser Ala Met Val
    515                  520                  525

Leu Thr Lys Met Lys Glu Thr Ala Glu Ala Tyr Leu Gly Lys Lys Val
    530                  535                  540

Thr His Ala Val Val Thr Val Pro Ala Tyr Phe Asn Asp Ala Gln Arg
545                  550                  555                  560

Gln Ala Thr Lys Asp Ala Gly Thr Ile Ala Gly Leu Asn Val Met Arg
                565                  570                  575

Ile Ile Asn Glu Pro Thr Ala Ala Ala Ile Ala Tyr Gly Leu Asp Lys
                580                  585                  590

Arg Glu Gly Glu Lys Asn Ile Leu Val Phe Asp Leu Gly Gly Gly Thr
    595                  600                  605

Phe Asp Val Ser Leu Leu Thr Ile Asp Asn Gly Val Phe Glu Val Val
    610                  615                  620
```

```
Ala Thr Asn Gly Asp Thr His Leu Gly Gly Glu Asp Phe Asp Gln Arg
625                 630                 635                 640

Val Met Glu His Phe Ile Lys Leu Tyr Lys Lys Lys Thr Gly Lys Asp
                    645                 650                 655

Val Arg Lys Asp Asn Arg Ala Val Gln Lys Leu Arg Arg Glu Val Glu
                660                 665                 670

Lys Ala Lys Arg Ala Leu Ser Ser Gln His Gln Ala Arg Ile Glu Ile
            675                 680                 685

Glu Ser Phe Tyr Glu Gly Glu Asp Phe Ser Glu Thr Leu Thr Arg Ala
        690                 695                 700

Lys Phe Glu Glu Leu Asn Met Asp Leu Phe Arg Ser Thr Met Lys Pro
705                 710                 715                 720

Val Gln Lys Val Leu Glu Asp Ser Asp Leu Lys Lys Ser Asp Ile Asp
                725                 730                 735

Glu Ile Val Leu Val Gly Gly Ser Thr Arg Ile Pro Lys Ile Gln Gln
                740                 745                 750

Leu Val Lys Glu Phe Phe Asn Gly Lys Glu Pro Ser Arg Gly Ile Asn
            755                 760                 765

Pro Asp Glu Ala Val Ala Tyr Gly Ala Ala Val Gln Ala Gly Val Leu
        770                 775                 780

Ser Gly Asp Gln Asp Thr Gly Asp Leu Val Leu Leu Asp Val Cys Pro
785                 790                 795                 800

Leu Thr Leu Gly Ile Glu Thr Val Gly Gly Val Met Thr Lys Leu Ile
                805                 810                 815

Pro Arg Asn Thr Val Val Pro Thr Lys Lys Ser Gln Ile Phe Ser Thr
                820                 825                 830

Ala Ser Asp Asn Gln Pro Thr Val Thr Ile Lys Val Tyr Glu Gly Glu
            835                 840                 845

Arg Pro Leu Thr Lys Asp Asn His Leu Leu Gly Thr Phe Asp Leu Thr
        850                 855                 860

Gly Ile Pro Pro Ala Pro Arg Gly Val Pro Gln Ile Glu Val Thr Phe
865                 870                 875                 880

Glu Ile Asp Val Asn Gly Ile Leu Arg Val Thr Ala Glu Asp Lys Gly
                885                 890                 895

Thr Gly Asn Lys Asn Lys Ile Thr Ile Thr Asn Asp Gln Asn Arg Leu
                900                 905                 910

Thr Pro Glu Glu Ile Glu Arg Met Val Asn Asp Ala Glu Lys Phe Ala
            915                 920                 925

Glu Glu Asp Lys Lys Leu Lys Glu Arg Ile Asp Thr Arg Asn Glu Leu
        930                 935                 940

Glu Ser Tyr Ala Tyr Ser Leu Lys Asn Gln Ile Gly Asp Lys Glu Lys
945                 950                 955                 960

Leu Gly Gly Lys Leu Ser Ser Glu Asp Lys Glu Thr Met Glu Lys Ala
                965                 970                 975

Val Glu Glu Lys Ile Glu Trp Leu Glu Ser His Gln Asp Ala Asp Ile
                980                 985                 990

Glu Asp Phe Lys Ala Lys Lys Lys  Glu Leu Glu Glu Ile  Val Gln Pro
            995                 1000                 1005

Ile Ile  Ser Lys Leu Tyr Gly  Ser Ala Gly Pro Pro  Pro Thr Gly
    1010                 1015                 1020

Glu Glu  Asp Thr Ala Glu Lys  Asp Glu Leu
    1025                 1030
```

```
<210> SEQ ID NO 33
<211> LENGTH: 1033
<212> TYPE: PRT
<213> ORGANISM: Artificial Sequence
<220> FEATURE:
<223> OTHER INFORMATION: 3E10 Fv-GRP78 amino acid sequence for a
      chimeric protein comprising a single chain Fv antibody fragment
      derived from Mus musculus 3E10 hybridoma and GRP78 from Homo
      sapiens joined by human CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
      signal sequence for secretion of fusion protein, provided by
      pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
      removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility
<220> FEATURE:
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting
      in enhanced cell penetration of the 3E10 monoclonal antibody and
      3E10 Fv antibody fragment
<220> FEATURE:
<221> NAME/KEY: MISC_FEATURE
```

```
<222> LOCATION: (264)..(264)
<223> OTHER INFORMATION: Asparagine (N) in place of aspartic acid in
      3E10 variable heavy chain, VH, conferring enhanced cell
      penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
      chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(373)
<223> OTHER INFORMATION: Homo sapiens immunoglobulin heavy chain
      constant domain, CH1, linker
<220> FEATURE:
<221> NAME/KEY: MISC_FEATURE
<222> LOCATION: (374)..(379)
<223> OTHER INFORMATION: Swivel sequence
<220> FEATURE:
<221> NAME/KEY: MISC_FEATURE
<222> LOCATION: (380)..(1033)
<223> OTHER INFORMATION: Homo sapiens GRP78 sequence

<400> SEQUENCE: 33

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
                85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
        195                 200                 205

Leu Glu Ile Lys Arg Ala Asp Ala Ala Pro Gly Gly Gly Gly Ser Gly
    210                 215                 220
```

```
Gly Gly Gly Ser Gly Gly Gly Gly Ser Glu Val Gln Leu Val Glu Ser
225             230             235             240

Gly Gly Gly Leu Val Lys Pro Gly Gly Ser Arg Lys Leu Ser Cys Ala
            245             250             255

Ala Ser Gly Phe Thr Phe Ser Asn Tyr Gly Met His Trp Val Arg Gln
            260             265             270

Ala Pro Glu Lys Gly Leu Glu Trp Val Ala Tyr Ile Ser Ser Gly Ser
        275             280             285

Ser Thr Ile Tyr Tyr Ala Asp Thr Val Lys Gly Arg Phe Thr Ile Ser
    290             295             300

Arg Asp Asn Ala Lys Asn Thr Leu Phe Leu Gln Met Thr Ser Leu Arg
305             310             315             320

Ser Glu Asp Thr Ala Met Arg Gly Leu Leu Leu Asp Tyr Trp Gly Gln
            325             330             335

Gly Thr Thr Leu Thr Val Ser Ser Leu Glu Gln Lys Leu Ile Ser Glu
            340             345             350

Glu Asp Leu Asn Ser Ala Val Asp Ala Ser Thr Lys Gly Pro Ser Val
            355             360             365

Phe Pro Leu Ala Pro Leu Glu Ser Ser Gly Ser Met Lys Leu Ser Leu
    370             375             380

Val Ala Ala Met Leu Leu Leu Leu Ser Ala Ala Arg Ala Glu Glu Glu
385             390             395             400

Asp Lys Lys Glu Asp Val Gly Thr Val Val Gly Ile Asp Leu Gly Thr
            405             410             415

Thr Tyr Ser Cys Val Gly Val Phe Lys Asn Gly Arg Val Glu Ile Ile
            420             425             430

Ala Asn Asp Gln Gly Asn Arg Ile Thr Pro Ser Tyr Val Ala Phe Thr
            435             440             445

Pro Glu Gly Glu Arg Leu Ile Gly Asp Ala Ala Lys Asn Gln Leu Thr
    450             455             460

Ser Asn Pro Glu Asn Thr Val Phe Asp Ala Lys Arg Leu Ile Gly Arg
465             470             475             480

Thr Trp Asn Asp Pro Ser Val Gln Gln Asp Ile Lys Phe Leu Pro Phe
            485             490             495

Lys Val Val Glu Lys Lys Thr Lys Pro Tyr Ile Gln Val Asp Ile Gly
            500             505             510

Gly Gly Gln Thr Lys Thr Phe Ala Pro Glu Glu Ile Ser Ala Met Val
            515             520             525

Leu Thr Lys Met Lys Glu Thr Ala Glu Ala Tyr Leu Gly Lys Lys Val
    530             535             540

Thr His Ala Val Val Thr Val Pro Ala Tyr Phe Asn Asp Ala Gln Arg
545             550             555             560

Gln Ala Thr Lys Asp Ala Gly Thr Ile Ala Gly Leu Asn Val Met Arg
            565             570             575

Ile Ile Asn Glu Pro Thr Ala Ala Ala Ile Ala Tyr Gly Leu Asp Lys
            580             585             590

Arg Glu Gly Glu Lys Asn Ile Leu Val Phe Asp Leu Gly Gly Gly Thr
        595             600             605

Phe Asp Val Ser Leu Leu Thr Ile Asp Asn Gly Val Phe Glu Val Val
    610             615             620

Ala Thr Asn Gly Asp Thr His Leu Gly Gly Glu Asp Phe Asp Gln Arg
625             630             635             640

Val Met Glu His Phe Ile Lys Leu Tyr Lys Lys Lys Thr Gly Lys Asp
```

-continued

```
                    645                 650                 655
Val Arg Lys Asp Asn Arg Ala Val Gln Lys Leu Arg Arg Glu Val Glu
                660                 665                 670

Lys Ala Lys Arg Ala Leu Ser Ser Gln His Gln Ala Arg Ile Glu Ile
                675                 680                 685

Glu Ser Phe Tyr Glu Gly Glu Asp Phe Ser Glu Thr Leu Thr Arg Ala
                690                 695                 700

Lys Phe Glu Glu Leu Asn Met Asp Leu Phe Arg Ser Thr Met Lys Pro
705                 710                 715                 720

Val Gln Lys Val Leu Glu Asp Ser Asp Leu Lys Lys Ser Asp Ile Asp
                725                 730                 735

Glu Ile Val Leu Val Gly Gly Ser Thr Arg Ile Pro Lys Ile Gln Gln
                740                 745                 750

Leu Val Lys Glu Phe Phe Asn Gly Lys Glu Pro Ser Arg Gly Ile Asn
                755                 760                 765

Pro Asp Glu Ala Val Ala Tyr Gly Ala Ala Val Gln Ala Gly Val Leu
                770                 775                 780

Ser Gly Asp Gln Asp Thr Gly Asp Leu Val Leu Leu Asp Val Cys Pro
785                 790                 795                 800

Leu Thr Leu Gly Ile Glu Thr Val Gly Gly Val Met Thr Lys Leu Ile
                805                 810                 815

Pro Arg Asn Thr Val Val Pro Thr Lys Lys Ser Gln Ile Phe Ser Thr
                820                 825                 830

Ala Ser Asp Asn Gln Pro Thr Val Thr Ile Lys Val Tyr Glu Gly Glu
                835                 840                 845

Arg Pro Leu Thr Lys Asp Asn His Leu Leu Gly Thr Phe Asp Leu Thr
                850                 855                 860

Gly Ile Pro Pro Ala Pro Arg Gly Val Pro Gln Ile Glu Val Thr Phe
865                 870                 875                 880

Glu Ile Asp Val Asn Gly Ile Leu Arg Val Thr Ala Glu Asp Lys Gly
                885                 890                 895

Thr Gly Asn Lys Asn Lys Ile Thr Ile Thr Asn Asp Gln Asn Arg Leu
                900                 905                 910

Thr Pro Glu Glu Ile Glu Arg Met Val Asn Asp Ala Glu Lys Phe Ala
                915                 920                 925

Glu Glu Asp Lys Lys Leu Lys Glu Arg Ile Asp Thr Arg Asn Glu Leu
                930                 935                 940

Glu Ser Tyr Ala Tyr Ser Leu Lys Asn Gln Ile Gly Asp Lys Glu Lys
945                 950                 955                 960

Leu Gly Gly Lys Leu Ser Ser Glu Asp Lys Glu Thr Met Glu Lys Ala
                965                 970                 975

Val Glu Glu Lys Ile Glu Trp Leu Glu Ser His Gln Asp Ala Asp Ile
                980                 985                 990

Glu Asp Phe Lys Ala Lys Lys Lys  Glu Leu Glu Glu Ile  Val Gln Pro
                995                 1000                1005

Ile Ile  Ser Lys Leu Tyr Gly  Ser Ala Gly Pro Pro  Pro Thr Gly
    1010                1015                1020

Glu Glu  Asp Thr Ala Glu Lys  Asp Glu Leu
    1025                1030
```

<210> SEQ ID NO 34
<211> LENGTH: 3342
<212> TYPE: DNA
<213> ORGANISM: Artificial Sequence

```
<220> FEATURE:
<223> OTHER INFORMATION: 3E10 Fv-Hsp90 nucleotide sequence encoding a
      chimeric protein comprising a single chain Fv antibody fragment
      derived from Mus musculus 3E10 hybridoma and Hsp90 from Homo
      sapiens joined by human CH1 linker and swivel sequence
<220> FEATURE:
<221> NAME/KEY: CDS
<222> LOCATION: (1)..(3336)
<223> OTHER INFORMATION: Coding sequence for a chimeric protein
      containing Saccharomyces cerevisiae alpha-factor secretory signal
      sequence, AGIH peptide, Mus musculus 3E10 Fv antibody fragment,
      Homo sapiens CH1 linker, swivel sequence, epitope tags, and Homo
      sapiens Hsp90 protein
<220> FEATURE:
<221> NAME/KEY: misc_feature
<222> LOCATION: (1)..(267)
<223> OTHER INFORMATION: Coding sequence: Saccharomyces cerevisiae
      alpha-factor secretory signal sequence for secretion of fusion
      protein, provided by pPicZalpha A expression vector
<220> FEATURE:
<221> NAME/KEY: misc_feature
<222> LOCATION: (253)..(258)
<223> OTHER INFORMATION: Kex2 signal cleavage site between Arg-Glu
      encoded by nucleotide positions 253-258 for removing Saccharomyces
      cerevisiae alpha-factor secretory signal
<220> FEATURE:
<221> NAME/KEY: misc_feature
<222> LOCATION: (259)..(264)
<223> OTHER INFORMATION: Ste13 signal cleavage site between Ala-Glu
      encoded by nucleotide positions 259-264 for removing Saccharomyces
      cerevisiae alpha-factor secretory signal
<220> FEATURE:
<221> NAME/KEY: misc_feature
<222> LOCATION: (265)..(270)
<223> OTHER INFORMATION: Ste13 signal cleavage site between Ala-Glu
      encoded by nucleotide positions 265-270 for removing Saccharomyces
      cerevisiae alpha-factor secretory signal
<220> FEATURE:
<221> NAME/KEY: misc_feature
<222> LOCATION: (268)..(273)
<223> OTHER INFORMATION: EcoRI restrictiom emzyme site
<220> FEATURE:
<221> NAME/KEY: misc_feature
<222> LOCATION: (274)..(291)
<223> OTHER INFORMATION: His6 tag
<220> FEATURE:
<221> NAME/KEY: misc_feature
<222> LOCATION: (292)..(303)
<223> OTHER INFORMATION: Coding sequence: AGIH increases solubility
<220> FEATURE:
<221> NAME/KEY: misc_feature
<222> LOCATION: (304)..(304)
<223> OTHER INFORMATION: Begin of coding sequence for Mus musculus 3E10
      immunoglobulin variable light chain kappa (Vk); begin 3E10 Fv
      antibody fragment
<220> FEATURE:
<221> NAME/KEY: misc_feature
<222> LOCATION: (406)..(417)
<223> OTHER INFORMATION: Coding sequence: CDR1 Vk
<220> FEATURE:
<221> NAME/KEY: misc_feature
<222> LOCATION: (466)..(483)
<223> OTHER INFORMATION: Coding sequence: CDR2 Vk
<220> FEATURE:
<221> NAME/KEY: misc_feature
<222> LOCATION: (580)..(606)
<223> OTHER INFORMATION: Coding sequence: CDR3 Vk
<220> FEATURE:
<221> NAME/KEY: misc_feature
<222> LOCATION: (654)..(654)
<223> OTHER INFORMATION: End of coding sequence for 3E10 immunoglobulin
      variable light chain kappa (Vk)
<220> FEATURE:
<221> NAME/KEY: misc_feature
<222> LOCATION: (655)..(699)
<223> OTHER INFORMATION: Coding sequence: (GGGGS)3 linker
<220> FEATURE:
<221> NAME/KEY: misc_feature
<222> LOCATION: (700)..(700)
```

<223> OTHER INFORMATION: Begin of coding sequence for Mus musculus 3E10
      immunoglobulin variable heavy chain (VH)
<220> FEATURE:
<221> NAME/KEY: misc_feature
<222> LOCATION: (790)..(804)
<223> OTHER INFORMATION: Coding sequence: CDR1 VH with mutation in the
      first codon of CDR1 resulting in a D31N change for 3E10 VH chain
      and enhanced cell penetration of the 3E10 monoclonal antibody and
      3E10 Fv antibody fragment
<220> FEATURE:
<221> NAME/KEY: misc_feature
<222> LOCATION: (847)..(897)
<223> OTHER INFORMATION: Coding sequence: CDR2 VH
<220> FEATURE:
<221> NAME/KEY: misc_feature
<222> LOCATION: (979)..(999)
<223> OTHER INFORMATION: Coding sequence: CDR3 VH
<220> FEATURE:
<221> NAME/KEY: misc_feature
<222> LOCATION: (1032)..(1032)
<223> OTHER INFORMATION: End of coding sequence for Mus musculus 3E10
      immunoglobulin heavy chain (VH); end of 3E10 Fv antibody fragment
<220> FEATURE:
<221> NAME/KEY: misc_feature
<222> LOCATION: (1036)..(1065)
<223> OTHER INFORMATION: Coding sequence: myc epitope tag
<220> FEATURE:
<221> NAME/KEY: misc_feature
<222> LOCATION: (1081)..(1119)
<223> OTHER INFORMATION: Coding sequence: Homo sapiens immunoglobulin
      heavy chain constant domain, CH1, linker
<220> FEATURE:
<221> NAME/KEY: misc_feature
<222> LOCATION: (1120)..(1137)
<223> OTHER INFORMATION: Coding sequence: swivel sequence
<220> FEATURE:
<221> NAME/KEY: misc_feature
<222> LOCATION: (1132)..(1137)
<223> OTHER INFORMATION: BamHI restriction enzyme site
<220> FEATURE:
<221> NAME/KEY: misc_feature
<222> LOCATION: (1138)..(3336)
<223> OTHER INFORMATION: Coding sequence: Homo sapiens Hsp90 sequence
<220> FEATURE:
<221> NAME/KEY: misc_feature
<222> LOCATION: (3334)..(3336)
<223> OTHER INFORMATION: Stop codon
<220> FEATURE:
<221> NAME/KEY: misc_feature
<222> LOCATION: (3337)..(3342)
<223> OTHER INFORMATION: XbaI restriction enzyme site

<400> SEQUENCE: 34 atg aga ttt cct tca ctt ttt act gct gtt tta ttc gca gca tcc tcc        48
Met Arg Phe Pro Ser Leu Phe Thr Ala Val Leu Phe Ala Ala Ser Ser
1               5                   10                  15 gca tta gct gct cca gtc aac act aca aca gaa gat gaa acg gca caa        96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc       144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg       192
Asp Val Ala Val Leu Pro Phe Ser Asn Ser Thr Asn Asn Gly Leu Leu
    50                  55                  60 ttt ata aat act act att gcc agc att gct gct aaa gaa gaa ggg gta       240
Phe Ile Asn Thr Thr Ile Ala Ser Ile Ala Ala Lys Glu Glu Gly Val
65                  70                  75                  80 tct ctc gag aaa aga gag gct gaa gct gaa ttc cat cac cat cac cat       288
Ser Leu Glu Lys Arg Glu Ala Glu Ala Glu Phe His His His His His
                85                  90                  95 cac gca ggg att cac gac att gtc ctg aca cag tct cct gct tcc tta       336

-continued

```
His Ala Gly Ile His Asp Ile Val Leu Thr Gln Ser Pro Ala Ser Leu
            100                 105                 110 gct gta tct ctg ggg cag agg gcc acc atc tcc tgc agg gcc agc aaa      384
Ala Val Ser Leu Gly Gln Arg Ala Thr Ile Ser Cys Arg Ala Ser Lys
            115                 120                 125 agt gtc agt aca tct agc tat agt tac atg cac tgg tac caa cag aaa      432
Ser Val Ser Thr Ser Ser Tyr Ser Tyr Met His Trp Tyr Gln Gln Lys
            130                 135                 140 cca gga cag cca ccc aaa ctc ctc atc aag tat gca tcc tac cta gaa      480
Pro Gly Gln Pro Pro Lys Leu Leu Ile Lys Tyr Ala Ser Tyr Leu Glu
145                 150                 155                 160 tct ggg gtt cct gcc agg ttc agt ggc agt ggg tct ggg aca gac ttc      528
Ser Gly Val Pro Ala Arg Phe Ser Gly Ser Gly Ser Gly Thr Asp Phe
                165                 170                 175 acc ctc aac atc cat cct gtg gag gag gag gat gct gca aca tat tac      576
Thr Leu Asn Ile His Pro Val Glu Glu Glu Asp Ala Ala Thr Tyr Tyr
            180                 185                 190 tgt cag cac agt agg gag ttt ccg tgg acg ttc ggt gga ggc acc aag      624
Cys Gln His Ser Arg Glu Phe Pro Trp Thr Phe Gly Gly Gly Thr Lys
            195                 200                 205 ctg gaa atc aaa cgg gct gat gct gca ccc ggg ggt ggc ggt tct ggc      672
Leu Glu Ile Lys Arg Ala Asp Ala Ala Pro Gly Gly Gly Gly Ser Gly
            210                 215                 220 ggt ggc ggt tct gga ggc ggt ggc tct gag gtg cag ctg gtg gag tct      720
Gly Gly Gly Ser Gly Gly Gly Gly Ser Glu Val Gln Leu Val Glu Ser
225                 230                 235                 240 ggg gga ggc tta gtg aag cct gga ggg tcc cgg aaa ctc tcc tgt gca      768
Gly Gly Gly Leu Val Lys Pro Gly Gly Ser Arg Lys Leu Ser Cys Ala
                245                 250                 255 gcc tct gga ttc act ttc agt aac tat gga atg cac tgg gtc cgt cag      816
Ala Ser Gly Phe Thr Phe Ser Asn Tyr Gly Met His Trp Val Arg Gln
                260                 265                 270 gct cca gag aag ggg ctg gag tgg gtt gca tac att agt agt ggc agt      864
Ala Pro Glu Lys Gly Leu Glu Trp Val Ala Tyr Ile Ser Ser Gly Ser
            275                 280                 285 agt acc atc tac tat gca gac aca gtg aag ggc cga ttc acc atc tcc      912
Ser Thr Ile Tyr Tyr Ala Asp Thr Val Lys Gly Arg Phe Thr Ile Ser
            290                 295                 300 aga gac aat gcc aag aac acc ctg ttc ctg caa atg acc agt cta agg      960
Arg Asp Asn Ala Lys Asn Thr Leu Phe Leu Gln Met Thr Ser Leu Arg
305                 310                 315                 320 tct gag gac aca gcc atg cgg ggg tta cta ctt gac tac tgg ggc caa     1008
Ser Glu Asp Thr Ala Met Arg Gly Leu Leu Leu Asp Tyr Trp Gly Gln
                325                 330                 335 ggc acc act ctc aca gtc tcc tca cta gaa caa aaa ctc atc tca gaa     1056
Gly Thr Thr Leu Thr Val Ser Ser Leu Glu Gln Lys Leu Ile Ser Glu
            340                 345                 350 gag gat ctg aat agc gcc gtc gac gct tcc acc aag ggc cca tcc gtc     1104
Glu Asp Leu Asn Ser Ala Val Asp Ala Ser Thr Lys Gly Pro Ser Val
            355                 360                 365 ttc ccc ctg gcg ccc ctg gag tct tcc gga tcc atg cct gag gaa acc     1152
Phe Pro Leu Ala Pro Leu Glu Ser Ser Gly Ser Met Pro Glu Glu Thr
            370                 375                 380 cag acc caa gac caa ccg atg gag gag gag gag gtt gag acg ttc gcc     1200
Gln Thr Gln Asp Gln Pro Met Glu Glu Glu Glu Val Glu Thr Phe Ala
385                 390                 395                 400 ttt cag gca gaa att gcc cag ttg atg tca ttg atc atc aat act ttc     1248
Phe Gln Ala Glu Ile Ala Gln Leu Met Ser Leu Ile Ile Asn Thr Phe
                405                 410                 415
```

```
tac tcg aac aaa gag atc ttt ctg aga gag ctc att tca aat tca tca    1296
Tyr Ser Asn Lys Glu Ile Phe Leu Arg Glu Leu Ile Ser Asn Ser Ser
            420             425             430 gat gca ttg gac aaa atc cgg tat gaa agc ttg aca gat ccc agt aaa    1344
Asp Ala Leu Asp Lys Ile Arg Tyr Glu Ser Leu Thr Asp Pro Ser Lys
            435             440             445 tta gac tct ggg aaa gag ctg cat att aac ctt ata ccg aac aaa caa    1392
Leu Asp Ser Gly Lys Glu Leu His Ile Asn Leu Ile Pro Asn Lys Gln
            450             455             460 gat cga act ctc act att gtg gat act gga att gga atg acc aag gct    1440
Asp Arg Thr Leu Thr Ile Val Asp Thr Gly Ile Gly Met Thr Lys Ala
465             470             475             480 gac ttg atc aat aac ctt ggt act atc gcc aag tct ggg acc aaa gcg    1488
Asp Leu Ile Asn Asn Leu Gly Thr Ile Ala Lys Ser Gly Thr Lys Ala
            485             490             495 ttc atg gaa gct ttg cag gct ggt gca gat atc tct atg att ggc cag    1536
Phe Met Glu Ala Leu Gln Ala Gly Ala Asp Ile Ser Met Ile Gly Gln
            500             505             510 ttc ggt gtt ggt ttt tat tct gct tat ttg gtt gct gag aaa gta act    1584
Phe Gly Val Gly Phe Tyr Ser Ala Tyr Leu Val Ala Glu Lys Val Thr
            515             520             525 gtg atc acc aaa cat aac gat gat gag cag tac gct tgg gag tcc tca    1632
Val Ile Thr Lys His Asn Asp Asp Glu Gln Tyr Ala Trp Glu Ser Ser
            530             535             540 gca ggg gga tca ttc aca gtg agg aca gac aca ggt gaa cct atg ggt    1680
Ala Gly Gly Ser Phe Thr Val Arg Thr Asp Thr Gly Glu Pro Met Gly
545             550             555             560 cgt gga aca aaa gtt atc cta cac ctg aaa gaa gac caa act gag tac    1728
Arg Gly Thr Lys Val Ile Leu His Leu Lys Glu Asp Gln Thr Glu Tyr
            565             570             575 ttg gag gaa cga aga ata aag gag att gtg aag aaa cat tct cag ttt    1776
Leu Glu Glu Arg Arg Ile Lys Glu Ile Val Lys Lys His Ser Gln Phe
            580             585             590 att gga tat ccc att act ctt ttt gtg gag aag gaa cgt gat aaa gaa    1824
Ile Gly Tyr Pro Ile Thr Leu Phe Val Glu Lys Glu Arg Asp Lys Glu
            595             600             605 gta agc gat gat gag gct gaa gaa aag gaa gac aaa gaa gaa gaa aaa    1872
Val Ser Asp Asp Glu Ala Glu Glu Lys Glu Asp Lys Glu Glu Glu Lys
            610             615             620 gaa aaa gaa gag aaa gag tcg gaa gac aaa cct gaa att gaa gat gtt    1920
Glu Lys Glu Glu Lys Glu Ser Glu Asp Lys Pro Glu Ile Glu Asp Val
625             630             635             640 ggt tct gat gag gaa gaa gaa aag aag gat ggt gac aag aag aag aag    1968
Gly Ser Asp Glu Glu Glu Glu Lys Lys Asp Gly Asp Lys Lys Lys Lys
            645             650             655 aag aag att aag gaa aag tac atc gat caa gaa gag ctc aac aaa aca    2016
Lys Lys Ile Lys Glu Lys Tyr Ile Asp Gln Glu Glu Leu Asn Lys Thr
            660             665             670 aag ccc atc tgg acc aga aat ccc gac gat att act aat gag gag tac    2064
Lys Pro Ile Trp Thr Arg Asn Pro Asp Asp Ile Thr Asn Glu Glu Tyr
            675             680             685 gga gaa ttc tat aag agc ttg acc aat gac tgg gaa gat cac ttg gca    2112
Gly Glu Phe Tyr Lys Ser Leu Thr Asn Asp Trp Glu Asp His Leu Ala
            690             695             700 gtg aag cat ttt tca gtt gaa gga cag ttg gaa ttc aga gcc ctt cta    2160
Val Lys His Phe Ser Val Glu Gly Gln Leu Glu Phe Arg Ala Leu Leu
705             710             715             720 ttt gtc cca cga cgt gct cct ttt gat ctg ttt gaa aac aga aag aaa    2208
Phe Val Pro Arg Arg Ala Pro Phe Asp Leu Phe Glu Asn Arg Lys Lys
            725             730             735
```

-continued

```
aag aac aac atc aaa ttg tat gta cgc aga gtt ttc atc atg gat aac      2256
Lys Asn Asn Ile Lys Leu Tyr Val Arg Arg Val Phe Ile Met Asp Asn
            740             745             750 tgt gag gag cta atc cct gaa tat ctg aac ttc att aga ggg gtg gta      2304
Cys Glu Glu Leu Ile Pro Glu Tyr Leu Asn Phe Ile Arg Gly Val Val
            755             760             765 gac tcg gag gat ctc cct cta aac ata tcc cgt gag atg ttg caa caa      2352
Asp Ser Glu Asp Leu Pro Leu Asn Ile Ser Arg Glu Met Leu Gln Gln
            770             775             780 agc aaa att ttg aaa gtt atc agg aag aat ttg gtc aaa aaa tgc tta      2400
Ser Lys Ile Leu Lys Val Ile Arg Lys Asn Leu Val Lys Lys Cys Leu
785             790             795             800 gaa ctc ttt act gaa ctg gcg gaa gat aaa gag aac tac aag aaa ttc      2448
Glu Leu Phe Thr Glu Leu Ala Glu Asp Lys Glu Asn Tyr Lys Lys Phe
            805             810             815 tat gag cag ttc tct aaa aac ata aag ctt gga ata cac gaa gac tct      2496
Tyr Glu Gln Phe Ser Lys Asn Ile Lys Leu Gly Ile His Glu Asp Ser
            820             825             830 caa aat cgg aag aag ctt tca gag ctg tta agg tac tac aca tct gcc      2544
Gln Asn Arg Lys Lys Leu Ser Glu Leu Leu Arg Tyr Tyr Thr Ser Ala
            835             840             845 tct ggt gat gag atg gtt tct ctc aag gac tac tgc acc aga atg aag      2592
Ser Gly Asp Glu Met Val Ser Leu Lys Asp Tyr Cys Thr Arg Met Lys
850             855             860 gag aac cag aaa cat atc tat tat atc aca ggt gag acc aag gac cag      2640
Glu Asn Gln Lys His Ile Tyr Tyr Ile Thr Gly Glu Thr Lys Asp Gln
865             870             875             880 gta gct aac tca gcc ttt gtg gaa cgt ctt cgg aaa cat ggc tta gaa      2688
Val Ala Asn Ser Ala Phe Val Glu Arg Leu Arg Lys His Gly Leu Glu
            885             890             895 gtg atc tat atg att gag ccc att gat gag tac tgt gtc caa cag ctg      2736
Val Ile Tyr Met Ile Glu Pro Ile Asp Glu Tyr Cys Val Gln Gln Leu
            900             905             910 aag gaa ttt gag ggg aag act tta gtg tca gtc acc aaa gaa ggc ctg      2784
Lys Glu Phe Glu Gly Lys Thr Leu Val Ser Val Thr Lys Glu Gly Leu
            915             920             925 gaa ctt cca gag gat gaa gaa gag aaa aag aag cag gaa gag aaa aaa      2832
Glu Leu Pro Glu Asp Glu Glu Glu Lys Lys Lys Gln Glu Glu Lys Lys
            930             935             940 aca aag ttt gag aac ctc tgc aaa atc atg aaa gac ata ttg gag aaa      2880
Thr Lys Phe Glu Asn Leu Cys Lys Ile Met Lys Asp Ile Leu Glu Lys
945             950             955             960 aaa gtt gaa aag gtg gtt gtg tca aac cga ttg gtg aca tct cca tgc      2928
Lys Val Glu Lys Val Val Val Ser Asn Arg Leu Val Thr Ser Pro Cys
            965             970             975 tgt att gtc aca agc aca tat ggc tgg aca gca aac atg gag aga atc      2976
Cys Ile Val Thr Ser Thr Tyr Gly Trp Thr Ala Asn Met Glu Arg Ile
            980             985             990 atg aaa gct caa gcc cta aga gac  aac tca aca atg ggt  tac atg gca      3024
Met Lys Ala Gln Ala Leu Arg Asp  Asn Ser Thr Met Gly  Tyr Met Ala
            995             1000            1005 gca aag aaa cac ctg gag ata  aac cct gac cat tcc  att att gag      3069
Ala Lys Lys His Leu Glu Ile  Asn Pro Asp His Ser  Ile Ile Glu
        1010            1015            1020 acc tta agg caa aag gca gag  gct gat aag aac gac  aag tct gtg      3114
Thr Leu Arg Gln Lys Ala Glu  Ala Asp Lys Asn Asp  Lys Ser Val
        1025            1030            1035 aag gat ctg gtc atc ttg ctt  tat gaa act gcg ctc  ctg tct tct      3159
Lys Asp Leu Val Ile Leu Leu  Tyr Glu Thr Ala Leu  Leu Ser Ser
```

-continued

```
        1040                1045                1050 ggc ttc agt ctg gaa gat ccc  cag aca cat gct aac  agg atc tac      3204
Gly Phe Ser Leu Glu Asp Pro  Gln Thr His Ala Asn  Arg Ile Tyr
    1055                1060                1065 agg atg atc aaa ctt ggt ctg  ggt att gat gaa gat  gac cct act      3249
Arg Met Ile Lys Leu Gly Leu  Gly Ile Asp Glu Asp  Asp Pro Thr
    1070                1075                1080 gct gat gat acc agt gct gct  gta act gaa gaa atg  cca ccc ctt      3294
Ala Asp Asp Thr Ser Ala Ala  Val Thr Glu Glu Met  Pro Pro Leu
    1085                1090                1095 gaa gga gat gac gac aca tca  cgc atg gaa gaa gta  gac taa tctaga    3342
Glu Gly Asp Asp Asp Thr Ser  Arg Met Glu Glu Val  Asp
    1100                1105                1110

<210> SEQ ID NO 35
<211> LENGTH: 1111
<212> TYPE: PRT
<213> ORGANISM: Artificial Sequence
<220> FEATURE:
<223> OTHER INFORMATION: Synthetic Construct

<400> SEQUENCE: 35

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
            85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
            115                 120                 125

Ser Val Ser Thr Ser Ser Tyr Ser Tyr Met His Trp Tyr Gln Gln Lys
            130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
                165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
            195                 200                 205

Leu Glu Ile Lys Arg Ala Asp Ala Ala Pro Gly Gly Gly Gly Ser Gly
        210                 215                 220

Gly Gly Gly Ser Gly Gly Gly Gly Ser Glu Val Gln Leu Val Glu Ser
225                 230                 235                 240

Gly Gly Gly Leu Val Lys Pro Gly Gly Ser Arg Lys Leu Ser Cys Ala
                245                 250                 255

Ala Ser Gly Phe Thr Phe Ser Asn Tyr Gly Met His Trp Val Arg Gln
            260                 265                 270
```

```
Ala Pro Glu Lys Gly Leu Glu Trp Val Ala Tyr Ile Ser Ser Gly Ser
        275                 280                 285

Ser Thr Ile Tyr Tyr Ala Asp Thr Val Lys Gly Arg Phe Thr Ile Ser
        290                 295                 300

Arg Asp Asn Ala Lys Asn Thr Leu Phe Leu Gln Met Thr Ser Leu Arg
305                 310                 315                 320

Ser Glu Asp Thr Ala Met Arg Gly Leu Leu Leu Asp Tyr Trp Gly Gln
                325                 330                 335

Gly Thr Thr Leu Thr Val Ser Ser Leu Glu Gln Lys Leu Ile Ser Glu
                340                 345                 350

Glu Asp Leu Asn Ser Ala Val Asp Ala Ser Thr Lys Gly Pro Ser Val
        355                 360                 365

Phe Pro Leu Ala Pro Leu Glu Ser Ser Gly Ser Met Pro Glu Glu Thr
        370                 375                 380

Gln Thr Gln Asp Gln Pro Met Glu Glu Glu Glu Val Glu Thr Phe Ala
385                 390                 395                 400

Phe Gln Ala Glu Ile Ala Gln Leu Met Ser Leu Ile Ile Asn Thr Phe
                405                 410                 415

Tyr Ser Asn Lys Glu Ile Phe Leu Arg Glu Leu Ile Ser Asn Ser Ser
                420                 425                 430

Asp Ala Leu Asp Lys Ile Arg Tyr Glu Ser Leu Thr Asp Pro Ser Lys
        435                 440                 445

Leu Asp Ser Gly Lys Glu Leu His Ile Asn Leu Ile Pro Asn Lys Gln
        450                 455                 460

Asp Arg Thr Leu Thr Ile Val Asp Thr Gly Ile Gly Met Thr Lys Ala
465                 470                 475                 480

Asp Leu Ile Asn Asn Leu Gly Thr Ile Ala Lys Ser Gly Thr Lys Ala
                485                 490                 495

Phe Met Glu Ala Leu Gln Ala Gly Ala Asp Ile Ser Met Ile Gly Gln
                500                 505                 510

Phe Gly Val Gly Phe Tyr Ser Ala Tyr Leu Val Ala Glu Lys Val Thr
                515                 520                 525

Val Ile Thr Lys His Asn Asp Asp Glu Gln Tyr Ala Trp Glu Ser Ser
        530                 535                 540

Ala Gly Gly Ser Phe Thr Val Arg Thr Asp Thr Gly Glu Pro Met Gly
545                 550                 555                 560

Arg Gly Thr Lys Val Ile Leu His Leu Lys Glu Asp Gln Thr Glu Tyr
                565                 570                 575

Leu Glu Glu Arg Arg Ile Lys Glu Ile Val Lys Lys His Ser Gln Phe
                580                 585                 590

Ile Gly Tyr Pro Ile Thr Leu Phe Val Glu Lys Glu Arg Asp Lys Glu
        595                 600                 605

Val Ser Asp Asp Glu Ala Glu Glu Lys Glu Asp Lys Glu Glu Glu Lys
        610                 615                 620

Glu Lys Glu Glu Lys Glu Ser Glu Asp Lys Pro Glu Ile Glu Asp Val
625                 630                 635                 640

Gly Ser Asp Glu Glu Glu Glu Lys Lys Asp Gly Asp Lys Lys Lys Lys
                645                 650                 655

Lys Lys Ile Lys Glu Lys Tyr Ile Asp Gln Glu Glu Leu Asn Lys Thr
                660                 665                 670

Lys Pro Ile Trp Thr Arg Asn Pro Asp Asp Ile Thr Asn Glu Glu Tyr
        675                 680                 685

Gly Glu Phe Tyr Lys Ser Leu Thr Asn Asp Trp Glu Asp His Leu Ala
```

```
            690             695             700

Val Lys His Phe Ser Val Glu Gly Gln Leu Glu Phe Arg Ala Leu Leu
705             710             715             720

Phe Val Pro Arg Arg Ala Pro Phe Asp Leu Phe Glu Asn Arg Lys Lys
            725             730             735

Lys Asn Asn Ile Lys Leu Tyr Val Arg Arg Val Phe Ile Met Asp Asn
            740             745             750

Cys Glu Glu Leu Ile Pro Glu Tyr Leu Asn Phe Ile Arg Gly Val Val
            755             760             765

Asp Ser Glu Asp Leu Pro Leu Asn Ile Ser Arg Glu Met Leu Gln Gln
            770             775             780

Ser Lys Ile Leu Lys Val Ile Arg Lys Asn Leu Val Lys Lys Cys Leu
785             790             795             800

Glu Leu Phe Thr Glu Leu Ala Glu Asp Lys Glu Asn Tyr Lys Lys Phe
            805             810             815

Tyr Glu Gln Phe Ser Lys Asn Ile Lys Leu Gly Ile His Glu Asp Ser
            820             825             830

Gln Asn Arg Lys Lys Leu Ser Glu Leu Leu Arg Tyr Tyr Thr Ser Ala
            835             840             845

Ser Gly Asp Glu Met Val Ser Leu Lys Asp Tyr Cys Thr Arg Met Lys
    850             855             860

Glu Asn Gln Lys His Ile Tyr Tyr Ile Thr Gly Glu Thr Lys Asp Gln
865             870             875             880

Val Ala Asn Ser Ala Phe Val Glu Arg Leu Arg Lys His Gly Leu Glu
            885             890             895

Val Ile Tyr Met Ile Glu Pro Ile Asp Glu Tyr Cys Val Gln Gln Leu
            900             905             910

Lys Glu Phe Glu Gly Lys Thr Leu Val Ser Val Thr Lys Glu Gly Leu
            915             920             925

Glu Leu Pro Glu Asp Glu Glu Glu Lys Lys Lys Gln Glu Glu Lys Lys
    930             935             940

Thr Lys Phe Glu Asn Leu Cys Lys Ile Met Lys Asp Ile Leu Glu Lys
945             950             955             960

Lys Val Glu Lys Val Val Val Ser Asn Arg Leu Val Thr Ser Pro Cys
            965             970             975

Cys Ile Val Thr Ser Thr Tyr Gly Trp Thr Ala Asn Met Glu Arg Ile
            980             985             990

Met Lys Ala Gln Ala Leu Arg Asp  Asn Ser Thr Met Gly  Tyr Met Ala
    995             1000            1005

Ala Lys  Lys His Leu Glu Ile  Asn Pro Asp His Ser  Ile Ile Glu
    1010            1015            1020

Thr Leu  Arg Gln Lys Ala Glu  Ala Asp Lys Asn Asp  Lys Ser Val
    1025            1030            1035

Lys Asp  Leu Val Ile Leu Leu  Tyr Glu Thr Ala Leu  Leu Ser Ser
    1040            1045            1050

Gly Phe  Ser Leu Glu Asp Pro  Gln Thr His Ala Asn  Arg Ile Tyr
    1055            1060            1065

Arg Met  Ile Lys Leu Gly Leu  Gly Ile Asp Glu Asp  Asp Pro Thr
    1070            1075            1080

Ala Asp  Asp Thr Ser Ala Ala  Val Thr Glu Glu Met  Pro Pro Leu
    1085            1090            1095

Glu Gly  Asp Asp Asp Thr Ser  Arg Met Glu Glu Val  Asp
    1100            1105            1110
```

-continued

```
<210> SEQ ID NO 36
<211> LENGTH: 1111
<212> TYPE: PRT
<213> ORGANISM: Artificial Sequence
<220> FEATURE:
<223> OTHER INFORMATION: 3E10 Fv-Hsp90 amino acid sequence for a
      chimeric protein comprising a single chain Fv antibody fragment
      derived from Mus musculus 3E10 hybridoma and Hsp90 from Homo
      sapiens joined by human CH1 linker and swivel sequence
<220> FEATURE:
<221> NAME/KEY: MISC_FEATURE
<222> LOCATION: (1)..(89)
<223> OTHER INFORMATION: Saccharomyces cerevisiae alpha-factor secretory
      signal sequence for secretion of fusion protein, provided by
      pPicZalpha A expression vector
<220> FEATURE:
<221> NAME/KEY: MISC_FEATURE
<222> LOCATION: (85)..(86)
<223> OTHER INFORMATION: Kex2 signal cleavage site between Arg-Glu for
      removing Saccharomyces cerevisiae alpha-factor secretory signal
<220> FEATURE:
<221> NAME/KEY: MISC_FEATURE
<222> LOCATION: (87)..(88)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (89)..(90)
<223> OTHER INFORMATION: Ste13 signal cleavage site between Ala-Glu for
      removing Saccharomyces cerevisiae alpha-factor secretory signal
<220> FEATURE:
<221> NAME/KEY: MISC_FEATURE
<222> LOCATION: (92)..(97)
<223> OTHER INFORMATION: His6 tag
<220> FEATURE:
<221> NAME/KEY: MISC_FEATURE
<222> LOCATION: (98)..(101)
<223> OTHER INFORMATION: AGIH increases solubility
<220> FEATURE:
<221> NAME/KEY: MISC_FEATURE
<222> LOCATION: (102)..(102)
<223> OTHER INFORMATION: Begin Mus musculus 3E10 immunoglobulin variable
      light chain kappa (Vk); begin 3E10 Fv antibody fragment
<220> FEATURE:
<221> NAME/KEY: MISC_FEATURE
<222> LOCATION: (136)..(139)
<223> OTHER INFORMATION: CDR1 Vk
<220> FEATURE:
<221> NAME/KEY: MISC_FEATURE
<222> LOCATION: (156)..(161)
<223> OTHER INFORMATION: CDR2 Vk
<220> FEATURE:
<221> NAME/KEY: MISC_FEATURE
<222> LOCATION: (194)..(202)
<223> OTHER INFORMATION: CDR3 Vk
<220> FEATURE:
<221> NAME/KEY: MISC_FEATURE
<222> LOCATION: (218)..(218)
<223> OTHER INFORMATION: End of 3E10 immunoglobulin variable light chain
      kappa (Vk)
<220> FEATURE:
<221> NAME/KEY: MISC_FEATURE
<222> LOCATION: (219)..(233)
<223> OTHER INFORMATION: (GGGGS)3 linker
<220> FEATURE:
<221> NAME/KEY: MISC_FEATURE
<222> LOCATION: (234)..(234)
<223> OTHER INFORMATION: Begin of Mus musculus 3E10 immunoglobulin
      variable heavy chain (VH)
<220> FEATURE:
<221> NAME/KEY: MISC_FEATURE
<222> LOCATION: (264)..(268)
<223> OTHER INFORMATION: CDR1 VH with mutation in the first amino acid
      of CDR1 corresponding to a D31N change of 3E10 VH chain resulting
      in enhanced cell penetration of the 3E10 monoclonal antibody and
      3E10 Fv antibody fragment
<220> FEATURE:
```

-continued

```
<221> NAME/KEY: MISC_FEATURE
<222> LOCATION: (264)..(264)
<223> OTHER INFORMATION: Asparagine (N) in place of aspartic acid in
      3E10 variable heavy chain, VH, conferring enhanced cell
      penetration; D31N mutation in CDR1 of 3E10 VH chain
<220> FEATURE:
<221> NAME/KEY: MISC_FEATURE
<222> LOCATION: (283)..(299)
<223> OTHER INFORMATION: CDR2 VH
<220> FEATURE:
<221> NAME/KEY: MISC_FEATURE
<222> LOCATION: (327)..(333)
<223> OTHER INFORMATION: CDR3 VH
<220> FEATURE:
<221> NAME/KEY: MISC_FEATURE
<222> LOCATION: (344)..(344)
<223> OTHER INFORMATION: End of Mus musculus 3E10 immunoglobulin heavy
      chain (VH); end of 3E10 Fv antibody fragment
<220> FEATURE:
<221> NAME/KEY: MISC_FEATURE
<222> LOCATION: (346)..(355)
<223> OTHER INFORMATION: myc epitope tag
<220> FEATURE:
<221> NAME/KEY: MISC_FEATURE
<222> LOCATION: (361)..(373)
<223> OTHER INFORMATION: Homo sapiens immunoglobulin heavy chain
      constant domain, CH1, linker
<220> FEATURE:
<221> NAME/KEY: MISC_FEATURE
<222> LOCATION: (374)..(379)
<223> OTHER INFORMATION: Swivel sequence
<220> FEATURE:
<221> NAME/KEY: MISC_FEATURE
<222> LOCATION: (380)..(1111)
<223> OTHER INFORMATION: Homo sapiens Hsp90 sequence

<400> SEQUENCE: 36

Met Arg Phe Pro Ser Leu Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe His His His His His
            85                  90                  95

His Ala Gly Ile His Asp Ile Val Leu Thr Gln Ser Pro Ala Ser Leu
            100                 105                 110

Ala Val Ser Leu Gly Gln Arg Ala Thr Ile Ser Cys Arg Ala Ser Lys
        115                 120                 125

Ser Val Ser Thr Ser Ser Tyr Ser Tyr Met His Trp Tyr Gln Gln Lys
    130                 135                 140

Pro Gly Gln Pro Pro Lys Leu Leu Ile Lys Tyr Ala Ser Tyr Leu Glu
145                 150                 155                 160

Ser Gly Val Pro Ala Arg Phe Ser Gly Ser Gly Ser Gly Thr Asp Phe
            165                 170                 175

Thr Leu Asn Ile His Pro Val Glu Glu Glu Asp Ala Ala Thr Tyr Tyr
            180                 185                 190

Cys Gln His Ser Arg Glu Phe Pro Trp Thr Phe Gly Gly Gly Thr Lys
        195                 200                 205

Leu Glu Ile Lys Arg Ala Asp Ala Ala Pro Gly Gly Gly Gly Ser Gly
    210                 215                 220
```

-continued

```
Gly Gly Gly Ser Gly Gly Gly Ser Glu Val Gln Leu Val Glu Ser
225             230             235             240

Gly Gly Gly Leu Val Lys Pro Gly Gly Ser Arg Lys Leu Ser Cys Ala
            245             250             255

Ala Ser Gly Phe Thr Phe Ser Asn Tyr Gly Met His Trp Val Arg Gln
            260             265             270

Ala Pro Glu Lys Gly Leu Glu Trp Val Ala Tyr Ile Ser Ser Gly Ser
            275             280             285

Ser Thr Ile Tyr Tyr Ala Asp Thr Val Lys Gly Arg Phe Thr Ile Ser
            290             295             300

Arg Asp Asn Ala Lys Asn Thr Leu Phe Leu Gln Met Thr Ser Leu Arg
305             310             315             320

Ser Glu Asp Thr Ala Met Arg Gly Leu Leu Leu Asp Tyr Trp Gly Gln
            325             330             335

Gly Thr Thr Leu Thr Val Ser Ser Leu Glu Gln Lys Leu Ile Ser Glu
            340             345             350

Glu Asp Leu Asn Ser Ala Val Asp Ala Ser Thr Lys Gly Pro Ser Val
            355             360             365

Phe Pro Leu Ala Pro Leu Glu Ser Ser Gly Ser Met Pro Glu Glu Thr
            370             375             380

Gln Thr Gln Asp Gln Pro Met Glu Glu Glu Glu Val Glu Thr Phe Ala
385             390             395             400

Phe Gln Ala Glu Ile Ala Gln Leu Met Ser Leu Ile Ile Asn Thr Phe
            405             410             415

Tyr Ser Asn Lys Glu Ile Phe Leu Arg Glu Leu Ile Ser Asn Ser Ser
            420             425             430

Asp Ala Leu Asp Lys Ile Arg Tyr Glu Ser Leu Thr Asp Pro Ser Lys
            435             440             445

Leu Asp Ser Gly Lys Glu Leu His Ile Asn Leu Ile Pro Asn Lys Gln
            450             455             460

Asp Arg Thr Leu Thr Ile Val Asp Thr Gly Ile Gly Met Thr Lys Ala
465             470             475             480

Asp Leu Ile Asn Asn Leu Gly Thr Ile Ala Lys Ser Gly Thr Lys Ala
            485             490             495

Phe Met Glu Ala Leu Gln Ala Gly Ala Asp Ile Ser Met Ile Gly Gln
            500             505             510

Phe Gly Val Gly Phe Tyr Ser Ala Tyr Leu Val Ala Glu Lys Val Thr
            515             520             525

Val Ile Thr Lys His Asn Asp Asp Glu Gln Tyr Ala Trp Glu Ser Ser
            530             535             540

Ala Gly Gly Ser Phe Thr Val Arg Thr Asp Thr Gly Glu Pro Met Gly
545             550             555             560

Arg Gly Thr Lys Val Ile Leu His Leu Lys Glu Asp Gln Thr Glu Tyr
            565             570             575

Leu Glu Glu Arg Arg Ile Lys Glu Ile Val Lys Lys His Ser Gln Phe
            580             585             590

Ile Gly Tyr Pro Ile Thr Leu Phe Val Glu Lys Glu Arg Asp Lys Glu
            595             600             605

Val Ser Asp Asp Glu Ala Glu Glu Lys Glu Asp Lys Glu Glu Glu Lys
            610             615             620

Glu Lys Glu Glu Lys Glu Ser Glu Asp Lys Pro Glu Ile Glu Asp Val
625             630             635             640
```

```
Gly Ser Asp Glu Glu Glu Glu Lys Lys Asp Gly Asp Lys Lys Lys Lys
              645             650             655

Lys Lys Ile Lys Glu Lys Tyr Ile Asp Gln Glu Glu Leu Asn Lys Thr
              660             665             670

Lys Pro Ile Trp Thr Arg Asn Pro Asp Asp Ile Thr Asn Glu Glu Tyr
              675             680             685

Gly Glu Phe Tyr Lys Ser Leu Thr Asn Asp Trp Glu Asp His Leu Ala
       690             695             700

Val Lys His Phe Ser Val Glu Gly Gln Leu Glu Phe Arg Ala Leu Leu
705             710             715             720

Phe Val Pro Arg Arg Ala Pro Phe Asp Leu Phe Glu Asn Arg Lys Lys
              725             730             735

Lys Asn Asn Ile Lys Leu Tyr Val Arg Arg Val Phe Ile Met Asp Asn
              740             745             750

Cys Glu Glu Leu Ile Pro Glu Tyr Leu Asn Phe Ile Arg Gly Val Val
       755             760             765

Asp Ser Glu Asp Leu Pro Leu Asn Ile Ser Arg Glu Met Leu Gln Gln
       770             775             780

Ser Lys Ile Leu Lys Val Ile Arg Lys Asn Leu Val Lys Lys Cys Leu
785             790             795             800

Glu Leu Phe Thr Glu Leu Ala Glu Asp Lys Glu Asn Tyr Lys Lys Phe
              805             810             815

Tyr Glu Gln Phe Ser Lys Asn Ile Lys Leu Gly Ile His Glu Asp Ser
       820             825             830

Gln Asn Arg Lys Lys Leu Ser Glu Leu Leu Arg Tyr Tyr Thr Ser Ala
       835             840             845

Ser Gly Asp Glu Met Val Ser Leu Lys Asp Tyr Cys Thr Arg Met Lys
       850             855             860

Glu Asn Gln Lys His Ile Tyr Tyr Ile Thr Gly Glu Thr Lys Asp Gln
865             870             875             880

Val Ala Asn Ser Ala Phe Val Glu Arg Leu Arg Lys His Gly Leu Glu
              885             890             895

Val Ile Tyr Met Ile Glu Pro Ile Asp Glu Tyr Cys Val Gln Gln Leu
              900             905             910

Lys Glu Phe Glu Gly Lys Thr Leu Val Ser Val Thr Lys Glu Gly Leu
       915             920             925

Glu Leu Pro Glu Asp Glu Glu Glu Lys Lys Lys Gln Glu Glu Lys Lys
       930             935             940

Thr Lys Phe Glu Asn Leu Cys Lys Ile Met Lys Asp Ile Leu Glu Lys
945             950             955             960

Lys Val Glu Lys Val Val Val Ser Asn Arg Leu Val Thr Ser Pro Cys
              965             970             975

Cys Ile Val Thr Ser Thr Tyr Gly Trp Thr Ala Asn Met Glu Arg Ile
              980             985             990

Met Lys Ala Gln Ala Leu Arg Asp  Asn Ser Thr Met Gly  Tyr Met Ala
       995             1000            1005

Ala Lys  Lys His Leu Glu Ile  Asn Pro Asp His Ser  Ile Ile Glu
       1010            1015            1020

Thr Leu  Arg Gln Lys Ala Glu  Ala Asp Lys Asn Asp  Lys Ser Val
       1025            1030            1035

Lys Asp  Leu Val Ile Leu Leu  Tyr Glu Thr Ala Leu  Leu Ser Ser
       1040            1045            1050

Gly Phe  Ser Leu Glu Asp Pro  Gln Thr His Ala Asn  Arg Ile Tyr
```

-continued

```
      1055                1060                1065

Arg Met  Ile Lys Leu Gly Leu  Gly Ile Asp Glu Asp  Asp Pro Thr
      1070                1075                1080

Ala Asp  Asp Thr Ser Ala Ala  Val Thr Glu Glu Met  Pro Pro Leu
      1085                1090                1095

Glu Gly  Asp Asp Asp Thr Ser  Arg Met Glu Glu Val  Asp
      1100                1105                1110
```